(12) United States Patent
Grammenos et al.

(10) Patent No.: US 9,815,798 B2
(45) Date of Patent: Nov. 14, 2017

(54) SUBSTITUTED [1,2,4]TRIAZOLE AND IMIDAZOLE COMPOUNDS AS FUNGICIDES

(71) Applicant: BASF SE, Ludwigshafen (DE)

(72) Inventors: Wassilios Grammenos, Ludwigshafen (DE); Nadege Boudet, Hirschberg (DE); Bernd Mueller, Frankenthal (DE); Maria Angelica Quintero Palomar, Mannheim (DE); Ana Escribano Cuesta, Mannheim (DE); Erica May Cambeis, Wachenheim (DE); Jan Klaas Lohmann, Lambsheim (DE); Thomas Grote, Wachenheim (DE); Manuel Kretschmer, Mannheim (DE); Ian Robert Craig, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/128,668

(22) PCT Filed: Mar. 16, 2015

(86) PCT No.: PCT/EP2015/055456
§ 371 (c)(1),
(2) Date: Sep. 23, 2016

(87) PCT Pub. No.: WO2015/144480
PCT Pub. Date: Oct. 1, 2015

(65) Prior Publication Data
US 2017/0107184 A1    Apr. 20, 2017

(30) Foreign Application Priority Data

Mar. 26, 2014 (EP) ...................................... 14161798
Apr. 2, 2014 (EP) ...................................... 14163135

(51) Int. Cl.
C07D 233/56   (2006.01)
C07D 249/08   (2006.01)
A01N 43/50    (2006.01)
A01N 43/653   (2006.01)

(52) U.S. Cl.
CPC ........... C07D 249/08 (2013.01); A01N 43/50 (2013.01); A01N 43/653 (2013.01); C07D 233/56 (2013.01)

(58) Field of Classification Search
CPC .... C07D 233/56; C07D 249/08; A01N 43/50; A01N 43/653
See application file for complete search history.

(56) References Cited

U.S. PATENT DOCUMENTS 4,609,668 A   9/1986   Schaub et al.
5,143,932 A   9/1992   Jautelat et al.

FOREIGN PATENT DOCUMENTS

| | | | | |
|---|---|---|---|---|
| EP | 0440950 | 8/1991 | | |
| GB | EP 0123160 A2 | * 10/1984 | ........... | A01N 43/653 |
| JP | 06329636 A | * 11/1994 | | |
| WO | WO 2013007767 | 1/2013 | | |
| WO | WO 2013092224 | 6/2013 | | |
| WO | WO 2013113715 | 8/2013 | | |
| WO | WO 2013135671 | 9/2013 | | |
| WO | WO 2013135672 | 9/2013 | | |
| WO | WO 2014009137 | 1/2014 | | |
| WO | WO 2014009293 | 1/2014 | | |
| WO | WO 2014056780 | 4/2014 | | |
| WO | WO 2014061197 | 4/2014 | | |
| WO | WO 2014082871 | 6/2014 | | |
| WO | WO 2014082872 | 6/2014 | | |
| WO | WO 2014082879 | 6/2014 | | |
| WO | WO 2014082880 | 6/2014 | | |
| WO | WO 2014082881 | 6/2014 | | |
| WO | WO 2014086601 | 6/2014 | | |
| WO | WO 2014095249 | 6/2014 | | |
| WO | WO 2014095381 | 6/2014 | | |
| WO | WO 2014095534 | 6/2014 | | |
| WO | WO 2014095547 | 6/2014 | | |
| WO | WO 2014095548 | 6/2014 | | |
| WO | WO 2014095555 | 6/2014 | | |
| WO | WO 2014095637 | 6/2014 | | |
| WO | WO 2014095655 | 6/2014 | | |
| WO | WO 2014095672 | 6/2014 | | |
| WO | WO 2014095932 | 6/2014 | | |
| WO | WO 2014095994 | 6/2014 | | |

(Continued)

OTHER PUBLICATIONS

International Search Report, issued in PCT/EP2015/055456, dated May 8, 2015.
International Preliminary Report on Patentability, issued in PCT/EP2015/055456, dated Sep. 27, 2016.
Office Action, issued in co-pending U.S. Appl. No. 15/103,529, dated Mar. 21, 2017.

*Primary Examiner* — Nathan W Schlientz
(74) *Attorney, Agent, or Firm* — Brinks Gilson & Lione

(57) ABSTRACT

The present invention relates to compounds of the formula I

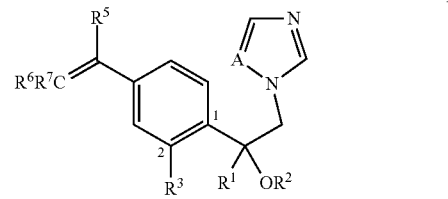

and their use as fungicides, wherein the variables are defined as described in the claims and the specification.

21 Claims, No Drawings

(56) References Cited

FOREIGN PATENT DOCUMENTS

| WO | WO 2014108286 | 7/2014 |
| WO | WO 2014108288 | 7/2014 |
| WO | WO 2014108299 | 7/2014 |
| WO | WO 2014124850 | 8/2014 |
| WO | WO 2014184236 | 11/2014 |
| WO | WO 2014184309 | 11/2014 |
| WO | WO 2014198553 | 12/2014 |
| WO | WO 2014198557 | 12/2014 |
| WO | WO 2014202421 | 12/2014 |
| WO | WO 2014202703 | 12/2014 |
| WO | WO 2014207052 | 12/2014 |
| WO | WO 2014207071 | 12/2014 |
| WO | WO 2015003908 | 1/2015 |
| WO | WO 2015036058 | 3/2015 |
| WO | WO 2015036059 | 3/2015 |
| WO | WO 2015086462 | 6/2015 |
| WO | WO 2015150135 | 10/2015 |
| WO | WO 2015150138 | 10/2015 |
| WO | WO 2015150139 | 10/2015 |
| WO | WO 2015150170 | 10/2015 |
| WO | WO 2015150343 | 10/2015 |

\* cited by examiner

SUBSTITUTED [1,2,4]TRIAZOLE AND IMIDAZOLE COMPOUNDS AS FUNGICIDES

This application is a National Stage application of International Application No. PCT/EP2015/055456, filed Mar. 16, 2015. This application also claims priority under 35 U.S.C. §119 to European Patent Application No. 14161798.5, filed Mar. 26, 2014, and European Patent Application No. 14163135.8, filed Apr. 2, 2014.

The present invention relates to substituted [1,2,4]triazole and imidazole compounds and the N-oxides and the salts thereof for combating phytopathogenic fungi, and to the use and methods for combating phytopathogenic fungi and to seeds coated with at least one such compound. The invention also relates to processes for preparing these compounds, intermediates, processes for preparing such intermediates, and to compositions comprising at least one compound I.

In many cases, in particular at low application rates, the fungicidal activity of known fungicidal compounds is unsatisfactory. Based on this, it was an object of the present invention to provide compounds having improved activity and/or a broader activity spectrum against phytopathogenic harmful fungi.

Surprisingly, this object is achieved by the use of the inventive substituted [1,2,4]triazol and imidazole compounds of formula I having favorable fungicidal activity against phytopathogenic fungi.

Accordingly, the present invention relates, to the compounds of the formula I

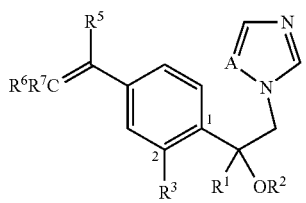

wherein
A is CH or N;
$R^1$ is $C_1$-$C_6$-alkyl, $C_2$-$C_6$-alkenyl, $C_2$-$C_6$-alkynyl or $C_3$-$C_6$-cycloalkyl;
wherein the aliphatic moieties of $R^1$ are not further substituted or carry one, two, three or up to the maximum possible number of identical or different groups $R^{1a}$ which independently of one another are selected from:
$R^{1a}$ halogen, OH, CN, $C_1$-$C_4$-alkoxy, $C_3$-$C_6$-cycloalkyl, $C_3$-$C_6$-halogencycloalkyl and $C_1$-$C_4$-halogenalkoxy;
wherein the cycloalkyl moieties of $R^1$ are not further substituted or carry one, two, three, four, five or up to the maximum number of identical or different groups $R^{1b}$ which independently of one another are selected from:
$R^{1b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl and $C_1$-$C_4$-halogenalkoxy;
$R^2$ is hydrogen, $C_1$-$C_4$-alkyl, $C_2$-$C_4$-alkenyl or $C_2$-$C_4$-alkynyl;
wherein the aliphatic moieties of $R^2$ are not further substituted or carry one, two, three or up to the maximum possible number of identical or different groups $R^{2a}$ which independently of one another are selected from:
$R^{2a}$ halogen, OH, CN, $C_1$-$C_4$-alkoxy, $C_3$-$C_6$-cycloalkyl, $C_3$-$C_6$-halogencycloalkyl and $C_1$-$C_4$-halogenalkoxy;

$R^3$ is selected from hydrogen, halogen, CN, $C_1$-$C_4$-alkyl, $C_1$-$C_4$-alkoxy, $C_2$-$C_4$-alkenyl, $C_2$-$C_4$-alkynyl, $C_3$-$C_6$-cycloalkyl and $S(O)_p(C_1$-$C_4$-alkyl), wherein p is 0, 1 or 2, and wherein each of $R^3$ is unsubstituted or further substituted by one, two, three or four $R^{3a}$; wherein
$R^{3a}$ is independently selected from halogen, CN, OH, $C_1$-$C_4$-alkyl, $C_1$-$C_4$-halogenalkyl, $C_3$-$C_6$-cycloalkyl, $C_3$-$C_6$-halogencycloalkyl, $C_1$-$C_4$-alkoxy and $C_1$-$C_4$-halogenalkoxy;
$R^5$ is hydrogen, halogen, CN, $C_1$-$C_6$-alkyl, $C_1$-$C_6$-halogenalkyl, $C_1$-$C_6$-alkoxy, $C_1$-$C_6$-halogenalkoxy, C(=O)—O—($C_1$-$C_6$-alkyl), $C_3$-$C_6$-cycloalkyl or saturated or partially unsaturated three-, four-, five-, six- or seven-membered heterocyclyl, wherein the heterocyclyl contains 1, 2, 3 or 4 heteroatoms selected from O, N and S, and wherein the cycloalkyl and heterocyclyl is unsubstituted (m=0) or substituted by $(R^4)_m$;
$R^6$ is hydrogen, halogen, CN, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy and $C_1$-$C_6$-halogenalkoxy; wherein the alkenyl and alkynyl moieties are not further substituted or carry one, two, three, four, five or up to the maximum number of identical or different groups $R^{6a}$ which independently of one another are selected from:
$R^{6a}$ halogen, $C_1$-$C_4$-alkyl, $C_1$-$C_4$-halogenalkyl, $Si(CH_3)_3$;
$R^7$ is hydrogen, halogen, CN, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy, $C_1$-$C_6$-halogenalkoxy, C(=O)—O—($C_1$-$C_6$-alkyl), $Si(CH_3)_3$, $C_3$-$C_6$-cycloalkyl or saturated or partially unsaturated three-, four-, five-, six- or seven-membered heterocyclyl, wherein the heterocyclyl contains 1, 2, 3 or 4 heteroatoms selected from O, N and S, and wherein the cycloalkyl and heterocyclyl is unsubstituted (m=0) or substituted by $(R^4)_m$; and wherein the alkenyl and alkynyl moieties are not further substituted or carry one, two, three, four, five or up to the maximum number of identical or different groups $R^{7a}$ which independently of one another are selected from:
$R^{7a}$ halogen, $C_1$-$C_4$-alkyl, $C_1$-$C_4$-halogenalkyl, $Si(CH_3)_3$;
wherein zero or one of $R^5$ and $R^7$ is selected from cycloalkyl and heterocycyl;
or $R^5$ and $R^7$ together with the carbon atoms to which they are bound form a $C_3$-$C_6$-cycloalkenyl, that is unsubstituted at the saturated chain or substituted by $(R^8)_n$; and $R^6$ is as defined above;
or $R^6$ and $R^7$ together with the carbon atoms to which they are bound form a $C_3$-$C_6$-cycloalkyl, that is unsubstituted or substituted by $(R^8)_n$; and $R^5$ is selected from hydrogen, halogen, CN, $C_1$-$C_6$-alkyl, $C_1$-$C_6$-halogenalkyl, $C_1$-$C_6$-alkoxy, $C_1$-$C_6$-halogenalkoxy and C(=O)—O—($C_1$-$C_6$-alkyl); wherein
m is 0, 1, 2, 3, 4 or 5;
$R^4$ is in each case independently selected from halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl and $C_3$-$C_6$-cycloalkyl, wherein each of $R^4$ is unsubstituted or further substituted by one, two, three or four $R^{4a}$ wherein
$R^{4a}$ is independently selected from halogen;
n is 0, 1, 2, 3, 4 or 5;
$R^8$ is in each case independently selected from the substituents as defined for $R^4$; wherein each of $R^8$ is unsubstituted or further substituted by one, two, three or four $R^{8a}$ that is in each case independently selected from the substituents as defined for $R^{4a}$;
and the N-oxides and the agriculturally acceptable salts thereof.

The inventive compounds can be prepared as follows.

A 4-halo, in particular 4-bromo, phenyl compound III can be transformed to the alkenyl component I using crosscoupling methodology known to the expert using e.g a boronic acid derivative such as reagent IV-3, wherein R' is preferably hydrogen or ($C_1$-$C_4$)-alkyl:

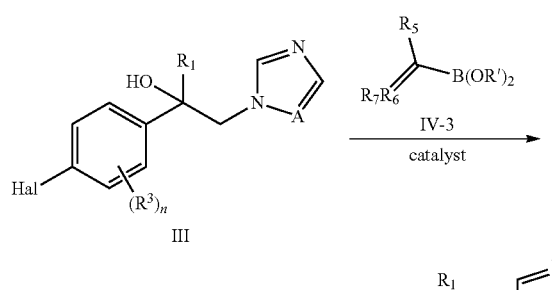

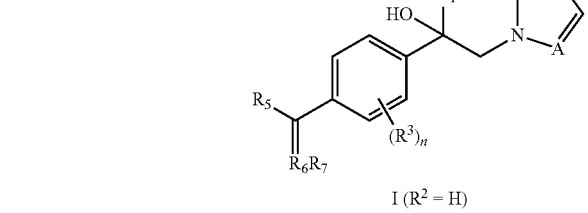

Hal = e.g. Br
A = in particular N

Alternatively, the halide III can be transformed into a boronic acid ester using reagent IV-1 or IV-2, for example, wherein R', R", R''' and R'''' are independently hydrogen or ($C_1$-$C_4$)-alkyl, leading to compounds II. A catalyst such as $PdCl_2$, $PdCl_2$ (dppf), or $Pd(PPh_3)_4$ can be used. In compounds II, "R" has the meaning corresponding to the substituents of the respective boro reagent IV-1 or IV-2 used. Then, II is coupled with a vinyl halide to result in compounds I (see, e.g. Lightfoot, Andrew P., Synlett, (3), 529-531; 2005; Hogan, Anne-Marie L. et al, Journal of Organic Chemistry, 73(15), 6041-6044; 2008). For the reaction of compounds II with a vinyl-halide a catalyst such as $PdCl_2$, $PdCl_2$ (dppf), or $Pd(PPh_3)_4$ can be used (Song, Chun et al Tetrahedron, 61(31), 7438-7446; 2005; Batey, Robert A. and Quach, Tan D. Tetrahedron Letters, 42(52), 9099-9103; 2001).

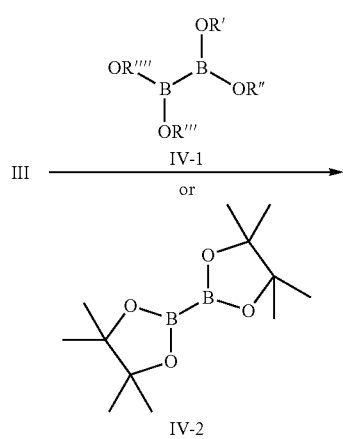

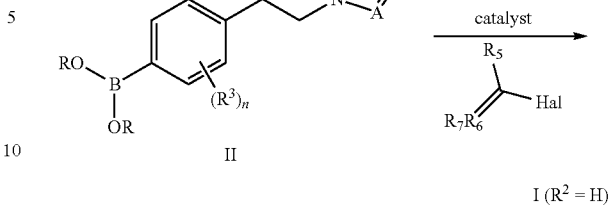

Alternatively, compounds I can be prepared by the reaction of halo, in particular bromo, compound III with a metallation agent "R-M" such as iPrMgCI or BuLi. The metallorganic species is then transformed into an aldehyde (IIb) or ketone (IIa) using DMF or a corresponding amide. Ketones IIa can also be obtained by reacting an aldehyde IIb with an organometallic species $R^5$-M (Magnesium, Lithium, etc.) and subsequent oxidation using Swern or Dess Martin conditions to yield ketones IIa.

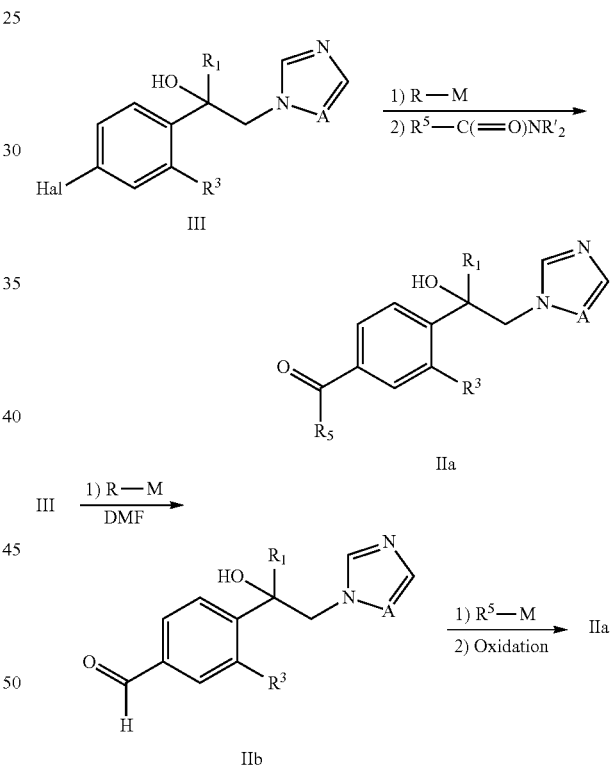

Hal = e.g. Br
A = in particular N

The so obtained ketones IIa can be transformed to an alkene using methodology known to the expert such as Wittig reactions and other olefination reactions (Heravi, Majid M.; Faghihi, Zeinab from Current Organic Chemistry (2012), 16(18), 2097-2123; Shindo, Mitsuru; Matsumoto, Kenji Topics in Current Chemistry (2012), 327 (Stereoselective Alkene Synthesis), 1-32; Hu, Yang; Zhang, X. Peter Topics in Current Chemistry (2012), 327 (Stereoselective Alkene Synthesis), 147-162, Odom, Aaron L. Dalton Transactions (2011), 40(12), 2689-2695).

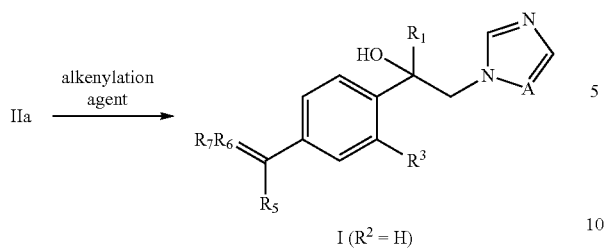

Halo compounds III can be prepared starting from known molecules. For example a substituted phenyl Grignard is generated and transformed to a ketone (in analogy to the compounds in for example WO 2013/07767). Epoxidation followed by reaction with triazole leads to bromide VI.

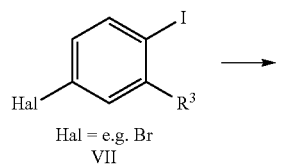

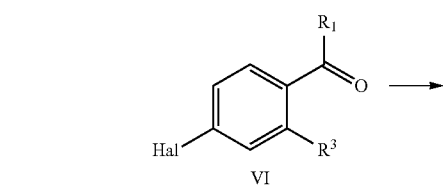

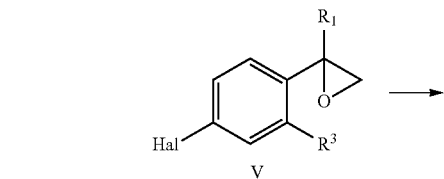

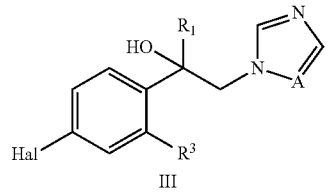

Alternatively, halo/bromo compounds III can be prepared using the following scheme: A Grignard is generated and the so-obtained acyl compound is chlorinated using a chlorination agent (e.g. $SO_2Cl_2$, NCS, $Cl_2$). Addition of a metal organic species (e.g. a Grignard compound) leads to a chloro alcohol, that can be subsequently transformed into halo/bromo compound III.

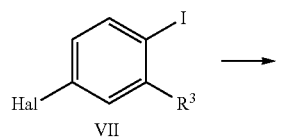

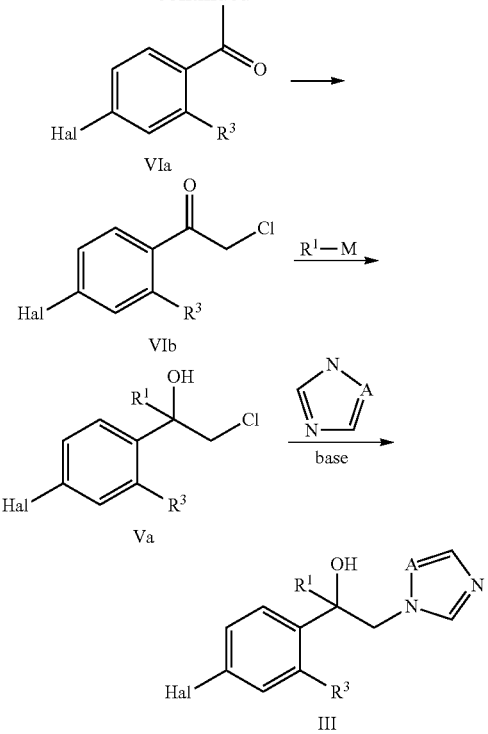

Compounds I, wherein $R^2$ is different from hydrogen can be obtained from alcohol compounds I ($R^2$=H) by reacting the alcohol compound with $R^2$-LG, wherein LG represents a nucleophilically replaceable leaving group, such as halogen, alkylsulfonyl, alkylsulfonyloxy and arylsulfonyloxy, preferably chloro, bromo or iodo, particularly preferably bromo, preferably in the presence of a base. A, $R^1$, $R^2$, $R^3$, $R^4$, $R^5$, $R^6$ and m are as defined herein.

The N-oxides may be prepared from the inventive compounds according to conventional oxidation methods, e. g. by treating compounds I with an organic peracid such as metachloroperbenzoic acid (cf. WO 03/64572 or J. Med. Chem. 38(11), 1892-903, 1995); or with inorganic oxidizing agents such as hydrogen peroxide (cf. J. Heterocyc. Chem. 18(7), 1305-8, 1981) or oxone (cf. J. Am. Chem. Soc. 123(25), 5962-5973, 2001). The oxidation may lead to pure mono-N-oxides or to a mixture of different N-oxides, which can be separated by conventional methods such as chromatography.

If the synthesis yields mixtures of isomers, a separation is generally not necessarily required since in some cases the individual isomers can be interconverted during work-up for use or during application (e. g. under the action of light, acids or bases). Such conversions may also take place after use, e. g. in the treatment of plants in the treated plant, or in the harmful fungus to be controlled.

In the following, the intermediate compounds are further described. A skilled person will readily understand that the preferences for the substituents, also in particular the ones given in the tables below for the respective substituents, given herein in connection with compounds I apply for the intermediates accordingly. Thereby, the substituents in each case have independently of each other or more preferably in combination the meanings as defined herein.

Compounds of formula VI are at least partially new. Consequently, a further embodiment of the present invention are compounds of formula VI (see above), wherein the variables are as defined and preferably defined for formula I herein.

Compounds of formula VIa are at least partially new. Consequently, a further embodiment of the present invention are compounds of formula VIa (see above), wherein the variables are as defined and preferably defined for formula I herein.

Compounds of formula VIb are at least partially new. Consequently, a further embodiment of the present invention are compounds of formula VIb (see above), wherein the variables are as defined and preferably defined for formula I herein.

Compounds of formula V are at least partially new. Consequently, a further embodiment of the present invention are compounds of formula V (see above), wherein the variables are as defined and preferably defined for formula I herein.

Compounds of formula Va are at least partially new. Consequently, a further embodiment of the present invention are compounds of formula Va (see above), wherein the variables are as defined and preferably defined for formula I herein.

Compounds of formula III are at least partially new. Consequently, a further embodiment of the present invention are compounds of formula III (see above), wherein the variables are as defined and preferably defined for formula I herein.

Compounds of formula II are at least partially new. Consequently, a further embodiment of the present invention are compounds of formula II (see above), wherein the variables are as defined and preferably defined for formula I herein.

Compounds of formula IIa are at least partially new. Consequently, a further embodiment of the present invention are compounds of formula IIa (see above), wherein the variables are as defined and preferably defined for formula I herein.

Compounds of formula IIb are at least partially new. Consequently, a further embodiment of the present invention are compounds of formula IIb (see above), wherein the variables are as defined and preferably defined for formula I herein.

In the definitions of the variables given above, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_6$-alkyl" refers to a straight-chained or branched saturated hydrocarbon group having 1 to 6 carbon atoms, e.g. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Likewise, the term "$C_2$-$C_4$-alkyl" refers to a straight-chained or branched alkyl group having 2 to 4 carbon atoms, such as ethyl, propyl (n-propyl), 1-methylethyl (iso-propoyl), butyl, 1-methylpropyl (sec.-butyl), 2-methylpropyl (iso-butyl), 1,1-dimethylethyl (tert.-butyl).

The term "$C_1$-$C_6$-halogenalkyl" refers to an alkyl group having 1 or 6 carbon atoms as defined above, wherein some or all of the hydrogen atoms in these groups may be replaced by halogen atoms as mentioned above. Examples are "$C_1$-$C_2$-halogenalkyl" groups such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl.

The term "$C_1$-$C_6$-hydroxyalkyl" refers to an alkyl group having 1 or 6 carbon atoms as defined above, wherein some or all of the hydrogen atoms in these groups may be replaced by OH groups.

The term "$C_2$-$C_6$-alkenyl" refers to a straight-chain or branched unsaturated hydrocarbon radical having 2 to 6 carbon atoms and a double bond in any position. Examples are "$C_2$-$C_4$-alkenyl" groups, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond. Examples are "$C_2$-$C_4$-alkynyl" groups, such as ethynyl, prop-1-ynyl, prop-2-ynyl (propargyl), but-1-ynyl, but-2-ynyl, but-3-ynyl, 1-methyl-prop-2-ynyl.

The term "$C_3$-$C_6$-cycloalkyl" refers to monocyclic saturated hydrocarbon radicals having 3 to 6 carbon ring members, such as cyclopropyl, cyclobutyl, cyclopentyl, cyclohexyl.

The term "$C_3$-$C_6$-cycloalkenyl" refers to monocyclic hydrocarbon radicals having 3 to 6 carbon ring members and one double bond, such as cyclopropenyl, cyclobutenyl, cyclopentenyl, cyclohexenyl.

The term "$C_3$-$C_6$-cycloalkyl-$C_1$-$C_4$-alkyl" refers to alkyl having 1 to 4 carbon atoms (as defined above), wherein one hydrogen atom of the alkyl radical is replaced by a cycloalkyl radical having 3 to 6 carbon atoms (as defined above).

The term "$C_1$-$C_6$-alkoxy" or "$C_1$-$C_4$-alkoxy" refers to a straight-chain or branched alkyl group having 1 to 6 or 1 to 4 carbon atoms which is bonded via an oxygen, at any position in the alkyl group. Examples are "$C_1$-$C_4$-alkoxy" groups, such as methoxy, ethoxy, n-propoxy, 1-methylethoxy, butoxy, 1-methyl-propoxy, 2-methylpropoxy or 1,1-dimethylethoxy.

The term "$C_1$-$C_6$-halogenalkoxy" or "$C_1$-$C_4$-halogenalkoxy" refers to a $C_1$-$C_6$-alkoxy or $C_1$-$C_4$-alkoxy radical as defined above, wherein one, some or all of the hydrogen atoms in these groups may be replaced by one or more halogen atoms as mentioned above. Examples are "$C_1$-$C_4$-halogenalkoxy" groups, such as OCH$_2$F, OCHF$_2$, OCF$_3$, OCH$_2$Cl, OCHCl$_2$, OCCl$_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloro-ethoxy, OC$_2$F$_5$, 2-fluoropropoxy, 3-fluoropropoxy, 2,2-difluoropropoxy, 2,3-difluoro-propoxy, 2 chloropropoxy, 3-chloropropoxy, 2,3-dichloropropoxy, 2-bromo-propoxy, 3 bromopropoxy, 3,3,3-trifluoropropoxy, 3,3,3-trichloropropoxy, $OCH_2\text{—}C_2F_5$, $OCF_2\text{—}C_2F_5$, 1-fluoromethyl-2-fluoroethoxy, 1-chloromethyl-2-chloroethoxy, 1-bromomethyl-2-bromo-ethoxy, 4-fluorobutoxy, 4-chlorobutoxy, 4-bromobutoxy or nonafluorobutoxy.

The term "$C_1$-$C_4$-alkoxy-$C_1$-$C_4$-alkyl" refers to alkyl having 1 to 4 carbon atoms (as defined above), wherein one hydrogen atom of the alkyl radical is replaced by a $C_1$-$C_4$-alkoxy group (as defined above). Likewise, the term "$C_1$-$C_6$-alkoxy-$C_1$-$C_4$-alkyl" refers to alkyl having 1 to 4 carbon atoms (as defined above), wherein one hydrogen atom of the alkyl radical is replaced by a $C_1$-$C_6$-alkoxy group (as defined above).

The term "$C_1$-$C_4$-alkylthio" as used herein refers to straight-chain or branched alkyl groups having 1 to 4 carbon atoms (as defined above) bonded via a sulfur atom. Accordingly, the term "$C_1$-$C_4$-halogenalkylthio" as used herein refers to straight-chain or branched halogenalkyl group having 1 to 4 carbon atoms (as defined above) bonded through a sulfur atom, at any position in the halogenalkyl group.

The term "$C_1$-$C_4$-alkylsulfinyl" refers to straight-chain or branched alkyl groups having 1 to 4 carbon atoms (as defined above) bonded through a —S(=O)— moiety, at any position in the alkyl group, for example methylsulfinyl and ethylsulfinyl, and the like. Accordingly, the term "$C_1$-$C_4$-halogenalkylsulfinyl" refers to straight-chain or branched halogenalkyl group having 1 to 4 carbon atoms (as defined above), bonded through a —S(=O)— moiety, at any position in the halogenalkyl group.

The term "$C_1$-$C_4$-alkylsulfonyl" refers to straight-chain or branched alkyl groups having 1 to 4 carbon atoms (as defined above), bonded through a —S(=O)$_2$— moiety, at any position in the alkyl group, for example methylsulfonyl. Accordingly, the term "$C_1$-$C_4$-halogenalkylsulfonyl" refers to straight-chain or branched halogenalkyl group having 1 to 4 carbon atoms (as defined above), bonded through a —S(=O)$_2$— moiety, at any position in the halogenalkyl group.

The term "$C_3$-$C_6$-cycloalkyl-$C_3$-$C_6$-cycloalkyl" refers to a cycloalkyl radical having 3 to 6 carbon atoms (as defined above), which is substituted by a further cycloalkyl radical having 3 to 6 carbon atoms.

The term "C(=O)—O—$C_1$-$C_4$-alkyl" refers to an ester radical which is attached through the carbon atom of the group C(=O).

The term "saturated or partially unsaturated three-, four-, five-, six- or seven-membered heterocyclyl, wherein the heterocyclyl contains 1, 2, 3 or 4 heteroatoms selected from O, N and S" is to be understood as meaning both saturated and partially unsaturated heterocycles, wherein the ring member atoms of the heterocycle include besides carbon atoms 1, 2, 3 or 4 heteroatoms independently selected from the group of O, N and S. For example:

a 3- or 4-membered saturated heterocycle which contains 1 or 2 heteroatoms from the group consisting of O, N and S as ring members such as oxirane, aziridine, thiirane, oxetane, azetidine, thiethane, [1,2]dioxetane, [1,2]dithietane, [1,2]diazetidine; and a 5- or 6-membered saturated or partially unsaturated heterocycle which contains 1, 2 or 3 heteroatoms from the group consisting of O, N and S as ring members such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl and also the corresponding -ylidene radicals; and a 7-membered saturated or partially unsaturated heterocycle such as tetra- and hexahydroazepinyl, such as 2,3,4,5-tetrahydro[1H]azepin-1-,-2-,-3-,-4-,-5-,-6- or -7-yl, 3,4,5,6-tetrahydro[2H]azepin-2-,-3-,-4-,-5-,-6- or -7-yl, 2,3,4,7-tetrahydro[1H]azepin-1-,-2-,-3-,-4-,-5-,-6- or -7-yl, 2,3,6,7-tetrahydro[1H]azepin-1-,-2-,-3-,-4-,-5-,-6- or -7-yl, hexahydroazepin-1-,-2-,-3- or -4-yl, tetra- and hexahydrooxepinyl such as 2,3,4,5-tetrahydro[1H]oxepin-2-,-3-,-4-,-5-,-6- or -7-yl, 2,3,4,7-tetrahydro[1H]oxepin-2-,-3-,-4-,-5-,-6- or -7-yl, 2,3,6,7-tetrahydro[1H]oxepin-2-,-3-,-4-,-5-,-6- or -7-yl, hexahydroazepin-1-,-2-,-3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding -ylidene radicals.

Agriculturally acceptable salts of the inventive compounds encompass especially the salts of those cations or the acid addition salts of those acids whose cations and anions, respectively, have no adverse effect on the fungicidal action of said compounds. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting such inventive compound with an acid of the corresponding anion, preferably of hydrochloric acid, hydrobromic acid, sulfuric acid, phosphoric acid or nitric acid.

The inventive compounds can be present in atropisomers arising from restricted rotation about a single bond of asymmetric groups. They also form part of the subject matter of the present invention.

Depending on the substitution pattern, the compounds of formula I and their N-oxides may have one or more centers of chirality, in which case they are present as pure enantiomers or pure diastereomers or as enantiomer or diastereomer mixtures. Both, the pure enantiomers or diastereomers and their mixtures are subject matter of the present invention.

In the following, particular embodiments of the inventive compounds are described. Therein, specific meanings of the respective substituents are further detailed, wherein the meanings are in each case on their own but also in any combination with one another, particular embodiments of the present invention.

Furthermore, in respect of the variables, generally, the embodiments of the compounds I also apply to the intermediates.

A according to the invention is N or CH. According to one embodiment A is N. According to a further embodiment A is CH.

$R^1$ according to the invention is $C_1$-$C_6$-alkyl, $C_2$-$C_6$-alkenyl, $C_2$-$C_6$-alkynyl or $C_3$-$C_6$-cycloalkyl; wherein the aliphatic moieties of $R^1$ are not further substituted or carry one, two, three or up to the maximum possible number of identical or different groups $R^{1a}$ which independently of one another are selected from $R^{1a}$ halogen, OH, CN, $C_1$-$C_4$-alkoxy, $C_3$-$C_6$-cycloalkyl, $C_3$-$C_8$-halogencycloalkyl and $C_1$-$C_4$-halogenalkoxy; and wherein the cycloalkyl moieties of $R^1$ are not further substituted or carry one, two, three, four, five or up to the maximum number of identical or different groups $R^{1b}$ which independently of one another are selected from $R^{1b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl and $C_1$-$C_4$-halogenalkoxy.

According to a further embodiment of the invention, $R^1$ is selected from $C_1$-$C_6$-alkyl, $C_2$-$C_6$-alkenyl, $C_2$-$C_6$-alkynyl, $C_3$-$C_6$-cycloalkyl and $C_3$-$C_6$-cycloalkyl-$C_1$-$C_4$-alkyl, wherein the $R^1$ are in each case unsubstituted or are substituted by $R^{1a}$ and/or $R^{1b}$ as defined and preferably defined herein. Specific embodiments thereof can be found in the below Table P1.

According to one particular embodiment, $R^1$ is $C_1$-$C_6$-alkyl, in particular $C_1$-$C_4$-alkyl, such as $CH_3$, $C_2H_5$, $CH(CH_3)_2$ or $C(CH_3)_3$. A further embodiment relates to compounds, wherein $R^1$ is $C_1$-$C_3$-alkyl, in particular $CH_3$, $C_2H_5$ or n-$C_3H_7$. A further embodiment relates to compounds, wherein $R^1$ is $C_1$-$C_6$-alkyl, in particular $C_1$-$C_4$-alkyl or $C_1$-$C_3$-alkyl, that is substituted by one, two or three or up to the maximum possible number of identical or different groups $R^{1a}$, as defined and preferably defined herein. According to a specific embodiment thereof, $R^1$ is $C_1$-$C_6$-halogenalkyl, in particular $C_1$-$C_4$-halogenalkyl or $C_1$-$C_3$-halogenalkyl, more particularly $C_1$-$C_2$-halogenalkyl such as $CF_3$ or $CHF_2$, $CF_2CH_3$, $CH_2CF_3$ or $CF_2CF_3$. According to a further specific embodiment thereof, $R^1$ is $C_1$-$C_4$-alkoxy-$C_1$-$C_6$-alkyl, in particular $C_1$-$C_4$-alkoxy-$C_1$-$C_4$-alkyl, such as $CH_2$-$OCH_3$. Further specific embodiments thereof can be found in the below Table P1.

According to still another embodiment, $R^1$ is $C_3$-$C_6$-cycloalkyl-$C_1$-$C_6$-alkyl, in particular $C_3$-$C_6$-cycloalkyl-$C_1$-$C_4$-alkyl. A further embodiment relates to compounds, wherein $R^1$ is $C_3$-$C_6$-cycloalkyl-$C_1$-$C_6$-alkyl, in particular $C_3$-$C_6$-cycloalkyl-$C_1$-$C_4$-alkyl, that is substituted by one, two or three or up to the maximum possible number of identical or different groups $R^{1a}$ in the alkyl moiety and/or substituted by one, two, three four or five or up to the maximum possible number of identical or different groups $R^{1b}$ in the cycloalkyl moiety. $R^{1a}$ are in each case as defined and preferably defined herein. Specific embodiments thereof can be found in the below Table P1.

According to another embodiment, $R^1$ is $C_2$-$C_6$-alkenyl, in particular $C_2$-$C_4$-alkenyl, such as $CH=CH_2$, $CH_2CH=CH_2$, $CH=CHCH_3$ or $C(CH_3)=CH_2$. A further embodiment relates to compounds, wherein $R^1$ is $C_2$-$C_6$-alkenyl, in particular $C_2$-$C_4$-alkenyl, that is substituted by one, two or three or up to the maximum possible number of identical or different groups $R^{1a}$ as defined and preferably defined herein. According to a specific embodiment thereof, $R^1$ is $C_2$-$C_6$-halogenalkenyl, in particular $C_2$-$C_4$-halogenalkenyl. Further specific embodiments thereof can be found in the below Table P1.

According to still another embodiment, $R^1$ is $C_2$-$C_6$-alkynyl, in particular $C_2$-$C_4$-alkynyl, such as $C\equiv CH$, $C\equiv CCH_3$, $CH_2$—$C\equiv C$—$H$ or $CH_2$—$C\equiv C$—$CH_3$.

A further embodiment relates to compounds, wherein $R^1$ is $C_2$-$C_6$-alkynyl, in particular $C_2$-$C_4$-alkynyl, that is substituted by one, two or three or up to the maximum possible number of identical or different groups $R^{1a}$, as defined and preferably defined herein. According to a specific embodiment thereof, $R^1$ is $C_2$-$C_6$-halogenalkynyl, in particular $C_2$-$C_4$-halogenalkynyl. According to a further specific embodiment thereof, $R^1$ is $C_3$-$C_6$-cycloalkyl-$C_2$-$C_6$-alkynyl or $C_3$-$C_6$-halogencycloalkyl-$C_2$-$C_6$-alkynyl, in particular $C_3$-$C_6$-cycloalkyl-$C_2$-$C_4$-alkynyl or $C_3$-$C_6$-halogencycloalkyl-$C_2$-$C_4$-alkynyl. Further specific embodiments thereof can be found in the below Table P1.

According to still another embodiment, $R^1$ is $C_3$-$C_6$-cycloalkyl, such as $C_3H_5$ (cyclopropyl), $C_4H_7$ (cyclobutyl), cyclopentyl or cyclohexyl. A further embodiment relates to compounds, wherein $R^1$ is $C_3$-$C_6$-cycloalkyl, such as $C_3H_5$ (cyclopropyl) or $C_4H_7$ (cyclobutyl), that is substituted by one, two, three four or five or up to the maximum possible number of identical or different groups $R^{1b}$ as defined and preferably defined herein. According to a specific embodiment thereof, $R^1$ is $C_3$-$C_6$-halogencycloalkyl, such as halogencyclopropyl, in particular 1-F-cyclopropyl or 1-Cl-cyclopropyl. According to a further specific embodiment thereof, $R^1$ $C_3$-$C_6$-cycloalkyl-$C_3$-$C_6$-cycloalkyl, wherein each of said cycloalkyl-cycloalkyl moieties is unsubstituted or carries one, two or three $R^{1b}$ as defined and preferably defined herein, such as 1-cyclopropyl-cyclopropyl or 2-cyclopropyl-cyclopropyl. Specific embodiments thereof can be found in the below Table P1.

Specifically, it may be preferred, according to one particular embodiment, if $R^1$ is selected from $C_1$-$C_4$-alkyl, such as methyl, ethyl, n-propyl, iso-propyl, tert-butyl, $CH_2C(CH_3)_3$ and $CH_2CH(CH_3)_2$ more particularly methyl, ethyl, n-propyl, $CH_2C(CH_3)_3$ and $CH_2CH(CH_3)_2$, $C_1$-$C_4$-halogenalkyl, such as $CF_3$, $C_2$-$C_6$-alkenyl, $C_2$-$C_6$-alkynyl, such as $C\equiv CCH_3$, and $C_3$-$C_6$-cycloalkyl, such as cyclopropyl.

In one further particular embodiment, $R^1$ is selected from methyl, ethyl, n-propyl, $CH_2C(CH_3)_3$, $CH_2CH(CH_3)_2$, $CF_3$, $C_2$-$C_6$-alkenyl, $C_2$-$C_6$-alkynyl and $C_3$-$C_6$-cycloalkyl.

Specifically, it may further be preferred, according to a further particular embodiment, if $R^1$ is selected from $C_1$-$C_3$-alkyl, such as methyl, ethyl, n-propyl and iso-propyl, more specifically methyl, ethyl and n-propyl, $C_1$-$C_3$-halogenalkyl, such as $CF_3$, $C_2$-$C_4$-alkenyl, $C_2$-$C_4$-alkynyl, such as $C{\equiv}CCH_3$, and $C_3$-$C_6$-cycloalkyl, such as cyclopropyl.

More specifically, it may be preferred, according to a further particular embodiment, if $R^1$ is selected from $C_1$-$C_3$-alkyl, selected from methyl, ethyl and n-propyl, $C_1$-$C_3$-halogenalkyl, $C_2$-$C_4$-alkenyl, $C_2$-$C_4$-alkynyl and $C_3$-$C_6$-cycloalkyl.

Particularly preferred embodiments of $R^1$ according to the invention are in Table P1 below, wherein each line of lines P1-1 to P1-138 corresponds to one particular embodiment of the invention, wherein P1-1 to P1-138 are also in any combination a preferred embodiment of the present invention.

TABLE P1

| line | $R^1$ |
|---|---|
| P1-1 | $CH_3$ |
| P1-2 | $CH_2CH_3$ |
| P1-3 | $CH_2CH_2CH_3$ |
| P1-4 | $CH(CH_3)_2$ |
| P1-5 | $C(CH_3)_3$ |
| P1-6 | $CH(CH_3)CH_2CH_3$ |
| P1-7 | $CH_2CH(CH_3)_2$ |
| P1-8 | $CH_2CH_2CH_2CH_3$ |
| P1-9 | $CF_3$ |
| P1-10 | $CHF_2$ |
| P1-11 | $CH_2F$ |
| P1-12 | $CHCl_2$ |
| P1-13 | $CH_2Cl$ |
| P1-14 | $CF_2CH_3$ |
| P1-15 | $CH_2CF_3$ |
| P1-16 | $CF_2CF_3$ |
| P1-17 | $CH_2OH$ |
| P1-18 | $CH_2CH_2OH$ |
| P1-19 | $CH_2CH_2CH_2OH$ |
| P1-20 | $CH(CH_3)CH_2OH$ |
| P1-21 | $CH_2CH(CH_3)OH$ |
| P1-22 | $CH_2CH_2CH_2CH_2OH$ |
| P1-23 | $CH(CH_3)CN$ |
| P1-24 | $CH_2CH_2CN$ |
| P1-25 | $CH_2CN$ |
| P1-26 | $CH_2CH_2CN$ |
| P1-27 | $CH_2CH_2CH_2CN$, |
| P1-28 | $CH(CH_3)CH_2CN$ |
| P1-29 | $CH_2CH(CH_3)CN$ |
| P1-30 | $CH_2CH_2CH_2CH_2CN$ |
| P1-31 | $CH_2OCH_3$ |
| P1-32 | $CH_2OCH_2CH_3$ |
| P1-33 | $CH(CH_3)OCH_3$ |
| P1-34 | $CH(CH_3)OCH_2CH_3$ |
| P1-35 | $CH_2CH_2OCH_2CH_3$ |
| P1-36 | $CH_2OCF_3$ |
| P1-37 | $CH_2CH_2OCF_3$ |
| P1-38 | $CH_2OCCl_3$ |
| P1-39 | $CH_2CH_2OCCl_3$ |
| P1-40 | $CH{=}CH_2$ |
| P1-41 | $CH_2CH{=}CH_2$ |
| P1-42 | $CH_2CH{=}CHCH_3$ |
| P1-43 | $CH_2C(CH_3){=}CH_2$ |
| P1-44 | $CH_2C(CH_3){=}CHCH_3$ |
| P1-45 | $CH_2C(CH_3){=}C(CH_3)_2$ |
| P1-46 | $CH{=}CHCH_3$ |
| P1-47 | $C(CH_3){=}CH_2$ |
| P1-48 | $CH{=}C(CH_3)_2$ |
| P1-49 | $C(CH_3){=}C(CH_3)_2$ |
| P1-50 | $C(CH_3){=}CH(CH_3)$ |
| P1-51 | $C(Cl){=}CH_2$ |
| P1-52 | $C(H){=}CHCl$ |
| P1-53 | $C(Cl){=}CHCl$ |
| P1-54 | $CH{=}CCl_2$ |
| P1-55 | $C(Cl){=}CCl_2$ |
| P1-56 | $C(H){=}CH(F)$ |
| P1-57 | $C(H){=}CF_2$ |
| P1-58 | $C(F){=}CF_2$ |
| P1-59 | $C(F){=}CHF$ |
| P1-60 | $CH{=}CHCH_2OH$ |
| P1-61 | $CH{=}CHOCH_3$ |
| P1-62 | $CH{=}CHCH_2OCH_3$ |
| P1-63 | $CH{=}CHCH_2OCF_3$ |
| P1-64 | $CH{=}CHCH_2OCCl_3$ |
| P1-65 | $CH{=}CH(C_3H_5)$ |
| P1-66 | $CH{=}CH(C_4H_7)$ |
| P1-67 | $CH{=}CH(1\text{-}Cl{-}C_3H_4)$ |
| P1-68 | $CH{=}CH(1\text{-}F{-}C_3H_4)$ |
| P1-69 | $CH{=}CH(1\text{-}Cl{-}C_4H_6)$ |
| P1-70 | $CH{=}CH(1\text{-}F{-}C_4H_6)$ |
| P1-71 | $C{\equiv}CH$ |
| P1-72 | $C{\equiv}CCH_3$ |
| P1-73 | $CH_2C{\equiv}CCH_3$ |
| P1-74 | $CH_2C{\equiv}CH$ |
| P1-75 | $CH_2C{\equiv}CCH_2CH_3$ |
| P1-76 | $C{\equiv}CCH(CH_3)_2$ |
| P1-77 | $C{\equiv}CC(CH_3)_3$ |
| P1-78 | $C{\equiv}C(C_3H_5)$ |
| P1-79 | $C{\equiv}C(C_4H_7)$ |
| P1-80 | $C{\equiv}C(1\text{-}Cl{-}C_3H_4)$ |
| P1-81 | $C{\equiv}C(1\text{-}Cl{-}C_4H_6)$ |
| P1-82 | $C{\equiv}CCl$ |
| P1-83 | $C{\equiv}CBr$ |
| P1-84 | $C{\equiv}C{-}I$ |
| P1-85 | $CH_2C{\equiv}CCl$ |
| P1-86 | $CH_2C{\equiv}CBr$ |
| P1-87 | $CH_2C{\equiv}C{-}I$ |
| P1-88 | $C{\equiv}CCH_2OCH_3$ |
| P1-89 | $C{\equiv}CCH(OH)CH_3$ |
| P1-90 | $C{\equiv}CCH(OCH_3)CH_3$ |
| P1-91 | $C{\equiv}COCH_3$ |
| P1-92 | $CH_2C{\equiv}COCH_3$ |
| P1-93 | $C{\equiv}CCH_2OCCl_3$ |
| P1-94 | $C{\equiv}CCH_2OCF_3$ |
| P1-95 | $C{\equiv}CCH_2(C_3H_5)$ |
| P1-96 | $C{\equiv}CCH_2(C_4H_7)$ |
| P1-97 | $C{\equiv}C(1\text{-}Cl{-}C_3H_4)$ |
| P1-98 | $C{\equiv}C(1\text{-}F{-}C_3H_4)$ |
| P1-99 | $C{\equiv}C(1\text{-}Cl{-}C_4H_6)$ |
| P1-100 | $C{\equiv}C(1\text{-}F{-}C_4H_6)$ |
| P1-101 | $C_3H_5$ (cyclopropyl) |
| P1-102 | $C_4H_7$ (cyclobutyl) |
| P1-103 | $C_5H_9$ (cyclopentyl) |
| P1-104 | cyclohexyl |
| P1-105 | $CH(CH_3){-}C_3H_5$ ($CH(CH_3)$-cyclopropyl) |
| P1-106 | $CH_2{-}C_3H_5$ ($CH_2$-cyclopropyl) |
| P1-107 | 1-(Cl)-cyclopropyl |
| P1-108 | 1-(F)-cyclopropyl |
| P1-109 | 1-($CH_3$)-cyclopropyl |
| P1-110 | 1-(CN)-cyclopropyl |
| P1-111 | 2-(Cl)-cyclopropyl |
| P1-112 | 2-(F)-cyclopropyl |
| P1-113 | 1-(Cl)-cyclobutyl |
| P1-114 | 1-(F)-cyclobutyl |
| P1-115 | 2-(Cl)-cyclobutyl |
| P1-116 | 3-(Cl)-cyclobutyl |
| P1-117 | 2-(F)-cyclobutyl |
| P1-118 | 3-(F)-cyclobutyl |
| P1-119 | 3,3-$Cl_2$-cyclobutyl |
| P1-120 | 3,3-$F_2$-cyclobutyl |
| P1-121 | 2-($CH_3$)-cyclopropyl |
| P1-122 | 1-($CH_3$)-cyclobutyl |
| P1-123 | 2-($CH_3$)-cyclobutyl |
| P1-124 | 3-($CH_3$)-cyclobutyl |
| P1-125 | 3,3-$(CH_3)_2$-cyclobutyl |
| P1-126 | 2-(CN)-cyclopropyl |
| P1-127 | 1-cyclopropyl-cyclopropyl |
| P1-128 | 2-cyclopropyl-cyclopropyl |
| P1-129 | $CH(CH_3)$(cyclobutyl) |

TABLE P1-continued

| line | $R^1$ |
|---|---|
| P1-130 | $CH_2$-(cyclobutyl) |
| P1-131 | $CH_2CH_2$-(cyclopropyl) |
| P1-132 | $CH_2CH_2$-(cyclobutyl) |
| P1-133 | $CH_2$-(1-Cl-cyclopropyl) |
| P1-134 | $CH_2$-(1-F-cyclopropyl) |
| P1-135 | $CH_2$-(1-Cl-cyclobutyl) |
| P1-136 | $CH_2$-(1-F-cyclobutyl) |
| P1-137 | $CHCH_3$-(1-Cl-cyclopropyl) |
| P1-138 | $C(CH_3)_2$-(1-F-cyclopropyl) |

$R^{1a}$ are the possible substituents for the aliphatic moieties of $R^1$.

$R^{1a}$ according to the invention is independently selected from halogen, OH, CN, $C_1$-$C_4$-alkoxy, $C_3$-$C_6$-cycloalkyl, $C_3$-$C_6$-halocycloalkyl and $C_1$-$C_4$-halogenalkoxy.

According to one embodiment $R^{1a}$ is independently selected from halogen, OH, CN, $C_1$-$C_2$-alkoxy, $C_3$-$C_6$-cycloalkyl, $C_3$-$C_6$-halocycloalkyl and $C_1$-$C_2$-halogenalkoxy. Specifically, $R^{1a}$ is independently selected from F, Cl, OH, CN, $C_1$-$C_2$-alkoxy, cyclopropyl, 1-F-cyclopropyl, 1-Cl-cyclopropyl and $C_1$-$C_2$-halogenalkoxy.

$R^{1b}$ are the possible substituents for the cycloalkyl moieties of $R^1$.

$R^{1b}$ according to the invention is independently selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halocycloalkyl and $C_1$-$C_4$-halogenalkoxy.

According to one embodiment thereof $R^{1b}$ is independently selected from halogen, CN, $C_1$-$C_2$-alkyl, $C_1$-$C_2$-alkoxy, $C_1$-$C_2$-halogenalkyl, $C_3$-$C_6$-cycloalkyl, $C_3$-$C_6$-halocycloalkyl and $C_1$-$C_2$-halogenalkoxy. Specifically, $R^{1b}$ is independently selected from F, Cl, OH, CN, $CH_3$, $OCH_3$, cyclopropyl, 1-F-cyclopropyl, 1-Cl-cyclopropyl and halogenmethoxy.

According to the invention, $R^2$ is hydrogen, $C_1$-$C_4$-alkyl, $C_2$-$C_4$-alkenyl, $C_2$-$C_4$-alkynyl, wherein the aliphatic moieties of $R^2$ are not further substituted or carry one, two, three or up to the maximum possible number of identical or different groups $R^{2a}$ which independently of one another are selected from halogen, OH, CN, $C_1$-$C_4$-alkoxy, $C_3$-$C_6$-cycloalkyl, $C_3$-$C_6$-halocycloalkyl and $C_1$-$C_4$-halogenalkoxy.

According to one embodiment, $R^2$ is H.

According to a further embodiment of the invention, $R^2$ is selected from $C_1$-$C_4$-alkyl, $C_2$-$C_4$-alkenyl, $C_2$-$C_4$-alkynyl.

According to a further embodiment of the invention, $R^2$ is selected from H, $C_1$-$C_4$-alkyl, in particular methyl or ethyl, $C_2$-$C_4$-alkenyl, in particular $CH_2CH=CH_2$, and $C_2$-$C_4$-alkynyl, in particular $CH_2C\equiv CH$. Specific embodiments thereof can be found in the below Table P2.

According to one particular embodiment, $R^2$ is $C_1$-$C_4$-alkyl, such as $CH_3$, $C_2H_5$, $CH(CH_3)_2$, $CH_2CH_2CH_3$, $CH_2CH_2CH_2CH_3$, $CH_2CH(CH_3)_2$. A further embodiment relates to compounds, wherein $R^2$ is $C_1$-$C_4$-alkyl, that is substituted by one, two or three or up to the maximum possible number of identical or different groups $R^{2a}$, as defined and preferably defined herein. According to a specific embodiment thereof, $R^2$ is $C_1$-$C_4$-halogenalkyl, more particularly $C_1$-$C_2$-halogenalkyl. According to a further specific embodiment thereof, $R^2$ is $C_1$-$C_4$-alkoxy-$C_1$-$C_4$-alkyl, such as $CH_2OCH_3$ or $CH_2CH_2OCH_3$. According to still a further specific embodiment thereof, $R^2$ is hydroxyl-$C_1$-$C_4$-alkyl, such as $CH_2CH_2OH$. Further specific embodiments thereof can be found in the below Table P2.

According to still another embodiment, $R^2$ is $C_3$-$C_6$-cycloalkyl-$C_1$-$C_4$-alkyl. A further embodiment relates to compounds, wherein $R^2$ is $C_3$-$C_6$-cycloalkyl-$C_1$-$C_4$-alkyl, more particularly $C_3$-$C_6$-cycloalkyl-$C_1$-$C_2$-alkyl, that is substituted by one, two or three or up to the maximum possible number of identical or different groups $R^{2a}$. A further embodiment relates to compounds, wherein $R^2$ is $C_3$-$C_6$-halocycloalkyl-$C_1$-$C_4$-alkyl, more particularly $C_3$-$C_6$-halocycloalkyl-$C_1$-$C_2$-alkyl. Specific embodiments thereof can be found in the below Table P2.

According to another embodiment, $R^2$ is $C_2$-$C_4$-alkenyl, such as $CH_2CH=CH_2$, $CH_2C(CH_3)=CH_2$ or $CH_2CH=CHCH_3$. A further embodiment relates to compounds, wherein $R^2$ is $C_2$-$C_4$-alkenyl that is substituted by one, two or three or up to the maximum possible number of identical or different groups $R^{2a}$ as defined and preferably defined herein. According to a specific embodiment thereof, $R^2$ is $C_2$-$C_4$-halogenalkenyl, such as $CH_2C(Cl)=CH_2$ and $CH_2C(H)=CHCl$. According to a further specific embodiment thereof, $R^2$ is $C_3$-$C_6$-cycloalkyl-$C_2$-$C_4$-alkenyl or $C_3$-$C_6$-halocycloalkyl-$C_2$-$C_4$-alkenyl. Further specific embodiments thereof can be found in the below Table P2.

According to still another embodiment, $R^2$ is $C_2$-$C_4$-alkynyl, such as $CH_2C\equiv CH$ or $CH_2C\equiv CCH_3$. A further embodiment relates to compounds, wherein $R^2$ is $C_2$-$C_4$-alkynyl that is substituted by one, two or three or up to the maximum possible number of identical or different groups $R^{2a}$, as defined and preferably defined herein. According to a specific embodiment thereof, $R^2$ is $C_2$-$C_4$-halogenalkynyl. According to a further specific embodiment thereof, $R^2$ is $C_3$-$C_6$-cycloalkyl-$C_2$-$C_4$-alkynyl or $C_3$-$C_6$-halocycloalkyl-$C_2$-$C_4$-alkynyl. Specific embodiments thereof can be found in the below Table P2.

Particularly preferred embodiments of $R^2$ according to the invention are in Table P2 below, wherein each line of lines P2-1 to P2-79 corresponds to one particular embodiment of the invention, wherein P2-1 to P2-79 are also in any combination a preferred embodiment of the present invention.

TABLE P2

| line | $R^2$ |
|---|---|
| P2-1 | H |
| P2-2 | $CH_3$ |
| P2-3 | $CH_2CH_3$ |
| P2-4 | $CH(CH_3)_2$ |
| P2-5 | $CH_2CH_2CH_3$ |
| P2-6 | $CH_2CH_2CH_2CH_3$ |
| P2-7 | $CH_2CH(CH_3)_2$ |
| P2-8 | $CF_3$ |
| P2-9 | $CHF_2$ |
| P2-10 | $CFH_2$ |
| P2-11 | $CCl_3$. |
| P2-12 | $CHCl_2$ |
| P2-13 | $CClH_2$ |
| P2-14 | $CH_2CF_3$ |
| P2-15 | $CH_2CHF_2$ |
| P2-16 | $CH_2CCl_3$ |
| P2-17 | $CH_2CHCl_2$ |
| P2-18 | $CH_2CH_2OCH_2CH_3$ |
| P2-19 | $CH(CH_3)OCH_2CH_3$ |
| P2-20 | $CH(CH_3)OCH_3$ |
| P2-21 | $CH_2OCH_3$ |
| P2-22 | $CH_2CH_2OCH_3$ |
| P2-23 | $CH_2OCF_3$ |
| P2-24 | $CH_2CH_2OCF_3$ |
| P2-25 | $CH_2OCCl_3$ |
| P2-26 | $CH_2CH_2OCCl_3$ |
| P2-27 | $CH_2CH_2OH$ |
| P2-28 | $CH_2OH$ |
| P2-29 | $CH_2CH_2CH_2OH$, |

TABLE P2-continued

| line | R² |
|---|---|
| P2-30 | CH(CH₃)CH₂OH |
| P2-31 | CH₂CH(CH₃)OH |
| P2-32 | CH₂CH₂CH₂CH₂OH |
| P2-33 | CH₂CN, |
| P2-34 | CH₂CH₂CN, |
| P2-35 | CH₂CH₂CH₂CN, |
| P2-36 | CH(CH₃)CH₂CN, |
| P2-37 | CH₂CH(CH₃)CN, |
| P2-38 | CH₂CH₂CH₂CH₂CN |
| P2-39 | CH=CH₂ |
| P2-40 | C(CH₃)=CH₂ |
| P2-41 | CH=CHCH₃ |
| P2-42 | CH₂CH=CH₂ |
| P2-43 | CH₂CH=CHCH₃ |
| P2-44 | CH₂C(CH₃)=CH₂ |
| P2-45 | C(CH₃)=CH(CH₃) |
| P2-46 | CH=C(CH₃)₂ |
| P2-47 | CH=C(Cl)₂ |
| P2-48 | C(CH₃)=CH₂ |
| P2-49 | CH₂C(Cl)=CH₂ |
| P2-50 | CH₂C(H)=CHCl |
| P2-51 | CH=CHCH₂OH |
| P2-52 | CH=C(CH₃)OH |
| P2-53 | CH=CHOCH₃ |
| P2-54 | CH=CHCH₂OCH₃ |
| P2-55 | CH₂CH=CHCH₂OCH₃ |
| P2-56 | CH=CHOCF₃ |
| P2-57 | CH=CHCH₂OCF₃ |
| P2-58 | CH=CHOCCl₃ |
| P2-59 | CH=CHCH₂OCCl₃ |
| P2-60 | CH₂CH=CH(C₃H₅) |
| P2-61 | CH₂CH=CH(C₄H₇) |
| P2-62 | CH₂CH=CH(1-Cl—C₃H₄) |
| P2-63 | CH₂CH=CH(1-F—C₃H₄) |
| P2-64 | CH₂C≡CH |
| P2-65 | CH₂C≡CCH₃ |
| P2-66 | CH₂C≡CCl |
| P2-67 | CH₂C≡CF |
| P2-68 | CH₂C≡C—I |
| P2-69 | CH₂C≡CCH₂OH |
| P2-70 | CH₂C≡CCH₂OCH₃ |
| P2-71 | CH₂C≡COCH₃ |
| P2-72 | C≡COCF₃ |
| P2-73 | CH₂C≡COCF₃ |
| P2-74 | C≡COCCl₃ |
| P2-75 | CH₂C≡COCCl₃ |
| P2-76 | CH₂-(cyclopropyl) |
| P2-77 | CH₂-(cyclobutyl) |
| P2-78 | CH₂-(1-Cl-cyclopropyl) |
| P2-79 | CH₂-(1-F-cyclopropyl) |

$R^3$ according to the present invention is selected from hydrogen, halogen, CN, $C_1$-$C_4$-alkyl, $C_1$-$C_4$-alkoxy, $C_2$-$C_4$-alkenyl, $C_2$-$C_4$-alkynyl, $C_3$-$C_6$-cycloalkyl and $S(O)_p(C_1$-$C_4$-alkyl), wherein each of $R^3$ is unsubstituted or further substituted by one, two, three or four $R^{3a}$; wherein $R^{3a}$ is independently selected from halogen, CN, OH, $C_1$-$C_4$-alkyl, $C_1$-$C_4$-halogenalkyl, $C_3$-$C_6$-cycloalkyl, $C_3$-$C_6$-halogencycloalkyl, $C_1$-$C_4$-alkoxy and $C_1$-$C_4$-halogenalkoxy, and wherein p is 0, 1 or 2.

$R^3$ according one embodiment is hydrogen.

$R^3$ according to a further embodiment is selected from halogen, CN, $C_1$-$C_4$-alkyl, $C_1$-$C_4$-alkoxy, $C_2$-$C_4$-alkenyl, $C_2$-$C_4$-alkynyl, $C_3$-$C_6$-cycloalkyl and $S(O)_p(C_1$-$C_4$-alkyl), wherein each of $R^3$ is unsubstituted or further substituted by one, two, three or four $R^{3a}$; wherein $R^{3a}$ is independently selected from halogen, CN, OH, $C_1$-$C_4$-alkyl, $C_1$-$C_4$-halogenalkyl, $C_3$-$C_6$-cycloalkyl, $C_3$-$C_6$-halogencycloalkyl, $C_1$-$C_4$-alkoxy and $C_1$-$C_4$-halogenalkoxy, and wherein p is 0, 1 or 2.

According to a further embodiment, $R^3$ is selected from H, F, Cl, Br, CN, $C_1$-$C_4$-alkyl, $C_1$-$C_4$-halogenalkyl, $C_1$-$C_4$-alkoxy, $C_1$-$C_4$-halogenalkoxy, $S(C_1$-$C_4$-alkyl), $S(O)(C_1$-$C_4$-alkyl) and $S(O)_2(C_1$-$C_4$-alkyl).

According to still a further embodiment, $R^3$ is selected from F, Cl, Br, CN, $C_1$-$C_4$-alkyl, $C_1$-$C_4$-halogenalkyl, $C_1$-$C_4$-alkoxy, $C_1$-$C_4$-halogenalkoxy, $S(C_1$-$C_4$-alkyl), $S(O)(C_1$-$C_4$-alkyl) and $S(O)_2(C_1$-$C_4$-alkyl).

According to a further embodiment, $R^3$ is selected from H, Cl, F, Br, CN, $C_1$-$C_2$-alkyl, in particular H, $CH_3$, $C_1$-$C_2$-halogenalkyl, in particular H, $CF_3$, $C_1$-$C_2$-alkoxy, in particular $OCH_3$, and $C_1$-$C_2$-halogenalkoxy, in particular $OCF_3$.

According to still a further embodiment, $R^3$ is selected from Cl, F, Br, $C_1$-$C_2$-alkyl, in particular $CH_3$, $C_1$-$C_2$-halogenalkyl, in particular $CF_3$, $C_1$-$C_2$-alkoxy, in particular $OCH_3$, and $C_1$-$C_2$-halogenalkoxy, in particular $OCF_3$.

According to a further embodiment, $R^3$ is selected from H, $C_2$-$C_4$-alkenyl, $C_2$-$C_4$-halogenalkenyl, $C_2$-$C_4$-alkynyl and $C_2$-$C_4$-halogenalkynyl. According to one particular embodiment, $R^3$ is H, $C_2$-$C_4$-alkenyl or $C_2$-$C_4$-halogenalkenyl, such as H or CH=CH₂. According to a further particular embodiment, $R^3$ is H, $C_2$-$C_4$-alkynyl or $C_2$-$C_4$-halogenalkynyl, such as H or C≡CH According to still a further embodiment, $R^3$ is selected from $C_2$-$C_4$-alkenyl, $C_2$-$C_4$-halogenalkenyl, $C_2$-$C_4$-alkynyl and $C_2$-$C_4$-halogenalkynyl. According to one particular embodiment, $R^3$ is $C_2$-$C_4$-alkenyl or $C_2$-$C_4$-halogenalkenyl, such as CH=CH₂. According to a further particular embodiment, $R^3$ is $C_2$-$C_4$-alkynyl or $C_2$-$C_4$-halogenalkynyl, such as C≡CH.

According to a further embodiment, $R^3$ is selected from H, $C_3$-$C_6$-cycloalkyl and $C_3$-$C_6$-halogencycloalkyl.

According to still a further embodiment, $R^3$ is selected from $C_3$-$C_6$-cycloalkyl and $C_3$-$C_6$-halogencycloalkyl.

According to a further embodiment, $R^3$ is selected from H, $S(C_1$-$C_2$-alkyl), $S(O)(C_1$-$C_2$-alkyl) and $S(O)_2(C_1$-$C_2$-alkyl). According to a particular embodiment thereof, $R^3$ is selected from H, $SCH_3$, $S(O)(CH_3)$ and $S(O)_2(CH_3)$.

According to still a further embodiment, $R^3$ is selected from $S(C_1$-$C_2$-alkyl), $S(O)(C_1$-$C_2$-alkyl) and $S(O)_2(C_1$-$C_2$-alkyl). According to a particular embodiment thereof, $R^3$ is selected from $SCH_3$, $S(O)(CH_3)$ and $S(O)_2(CH_3)$.

According to one specific embodiment, $R^3$ is H or halogen, in particular H, Br, F or Cl, more specifically H, F or Cl.

According to a further specific embodiment, $R^3$ is halogen, in particular Br, F or Cl, more specifically F or Cl.

According to a further specific embodiment, $R^3$ is H or CN.

According to still a further specific embodiment, $R^3$ is CN.

According to still a further specific embodiment, $R^3$ is H, $C_1$-$C_4$-alkyl, such as $CH_3$, or $C_1$-$C_4$-halogenalkyl, such as $CF_3$, $CHF_2$, $CH_2F$, $CCl_3$, $CHCl_2$ or $CH_2Cl$.

According to still a further specific embodiment, $R^3$ is $C_1$-$C_4$-alkyl, such as $CH_3$, or $C_1$-$C_4$-halogenalkyl, such as $CF_3$, $CHF_2$, $CH_2F$, $CCl_3$, $CHCl_2$ or $CH_2Cl$.

According to a further specific embodiment, $R^3$ is H, $C_1$-$C_4$-alkoxy, more specifically $C_1$-$C_2$-alkoxy such as $OCH_3$ or $OCH_2CH_3$, or $C_1$-$C_4$-halogenalkoxy, more specifically $C_1$-$C_2$-halogenalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to a further specific embodiment, $R^3$ is $C_1$-$C_4$-alkoxy, more specifically $C_1$-$C_2$-alkoxy such as $OCH_3$ or $OCH_2CH_3$, or $C_1$-$C_4$-halogenalkoxy, more specifically $C_1$-$C_2$-halogenalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

$R^{3a}$ is selected from halogen, CN, OH, $C_1$-$C_4$-alkyl, $C_1$-$C_4$-halogenalkyl, $C_3$-$C_6$-cycloalkyl, $C_3$-$C_8$-halogencycloalkyl, $C_1$-$C_4$-alkoxy and $C_1$-$C_4$-halogenalkoxy, in particular selected from halogen, CN, $C_1$-$C_2$-alkyl, $C_1$-$C_2$-halogenalkyl, $C_3$-$C_6$-cycloalkyl, $C_3$-$C_6$-halogencycloalkyl, $C_1$-$C_2$-alkoxy and $C_1$-$C_2$-halogenalkoxy. Specifically, $R^{3a}$ is independently selected from F, Cl, CN, OH, $CH_3$, halogenmethyl, cyclopropyl, halogencyclopropyl, $OCH_3$ and halogenmethoxy.

Particularly preferred embodiments of $R^3$ according to the invention are in Table P3 below, wherein each line of lines P3-1 to P5-16 corresponds to one particular embodiment of the invention, wherein P3-1 to P3-16 are also in any combination with one another a preferred embodiment of the present invention. Thereby, for every $R^3$ that is present in the inventive compounds, these specific embodiments and preferences apply independently of the meaning of any other $R^3$ that may be present in the phenyl ring:

TABLE P3

| No. | $R^3$ |
|---|---|
| P3-1 | H |
| P3-2 | Cl |
| P3-3 | F |
| P3-4 | CN |
| P3-5 | $CH_3$ |
| P3-6 | $CH_2CH_3$ |
| P3-7 | $CF_3$ |
| P3-8 | $CHF_2$ |
| P3-9 | $OCH_3$ |
| P3-10 | $OCH_2CH_3$ |
| P3-11 | $OCF_3$ |
| P3-12 | $OCHF_2$ |
| P3-13 | $SCH_3$ |
| P3-14 | $SOCH_3$ |
| P3-15 | $SO_2CH_3$ |
| P3-16 | Br |

$R^5$ according to the invention is hydrogen, halogen, CN, $C_1$-$C_6$-alkyl, $C_1$-$C_6$-halogenalkyl, $C_1$-$C_6$-alkoxy, $C_1$-$C_6$-halogenalkoxy, C(=O)—O—($C_1$-$C_6$-alkyl), $C_3$-$C_6$-cycloalkyl or saturated or partially unsaturated three-, four-, five-, six- or seven-membered heterocyclyl, wherein the heterocyclyl contains 1, 2, 3 or 4 heteroatoms selected from O, N and S, and wherein the cycloalkyl and heterocyclyl is unsubstituted (m=0) or substituted by $(R^4)_m$; or $R^5$ together with $R^7$ and the carbon atoms to which they are bound forms a $C_3$-$C_6$-cycloalkenyl, that is unsubstituted at the saturated chain or substituted by $(R^8)_n$; wherein $R^6$ is as defined and preferably defined herein. In particular, $R^5$ is hydrogen, Cl, F, Br, CN, $C_1$-$C_4$-alkyl, $C_1$-$C_4$-halogenalkyl, $C_1$-$C_4$-alkoxy, $C_1$-$C_4$-halogenalkoxy, C(=O)—O—($C_1$-$C_4$-alkyl), $C_3$-$C_6$-cycloalkyl or saturated or partially unsaturated three-, four-, five-, six- or seven-membered heterocyclyl, wherein the heterocyclyl contains 1, 2, 3 or 4 heteroatoms selected from O, N and S, and wherein the cycloalkyl and heterocyclyl is unsubstituted (m=0) or substituted by $(R^4)_m$; or $R^5$ together with $R^7$ and the carbon atoms to which they are bound forms a $C_3$-$C_6$-cycloalkenyl, that is unsubstituted at the saturated chain or substituted by $(R^8)_n$; wherein $R^6$ is as defined and preferably defined herein.

According to one embodiment, $R^5$ is hydrogen.

According to a further embodiment, $R^5$ is halogen, CN, $C_1$-$C_6$-alkyl, $C_1$-$C_6$-halogenalkyl, $C_1$-$C_6$-alkoxy, $C_1$-$C_6$-halogenalkoxy, C(=O)—O—($C_1$-$C_6$-alkyl), $C_3$-$C_6$-cycloalkyl or saturated or partially unsaturated three-, four-, five-, six- or seven-membered heterocyclyl, wherein the heterocyclyl contains 1, 2, 3 or 4 heteroatoms selected from O, N and S, and wherein the cycloalkyl and heterocyclyl is unsubstituted (m=0) or substituted by $(R^4)_m$; or $R^5$ together with $R^7$ and the carbon atoms to which they are bound forms a $C_3$-$C_6$-cycloalkenyl, that is unsubstituted at the saturated chain or substituted by $(R^8)_n$; wherein $R^6$ is as defined herein. In particular, $R^5$ is, Cl, F, Br, CN, $C_1$-$C_4$-alkyl, $C_1$-$C_4$-halogenalkyl, $C_1$-$C_4$-alkoxy, $C_1$-$C_4$-halogenalkoxy, C(=O)—O—($C_1$-$C_4$-alkyl), $C_3$-$C_6$-cycloalkyl or saturated or partially unsaturated three-, four-, five-, six- or seven-membered heterocyclyl, wherein the heterocyclyl contains 1, 2, 3 or 4 heteroatoms selected from O, N and S, and wherein the cycloalkyl and heterocyclyl is unsubstituted (m=0) or substituted by $(R^4)_m$; or $R^5$ together with $R^7$ and the carbon atoms to which they are bound forms a $C_3$-$C_6$-cycloalkenyl, that is unsubstituted at the saturated chain or substituted by $(R^8)_n$; wherein $R^6$ is as defined and preferably defined herein.

According to a further embodiment, $R^5$ is hydrogen, halogen, CN, $C_1$-$C_6$-alkyl, $C_1$-$C_6$-halogenalkyl, $C_1$-$C_6$-alkoxy, $C_1$-$C_6$-halogenalkoxy or C(=O)—O—($C_1$-$C_6$-alkyl), in particular hydrogen, F, Cl, Br, CN, $C_1$-$C_4$-alkyl, $C_1$-$C_4$-halogenalkyl, $C_1$-$C_4$-alkoxy, $C_1$-$C_4$-halogenalkoxy or C(=O)—O—($C_1$-$C_4$-alkyl).

According to still a further embodiment, $R^5$ is halogen, CN, $C_1$-$C_6$-alkyl, $C_1$-$C_6$-halogenalkyl, $C_1$-$C_6$-alkoxy, $C_1$-$C_6$-halogenalkoxy or C(=O)—O—($C_1$-$C_6$-alkyl), in particular hydrogen, F, Cl, Br, CN, $C_1$-$C_4$-alkyl, $C_1$-$C_4$-halogenalkyl, $C_1$-$C_4$-alkoxy, $C_1$-$C_4$-halogenalkoxy or C(=O)—O—($C_1$-$C_4$-alkyl).

According to a further embodiment, $R^5$ is hydrogen, halogen, $C_1$-$C_6$-alkyl or $C_1$-$C_6$-halogenalkyl, in particular hydrogen, F, Cl, Br, $C_1$-$C_4$-alkyl or $C_1$-$C_4$-halogenalkyl, more specifically hydrogen, F, Cl, Br, $C_1$-$C_2$-alkyl or $C_1$-$C_2$-halogenalkyl.

According to still a further embodiment, $R^5$ is halogen, $C_1$-$C_6$-alkyl or $C_1$-$C_6$-halogenalkyl, in particular F, Cl, Br, $C_1$-$C_4$-alkyl or $C_1$-$C_4$-halogenalkyl, more specifically hydrogen, F, Cl, Br, $C_1$-$C_2$-alkyl or $C_1$-$C_2$-halogenalkyl.

According to a specific embodiment, $R^5$ is hydrogen or halogen, such as F, Cl, Br. According to one particular embodiment thereof, $R^5$ is H or F. According to a further particular embodiment thereof, $R^5$ is H or Cl. According to still a further particular embodiment thereof, $R^5$ is H or Br.

According to still a specific embodiment, $R^5$ is halogen such as F, Cl, Br. According to one particular embodiment thereof, $R^5$ is F. According to a further particular embodiment thereof, $R^5$ is Cl. According to still a further particular embodiment thereof, $R^5$ is Br.

According to a further embodiment, $R^5$ is H or CN.

According to still a further embodiment, $R^5$ is CN.

According to still a further specific embodiment, $R^5$ is hydrogen, $C_1$-$C_6$-alkyl, more specifically $C_1$-$C_4$-alkyl, such as $CH_3$, $C_2H_5$, iso-$C_3H_7$, n-$C_4H_9$, tert-$C_4H_9$ or iso-$C_4H_9$, or $C_1$-$C_6$-halogenalkyl, more specifically $C_1$-$C_4$-halogenalkyl, such as $CF_3$. According to one particular embodiment thereof, $R^5$ is hydrogen or $CH_3$. According to one particular embodiment thereof, $R^5$ is hydrogen or $CF_3$.

According to still a further specific embodiment, $R^5$ is $C_1$-$C_6$-alkyl, more specifically $C_1$-$C_4$-alkyl, such as $CH_3$, $C_2H_5$, iso-$C_3H_7$, n-$C_4H_9$, tert-$C_4H_9$ or iso-$C_4H_9$, or $C_1$-$C_6$-halogenalkyl, more specifically $C_1$-$C_4$-halogenalkyl, such as $CF_3$. According to one particular embodiment thereof, $R^5$ is $CH_3$. According to one particular embodiment thereof, $R^5$ is $CF_3$.

According to a further specific embodiment, $R^5$ is hydrogen, $C_1$-$C_6$-alkoxy, more specifically $C_1$-$C_4$-alkoxy, such as $OCH_3$, $OC_2H_5$, O-iso-$C_3H_7$, O-n-$C_4H_9$, O-tert-$C_4H_9$ or O-iso-$C_4H_9$, or $C_1$-$C_6$-halogenalkoxy, more specifically $C_1$-$C_4$-halogenalkoxy, such as $OCF_3$. According to one particular embodiment thereof, $R^5$ is hydrogen or $OCH_3$. According to one particular embodiment thereof, $R^5$ is hydrogen or $OCF_3$.

According to a further specific embodiment, $R^5$ is $C_1$-$C_6$-alkoxy, more specifically $C_1$-$C_4$-alkoxy, such as $OCH_3$, $OC_2H_5$, O-iso-$C_3H_7$, O-n-$C_4H_9$, O-tert-$C_4H_9$ or O-iso-$C_4H_9$, or $C_1$-$C_6$-halogenalkoxy, more specifically $C_1$-$C_4$-halogenalkoxy, such as $OCF_3$.

According to a further specific embodiment, $R^5$ is hydrogen or C(=O)—O—($C_1$-$C_6$-alkyl), in particular hydrogen or C(=O)—O—($C_1$-$C_4$-alkyl), such as hydrogen, C(=O)OCH$_3$ or C(=O)OC$_2$H$_5$.

According to still a further specific embodiment, $R^5$ is C(=O)—O—($C_1$-$C_6$-alkyl), in particular C(=O)—O—($C_1$-$C_4$-alkyl), such as C(=O)OCH$_3$ or C(=O)OC$_2$H$_5$.

According to a further specific embodiment, $R^5$ is hydrogen, CN or C(=O)—O—($C_1$-$C_6$-alkyl), in particular hydrogen, CN or C(=O)—O—($C_1$-$C_4$-alkyl), such as hydrogen, CN, C(=O)OCH$_3$ or C(=O)OC$_2$H$_5$.

According to a further specific embodiment, $R^5$ is CN or C(=O)—O—($C_1$-$C_6$-alkyl), in particular CN or C(=O)—O—($C_1$-$C_4$-alkyl), such as CN, C(=O)OCH$_3$ or C(=O)OC$_2$H$_5$.

According to a further embodiment, $R^5$ is $C_3$-$C_6$-cycloalkyl that is unsubstituted (m=0) or substituted by $(R^4)_m$. According to one embodiment thereof, m is 0, 1, 2 or 3. According to a further embodiment thereof, n is 0. According to still a further one embodiment thereof, n is 1 or 2.

According to a specific embodiment thereof, $R^5$ is cyclopropyl that is unsubstituted (m=0) or substituted by $(R^4)_m$. According to one embodiment thereof, m is 0, 1, 2 or 3. According to a further embodiment thereof, n is 0. According to still a further one embodiment thereof, n is 1 or 2.

According to a further specific embodiment thereof, $R^5$ is cyclobutyl that is unsubstituted (m=0) or substituted by $(R^4)_m$. According to one embodiment thereof, m is 0, 1, 2 or 3. According to a further embodiment thereof, n is 0. According to still a further one embodiment thereof, n is 1 or 2.

According to still a further specific embodiment thereof, $R^5$ is cyclopentyl that is unsubstituted (m=0) or substituted by $(R^4)_m$. According to one embodiment thereof, m is 0, 1, 2 or 3. According to a further embodiment thereof, n is 0. According to still a further one embodiment thereof, n is 1 or 2.

According to still a further specific embodiment thereof, $R^5$ is cyclohexyl that is unsubstituted (m=0) or substituted by $(R^4)_m$. According to one embodiment thereof, m is 0, 1, 2 or 3. According to a further embodiment thereof, m is 0. According to still a further one embodiment thereof, m is 1 or 2.

According to a further embodiment, $R^5$ is a saturated or partially unsaturated three-, four-, five-, six- or seven-membered heterocyclyl, wherein the heterocyclyl contains 1, 2, 3 or 4 heteroatoms selected from O, N and S, that is unsubstituted (m=0) or substituted by $(R^4)_m$. According to one embodiment thereof, m is 0, 1, 2 or 3. According to a further embodiment thereof, m is 0. According to still a further one embodiment thereof, m is 1 or 2.

According to one embodiment thereof, $R^5$ is a 4-membered saturated heterocycle which contains 1 or 2 heteroatoms, in particular 1 heteroatom, from the group consisting of N, O and S as ring members. For example, $R^5$ is oxetane. According to one embodiment thereof, m is 0, 1, 2 or 3. According to a further embodiment thereof, m is 0. According to still a further one embodiment thereof, m is 1 or 2.

According to a further embodiment thereof, $R^5$ is a 5-membered saturated heterocycle which contains 1, 2 or 3, in particular 1 or 2, heteroatoms from the group consisting of N, O and S as ring members. According to one embodiment thereof, m is 0, 1, 2 or 3. According to a further embodiment thereof, m is 0. According to still a further one embodiment thereof, m is 1 or 2.

According to a further embodiment thereof, $R^5$ is a 6-membered saturated heterocycle which contains 1, 2 or 3, in particular 1 or 2, heteroatoms from the group consisting of N, O and S as ring members. According to one embodiment thereof, m is 0, 1, 2 or 3. According to a further embodiment thereof, m is 0. According to still a further one embodiment thereof, m is 1 or 2.

According to a further embodiment thereof, $R^5$ is a 7-membered saturated heterocycle which contains 1, 2 or 3, in particular 1 or 2, heteroatoms from the group consisting of N, O and S as ring members. According to one embodiment thereof, m is 0, 1, 2 or 3. According to a further embodiment thereof, m is 0. According to still a further one embodiment thereof, m is 1 or 2.

$R^6$ according to the invention is hydrogen, halogen, CN, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy and $C_1$-$C_6$-halogenalkoxy, wherein the alkenyl and alkynyl moieties are not further substituted or carry one, two, three, four, five or up to the maximum number of identical or different groups $R^{6a}$ which independently of one another are selected from: $R^{6a}$ halogen, $C_1$-$C_4$-alkyl, $C_1$-$C_4$-halogenalkyl, Si(CH$_3$)$_3$;

or $R^6$ and $R^7$ together with the carbon atoms to which they are bound form a $C_3$-$C_6$-cycloalkyl, that is unsubstituted or substituted by $(R^8)_n$; and, in this case, $R^5$ is selected from hydrogen, halogen, CN, $C_1$-$C_6$-alkyl, $C_1$-$C_6$-halogenalkyl, $C_1$-$C_6$-alkoxy, $C_1$-$C_6$-halogenalkoxy and C(=O)—O—($C_1$-$C_6$-alkyl).

In particular, $R^6$ is H, Cl, F, Br, CN, $C_1$-$C_4$-alkyl, $C_1$-$C_4$-halogenalkyl, $C_2$-$C_4$-alkenyl, $C_2$-$C_4$-alkynyl, $C_1$-$C_4$-alkoxy, $C_1$-$C_4$-halogenalkoxy, or $R^6$ and $R^7$ together with the carbon atoms to which they are bound form a $C_3$-$C_6$-cycloalkyl, that is unsubstituted or substituted by $(R^8)_n$. The alkenyl and alkynyl moieties are not further substituted or carry one, two, three or four identical or different groups $R^{6a}$ which independently of one another are selected from: $R^{6a}$ Cl, F, Br, $C_1$-$C_2$-alkyl, $C_1$-$C_2$-halogenalkyl and Si(CH$_3$)$_3$.

According to one embodiment, $R^6$ is hydrogen.

According to a further embodiment, $R^6$ is halogen, CN, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy and $C_1$-$C_6$-halogenalkoxy; or $R^6$ and $R^7$ together with the carbon atoms to which they are bound form a $C_3$-$C_6$-cycloalkyl, that is unsubstituted or substituted by $(R^8)_n$; and, this case, $R^5$ is selected from hydrogen, halogen, CN, $C_1$-$C_6$-alkyl, $C_1$-$C_6$-halogenalkyl, $C_1$-$C_6$-alkoxy, $C_1$-$C_6$-halogenalkoxy and C(=O)—O—($C_1$-$C_6$-alkyl). In particular, $R^6$ is Cl, F, Br, CN, $C_1$-$C_4$-alkyl, $C_1$-$C_4$-halogenalkyl, $C_2$-$C_4$-alkenyl, $C_2$-$C_4$-alkynyl, $C_1$-$C_4$-alkoxy, $C_1$-$C_4$-halogenalkoxy, or $R^6$ and $R^7$ together with the carbon atoms to which they are bound form a $C_3$-$C_6$-cycloalkyl, that is unsubstituted or substituted by $(R^8)_n$. The alkenyl and alkynyl moieties are not further substituted or carry one, two, three or four identical or different groups $R^{6a}$ which independently of one another are selected from: $R^{6a}$ Cl, F, Br, $C_1$-$C_2$-alkyl, $C_1$-$C_2$-halogenalkyl and Si(CH$_3$)$_3$.

According to a further embodiment, $R^6$ is hydrogen, halogen, CN, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy or $C_1$-$C_6$-halogenalkoxy, in particular hydrogen, F, Cl, Br, CN, $C_1$-$C_4$-alkyl, $C_1$-$C_4$-halogenalkyl, $C_2$-$C_4$-alkenyl, $C_2$-$C_4$-alkynyl, $C_1$-$C_4$-alkoxy or $C_1$-$C_4$-halogenalkoxy. The alkenyl and alkynyl moieties are not further substituted or carry one, two, three or four identical or different groups $R^{6a}$ which independently of one another are selected from: $R^{6a}$ Cl, F, Br, $C_1$-$C_2$-alkyl, $C_1$-$C_2$-halogenalkyl and $Si(CH_3)_3$.

According to still a further embodiment, $R^6$ is halogen, CN, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy or $C_1$-$C_6$-halogenalkoxy, in particular hydrogen, F, Cl, Br, CN, $C_1$-$C_4$-alkyl, $C_1$-$C_4$-halogenalkyl, $C_2$-$C_4$-alkenyl, $C_2$-$C_4$-alkynyl, $C_1$-$C_4$-alkoxy or $C_1$-$C_4$-halogenalkoxy. The alkenyl and alkynyl moieties are not further substituted or carry one, two, three or four identical or different groups $R^{6a}$ which independently of one another are selected from: $R^{6a}$ Cl, F, Br, $C_1$-$C_2$-alkyl, $C_1$-$C_2$-halogenalkyl and $Si(CH_3)_3$.

According to a further embodiment, $R^6$ is hydrogen, halogen, $C_1$-$C_6$-alkyl, $C_1$-$C_6$-halogenalkyl, $C_2$-$C_6$-alkenyl or $C_2$-$C_6$-alkynyl, in particular hydrogen, F, Cl, Br, $C_1$-$C_4$-alkyl, $C_1$-$C_4$-halogenalkyl, $C_2$-$C_4$-alkenyl or $C_2$-$C_4$-alkynyl, The alkenyl and alkynyl moieties are not further substituted or carry one, two, three or four identical or different groups $R^{6a}$ which independently of one another are selected from: $R^{6a}$ Cl, F, Br, $C_1$-$C_2$-alkyl, $C_1$-$C_2$-halogenalkyl and $Si(CH_3)_3$. More specifically, $R^6$ is hydrogen, F, Cl, Br, $C_1$-$C_2$-alkyl, $C_1$-$C_2$-halogenalkyl, $C_2$-$C_3$-alkenyl, $C_2$-$C_3$-halogenalkenyl, $C_2$-$C_3$-alkynyl or $C_2$-$C_3$-halogenalkynyl.

According to still a further embodiment, $R^6$ is halogen, $C_1$-$C_6$-alkyl, $C_1$-$C_6$-halogenalkyl, $C_2$-$C_6$-alkenyl or $C_2$-$C_6$-alkynyl, in particular F, Cl, Br, $C_1$-$C_4$-alkyl, $C_1$-$C_4$-halogenalkyl, $C_2$-$C_4$-alkenyl or $C_2$-$C_4$-alkynyl, The alkenyl and alkynyl moieties are not further substituted or carry one, two, three or four identical or different groups $R^{6a}$ which independently of one another are selected from: $R^{6a}$ Cl, F, Br, $C_1$-$C_2$-alkyl, $C_1$-$C_2$-halogenalkyl and $Si(CH_3)_3$. More specifically, $R^6$ is F, Cl, Br, $C_1$-$C_2$-alkyl, $C_1$-$C_2$-halogenalkyl, $C_2$-$C_3$-alkenyl, $C_2$-$C_3$-halogenalkenyl, $C_2$-$C_3$-alkynyl or $C_2$-$C_3$-halogenalkynyl.

According to a specific embodiment, $R^6$ is hydrogen or halogen, such as F, Cl, Br. According to one particular embodiment thereof, $R^6$ is H or F. According to a further particular embodiment thereof, $R^6$ is H or Cl. According to still a further particular embodiment thereof, $R^6$ is H or Br.

According to still a specific embodiment, $R^6$ is halogen such as F, Cl, Br. According to one particular embodiment thereof, $R^6$ is F. According to a further particular embodiment thereof, $R^6$ is Cl. According to still a further particular embodiment thereof, $R^6$ is Br.

According to a further embodiment, $R^6$ is H or CN.

According to still a further embodiment, $R^6$ is CN.

According to a further specific embodiment, $R^6$ is hydrogen, $C_1$-$C_6$-alkyl, more specifically $C_1$-$C_4$-alkyl, such as $CH_3$, $C_2H_5$, iso-$C_3H_7$, n-$C_4H_9$, tert-$C_4H_9$ or iso-$C_4H_9$, or $C_1$-$C_6$-halogenalkyl, more specifically $C_1$-$C_4$-halogenalkyl, such as $CF_3$. According to one particular embodiment thereof, $R^6$ is hydrogen or $CH_3$. According to one particular embodiment thereof, $R^6$ is hydrogen or $CF_3$.

According to still a further specific embodiment, $R^6$ is $C_1$-$C_6$-alkyl, more specifically $C_1$-$C_4$-alkyl, such as $CH_3$, $C_2H_5$, iso-$C_3H_7$, n-$C_4H_9$, tert-$C_4H_9$ or iso-$C_4H_9$, or $C_1$-$C_6$-halogenalkyl, more specifically $C_1$-$C_4$-halogenalkyl, such as $CF_3$. According to one particular embodiment thereof, $R^6$ is $CH_3$. According to one particular embodiment thereof, $R^6$ is $CF_3$.

According to a further specific embodiment, $R^6$ is hydrogen or $C_2$-$C_6$-alkenyl, more specifically hydrogen or $C_2$-$C_4$-alkenyl, such as $C_2$-alkenyl or $C_3$-alkenyl, wherein the alkenyl are not further substituted or carry one, two, three or four identical or different groups $R^{6a}$ which independently of one another are selected from: $R^{6a}$ Cl, F, Br, $C_1$-$C_2$-alkyl, $C_1$-$C_2$-halogenalkyl and $Si(CH_3)_3$. Specifically, in this embodiment, $R^6$ is selected from H, CHC=CH, CH=$CHCH_3$, CH=$C(CH_3)_2$, CH=$CCl_2$, C(Cl)=$CH_2$, C(Cl)=$CCl_2$ and C($CH_3$)=$CCl_2$.

According to still a further specific embodiment, $R^6$ is $C_2$-$C_6$-alkenyl, more specifically $C_2$-$C_4$-alkenyl, such as $C_2$-alkenyl or $C_3$-alkenyl, wherein the alkenyl are not further substituted or carry one, two, three or four identical or different groups $R^{6a}$ which independently of one another are selected from: $R^{6a}$ Cl, F, Br, $C_1$-$C_2$-alkyl, $C_1$-$C_2$-halogenalkyl and $Si(CH_3)_3$. Specifically, in this embodiment, $R^6$ is selected from CHC=CH, CH=$CHCH_3$, CH=$C(CH_3)_2$, CH=$CCl_2$, C(Cl)=$CH_2$, C(Cl)=$CCl_2$ and C($CH_3$)=$CCl_2$.

According to a further specific embodiment, $R^6$ is hydrogen or $C_2$-$C_6$-alkynyl, more specifically hydrogen or $C_2$-$C_4$-alkynyl, such as $C_2$-alkynyl or $C_3$-alkynyl, wherein the alkynyl are not further substituted or carry one, two, three or four identical or different groups $R^{6a}$ which independently of one another are selected from: $R^{6a}$ Cl, F, Br, $C_1$-$C_2$-alkyl, $C_1$-$C_2$-halogenalkyl and $Si(CH_3)_3$. Specifically, in this embodiment, $R^6$ is selected from C≡CH, C≡C—$CH_3$, C≡CCl, C≡CBr and C≡C—I.

According to still a further specific embodiment, $R^6$ is hydrogen or $C_2$-$C_6$-alkynyl, more specifically hydrogen or $C_2$-$C_4$-alkynyl, such as $C_2$-alkynyl or $C_3$-alkynyl, wherein the alkynyl are not further substituted or carry one, two, three or four identical or different groups $R^{6a}$ which independently of one another are selected from: $R^{6a}$ Cl, F, Br, $C_1$-$C_2$-alkyl, $C_1$-$C_2$-halogenalkyl and $Si(CH_3)_3$. Specifically, in this embodiment, $R^6$ is selected from C≡CH, C≡C—$CH_3$, C≡CCl, C≡CBr and C≡C—I.

According to a further specific embodiment, $R^6$ is hydrogen, $C_1$-$C_6$-alkoxy, more specifically $C_1$-$C_4$-alkoxy, such as $OCH_3$, $OC_2H_5$, O-iso-$C_3H_7$, O-n-$C_4H_9$, O-tert-$C_4H_9$ or O-iso-$C_4H_9$, or $C_1$-$C_6$-halogenalkoxy, more specifically $C_1$-$C_4$-halogenalkoxy, such as $OCF_3$. According to one particular embodiment thereof, $R^6$ is hydrogen or $OCH_3$. According to one particular embodiment thereof, $R^6$ is hydrogen or $OCF_3$ According to a further specific embodiment, $R^6$ is $C_1$-$C_6$-alkoxy, more specifically $C_1$-$C_4$-alkoxy, such as $OCH_3$, $OC_2H_5$, O-iso-$C_3H_7$, O-n-$C_4H_9$, O-tert-$C_4H_9$ or O-iso-$C_4H_9$, or $C_1$-$C_6$-halogenalkoxy, more specifically $C_1$-$C_4$-halogenalkoxy, such as $OCF_3$.

$R^7$ according to the invention is hydrogen, halogen, CN, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy, $C_1$-$C_6$-halogenalkoxy, C(=O)—O—($C_1$-$C_6$-alkyl), $Si(CH_3)_3$, $C_3$-$C_6$-cycloalkyl or saturated or partially unsaturated three-, four-, five-, six- or seven-membered heterocyclyl, wherein the heterocyclyl contains 1, 2, 3 or 4 heteroatoms selected from O, N and S, and wherein the cycloalkyl and heterocyclyl is unsubstituted (m=0) or substituted by $(R^4)_m$; and wherein the alkenyl and alkynyl moieties are not further substituted or carry one, two, three, four, five or up to the maximum number of identical or different groups $R^{7a}$ which independently of one another are selected from halogen, $C_1$-$C_4$-alkyl, $C_1$-$C_4$-halogenalkyl and $Si(CH_3)_3$. Or $R^5$ and $R^7$ together with the carbon atoms to which they are bound form a $C_3$-$C_6$-cycloalkenyl, that is unsubstituted at the saturated chain or substituted by $(R^8)_n$; and $R^6$ is as defined or preferably defined above; or $R^6$ and $R^7$ together with the carbon atoms to which they are bound form a $C_3$-$C_6$-cycloalkyl, that is unsubstituted or substituted by $(R^8)_n$; and $R^5$ is selected from hydrogen, halogen, CN, $C_1$-$C_6$-alkyl, $C_1$-$C_6$-halogenalkyl, $C_1$-$C_6$-alkoxy, $C_1$-$C_6$-halogenalkoxy and C(=O)—O—($C_1$-$C_6$-alkyl), or as preferably defined herein.

According to one embodiment, $R^7$ is hydrogen.

According to a further embodiment, $R^7$ is halogen, CN, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy, $C_1$-$C_6$-halogenalkoxy, C(=O)—O—($C_1$-$C_6$-alkyl), Si(CH$_3$)$_3$, $C_3$-$C_6$-cycloalkyl or saturated or partially unsaturated three-, four-, five-, six- or seven-membered heterocyclyl, wherein the heterocyclyl contains 1, 2, 3 or 4 heteroatoms selected from O, N and S, and wherein the cycloalkyl and heterocyclyl is unsubstituted (m=0) or substituted by $(R^4)_m$; or $R^5$ and $R^7$ together with the carbon atoms to which they are bound form a $C_3$-$C_6$-cycloalkenyl, that is unsubstituted at the saturated chain or substituted by $(R^8)_n$; and $R^6$ is as defined or preferably defined above; or $R^6$ and $R^7$ together with the carbon atoms to which they are bound form a $C_3$-$C_6$-cycloalkyl, that is unsubstituted or substituted by $(R^8)_n$. Preferably, the alkenyl and alkynyl moieties are not further substituted or carry one, two, three or four identical or different groups $R^{7a}$ which independently of one another are selected from: $R^{6a}$ Cl, F, Br, $C_1$-$C_2$-alkyl, $C_1$-$C_2$-halogenalkyl and Si(CH$_3$)$_3$.

According to a further embodiment, $R^7$ is hydrogen, halogen, CN, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy, $C_1$-$C_6$-halogenalkoxy, C(=O)—O—($C_1$-$C_6$-alkyl) or Si(CH$_3$)$_3$, in particular hydrogen, F, Cl, Br, CN, $C_1$-$C_4$-alkyl, $C_1$-$C_4$-halogenalkyl, $C_2$-$C_4$-alkenyl, $C_2$-$C_4$-alkynyl, $C_1$-$C_4$-alkoxy, $C_1$-$C_4$-halogenalkoxy or C(=O)—O—($C_1$-$C_4$-alkyl). The alkenyl and alkynyl moieties are not further substituted or carry one, two, three or four identical or different groups $R^{7a}$ which independently of one another are selected from: $R^{6a}$ Cl, F, Br, $C_1$-$C_2$-alkyl, $C_1$-$C_2$-halogenalkyl and Si(CH$_3$)$_3$.

According to still a further embodiment, $R^7$ is halogen, CN, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy, $C_1$-$C_6$-halogenalkoxy, C(=O)—O—($C_1$-$C_6$-alkyl) or Si(CH$_3$)$_3$, in particular hydrogen, F, Cl, Br, CN, $C_1$-$C_4$-alkyl, $C_1$-$C_4$-halogenalkyl, $C_2$-$C_4$-alkenyl, $C_2$-$C_4$-alkynyl, $C_1$-$C_4$-alkoxy, $C_1$-$C_4$-halogenalkoxy or C(=O)—O—($C_1$-$C_4$-alkyl). The alkenyl and alkynyl moieties are not further substituted or carry one, two, three or four identical or different groups $R^{7a}$ which independently of one another are selected from: $R^{7a}$ Cl, F, Br, $C_1$-$C_2$-alkyl, $C_1$-$C_2$-halogenalkyl and Si(CH$_3$)$_3$.

According to a further embodiment, $R^7$ is hydrogen, halogen, $C_1$-$C_6$-alkyl, $C_1$-$C_6$-halogenalkyl, $C_2$-$C_6$-alkenyl or $C_2$-$C_6$-alkynyl, in particular hydrogen, F, Cl, Br, $C_1$-$C_4$-alkyl, $C_1$-$C_4$-halogenalkyl, $C_2$-$C_4$-alkenyl or $C_2$-$C_4$-alkynyl. The alkenyl and alkynyl moieties are not further substituted or carry one, two, three or four identical or different groups $R^{7a}$ which independently of one another are selected from: $R^{7a}$ Cl, F, Br, $C_1$-$C_2$-alkyl, $C_1$-$C_2$-halogenalkyl and Si(CH$_3$)$_3$. More specifically, $R^7$ is hydrogen, F, Cl, Br, $C_1$-$C_2$-alkyl, $C_1$-$C_2$-halogenalkyl, $C_2$-$C_3$-alkenyl, $C_2$-$C_3$-halogenalkenyl, $C_2$-$C_3$-alkynyl or $C_2$-$C_3$-halogenalkynyl.

According to still a further embodiment, $R^7$ is halogen, $C_1$-$C_6$-alkyl, $C_1$-$C_6$-halogenalkyl, $C_2$-$C_6$-alkenyl or $C_2$-$C_6$-alkynyl, in particular F, Cl, Br, $C_1$-$C_4$-alkyl, $C_1$-$C_4$-halogenalkyl, $C_2$-$C_4$-alkenyl or $C_2$-$C_4$-alkynyl. The alkenyl and alkynyl moieties are not further substituted or carry one, two, three or four identical or different groups $R^{7a}$ which independently of one another are selected from: $R^{7a}$ Cl, F, Br, $C_1$-$C_2$-alkyl, $C_1$-$C_2$-halogenalkyl and Si(CH$_3$)$_3$. More specifically, $R^7$ is F, Cl, Br, $C_1$-$C_2$-alkyl, $C_1$-$C_2$-halogenalkyl, $C_2$-$C_3$-alkenyl, $C_2$-$C_3$-halogenalkenyl, $C_2$-$C_3$-alkynyl or $C_2$-$C_3$-halogenalkynyl.

According to a specific embodiment, $R^7$ is hydrogen or halogen, such as F, Cl, Br. According to one particular embodiment thereof, $R^7$ is H or F. According to a further particular embodiment thereof, $R^7$ is H or Cl. According to still a further particular embodiment thereof, $R^7$ is H or Br.

According to still a specific embodiment, $R^7$ is halogen such as F, Cl, Br. According to one particular embodiment thereof, $R^7$ is F. According to a further particular embodiment thereof, $R^7$ is Cl. According to still a further particular embodiment thereof, $R^7$ is Br.

According to a further embodiment, $R^7$ is H or CN.

According to still a further embodiment, $R^7$ is CN.

According to a further specific embodiment, $R^7$ is hydrogen, $C_1$-$C_6$-alkyl, more specifically $C_1$-$C_4$-alkyl, such as CH$_3$, $C_2$H$_5$, iso-$C_3$H$_7$, n-$C_4$H$_9$, tert-$C_4$H$_9$ or iso-$C_4$H$_9$, or $C_1$-$C_6$-halogenalkyl, more specifically $C_1$-$C_4$-halogenalkyl, such as CF$_3$. According to one particular embodiment thereof, $R^7$ is hydrogen or CH$_3$. According to one particular embodiment thereof, $R^7$ is hydrogen or CF$_3$.

According to still a further specific embodiment, $R^7$ is $C_1$-$C_6$-alkyl, more specifically $C_1$-$C_4$-alkyl, such as CH$_3$, $C_2$H$_5$, iso-$C_3$H$_7$, n-$C_4$H$_9$, tert-$C_4$H$_9$ or iso-$C_4$H$_9$, or $C_1$-$C_6$-halogenalkyl, more specifically $C_1$-$C_4$-halogenalkyl, such as CF$_3$. According to one particular embodiment thereof, $R^7$ is CH$_3$. According to one particular embodiment thereof, $R^7$ is CF$_3$.

According to a further specific embodiment, $R^7$ is hydrogen or $C_2$-$C_6$-alkenyl, more specifically hydrogen or $C_2$-$C_4$-alkenyl, such as $C_2$-alkenyl or $C_3$-alkenyl, wherein the alkenyl are not further substituted or carry one, two, three or four identical or different groups $R^{7a}$ which independently of one another are selected from: $R^{7a}$ Cl, F, Br, $C_1$-$C_2$-alkyl, $C_1$-$C_2$-halogenalkyl and Si(CH$_3$)$_3$. Specifically, in this embodiment, $R^7$ is selected from H, CHC=CH, CH=CHCH$_3$, CH=C(CH$_3$)$_2$, CH=CCl$_2$, C(Cl)=CH$_2$, C(Cl)=CCl$_2$ and C(CH$_3$)=CCl$_2$.

According to still a further specific embodiment, $R^7$ is $C_2$-$C_6$-alkenyl, more specifically $C_2$-$C_4$-alkenyl, such as $C_2$-alkenyl or $C_3$-alkenyl, wherein the alkenyl are not further substituted or carry one, two, three or four identical or different groups $R^{7a}$ which independently of one another are selected from: $R^{7a}$ Cl, F, Br, $C_1$-$C_2$-alkyl, $C_1$-$C_2$-halogenalkyl and Si(CH$_3$)$_3$. Specifically, in this embodiment, $R^7$ is selected from CHC=CH, CH=CHCH$_3$, CH=C(CH$_3$)$_2$, CH=CCl$_2$, C(Cl)=CH$_2$, C(Cl)=CCl$_2$ and C(CH$_3$)=CCl$_2$.

According to a further specific embodiment, $R^7$ is hydrogen or $C_2$-$C_6$-alkynyl, more specifically hydrogen or $C_2$-$C_4$-alkynyl, such as $C_2$-alkynyl or $C_3$-alkynyl, wherein the alkynyl are not further substituted or carry one, two, three or four identical or different groups $R^{7a}$ which independently of one another are selected from: $R^{7a}$ Cl, F, Br, $C_1$-$C_2$-alkyl, $C_1$-$C_2$-halogenalkyl and Si(CH$_3$)$_3$. Specifically, in this embodiment, $R^7$ is selected from C≡CH, C≡C—CH$_3$, C≡CCl, C≡CBr and C≡C—I.

According to still a further specific embodiment, $R^7$ is hydrogen or $C_2$-$C_6$-alkynyl, more specifically hydrogen or $C_2$-$C_4$-alkynyl, such as $C_2$-alkynyl or $C_3$-alkynyl, wherein the alkynyl are not further substituted or carry one, two, three or four identical or different groups $R^{7a}$ which independently of one another are selected from: $R^{7a}$ Cl, F, Br, $C_1$-$C_2$-alkyl, $C_1$-$C_2$-halogenalkyl and Si(CH$_3$)$_3$. Specifically, in this embodiment, $R^7$ is selected from C≡CH, C≡C—CH$_3$, C≡CCl, C≡CBr and C≡C—I.

According to still a further specific embodiment, $R^7$ is C(=O)—O—($C_1$-$C_6$-alkyl), in particular C(=O)—O—($C_1$-$C_4$-alkyl), such as C(=O)OCH$_3$ or C(=O)OC$_2$H$_5$.

According to a further specific embodiment, $R^7$ is hydrogen, CN or C(=O)—O—($C_1$-$C_6$-alkyl), in particular hydrogen, CN or C(=O)—O—($C_1$-$C_4$-alkyl), such as hydrogen, CN, C(=O)$OCH_3$ or C(=O)$OC_2H_5$.

According to a further specific embodiment, $R^7$ is CN or C(=O)—O—($C_1$-$C_6$-alkyl), in particular CN or C(=O)—O—($C_1$-$C_4$-alkyl), such as CN, C(=O)$OCH_3$ or C(=O)$OC_2H_5$.

According to a further specific embodiment, $R^7$ is H or $Si(CH_3)_3$.

According to a further specific embodiment, $R^7$ is $Si(CH_3)_3$.

According to a further specific embodiment, $R^7$ is hydrogen, $C_1$-$C_6$-alkoxy, more specifically $C_1$-$C_4$-alkoxy, such as $OCH_3$, $OC_2H_5$, O-iso-$C_3H_7$, O-n-$C_4H_9$, O-tert-$C_4H_9$ or O-iso-$C_4H_9$, or $C_1$-$C_6$-halogenalkoxy, more specifically $C_1$-$C_4$-halogenalkoxy, such as $OCF_3$. According to one particular embodiment thereof, $R^7$ is hydrogen or $OCH_3$. According to one particular embodiment thereof, $R^7$ is hydrogen or $OCF_3$.

According to a further specific embodiment, $R^7$ is $C_1$-$C_6$-alkoxy, more specifically $C_1$-$C_4$-alkoxy, such as $OCH_3$, $OC_2H_5$, O-iso-$C_3H_7$, O-n-$C_4H_9$, O-tert-$C_4H_9$ or O-iso-$C_4H_9$, or $C_1$-$C_6$-halogenalkoxy, more specifically $C_1$-$C_4$-halogenalkoxy, such as $OCF_3$. According to one particular embodiment thereof, $R^7$ is $OCH_3$. According to one particular embodiment thereof, $R^7$ is $OCF_3$.

According to a further embodiment, $R^7$ is $C_3$-$C_6$-cycloalkyl that is unsubstituted (m=0) or substituted by $(R^4)_m$; at the same time, $R^5$ is selected from hydrogen, halogen, CN, $C_1$-$C_6$-alkyl, $C_1$-$C_6$-halogenalkyl, $C_1$-$C_6$-alkoxy, $C_1$-$C_6$-halogenalkoxy and C(=O)—O—($C_1$-$C_6$-alkyl) or any preferred meaning as defined herein, and $R^6$ is selected from hydrogen, halogen, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy and $C_1$-$C_6$-halogenalkoxy or any preferred meaning as defined herein. According to one embodiment thereof, m is 0, 1, 2 or 3. According to a further embodiment thereof, m is 0. According to still a further one embodiment thereof, m is 1 or 2.

According to a specific embodiment thereof, $R^7$ is cyclopropyl that is unsubstituted (m=0) or substituted by $(R^4)_m$. According to one embodiment thereof, m is 0, 1, 2 or 3. According to a further embodiment thereof, m is 0. According to still a further one embodiment thereof, m is 1 or 2.

According to a further specific embodiment thereof, $R^7$ is cyclobutyl that is unsubstituted (m=0) or substituted by $(R^4)_m$. According to one embodiment thereof, m is 0, 1, 2 or 3. According to a further embodiment thereof, m is 0. According to still a further one embodiment thereof, m is 1 or 2.

According to still a further specific embodiment thereof, $R^7$ is cyclopentyl that is unsubstituted (m=0) or substituted by $(R^4)_m$. According to one embodiment thereof, m is 0, 1, 2 or 3. According to a further embodiment thereof, m is 0. According to still a further one embodiment thereof, m is 1 or 2.

According to still a further specific embodiment thereof, $R^7$ is cyclohexyl that is unsubstituted (m=0) or substituted by $(R^4)_m$. According to one embodiment thereof, m is 0, 1, 2 or 3. According to a further embodiment thereof, m is 0. According to still a further one embodiment thereof, m is 1 or 2.

According to a further embodiment, $R^7$ is a saturated or partially unsaturated three-, four-, five-, six- or seven-membered heterocyclyl, wherein the heterocyclyl contains 1, 2, 3 or 4 heteroatoms selected from O, N and S, that is unsubstituted (m=0) or substituted by $(R^4)_m$.

According to one embodiment thereof, m is 0, 1, 2 or 3. According to a further embodiment thereof, m is 0. According to still a further one embodiment thereof, m is 1 or 2.

According to one embodiment thereof, $R^7$ is a 4-membered saturated heterocycle which contains 1 or 2 heteroatoms, in particular 1 heteroatom, from the group consisting of N, O and S as ring members. For example, $R^7$ is oxetane. According to one embodiment thereof, m is 0, 1, 2 or 3. According to a further embodiment thereof, m is 0. According to still a further one embodiment thereof, m is 1 or 2.

According to a further embodiment thereof, $R^7$ is a 5-membered saturated heterocycle which contains 1, 2 or 3, in particular 1 or 2, heteroatoms from the group consisting of N, O and S as ring members. According to one embodiment thereof, m is 0, 1, 2 or 3. According to a further embodiment thereof, m is 0. According to still a further one embodiment thereof, m is 1 or 2.

According to a further embodiment thereof, $R^7$ is a 6-membered saturated heterocycle which contains 1, 2 or 3, in particular 1 or 2, heteroatoms from the group consisting of N, O and S as ring members. According to one embodiment thereof, m is 0, 1, 2 or 3. According to a further embodiment thereof, m is 0. According to still a further one embodiment thereof, m is 1 or 2.

According to a further embodiment thereof, $R^7$ is a 7-membered saturated heterocycle which contains 1, 2 or 3, in particular 1 or 2, heteroatoms from the group consisting of N, O and S as ring members. According to one embodiment thereof, m is 0, 1, 2 or 3. According to a further embodiment thereof, m is 0. According to still a further one embodiment thereof, m is 1 or 2.

In one particular embodiment, $R^5$ is selected from hydrogen, halogen, CN, $C_1$-$C_6$-alkyl, $C_1$-$C_6$-halogenalkyl, $C_1$-$C_6$-alkoxy, $C_1$-$C_6$-halogenalkoxy and C(=O)—O—($C_1$-$C_6$-alkyl), $R^6$ is selected from hydrogen, halogen, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy and $C_1$-$C_6$-halogenalkoxy and $R^7$ is selected from hydrogen, halogen, CN, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy, $C_1$-$C_6$-halogenalkoxy and C(=O)—O—($C_1$-$C_6$-alkyl), or for each of the substituents, any preferred meaning as given above.

In one further particular embodiment, $R^5$ is unsubstituted or substituted $C_3$-$C_6$-cycloalkyl as defined and preferably defined above, $R^6$ is selected from hydrogen, halogen, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy and $C_1$-$C_6$-halogenalkoxy, preferably selected from hydrogen, F, Cl, Br, $C_1$-$C_4$-alkyl, $C_1$-$C_4$-halogenalkyl, $C_1$-$C_4$-alkoxy and $C_1$-$C_4$-halogenalkoxy and $R^7$ is selected from hydrogen, halogen, CN, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy, $C_1$-$C_6$-halogenalkoxy and C(=O)—O—($C_1$-$C_6$-alkyl), preferably selected from hydrogen, F, Cl, Br, CN, $C_1$-$C_4$-alkyl, $C_1$-$C_4$-halogenalkyl, $C_2$-$C_4$-alkenyl, $C_2$-$C_4$-alkynyl, $C_1$-$C_4$-alkoxy and $C_1$-$C_4$-halogenalkoxy, or, for each of the substituents, any preferred meaning as given above.

In still one further particular embodiment, $R^5$ is unsubstituted or substituted heterocyclyl as defined and preferably defined above, $R^6$ is selected from hydrogen, halogen, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy and $C_1$-$C_6$-halogenalkoxy, preferably selected from hydrogen, F, Cl, Br, $C_1$-$C_4$-alkyl, $C_1$-$C_4$-halogenalkyl, $C_1$-$C_4$-alkoxy and $C_1$-$C_4$-halogenalkoxy and $R^7$ is selected from hydrogen, halogen, CN, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy, $C_1$-$C_6$-halogenalkoxy and C(=O)—O—($C_1$-$C_6$-alkyl), preferably selected from hydrogen, F, Cl, Br, CN, $C_1$-$C_4$-alkyl, $C_1$-$C_4$-halogenalkyl, $C_2$-$C_4$-alkenyl, $C_2$-$C_4$-alkynyl, $C_1$-$C_4$-alkoxy and $C_1$-$C_4$-halogenalkoxy, or, for each of the substituents, any preferred meaning as given above.

In still one further particular embodiment, $R^5$ is selected from hydrogen, halogen, CN, $C_1$-$C_6$-alkyl, $C_1$-$C_6$-halogenalkyl, $C_1$-$C_6$-alkoxy, $C_1$-$C_6$-halogenalkoxy and C(=O)—O—($C_1$-$C_6$-alkyl), $R^6$ is selected from hydrogen, halogen, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy and $C_1$-$C_6$-halogenalkoxy, preferably selected from hydrogen, F, Cl, Br, $C_1$-$C_4$-alkyl, $C_1$-$C_4$-halogenalkyl, $C_1$-$C_4$-alkoxy and $C_1$-$C_4$-halogenalkoxy or, for each of the substituents, any preferred meaning as given above, and $R^7$ is unsubstituted or substituted $C_3$-$C_6$-cycloalkyl as defined and preferably defined above.

In still one further particular embodiment, $R^5$ is selected from hydrogen, halogen, CN, $C_1$-$C_6$-alkyl, $C_1$-$C_6$-halogenalkyl, $C_1$-$C_6$-alkoxy, $C_1$-$C_6$-halogenalkoxy and C(=O)—O—($C_1$-$C_6$-alkyl), preferably selected from hydrogen, F, Cl, Br, CN, $C_1$-$C_4$-alkyl, $C_1$-$C_4$-halogenalkyl, $C_1$-$C_4$-alkoxy and $C_1$-$C_4$-halogenalkoxy, $R^6$ is selected from hydrogen, halogen, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy and $C_1$-$C_6$-halogenalkoxy, preferably selected from hydrogen, F, Cl, Br, $C_1$-$C_4$-alkyl, $C_1$-$C_4$-halogenalkyl, $C_1$-$C_4$-alkoxy and $C_1$-$C_4$-halogenalkoxy or, for each of the substituents, any preferred meaning as given above, and $R^7$ is unsubstituted or substituted heterocyclyl as defined and preferably defined above.

According to a further embodiment, $R^5$ together with $R^7$ and the carbon atoms to which they are bound forms a $C_3$-$C_6$-cycloalkenyl, that is unsubstituted at the saturated chain or substituted by $(R^8)_n$; wherein $R^6$ is as defined herein. According to one embodiment thereof, n is 0, 1 or 2. According to a further embodiment thereof, n is 0. According to still a further one embodiment thereof, n is 1 or 2. According to one embodiment thereof, n is 0, 1, 2 or 3. According to a further embodiment thereof, n is 0. According to still a further one embodiment thereof, n is 1 or 2.

According to a specific embodiment thereof, $R^5$ together with $R^7$ and the carbon atoms to which they are bound forms a cyclopropenyl that is unsubstituted (n=0) or substituted by $(R^8)_n$. According to one embodiment thereof, n is 0, 1 or 2. According to a further embodiment thereof, n is 0. According to still a further one embodiment thereof, n is 1 or 2.

According to a further specific embodiment thereof, $R^5$ together with $R^7$ and the carbon atoms to which they are bound forms a cyclobutenyl that is unsubstituted (n=0) or substituted by $(R^8)_n$. According to one embodiment thereof, n is 0, 1 or 2. According to a further embodiment thereof, n is 0. According to still a further one embodiment thereof, n is 1 or 2.

According to a specific embodiment thereof, $R^5$ together with $R^7$ and the carbon atoms to which they are bound forms a cyclopentenyl that is unsubstituted (n=0) or substituted by $(R^8)_n$. According to one embodiment thereof, n is 0, 1 or 2. According to a further embodiment thereof, n is 0. According to still a further one embodiment thereof, n is 1 or 2.

According to a specific embodiment thereof, $R^5$ together with $R^7$ and the carbon atoms to which they are bound forms a cyclohexenyl that is unsubstituted (n=0) or substituted by $(R^8)_n$. According to one embodiment thereof, n is 0, 1 or 2. According to a further embodiment thereof, n is 0. According to still a further one embodiment thereof, n is 1 or 2.

According to a further embodiment, $R^6$ and $R^7$ together with the carbon atoms to which they are bound form a $C_3$-$C_6$-cycloalkyl, that is unsubstituted or substituted by $(R^8)_n$, as defined and preferably defined herein, and $R^5$ is selected from hydrogen, halogen, CN, $C_1$-$C_6$-alkyl, $C_1$-$C_6$-halogenalkyl, $C_1$-$C_6$-alkoxy, $C_1$-$C_6$-halogenalkoxy and C(=O)—O—($C_1$-$C_6$-alkyl) or any preferred meaning as given herein. According to one embodiment thereof, n is 0, 1 or 2. According to a further embodiment thereof, n is 0. According to still a further one embodiment thereof, n is 1 or 2.

According to a specific embodiment thereof, $R^6$ together with $R^7$ and the carbon atoms to which they are bound forms a cyclopropyl that is unsubstituted (n=0) or substituted by $(R^8)_n$. According to one embodiment thereof, n is 0, 1 or 2. According to a further embodiment thereof, n is 0. According to still a further one embodiment thereof, n is 1 or 2.

According to a further specific embodiment thereof, $R^6$ together with $R^7$ and the carbon atoms to which they are bound forms a cyclobutyl that is unsubstituted (n=0) or substituted by $(R^8)_n$. According to one embodiment thereof, n is 0, 1 or 2. According to a further embodiment thereof, n is 0. According to still a further one embodiment thereof, n is 1 or 2.

According to a specific embodiment thereof, $R^6$ together with $R^7$ and the carbon atoms to which they are bound forms a cyclopentyl that is unsubstituted (n=0) or substituted by $(R^8)_n$. According to one embodiment thereof, n is 0, 1 or 2. According to a further embodiment thereof, n is 0. According to still a further one embodiment thereof, n is 1 or 2.

According to a specific embodiment thereof, $R^6$ together with $R^7$ and the carbon atoms to which they are bound forms a cyclohexyl that is unsubstituted (n=0) or substituted by $(R^8)_n$. According to one embodiment thereof, n is 0, 1 or 2. According to a further embodiment thereof, n is 0. According to still a further one embodiment thereof, n is 1 or 2.

According to the invention, there can be zero, one, two, three, four or five $R^4$ present, namely for m is 0, 1, 2, 3, 4 or 5. In particular, m is 0, 1, 2 or 3. According to one embodiment, m is 0, 1 or 2.

According to one particular embodiment, m is 0.

According to a further embodiment, m is 1, 2 or 3, in particular 1 or 2, more specifically 1. According to one specific embodiment thereof, m is 1, according to a further specific embodiment, m is 2.

According to still a further embodiment, m is 2, 3 or 4.

According to still a further embodiment, m is 3.

For every $R^4$ that is present in the inventive compounds, the following embodiments and preferences apply independently of the meaning of any other $R^4$ that may be present in the phenyl ring. Furthermore, the particular embodiments and preferences given herein for $R^4$ apply independently for each of m=1, m=2, m=3, m=4 and m=5.

Each $R^4$ is independently selected from halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl and $C_3$-$C_6$-cycloalkyl, wherein each of $R^4$ is unsubstituted or further substituted by one, two, three or four $R^{4a}$ wherein $R^{4a}$ is independently selected from halogen.

According to one embodiment, $R^4$ is independently selected from halogen, CN, $NO_2$, $C_1$-$C_4$-alkyl, $C_1$-$C_4$-alkoxy, $C_2$-$C_4$-alkenyl, $C_2$-$C_4$-alkynyl and $C_3$-$C_6$-cycloalkyl, wherein each of $R^4$ is unsubstituted or further substituted by one, two, three or four independently selected halogen $(R^{4a})$.

According to a further embodiment, $R^4$ is independently selected from halogen, CN, $NO_2$, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl and $C_3$-$C_6$-halocycloalkyl.

According to a further embodiment, $R^4$ is independently selected from halogen, CN, $NO_2$, $C_1$-$C_2$-alkyl, $C_1$-$C_2$-haloalkyl, $C_1$-$C_2$-alkoxy and $C_1$-$C_2$-haloalkoxy According to a further embodiment, $R^4$ is independently selected from F, Cl, Br, CN, $C_1$-$C_4$-alkyl, $C_1$-$C_4$-haloalkyl, $C_1$-$C_4$-alkoxy and $C_1$-$C_4$-haloalkoxy.

According to a further embodiment, $R^4$ is independently selected from F, Cl, Br, CN, methyl, $C_1$-haloalkyl, methoxy and $C_1$-haloalkoxy, more specifically selected from F, Cl, CN and methyl.

According to still a further specific embodiment, $R^4$ is independently selected from halogen, in particular from Br, F and Cl, more specifically from F and Cl.

According to a further specific embodiment, $R^4$ is CN.

According to a further specific embodiment, $R^4$ is $C_1$-$C_4$-alkyl, such as $CH_3$. Further appropriate alkyls are ethyl, n-propyl, i-propyl, n-butyl, i-butyl and t-butyl.

According to a further specific embodiment, $R^4$ is $C_1$-$C_4$-haloalkyl, such as $CF_3$, $CHF_2$, $CH_2F$, $CCl_3$, $CHCl_2$ or $CH_2Cl$.

According to a further specific embodiment $R^4$ is $C_1$-$C_4$-alkoxy, more specifically $C_1$-$C_2$-alkoxy such as $OCH_3$ or $OCH_2CH_3$.

According to a further specific embodiment, $R^4$ is $C_1$-$C_4$-haloalkoxy, more specifically $C_1$-$C_2$-haloalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to still a further embodiment, $R^4$ is $C_2$-$C_6$-alkenyl or $C_2$-$C_6$-haloalkenyl, in particular $C_2$-$C_4$-alkenyl or $C_2$-$C_4$-haloalkenyl, such as CH=$CH_2$, $CH_2$CH=$CH_2$, CH=$CHCH_3$ or $C(CH_3)$=$CH_2$.

According to still a further embodiment, $R^4$ is $C_2$-$C_6$-alkynyl or $C_2$-$C_6$-haloalkynyl, in particular $C_2$-$C_4$-alkynyl or $C_2$-$C_4$-haloalkynyl, such as C≡CH, $CH_2$CCH or $CH_2$CC$CH_3$.

According to another embodiment $R^4$ is $C_3$-$C_6$-cycloalkyl, preferably cyclopropyl, cyclobutyl, cyclopentyl or cyclohexyl, in particular cyclopropyl or cyclobutyl. In a special embodiment $R^4$ is cyclopropyl. In a further special embodiment $R^4$ is cyclobutyl. In a further special embodiment $R^4$ is cyclopentyl. In a further special embodiment $R^4$ is cyclohexyl.

According to a specific embodiment $R^4$ is fully or partially halogenated $C_3$-$C_6$-cycloalkyl. In a special embodiment $R^4$ is fully or partially halogenated cyclopropyl. In a further special embodiment $R^4$ is 1-Cl-cyclopropyl. In a further special embodiment $R^4$ is 2-Cl-cyclopropyl. In a further special embodiment $R^4$ is 1-F-cyclopropyl. In a further special embodiment $R^4$ is 2-F-cyclopropyl. In a further special embodiment $R^4$ is fully or partially halogenated cyclobutyl. In a further special embodiment $R^4$ is 1-Cl-cyclobutyl. In a further special embodiment $R^4$ is 1-F-cyclobutyl. In a further special embodiment $R^4$ is 3,3-$Cl_2$-cyclobutyl. In a further special embodiment $R^4$ is 3,3-$F_2$-cyclobutyl.

$R^{4a}$ is halogen, in particular independently selected from F, Cl and Br.

According to the invention, there can be zero, one, two, three, four or five $R^8$ present, namely for n is 0, 1, 2, 3, 4 or 5. In particular, n is 0, 1, 2 or 3. According to one embodiment, n is 0, 1 or 2.

According to one particular embodiment, n is 0.

According to a further embodiment, n is 1, 2 or 3, in particular 1 or 2, more specifically 1. According to one specific embodiment thereof, n is 1, according to a further specific embodiment, n is 2.

According to still a further embodiment, n is 2, 3 or 4.

According to still a further embodiment, n is 3.

For every $R^8$ that is present in the inventive compounds, the following embodiments and preferences apply independently of the meaning of any other $R^8$ that may be present in the phenyl ring. Furthermore, the particular embodiments and preferences given herein for $R^8$ apply independently for each of n=1, n=2, m=3, n=4 and n=5.

$R^8$ is in each case independently selected from the substituents and preferred substituents as defined for $R^4$; wherein each of $R^8$ is unsubstituted or further substituted by one, two, three or four $R^{8a}$ that is in each case independently selected from the substituents and preferred substituents as defined for $R^{4a}$.

One embodiment relates to compounds I, wherein A is N (I.A), in particular compounds I.Aa and I.Ab, depending on the position of $R^6$ and $R^7$, respectively:

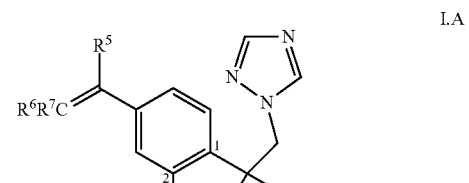

I.A

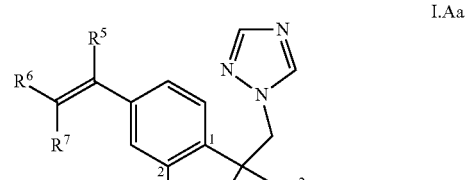

I.Aa

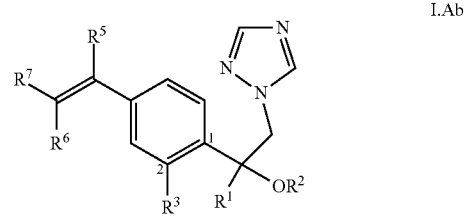

I.Ab

One specific embodiment is compounds I.A1, wherein A=N and $R^5$ is hydrogen, namely I.A1a and I.A1b, depending on the position of $R^6$ and $R^7$:

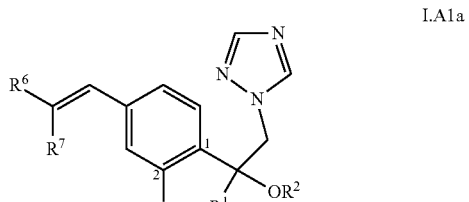

I.A1a

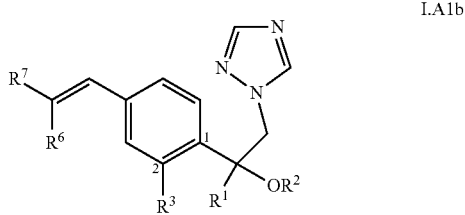

I.A1b

A further specific embodiment is compounds I.A1a, wherein $R^7$ is unsubstituted or substituted cycloalkyl, in particular compounds I.A1a-1, wherein $R^7$ is cyclopropyl, that is unsubstituted or substituted by $(R^4)_m$. Still a further specific embodiment is compounds I.A1b, wherein $R^7$ is unsubstituted or substituted cycloalkyl, in particular compounds I.A1b-1, wherein $R^7$ is cyclopropyl, that is unsubstituted or substituted by $(R^4)_m$:

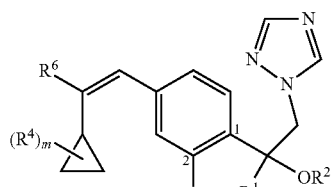

I.A1a-1

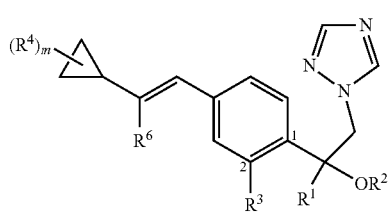

I.A1b-1

A further specific embodiment is compounds I.A1a, wherein $R^7$ is unsubstituted or substituted saturated or partially unsaturated three-, four-, five-, six- or seven-membered heterocyclyl, wherein the heterocyclyl contains 1, 2, 3 or 4 heteroatoms selected from O, N and S, in particular $R^7$ is unsubstituted or substituted saturated three-, four-, five-, six- or seven-membered heterocyclyl, wherein the heterocyclyl contains 1, 2 or 3 heteroatoms selected from O, N and S, specifically compounds I.A1a-2, wherein $R^7$ is 3-oxetanyl, that is unsubstituted or substituted by $(R^4)_m$. Still a further specific embodiment is compounds I.A1b, wherein $R^7$ is unsubstituted or substituted saturated or partially unsaturated three-, four-, five-, six- or seven-membered heterocyclyl, wherein the heterocyclyl contains 1, 2, 3 or 4 heteroatoms selected from O, N and S, in particular $R^7$ is unsubstituted or substituted saturated three-, four-, five-, six- or seven-membered heterocyclyl, wherein the heterocyclyl contains 1, 2 or 3 heteroatoms selected from O, N and S, specifically, compounds I.A1a-2, wherein $R^7$ is 3-oxetanyl, that is unsubstituted or substituted by $(R^4)_m$:

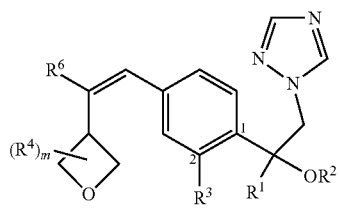

I.A1a-2

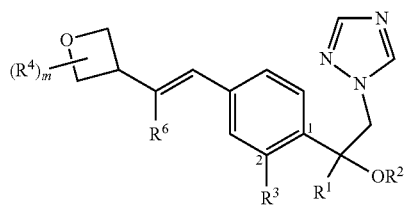

I.A1b-2

A further embodiment is compounds I.A2, wherein A=N and $R^5$ is unsubstituted or substituted cycloalkyl, in particular compounds I.A2-1, wherein $R^5$ is cyclopropyl, that is unsubstituted or substituted by $(R^4)_m$. A further specific embodiment thereof is compounds I.A2-1a, wherein $R^6$ and $R^7$ are hydrogen:

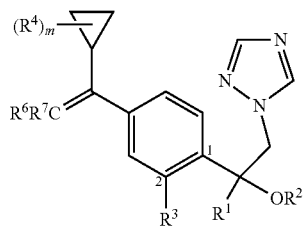

I.A2-1

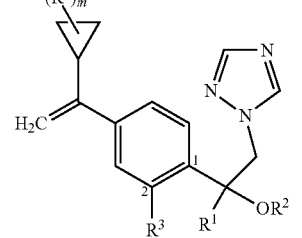

I.A2-1a

A further embodiment is compounds I.A3, wherein $R^5$ is unsubstituted or substituted saturated or partially unsaturated three-, four-, five-, six- or seven-membered heterocyclyl, wherein the heterocyclyl contains 1, 2, 3 or 4 heteroatoms selected from O, N and S, in particular $R^7$ is unsubstituted or substituted saturated three-, four-, five-, six- or seven-membered heterocyclyl, wherein the heterocyclyl contains 1, 2 or 3 heteroatoms selected from O, N and S. Specifically, one embodiment relates to compounds I.A3-1, wherein $R^5$ is 3-oxetanyl, that is unsubstituted or substituted by $(R^4)_m$. A specific embodiment thereof is compounds I.A3-1a, wherein $R^6$ and $R^7$ are hydrogen:

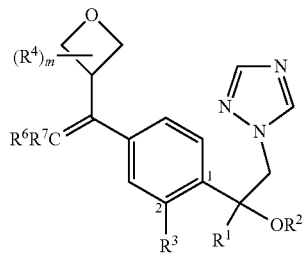

I.A3-1

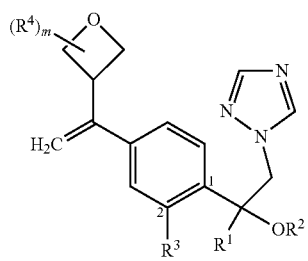

I.A3-1a

A further embodiment is compounds I.A4, wherein A=N and $R^6$ is hydrogen, namely I.A4a and I.A4b, depending on the position of $R^6$ and $R^7$. A specific embodiment thereof are compounds I.A4-1, wherein A=N and $R^7$ is also hydrogen:

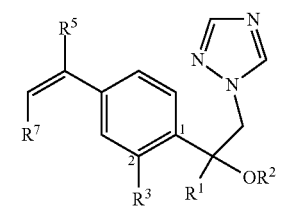

I.A4a

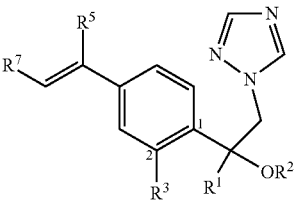

I.A4b

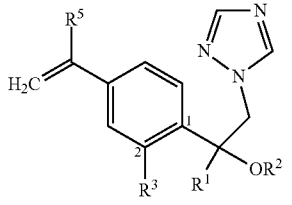

I.A4-1

A further specific embodiment of the invention are compounds I.A5, wherein A=N and $R^7$ is unsubstituted or substituted cycloalkyl, in particular compounds I.A5-1a and I.A5-1b, wherein $R^5$ is cyclopropyl, that is unsubstituted or substituted by $(R^4)_m$, depending on the position of the cyclopropyl. One particular embodiment thereof is compounds I.A5-1aa and I.A5-1ba, where $R^6$ is hydrogen:

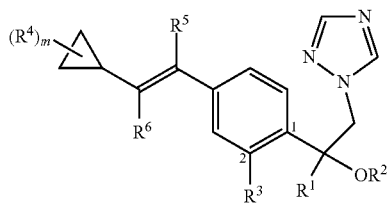

I.A5-1a

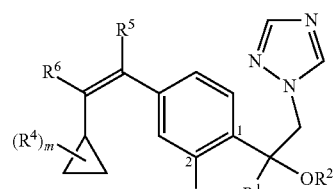

I.A5-1b

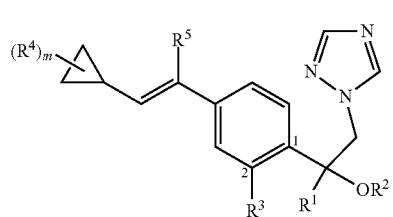

I.A5-1aa

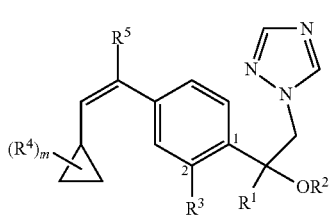

I.A5-1ba

A further specific embodiment of the invention are compounds I.A6, wherein A=N and $R^7$ is unsubstituted or substituted saturated or partially unsaturated three-, four-, five-, six- or seven-membered heterocyclyl, wherein the heterocyclyl contains 1, 2, 3 or 4 heteroatoms selected from O, N and S, in particular $R^7$ is unsubstituted or substituted saturated three-, four-, five-, six- or seven-membered heterocyclyl, wherein the heterocyclyl contains 1, 2 or 3 heteroatoms selected from O, N and S. Specifically, one embodiment relates to compounds I.A6-1a and I.A6-1b, wherein $R^5$ is 3-oxetanyl, that is unsubstituted or substituted by $(R^4)_m$. One particular embodiment thereof is compounds I.A6-1aa and I.A6-1ba, where $R^6$ is hydrogen

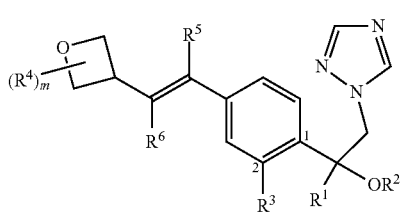

I.A6-1a

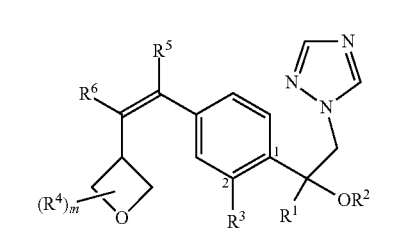

I.A6-1b

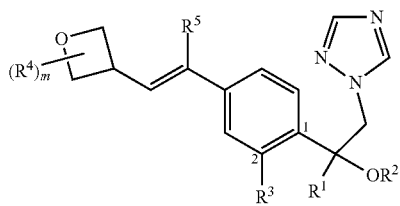
I.A6-1aa

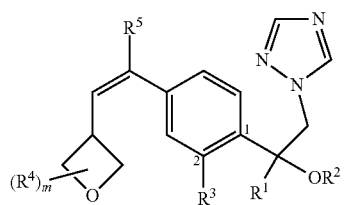
I.A6-1ba

Still a further specific embodiment is compounds I.A7, wherein $R^5$ and $R^6$ are hydrogen, namely compounds I.A7a and I.A7b, depending on the position of $R^7$:

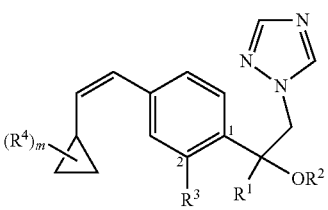
I.A7a

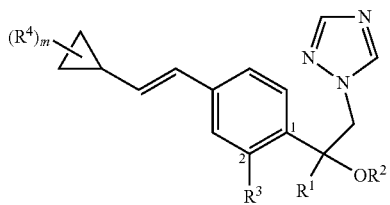
I.A7b

In a specific embodiment thereof, $R^7$ is unsubstituted or substituted cycloalkyl, in particular compounds I.A7a-1 and I.A7b-1, wherein $R^7$ is cyclopropyl, that is unsubstituted or substituted by $(R^4)_m$:

I.A7a-1

I.A7b-1

In a further specific embodiment thereof, $R^7$ is unsubstituted or substituted saturated or partially unsaturated three-, four-, five-, six- or seven-membered heterocyclyl, wherein the heterocyclyl contains 1, 2, 3 or 4 heteroatoms selected from O, N and S, in particular $R^7$ is unsubstituted or substituted saturated three-, four-, five-, six- or seven-membered heterocyclyl, wherein the heterocyclyl contains 1, 2 or 3 heteroatoms selected from O, N and S. Specifically, compounds I.A7a-2 and I.A7b-2, wherein $R^7$ is 3-oxetanyl, that is unsubstituted or substituted by $(R^4)_m$:

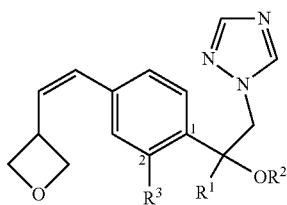
I.A7a-1

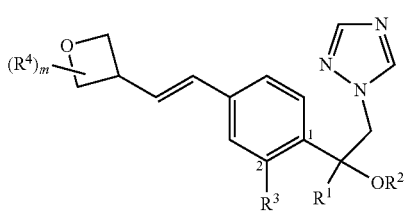
I.A7b-2

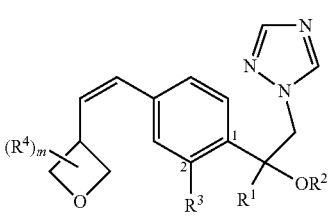
I.A7a-2

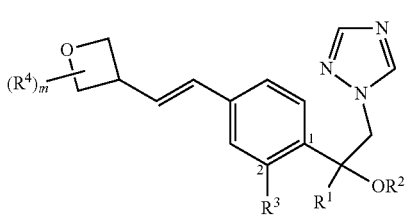
I.A7b-2

Still a further embodiment is compounds I.A8, where $R^5$ and $R^7$ together with the carbon atoms to which they are bound form a $C_3$-$C_6$-cycloloalkenyl, that is unsubstituted at the saturated chain or substituted by $(R^8)_n$; and $R^6$ is as defined and preferably defined herein. In one particular embodiment thereof, $R^5$ and $R^7$ together with the carbon atoms to which they are bound form a $C_5$-cycloalkenyl, that is unsubstituted at the saturated chain or substituted by $(R^8)_n$, namely compounds I.A8-1. In one further particular embodiment thereof, $R^5$ and $R^7$ together with the carbon atoms to which they are bound form a $C_6$-cycloalkenyl, that is unsubstituted at the saturated chain or substituted by $(R^8)_n$, namely compounds I.A8-2:

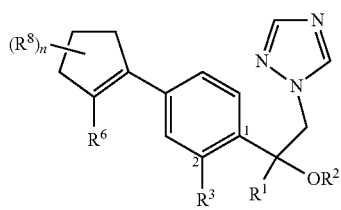

I.A8-1

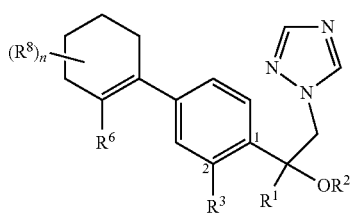

I.A8-2

Still a further embodiment is compounds I.A9, where $R^6$ and $R^7$ together with the carbon atoms to which they are bound form a $C_3$-$C_6$-cycloalkyl, that is unsubstituted or substituted by $(R^8)_n$; and $R^5$ is selected from hydrogen, halogen, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy, $C_1$-$C_6$-halogenalkoxy and $C(=O)$—O—$(C_1$-$C_6$-alkyl). In one particular embodiment thereof, $R^6$ and $R^7$ together with the carbon atoms to which they are bound form a $C_4$-cycloalkyl, that is unsubstituted or substituted by $(R^8)_n$, namely compounds I.A9-1. In one further particular embodiment thereof, $R^6$ and $R^7$ together with the carbon atoms to which they are bound form a $C_5$-cycloalkyl, that is unsubstituted or substituted by $(R^8)_n$, namely compounds I.A9-2:

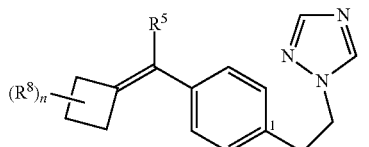

I.A9-1

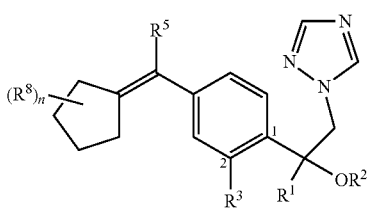

I.A9-2

A further embodiment relates to compounds I.A10, where $R^7$ is $C_2$-$C_6$-alkyne, that is not further substituted or carries one, two, three, four, five or up to the maximum number of identical or different groups $R^{7a}$ which independently of one another are selected from halogen, $C_1$-$C_4$-alkyl and $C_1$-$C_4$-halogenalkyl. In a specific embodiment, $R^7$ is $C_2$-alkyne, that may be substituted by $R^{7a}$, in particular selected from halogen, $C_1$-$C_2$-akyl and $C_1$-$C_2$-halogenalky, namely compounds I.A10-1a and I.A10-1b, depending on the position of $R^7$:

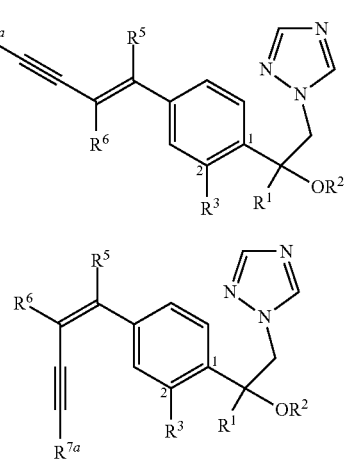

I.A10-1a

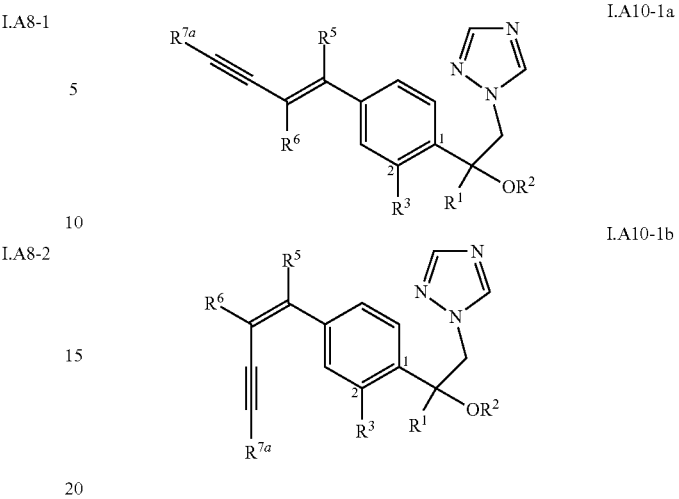

I.A10-1b

Particular embodiments are compounds I.A10-1a and I.A10-1b, respectively, wherein $R^6$ is hydrogen, namely compounds I.A10-1aa and I.A10-1ba:

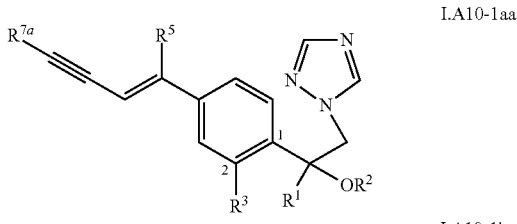

I.A10-1aa

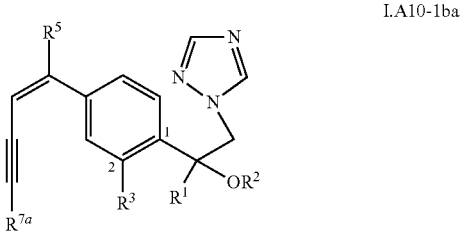

I.A10-1ba

Even more particularly, the triple bond is not substituted in compounds I.A10-1a and I.A10-1b, being compounds I.A11-1 and I.A11-2:

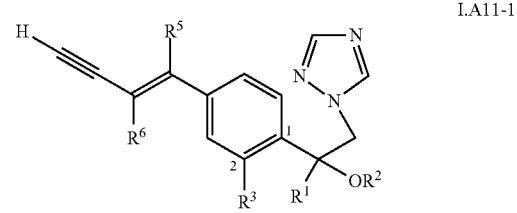

I.A11-1

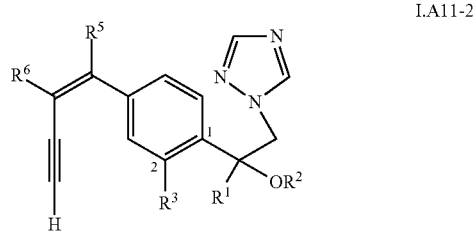

I.A11-2

Particular embodiments are compounds I.A11-1 and I.A11-2, respectively, wherein $R^6$ is hydrogen, namely compounds I.A11-1a and I.A11-2a:

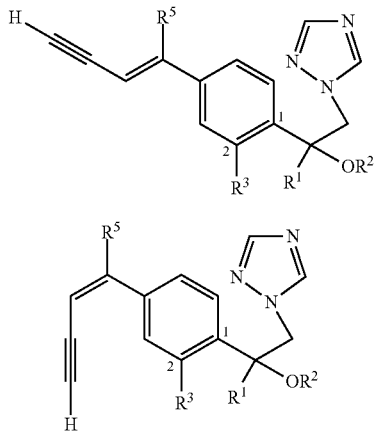

A further embodiment relates to compounds I, wherein A is CH (I.B), including the respective embodiments as detailed above for the triazoles.

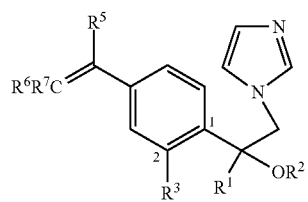

In particular with a view to their use, according to one embodiment, preference is given to the compounds of the formula I that are compiled in the Tables 1a to 49a, Tables 1b to 42b, Tables 1c to 42c, Tables 1d to 63d, Tables 1e to 28e, Tables 1f to 28f, Tables 1g to 56g, Tables 1h to 112h, Tables 1i to 112i, Tables 1j to 90j, Tables 1k to 90k, Tables 1l to 28l, Tables 1m to 18m, Tables 1ma to 18ma, Tables 1n to 7n, Tables 1o to 7o, Tables 1p to 21p and Tables 1q to 21q below. Each of the groups mentioned for a substituent in the tables is furthermore per se, independently of the combination in which it is mentioned, a particularly preferred aspect of the substituent in question.

Table 1a Compounds of the formula I.A7a in which the combination of $R^3$ and $R^7$ corresponds to line D1-1 of Table D1 and the meaning for the combination of $R^1$ and $R^2$ for each individual compound corresponds in each case to one line of Table B (compounds I.A7a.D1-1.B1 to I.A7a.D1-1.B550).

Table 2a Compounds of the formula I.A7a in which the combination of $R^3$ and $R^7$ corresponds to line D1-2 of Table D1 and the meaning for the combination of $R^1$ and $R^2$ for each individual compound corresponds in each case to one line of Table B (compounds I.A7a.D1-2.B1 to I.A7a.D1-2.B550).

Table 3a Compounds of the formula I.A7a in which the combination of $R^3$ and $R^7$ corresponds to line D1-3 of Table D1 and the meaning for the combination of $R^1$ and $R^2$ for each individual compound corresponds in each case to one line of Table B (compounds I.A7a.D1-3.B1 to I.A7a.D1-3.B550).

Table 4a Compounds of the formula I.A7a in which the combination of $R^3$ and $R^7$ corresponds to line D1-4 of Table D1 and the meaning for the combination of $R^1$ and $R^2$ for each individual compound corresponds in each case to one line of Table B (compounds I.A7a.D1-4.B1 to I.A7a.D1-4.B550).

Table 5a Compounds of the formula I.A7a in which the combination of $R^3$ and $R^7$ corresponds to line D1-5 of Table D1 and the meaning for the combination of $R^1$ and $R^2$ for each individual compound corresponds in each case to one line of Table B (compounds I.A7a.D1-5.B1 to I.A7a.D1-5.B550).

Table 6a Compounds of the formula I.A7a in which the combination of $R^3$ and $R^7$ corresponds to line D1-6 of Table D1 and the meaning for the combination of $R^1$ and $R^2$ for each individual compound corresponds in each case to one line of Table B (compounds I.A7a.D1-6.B1 to I.A7a.D1-6.B550).

Table 7a Compounds of the formula I.A7a in which the combination of $R^3$ and $R^7$ corresponds to line D1-7 of Table D1 and the meaning for the combination of $R^1$ and $R^2$ for each individual compound corresponds in each case to one line of Table B (compounds I.A7a.D1-7.B1 to I.A7a.D1-7.B550).

Table 8a Compounds of the formula I.A7a in which the combination of $R^3$ and $R^7$ corresponds to line D1-8 of Table D1 and the meaning for the combination of $R^1$ and $R^2$ for each individual compound corresponds in each case to one line of Table B (compounds I.A7a.D1-8.B1 to I.A7a.D1-8.B550).

Table 9a Compounds of the formula I.A7a in which the combination of $R^3$ and $R^7$ corresponds to line D1-9 of Table D1 and the meaning for the combination of $R^1$ and $R^2$ for each individual compound corresponds in each case to one line of Table B (compounds I.A7a.D1-9.B1 to I.A7a.D1-9.B550).

Table 10a Compounds of the formula I.A7a in which the combination of $R^3$ and $R^7$ corresponds to line D1-10 of Table D1 and the meaning for the combination of $R^1$ and $R^2$ for each individual compound corresponds in each case to one line of Table B (compounds I.A7a.D1-10.B1 to I.A7a.D1-10.B550).

Table 11a Compounds of the formula I.A7a in which the combination of $R^3$ and $R^7$ corresponds to line D1-11 of Table D1 and the meaning for the combination of $R^1$ and $R^2$ for each individual compound corresponds in each case to one line of Table B (compounds I.A7a.D1-11.B1 to I.A7a.D1-11.B550).

Table 12a Compounds of the formula I.A7a in which the combination of $R^3$ and $R^7$ corresponds to line D1-12 of Table D1 and the meaning for the combination of $R^1$ and $R^2$ for each individual compound corresponds in each case to one line of Table B (compounds I.A7a.D1-12.B1 to I.A7a.D1-12.B550).

Table 13a Compounds of the formula I.A7a in which the combination of $R^3$ and $R^7$ corresponds to line D1-13 of Table D1 and the meaning for the combination of $R^1$ and $R^2$ for each individual compound corresponds in each case to one line of Table B (compounds I.A7a.D1-13.B1 to I.A7a.D1-13.B550).

Table 14a Compounds of the formula I.A7a in which the combination of $R^3$ and $R^7$ corresponds to line D1-14 of Table D1 and the meaning for the combination of $R^1$ and $R^2$ for each individual compound corresponds in each case to one line of Table B (compounds I.A7a.D1-14.B1 to I.A7a.D1-14.B550).

Table 15a Compounds of the formula I.A7a in which the combination of $R^3$ and $R^7$ corresponds to line D1-15 of Table D1 and the meaning for the combination of $R^1$ and $R^2$ for each individual compound corresponds in each case to one line of Table B (compounds I.A7a.D1-15.B1 to I.A7a.D1-15.B550).

Table 16a Compounds of the formula I.A7a in which the combination of $R^3$ and $R^7$ corresponds to line D1-16 of Table D1 and the meaning for the combination of $R^1$ and $R^2$ for each individual compound corresponds in each case to one line of Table B (compounds I.A7a.D1-16.B1 to I.A7a.D1-16.B550).

Table 17a Compounds of the formula I.A7a in which the combination of $R^3$ and $R^7$ corresponds to line D1-17 of Table D1 and the meaning for the combination of $R^1$ and $R^2$ for each individual compound corresponds in each case to one line of Table B (compounds I.A7a.D1-17.B1 to I.A7a.D1-17.B550).

Table 18a Compounds of the formula I.A7a in which the combination of $R^3$ and $R^7$ corresponds to line D1-18 of Table D1 and the meaning for the combination of $R^1$ and $R^2$ for each individual compound corresponds in each case to one line of Table B (compounds I.A7a.D1-18.B1 to I.A7a.D1-18.B550).

Table 19a Compounds of the formula I.A7a in which the combination of $R^3$ and $R^7$ corresponds to line D1-19 of Table D1 and the meaning for the combination of $R^1$ and $R^2$ for each individual compound corresponds in each case to one line of Table B (compounds I.A7a.D1-19.B1 to I.A7a.D1-19.B550).

Table 20a Compounds of the formula I.A7a in which the combination of $R^3$ and $R^7$ corresponds to line D1-20 of Table D1 and the meaning for the combination of $R^1$ and $R^2$ for each individual compound corresponds in each case to one line of Table B (compounds I.A7a.D1-20.B1 to I.A7a.D1-20.B550).

Table 21a Compounds of the formula I.A7a in which the combination of $R^3$ and $R^7$ corresponds to line D1-21 of Table D1 and the meaning for the combination of $R^1$ and $R^2$ for each individual compound corresponds in each case to one line of Table B (compounds I.A7a.D1-21.B1 to I.A7a.D1-21.B550).

Table 22a Compounds of the formula I.A7a in which the combination of $R^3$ and $R^7$ corresponds to line D1-22 of Table D1 and the meaning for the combination of $R^1$ and $R^2$ for each individual compound corresponds in each case to one line of Table B (compounds I.A7a.D1-22.B1 to I.A7a.D1-22.B550).

Table 23a Compounds of the formula I.A7a in which the combination of $R^3$ and $R^7$ corresponds to line D1-23 of Table D1 and the meaning for the combination of $R^1$ and $R^2$ for each individual compound corresponds in each case to one line of Table B (compounds I.A7a.D1-23.B1 to I.A7a.D1-23.B550).

Table 24a Compounds of the formula I.A7a in which the combination of $R^3$ and $R^7$ corresponds to line D1-24 of Table D1 and the meaning for the combination of $R^1$ and $R^2$ for each individual compound corresponds in each case to one line of Table B (compounds I.A7a.D1-24.B1 to I.A7a.D1-24.B550).

Table 25a Compounds of the formula I.A7a in which the combination of $R^3$ and $R^7$ corresponds to line D1-25 of Table D1 and the meaning for the combination of $R^1$ and $R^2$ for each individual compound corresponds in each case to one line of Table B (compounds I.A7a.D1-25.B1 to I.A7a.D1-25.B550).

Table 26a Compounds of the formula I.A7a in which the combination of $R^3$ and $R^7$ corresponds to line D1-26 of Table D1 and the meaning for the combination of $R^1$ and $R^2$ for each individual compound corresponds in each case to one line of Table B (compounds I.A7a.D1-26.B1 to I.A7a.D1-26.B550).

Table 27a Compounds of the formula I.A7a in which the combination of $R^3$ and $R^7$ corresponds to line D1-27 of Table D1 and the meaning for the combination of $R^1$ and $R^2$ for each individual compound corresponds in each case to one line of Table B (compounds I.A7a.D1-27.B1 to I.A7a.D1-27.B550).

Table 28a Compounds of the formula I.A7a in which the combination of $R^3$ and $R^7$ corresponds to line D1-28 of Table D1 and the meaning for the combination of $R^1$ and $R^2$ for each individual compound corresponds in each case to one line of Table B (compounds I.A7a.D1-28.B1 to I.A7a.D1-28.B550).

Table 29a Compounds of the formula I.A7a in which the combination of $R^3$ and $R^7$ corresponds to line D1-29 of Table D1 and the meaning for the combination of $R^1$ and $R^2$ for each individual compound corresponds in each case to one line of Table B (compounds I.A7a.D1-29.B1 to I.A7a.D1-29.B550).

Table 30a Compounds of the formula I.A7a in which the combination of $R^3$ and $R^7$ corresponds to line D1-30 of Table D1 and the meaning for the combination of $R^1$ and $R^2$ for each individual compound corresponds in each case to one line of Table B (compounds I.A7a.D1-30.B1 to I.A7a.D1-30.B550).

Table 31a Compounds of the formula I.A7a in which the combination of $R^3$ and $R^7$ corresponds to line D1-31 of Table D1 and the meaning for the combination of $R^1$ and $R^2$ for each individual compound corresponds in each case to one line of Table B (compounds I.A7a.D1-31.B1 to I.A7a.D1-31.B550).

Table 32a Compounds of the formula I.A7a in which the combination of $R^3$ and $R^7$ corresponds to line D1-32 of Table D1 and the meaning for the combination of $R^1$ and $R^2$ for each individual compound corresponds in each case to one line of Table B (compounds I.A7a.D1-32.B1 to I.A7a.D1-32.B550).

Table 33a Compounds of the formula I.A7a in which the combination of $R^3$ and $R^7$ corresponds to line D1-33 of Table D1 and the meaning for the combination of $R^1$ and $R^2$ for each individual compound corresponds in each case to one line of Table B (compounds I.A7a.D1-33.B1 to I.A7a.D1-33.B550).

Table 34a Compounds of the formula I.A7a in which the combination of $R^3$ and $R^7$ corresponds to line D1-34 of Table D1 and the meaning for the combination of $R^1$ and $R^2$ for each individual compound corresponds in each case to one line of Table B (compounds I.A7a.D1-34.B1 to I.A7a.D1-34.B550).

Table 35a Compounds of the formula I.A7a in which the combination of $R^3$ and $R^7$ corresponds to line D1-35 of Table D1 and the meaning for the combination of $R^1$ and $R^2$ for each individual compound corresponds in each case to one line of Table B (compounds I.A7a.D1-35.B1 to I.A7a.D1-35.B550).

Table 36a Compounds of the formula I.A7a in which the combination of $R^3$ and $R^7$ corresponds to line D1-36 of Table D1 and the meaning for the combination of $R^1$ and $R^2$ for each individual compound corresponds in each case to one line of Table B (compounds I.A7a.D1-36.B1 to I.A7a.D1-36.B550).

Table 37a Compounds of the formula I.A7a in which the combination of $R^3$ and $R^7$ corresponds to line D1-37 of Table D1 and the meaning for the combination of $R^1$ and $R^2$ for each individual compound corresponds in each case to one line of Table B (compounds I.A7a.D1-37.B1 to I.A7a.D1-37.B550).

Table 38a Compounds of the formula I.A7a in which the combination of $R^3$ and $R^7$ corresponds to line D1-38 of Table D1 and the meaning for the combination of $R^1$ and $R^2$ for each individual compound corresponds in each case to one line of Table B (compounds I.A7a.D1-38.B1 to I.A7a.D1-38.B550).

Table 39a Compounds of the formula I.A7a in which the combination of $R^3$ and $R^7$ corresponds to line D1-39 of Table D1 and the meaning for the combination of $R^1$ and $R^2$ for each individual compound corresponds in each case to one line of Table B (compounds I.A7a.D1-39.B1 to I.A7a.D1-39.B550).

Table 40a Compounds of the formula I.A7a in which the combination of $R^3$ and $R^7$ corresponds to line D1-40 of Table D1 and the meaning for the combination of $R^1$ and $R^2$ for each individual compound corresponds in each case to one line of Table B (compounds I.A7a.D1-40.B1 to I.A7a.D1-40.B550).

Table 41a Compounds of the formula I.A7a in which the combination of $R^3$ and $R^7$ corresponds to line D1-41 of Table D1 and the meaning for the combination of $R^1$ and $R^2$ for each individual compound corresponds in each case to one line of Table B (compounds I.A7a.D1-41.B1 to I.A7a.D1-41.B550).

Table 42a Compounds of the formula I.A7a in which the combination of $R^3$ and $R^7$ corresponds to line D1-42 of Table D1 and the meaning for the combination of $R^1$ and $R^2$ for each individual compound corresponds in each case to one line of Table B (compounds I.A7a.D1-42.B1 to I.A7a.D1-42.B550).

Table 43a Compounds of the formula I.A7a in which the combination of $R^3$ and $R^7$ corresponds to line D1-43 of Table D1 and the meaning for the combination of $R^1$ and $R^2$ for each individual compound corresponds in each case to one line of Table B (compounds I.A7a.D1-43.B1 to I.A7a.D1-43.B550).

Table 44a Compounds of the formula I.A7a in which the combination of $R^3$ and $R^7$ corresponds to line D1-44 of Table D1 and the meaning for the combination of $R^1$ and $R^2$ for each individual compound corresponds in each case to one line of Table B (compounds I.A7a.D1-44.B1 to I.A7a.D1-44.B550).

Table 45a Compounds of the formula I.A7a in which the combination of $R^3$ and $R^7$ corresponds to line D1-45 of Table D1 and the meaning for the combination of $R^1$ and $R^2$ for each individual compound corresponds in each case to one line of Table B (compounds I.A7a.D1-45.B1 to I.A7a.D1-45.B550).

Table 46a Compounds of the formula I.A7a in which the combination of $R^3$ and $R^7$ corresponds to line D1-46 of Table D1 and the meaning for the combination of $R^1$ and $R^2$ for each individual compound corresponds in each case to one line of Table B (compounds I.A7a.D1-46.B1 to I.A7a.D1-46.B550).

Table 47a Compounds of the formula I.A7a in which the combination of $R^3$ and $R^7$ corresponds to line D1-47 of Table D1 and the meaning for the combination of $R^1$ and $R^2$ for each individual compound corresponds in each case to one line of Table B (compounds I.A7a.D1-47.B1 to I.A7a.D1-47.B550).

Table 48a Compounds of the formula I.A7a in which the combination of $R^3$ and $R^7$ corresponds to line D1-48 of Table D1 and the meaning for the combination of $R^1$ and $R^2$ for each individual compound corresponds in each case to one line of Table B (compounds I.A7a.D1-48.B1 to I.A7a.D1-48.B550).

Table 49a Compounds of the formula I.A7a in which the combination of $R^3$ and $R^7$ corresponds to line D1-49 of Table D1 and the meaning for the combination of $R^1$ and $R^2$ for each individual compound corresponds in each case to one line of Table B (compounds I.A7a.D1-49.B1 to I.A7a.D1-49.B550).

Table 1b Compounds of the formula I.A7b in which the combination of $R^3$ and $R^7$ corresponds to line D1-8 of Table D1 and the meaning for the combination of $R^1$ and $R^2$ for each individual compound corresponds in each case to one line of Table B (compounds I.A7b.D1-8.B1 to I.A7b.D1-8.B550).

Table 2b Compounds of the formula I.A7b in which the combination of $R^3$ and $R^7$ corresponds to line D1-9 of Table D1 and the meaning for the combination of $R^1$ and $R^2$ for each individual compound corresponds in each case to one line of Table B (compounds I.A7b.D1-9.B1 to I.A7b.D1-9.B550).

Table 3b Compounds of the formula I.A7b in which the combination of $R^3$ and $R^7$ corresponds to line D1-10 of Table D1 and the meaning for the combination of $R^1$ and $R^2$ for each individual compound corresponds in each case to one line of Table B (compounds I.A7b.D1-10.B1 to I.A7b.D1-10.B550).

Table 4b Compounds of the formula I.A7b in which the combination of $R^3$ and $R^7$ corresponds to line D1-11 of Table D1 and the meaning for the combination of $R^1$ and $R^2$ for each individual compound corresponds in each case to one line of Table B (compounds I.A7b.D1-11.B1 to I.A7b.D1-11.B550).

Table 5b Compounds of the formula I.A7b in which the combination of $R^3$ and $R^7$ corresponds to line D1-12 of Table D1 and the meaning for the combination of $R^1$ and $R^2$ for each individual compound corresponds in each case to one line of Table B (compounds I.A7b.D1-12.B1 to I.A7b.D1-12.B550).

Table 6b Compounds of the formula I.A7b in which the combination of $R^3$ and $R^7$ corresponds to line D1-13 of Table D1 and the meaning for the combination of $R^1$ and $R^2$ for each individual compound corresponds in each case to one line of Table B (compounds I.A7b.D1-13.B1 to I.A7b.D1-13.B550).

Table 7b Compounds of the formula I.A7b in which the combination of $R^3$ and $R^7$ corresponds to line D1-14 of Table D1 and the meaning for the combination of $R^1$ and $R^2$ for each individual compound corresponds in each case to one line of Table B (compounds I.A7b.D1-14.B1 to I.A7b.D1-14.B550).

Table 8b Compounds of the formula I.A7b in which the combination of $R^3$ and $R^7$ corresponds to line D1-15 of Table D1 and the meaning for the combination of $R^1$ and $R^2$ for each individual compound corresponds in each case to one line of Table B (compounds I.A7b.D1-15.B1 to I.A7b.D1-15.B550).

Table 9b Compounds of the formula I.A7b in which the combination of $R^3$ and $R^7$ corresponds to line D1-16 of Table D1 and the meaning for the combination of $R^1$ and $R^2$ for each individual compound corresponds in each case to one line of Table B (compounds I.A7b.D1-16.B1 to I.A7b.D1-16.B550).

Table 10b Compounds of the formula I.A7b in which the combination of $R^3$ and $R^7$ corresponds to line D1-17 of Table D1 and the meaning for the combination of $R^1$ and $R^2$ for each individual compound corresponds in each case to one line of Table B (compounds I.A7b.D1-17.B1 to I.A7b.D1-17.B550).

Table 11b Compounds of the formula I.A7b in which the combination of $R^3$ and $R^7$ corresponds to line D1-18 of Table D1 and the meaning for the combination of $R^1$ and $R^2$ for each individual compound corresponds in each case to one line of Table B (compounds I.A7b.D1-18.B1 to I.A7b.D1-18.B550).

Table 12b Compounds of the formula I.A7b in which the combination of $R^3$ and $R^7$ corresponds to line D1-19 of Table D1 and the meaning for the combination of $R^1$ and $R^2$ for each individual compound corresponds in each case to one line of Table B (compounds I.A7b.D1-19.B1 to I.A7b.D1-19.B550).

Table 13b Compounds of the formula I.A7b in which the combination of $R^3$ and $R^7$ corresponds to line D1-20 of Table D1 and the meaning for the combination of $R^1$ and $R^2$ for each individual compound corresponds in each case to one line of Table B (compounds I.A7b.D1-20.B1 to I.A7b.D1-20.B550).

Table 14b Compounds of the formula I.A7b in which the combination of $R^3$ and $R^7$ corresponds to line D1-21 of Table D1 and the meaning for the combination of $R^1$ and $R^2$ for each individual compound corresponds in each case to one line of Table B (compounds I.A7b.D1-21.B1 to I.A7b.D1-21.B550).

Table 15b Compounds of the formula I.A7b in which the combination of $R^3$ and $R^7$ corresponds to line D1-22 of Table D1 and the meaning for the combination of $R^1$ and $R^2$ for each individual compound corresponds in each case to one line of Table B (compounds I.A7b.D1-22.B1 to I.A7b.D1-22.B550).

Table 16b Compounds of the formula I.A7b in which the combination of $R^3$ and $R^7$ corresponds to line D1-23 of Table D1 and the meaning for the combination of $R^1$ and $R^2$ for each individual compound corresponds in each case to one line of Table B (compounds I.A7b.D1-23.B1 to I.A7b.D1-23.B550).

Table 17b Compounds of the formula I.A7b in which the combination of $R^3$ and $R^7$ corresponds to line D1-24 of Table D1 and the meaning for the combination of $R^1$ and $R^2$ for each individual compound corresponds in each case to one line of Table B (compounds I.A7b.D1-24.B1 to I.A7b.D1-24.B550).

Table 18b Compounds of the formula I.A7b in which the combination of $R^3$ and $R^7$ corresponds to line D1-25 of Table D1 and the meaning for the combination of $R^1$ and $R^2$ for each individual compound corresponds in each case to one line of Table B (compounds I.A7b.D1-25.B1 to I.A7b.D1-25.B550).

Table 19b Compounds of the formula I.A7b in which the combination of $R^3$ and $R^7$ corresponds to line D1-26 of Table D1 and the meaning for the combination of $R^1$ and $R^2$ for each individual compound corresponds in each case to one line of Table B (compounds I.A7b.D1-26.B1 to I.A7b.D1-26.B550).

Table 20b Compounds of the formula I.A7b in which the combination of $R^3$ and $R^7$ corresponds to line D1-27 of Table D1 and the meaning for the combination of $R^1$ and $R^2$ for each individual compound corresponds in each case to one line of Table B (compounds I.A7b.D1-27.B1 to I.A7b.D1-27.B550).

Table 21b Compounds of the formula I.A7b in which the combination of $R^3$ and $R^7$ corresponds to line D1-28 of Table D1 and the meaning for the combination of $R^1$ and $R^2$ for each individual compound corresponds in each case to one line of Table B (compounds I.A7b.D1-28.B1 to I.A7b.D1-28.B550).

Table 22b Compounds of the formula I.A7b in which the combination of $R^3$ and $R^7$ corresponds to line D1-29 of Table D1 and the meaning for the combination of $R^1$ and $R^2$ for each individual compound corresponds in each case to one line of Table B (compounds I.A7b.D1-29.B1 to I.A7b.D1-29.B550).

Table 23b Compounds of the formula I.A7b in which the combination of $R^3$ and $R^7$ corresponds to line D1-30 of Table D1 and the meaning for the combination of $R^1$ and $R^2$ for each individual compound corresponds in each case to one line of Table B (compounds I.A7b.D1-30.B1 to I.A7b.D1-30.B550).

Table 24b Compounds of the formula I.A7b in which the combination of $R^3$ and $R^7$ corresponds to line D1-31 of Table D1 and the meaning for the combination of $R^1$ and $R^2$ for each individual compound corresponds in each case to one line of Table B (compounds I.A7b.D1-31.B1 to I.A7b.D1-31.B550).

Table 25b Compounds of the formula I.A7b in which the combination of $R^3$ and $R^7$ corresponds to line D1-32 of Table D1 and the meaning for the combination of $R^1$ and $R^2$ for each individual compound corresponds in each case to one line of Table B (compounds I.A7b.D1-32.B1 to I.A7b.D1-32.B550).

Table 26b Compounds of the formula I.A7b in which the combination of $R^3$ and $R^7$ corresponds to line D1-33 of Table D1 and the meaning for the combination of $R^1$ and $R^2$ for each individual compound corresponds in each case to one line of Table B (compounds I.A7b.D1-33.B1 to I.A7b.D1-33.B550).

Table 27b Compounds of the formula I.A7b in which the combination of $R^3$ and $R^7$ corresponds to line D1-34 of Table D1 and the meaning for the combination of $R^1$ and $R^2$ for each individual compound corresponds in each case to one line of Table B (compounds I.A7b.D1-34.B1 to I.A7b.D1-34.B550).

Table 28b Compounds of the formula I.A7b in which the combination of $R^3$ and $R^7$ corresponds to line D1-35 of Table D1 and the meaning for the combination of $R^1$ and $R^2$ for each individual compound corresponds in each case to one line of Table B (compounds I.A7b.D1-35.B1 to I.A7b.D1-35.B550).

Table 29b Compounds of the formula I.A7b in which the combination of $R^3$ and $R^7$ corresponds to line D1-36 of Table D1 and the meaning for the combination of $R^1$ and $R^2$ for each individual compound corresponds in each case to one line of Table B (compounds I.A7b.D1-36.B1 to I.A7b.D1-36.B550).

Table 30b Compounds of the formula I.A7b in which the combination of $R^3$ and $R^7$ corresponds to line D1-37 of Table D1 and the meaning for the combination of $R^1$ and $R^2$ for each individual compound corresponds in each case to one line of Table B (compounds I.A7b.D1-37.B1 to I.A7b.D1-37.B550).

Table 31b Compounds of the formula I.A7b in which the combination of $R^3$ and $R^7$ corresponds to line D1-38 of Table D1 and the meaning for the combination of $R^1$ and $R^2$ for each individual compound corresponds in each case to one line of Table B (compounds I.A7b.D1-38.B1 to I.A7b.D1-38.B550).

Table 32b Compounds of the formula I.A7b in which the combination of $R^3$ and $R^7$ corresponds to line D1-39 of Table D1 and the meaning for the combination of $R^1$ and $R^2$ for each individual compound corresponds in each case to one line of Table B (compounds I.A7b.D1-39.B1 to I.A7b.D1-39.B550).

Table 33b Compounds of the formula I.A7b in which the combination of $R^3$ and $R^7$ corresponds to line D1-40 of Table D1 and the meaning for the combination of $R^1$ and $R^2$ for each individual compound corresponds in each case to one line of Table B (compounds I.A7b.D1-40.B1 to I.A7b.D1-40.B550).

Table 34b Compounds of the formula I.A7b in which the combination of $R^3$ and $R^7$ corresponds to line D1-41 of Table D1 and the meaning for the combination of $R^1$ and $R^2$ for each individual compound corresponds in each case to one line of Table B (compounds I.A7b.D1-41.B1 to I.A7b.D1-41.B550).

Table 35b Compounds of the formula I.A7b in which the combination of $R^3$ and $R^7$ corresponds to line D1-42 of Table D1 and the meaning for the combination of $R^1$ and $R^2$ for each individual compound corresponds in each case to one line of Table B (compounds I.A7b.D1-42.B1 to I.A7b.D1-42.B550).

Table 36b Compounds of the formula I.A7b in which the combination of $R^3$ and $R^7$ corresponds to line D1-43 of Table D1 and the meaning for the combination of $R^1$ and $R^2$ for each individual compound corresponds in each case to one line of Table B (compounds I.A7b.D1-43.B1 to I.A7b.D1-43.B550).

Table 37b Compounds of the formula I.A7b in which the combination of $R^3$ and $R^7$ corresponds to line D1-44 of Table D1 and the meaning for the combination of $R^1$ and $R^2$ for each individual compound corresponds in each case to one line of Table B (compounds I.A7b.D1-44.B1 to I.A7b.D1-44.B550).

Table 38b Compounds of the formula I.A7b in which the combination of $R^3$ and $R^7$ corresponds to line D1-45 of Table D1 and the meaning for the combination of $R^1$ and $R^2$ for each individual compound corresponds in each case to one line of Table B (compounds I.A7b.D1-45.B1 to I.A7b.D1-45.B550).

Table 39b Compounds of the formula I.A7b in which the combination of $R^3$ and $R^7$ corresponds to line D1-46 of Table D1 and the meaning for the combination of $R^1$ and $R^2$ for each individual compound corresponds in each case to one line of Table B (compounds I.A7b.D1-46.B1 to I.A7b.D1-46.B550).

Table 40b Compounds of the formula I.A7b in which the combination of $R^3$ and $R^7$ corresponds to line D1-47 of Table D1 and the meaning for the combination of $R^1$ and $R^2$ for each individual compound corresponds in each case to one line of Table B (compounds I.A7b.D1-47.B1 to I.A7b.D1-47.B550).

Table 41b Compounds of the formula I.A7b in which the combination of $R^3$ and $R^7$ corresponds to line D1-48 of Table D1 and the meaning for the combination of $R^1$ and $R^2$ for each individual compound corresponds in each case to one line of Table B (compounds I.A7b.D1-48.B1 to I.A7b.D1-48.B550).

Table 42b Compounds of the formula I.A7b in which the combination of $R^3$ and $R^7$ corresponds to line D1-49 of Table D1 and the meaning for the combination of $R^1$ and $R^2$ for each individual compound corresponds in each case to one line of Table B (compounds I.A7b.D1-49.B1 to I.A7b.D1-49.B550).

Table 1c Compounds of the formula I.A4-1 in which the combination of $R^3$ and $R^5$ corresponds to line D2-1 of Table D2 and the meaning for the combination of $R^1$ and $R^2$ for each individual compound corresponds in each case to one line of Table B (compounds I.A4-1.D2-1.B1 to I.A4-1.D2-1.B550).

Table 2c Compounds of the formula I.A4-1 in which the combination of $R^3$ and $R^5$ corresponds to line D2-2 of Table D2 and the meaning for the combination of $R^1$ and $R^2$ for each individual compound corresponds in each case to one line of Table B (compounds I.A4-1.D2-2.B1 to I.A4-1.D2-2.B550).

Table 3c Compounds of the formula I.A4-1 in which the combination of $R^3$ and $R^5$ corresponds to line D2-3 of Table D2 and the meaning for the combination of $R^1$ and $R^2$ for each individual compound corresponds in each case to one line of Table B (compounds I.A4-1.D2-3.B1 to I.A4-1.D2-3.B550).

Table 4c Compounds of the formula I.A4-1 in which the combination of $R^3$ and $R^5$ corresponds to line D2-4 of Table D2 and the meaning for the combination of $R^1$ and $R^2$ for each individual compound corresponds in each case to one line of Table B (compounds I.A4-1.D2-4.B1 to I.A4-1.D2-4.B550).

Table 5c Compounds of the formula I.A4-1 in which the combination of $R^3$ and $R^5$ corresponds to line D2-5 of Table D2 and the meaning for the combination of $R^1$ and $R^2$ for each individual compound corresponds in each case to one line of Table B (compounds I.A4-1.D2-5.B1 to I.A4-1.D2-5.B550).

Table 6c Compounds of the formula I.A4-1 in which the combination of $R^3$ and $R^5$ corresponds to line D2-6 of Table D2 and the meaning for the combination of $R^1$ and $R^2$ for each individual compound corresponds in each case to one line of Table B (compounds I.A4-1.D2-6.B1 to I.A4-1.D2-6.B550).

Table 7c Compounds of the formula I.A4-1 in which the combination of $R^3$ and $R^5$ corresponds to line D2-7 of Table D2 and the meaning for the combination of $R^1$ and $R^2$ for each individual compound corresponds in each case to one line of Table B (compounds I.A4-1.D2-7.B1 to I.A4-1.D2-7.B550).

Table 8c Compounds of the formula I.A4-1 in which the combination of $R^3$ and $R^5$ corresponds to line D2-8 of Table D2 and the meaning for the combination of $R^1$ and $R^2$ for each individual compound corresponds in each case to one line of Table B (compounds I.A4-1.D2-8.B1 to I.A4-1.D2-8.B550).

Table 9c Compounds of the formula I.A4-1 in which the combination of $R^3$ and $R^5$ corresponds to line D2-9 of Table D2 and the meaning for the combination of $R^1$ and $R^2$ for each individual compound corresponds in each case to one line of Table B (compounds I.A4-1.D2-9.B1 to I.A4-1.D2-9.B550).

Table 10c Compounds of the formula I.A4-1 in which the combination of $R^3$ and $R^5$ corresponds to line D2-10 of Table D2 and the meaning for the combination of $R^1$ and $R^2$ for each individual compound corresponds in each case to one line of Table B (compounds I.A4-1.D2-10.B1 to I.A4-1.D2-10.B550).

Table 11c Compounds of the formula I.A4-1 in which the combination of $R^3$ and $R^5$ corresponds to line D2-11 of Table D2 and the meaning for the combination of $R^1$ and $R^2$ for each individual compound corresponds in each case to one line of Table B (compounds I.A4-1.D2-11.B1 to I.A4-1.D2-11.B550).

Table 12c Compounds of the formula I.A4-1 in which the combination of $R^3$ and $R^5$ corresponds to line D2-12 of Table D2 and the meaning for the combination of $R^1$ and $R^2$ for each individual compound corresponds in each case to one line of Table B (compounds I.A4-1.D2-12.B1 to I.A4-1.D2-12.B550).

Table 13c Compounds of the formula I.A4-1 in which the combination of $R^3$ and $R^5$ corresponds to line D2-13 of Table D2 and the meaning for the combination of $R^1$ and $R^2$ for each individual compound corresponds in each case to one line of Table B (compounds I.A4-1.D2-13.B1 to I.A4-1.D2-13.B550).

Table 14c Compounds of the formula I.A4-1 in which the combination of $R^3$ and $R^5$ corresponds to line D2-14 of Table D2 and the meaning for the combination of $R^1$ and $R^2$ for each individual compound corresponds in each case to one line of Table B (compounds I.A4-1.D2-14.B1 to I.A4-1.D2-14.B550).

Table 15c Compounds of the formula I.A4-1 in which the combination of $R^3$ and $R^5$ corresponds to line D2-15 of Table D2 and the meaning for the combination of $R^1$ and $R^2$ for each individual compound corresponds in each case to one line of Table B (compounds I.A4-1.D2-15.B1 to I.A4-1.D2-15.B550).

Table 16c Compounds of the formula I.A4-1 in which the combination of $R^3$ and $R^5$ corresponds to line D2-16 of Table D2 and the meaning for the combination of $R^1$ and $R^2$ for each individual compound corresponds in each case to one line of Table B (compounds I.A4-1.D2-16.B1 to I.A4-1.D2-16.B550).

Table 17c Compounds of the formula I.A4-1 in which the combination of $R^3$ and $R^5$ corresponds to line D2-17 of Table D2 and the meaning for the combination of $R^1$ and $R^2$ for each individual compound corresponds in each case to one line of Table B (compounds I.A4-1.D2-17.B1 to I.A4-1.D2-17.B550).

Table 18c Compounds of the formula I.A4-1 in which the combination of $R^3$ and $R^5$ corresponds to line D2-18 of Table D2 and the meaning for the combination of $R^1$ and $R^2$ for each individual compound corresponds in each case to one line of Table B (compounds I.A4-1.D2-18.B1 to I.A4-1.D2-18.B550).

Table 19c Compounds of the formula I.A4-1 in which the combination of $R^3$ and $R^5$ corresponds to line D2-19 of Table D2 and the meaning for the combination of $R^1$ and $R^2$ for each individual compound corresponds in each case to one line of Table B (compounds I.A4-1.D2-19.B1 to I.A4-1.D2-19.B550).

Table 20c Compounds of the formula I.A4-1 in which the combination of $R^3$ and $R^5$ corresponds to line D2-20 of Table D2 and the meaning for the combination of $R^1$ and $R^2$ for each individual compound corresponds in each case to one line of Table B (compounds I.A4-1.D2-20.B1 to I.A4-1.D2-20.B550).

Table 21c Compounds of the formula I.A4-1 in which the combination of $R^3$ and $R^5$ corresponds to line D2-21 of Table D2 and the meaning for the combination of $R^1$ and $R^2$ for each individual compound corresponds in each case to one line of Table B (compounds I.A4-1.D2-21.B1 to I.A4-1.D2-21.B550).

Table 22c Compounds of the formula I.A4-1 in which the combination of $R^3$ and $R^5$ corresponds to line D2-22 of Table D2 and the meaning for the combination of $R^1$ and $R^2$ for each individual compound corresponds in each case to one line of Table B (compounds I.A4-1.D2-22.B1 to I.A4-1.D2-22.B550).

Table 23c Compounds of the formula I.A4-1 in which the combination of $R^3$ and $R^5$ corresponds to line D2-23 of Table D2 and the meaning for the combination of $R^1$ and $R^2$ for each individual compound corresponds in each case to one line of Table B (compounds I.A4-1.D2-23.B1 to I.A4-1.D2-23.B550).

Table 24c Compounds of the formula I.A4-1 in which the combination of $R^3$ and $R^5$ corresponds to line D2-24 of Table D2 and the meaning for the combination of $R^1$ and $R^2$ for each individual compound corresponds in each case to one line of Table B (compounds I.A4-1.D2-24.B1 to I.A4-1.D2-24.B550).

Table 25c Compounds of the formula I.A4-1 in which the combination of $R^3$ and $R^5$ corresponds to line D2-25 of Table D2 and the meaning for the combination of $R^1$ and $R^2$ for each individual compound corresponds in each case to one line of Table B (compounds I.A4-1.D2-25.B1 to I.A4-1.D2-25.B550).

Table 26c Compounds of the formula I.A4-1 in which the combination of $R^3$ and $R^5$ corresponds to line D2-26 of Table D2 and the meaning for the combination of $R^1$ and $R^2$ for each individual compound corresponds in each case to one line of Table B (compounds I.A4-1.D2-26.B1 to I.A4-1.D2-26.B550).

Table 27c Compounds of the formula I.A4-1 in which the combination of $R^3$ and $R^5$ corresponds to line D2-27 of Table D2 and the meaning for the combination of $R^1$ and $R^2$ for each individual compound corresponds in each case to one line of Table B (compounds I.A4-1.D2-27.B1 to I.A4-1.D2-27.B550).

Table 28c Compounds of the formula I.A4-1 in which the combination of $R^3$ and $R^5$ corresponds to line D2-28 of Table D2 and the meaning for the combination of $R^1$ and $R^2$ for each individual compound corresponds in each case to one line of Table B (compounds I.A4-1.D2-28.B1 to I.A4-1.D2-28.B550).

Table 29c Compounds of the formula I.A4-1 in which the combination of $R^3$ and $R^5$ corresponds to line D2-29 of Table D2 and the meaning for the combination of $R^1$ and $R^2$ for each individual compound corresponds in each case to one line of Table B (compounds I.A4-1.D2-29.B1 to I.A4-1.D2-29.B550).

Table 30c Compounds of the formula I.A4-1 in which the combination of $R^3$ and $R^5$ corresponds to line D2-30 of Table D2 and the meaning for the combination of $R^1$ and $R^2$ for each individual compound corresponds in each case to one line of Table B (compounds I.A4-1.D2-30.B1 to I.A4-1.D2-30.B550).

Table 31c Compounds of the formula I.A4-1 in which the combination of $R^3$ and $R^5$ corresponds to line D2-31 of Table D2 and the meaning for the combination of $R^1$ and $R^2$ for each individual compound corresponds in each case to one line of Table B (compounds I.A4-1.D2-31.B1 to I.A4-1.D2-31.B550).

Table 32c Compounds of the formula I.A4-1 in which the combination of $R^3$ and $R^5$ corresponds to line D2-32 of Table D2 and the meaning for the combination of $R^1$ and $R^2$ for each individual compound corresponds in each case to one line of Table B (compounds I.A4-1.D2-32.B1 to I.A4-1.D2-32.B550).

Table 33c Compounds of the formula I.A4-1 in which the combination of $R^3$ and $R^5$ corresponds to line D2-33 of Table D2 and the meaning for the combination of $R^1$ and $R^2$ for each individual compound corresponds in each case to one line of Table B (compounds I.A4-1.D2-33.B1 to I.A4-1.D2-33.B550).

Table 34c Compounds of the formula I.A4-1 in which the combination of $R^3$ and $R^5$ corresponds to line D2-34 of Table D2 and the meaning for the combination of $R^1$ and $R^2$ for each individual compound corresponds in each case to one line of Table B (compounds I.A4-1.D2-34.B1 to I.A4-1.D2-34.B550).

Table 35c Compounds of the formula I.A4-1 in which the combination of $R^3$ and $R^5$ corresponds to line D2-35 of Table D2 and the meaning for the combination of $R^1$ and $R^2$ for each individual compound corresponds in each case to one line of Table B (compounds I.A4-1.D2-35.B1 to I.A4-1.D2-35.B550).

Table 36c Compounds of the formula I.A4-1 in which the combination of $R^3$ and $R^5$ corresponds to line D2-36 of Table D2 and the meaning for the combination of $R^1$ and $R^2$ for each individual compound corresponds in each case to one line of Table B (compounds I.A4-1.D2-36.B1 to I.A4-1.D2-36.B550).

Table 37c Compounds of the formula I.A4-1 in which the combination of $R^3$ and $R^5$ corresponds to line D2-37 of Table D2 and the meaning for the combination of $R^1$ and $R^2$ for each individual compound corresponds in each case to one line of Table B (compounds I.A4-1.D2-37.B1 to I.A4-1.D2-37.B550).

Table 38c Compounds of the formula I.A4-1 in which the combination of $R^3$ and $R^5$ corresponds to line D2-38 of Table D2 and the meaning for the combination of $R^1$ and $R^2$ for each individual compound corresponds in each case to one line of Table B (compounds I.A4-1.D2-38.B1 to I.A4-1.D2-38.B550).

Table 39c Compounds of the formula I.A4-1 in which the combination of $R^3$ and $R^5$ corresponds to line D2-39 of Table D2 and the meaning for the combination of $R^1$ and $R^2$ for each individual compound corresponds in each case to one line of Table B (compounds I.A4-1.D2-39.B1 to I.A4-1.D2-39.B550).

Table 40c Compounds of the formula I.A4-1 in which the combination of $R^3$ and $R^5$ corresponds to line D2-40 of Table D2 and the meaning for the combination of $R^1$ and $R^2$ for each individual compound corresponds in each case to one line of Table B (compounds I.A4-1.D2-40.B1 to I.A4-1.D2-40.B550).

Table 41c Compounds of the formula I.A4-1 in which the combination of $R^3$ and $R^5$ corresponds to line D2-41 of Table D2 and the meaning for the combination of $R^1$ and $R^2$ for each individual compound corresponds in each case to one line of Table B (compounds I.A4-1.D2-41.B1 to I.A4-1.D2-41.B550).

Table 42c Compounds of the formula I.A4-1 in which the combination of $R^3$ and $R^5$ corresponds to line D2-42 of Table D2 and the meaning for the combination of $R^1$ and $R^2$ for each individual compound corresponds in each case to one line of Table B (compounds I.A4-1.D2-42.B1 to I.A4-1.D2-42.B550).

Table 1d Compounds of the formula I.A1a in which the combination of $R^3$, $R^6$ and $R^7$ corresponds to line D3-1 of Table D3 and the meaning for the combination of $R^1$ and $R^2$ for each individual compound corresponds in each case to one line of Table B (compounds I.A1a.D3-1.B1 to I.A1a.D3-1.B550).

Table 2d Compounds of the formula I.A1a in which the combination of $R^3$, $R^6$ and $R^7$ corresponds to line D3-2 of Table D3 and the meaning for the combination of $R^1$ and $R^2$ for each individual compound corresponds in each case to one line of Table B (compounds I.A1a.D3-2.B1 to I.A1a.D3-2.B550).

Table 3d Compounds of the formula I.A1a in which the combination of $R^3$, $R^6$ and $R^7$ corresponds to line D3-3 of Table D3 and the meaning for the combination of $R^1$ and $R^2$ for each individual compound corresponds in each case to one line of Table B (compounds I.A1a.D3-3.B1 to I.A1a.D3-3.B550).

Table 4d Compounds of the formula I.A1a in which the combination of $R^3$, $R^6$ and $R^7$ corresponds to line D3-4 of Table D3 and the meaning for the combination of $R^1$ and $R^2$ for each individual compound corresponds in each case to one line of Table B (compounds I.A1a.D3-4.B1 to I.A1a.D3-4.B550).

Table 5d Compounds of the formula I.A1a in which the combination of $R^3$, $R^6$ and $R^7$ corresponds to line D3-5 of Table D3 and the meaning for the combination of $R^1$ and $R^2$ for each individual compound corresponds in each case to one line of Table B (compounds I.A1a.D3-5.B1 to I.A1a.D3-5.B550).

Table 6d Compounds of the formula I.A1a in which the combination of $R^3$, $R^6$ and $R^7$ corresponds to line D3-6 of Table D3 and the meaning for the combination of $R^1$ and $R^2$ for each individual compound corresponds in each case to one line of Table B (compounds I.A1a.D3-6.B1 to I.A1a.D3-6.B550).

Table 7d Compounds of the formula I.A1a in which the combination of $R^3$, $R^6$ and $R^7$ corresponds to line D3-7 of Table D3 and the meaning for the combination of $R^1$ and $R^2$ for each individual compound corresponds in each case to one line of Table B (compounds I.A1a.D3-7.B1 to I.A1a.D3-7.B550).

Table 8d Compounds of the formula I.A1a in which the combination of $R^3$, $R^6$ and $R^7$ corresponds to line D3-8 of Table D3 and the meaning for the combination of $R^1$ and $R^2$ for each individual compound corresponds in each case to one line of Table B (compounds I.A1a.D3-8.B1 to I.A1a.D3-8.B550).

Table 9d Compounds of the formula I.A1a in which the combination of $R^3$, $R^6$ and $R^7$ corresponds to line D3-9 of Table D3 and the meaning for the combination of $R^1$ and $R^2$ for each individual compound corresponds in each case to one line of Table B (compounds I.A1a.D3-9.B1 to I.A1a.D3-9.B550).

Table 10d Compounds of the formula I.A1a in which the combination of $R^3$, $R^6$ and $R^7$ corresponds to line D3-10 of Table D3 and the meaning for the combination of $R^1$ and $R^2$ for each individual compound corresponds in each case to one line of Table B (compounds I.A1a.D3-10.B1 to I.A1a.D3-10.B550).

Table 11d Compounds of the formula I.A1a in which the combination of $R^3$, $R^6$ and $R^7$ corresponds to line D3-11 of Table D3 and the meaning for the combination of $R^1$ and $R^2$ for each individual compound corresponds in each case to one line of Table B (compounds I.A1a.D3-11.B1 to I.A1a.D3-11.B550).

Table 12d Compounds of the formula I.A1a in which the combination of $R^3$, $R^6$ and $R^7$ corresponds to line D3-12 of Table D3 and the meaning for the combination of $R^1$ and $R^2$ for each individual compound corresponds in each case to one line of Table B (compounds I.A1a.D3-12.B1 to I.A1a.D3-12.B550).

Table 13d Compounds of the formula I.A1a in which the combination of $R^3$, $R^6$ and $R^7$ corresponds to line D3-13 of Table D3 and the meaning for the combination of $R^1$ and $R^2$ for each individual compound corresponds in each case to one line of Table B (compounds I.A1a.D3-13.B1 to I.A1a.D3-13.B550).

Table 14d Compounds of the formula I.A1a in which the combination of $R^3$, $R^6$ and $R^7$ corresponds to line D3-14 of Table D3 and the meaning for the combination of $R^1$ and $R^2$ for each individual compound corresponds in each case to one line of Table B (compounds I.A1a.D3-14.B1 to I.A1a.D3-14.B550).

Table 15d Compounds of the formula I.A1a in which the combination of $R^3$, $R^6$ and $R^7$ corresponds to line D3-15 of Table D3 and the meaning for the combination of $R^1$ and $R^2$ for each individual compound corresponds in each case to one line of Table B (compounds I.A1a.D3-15.B1 to I.A1a.D3-15.B550).

Table 16d Compounds of the formula I.A1a in which the combination of $R^3$, $R^6$ and $R^7$ corresponds to line D3-16 of Table D3 and the meaning for the combination of $R^1$ and $R^2$ for each individual compound corresponds in each case to one line of Table B (compounds I.A1a.D3-16.B1 to I.A1a.D3-16.B550).

Table 17d Compounds of the formula I.A1a in which the combination of $R^3$, $R^6$ and $R^7$ corresponds to line D3-17 of Table D3 and the meaning for the combination of $R^1$ and $R^2$ for each individual compound corresponds in each case to one line of Table B (compounds I.A1a.D3-17.B1 to I.A1a.D3-17.B550).

Table 18d Compounds of the formula I.A1a in which the combination of $R^3$, $R^6$ and $R^7$ corresponds to line D3-18 of Table D3 and the meaning for the combination of $R^1$ and $R^2$ for each individual compound corresponds in each case to one line of Table B (compounds I.A1a.D3-18.B1 to I.A1a.D3-18.B550).

Table 19d Compounds of the formula I.A1a in which the combination of $R^3$, $R^6$ and $R^7$ corresponds to line D3-19 of Table D3 and the meaning for the combination of $R^1$ and $R^2$ for each individual compound corresponds in each case to one line of Table B (compounds I.A1a.D3-19.B1 to I.A1a.D3-19.B550).

Table 20d Compounds of the formula I.A1a in which the combination of $R^3$, $R^6$ and $R^7$ corresponds to line D3-20 of Table D3 and the meaning for the combination of $R^1$ and $R^2$ for each individual compound corresponds in each case to one line of Table B (compounds I.A1a.D3-20.B1 to I.A1a.D3-20.B550).

Table 21d Compounds of the formula I.A1a in which the combination of $R^3$, $R^6$ and $R^7$ corresponds to line D3-21 of Table D3 and the meaning for the combination of $R^1$ and $R^2$ for each individual compound corresponds in each case to one line of Table B (compounds I.A1a.D3-21.B1 to I.A1a.D3-21.B550).

Table 22d Compounds of the formula I.A1a in which the combination of $R^3$, $R^6$ and $R^7$ corresponds to line D3-22 of Table D3 and the meaning for the combination of $R^1$ and $R^2$ for each individual compound corresponds in each case to one line of Table B (compounds I.A1a.D3-22.B1 to I.A1a.D3-22.B550).

Table 23d Compounds of the formula I.A1a in which the combination of $R^3$, $R^6$ and $R^7$ corresponds to line D3-23 of Table D3 and the meaning for the combination of $R^1$ and $R^2$ for each individual compound corresponds in each case to one line of Table B (compounds I.A1a.D3-23.B1 to I.A1a.D3-23.B550).

Table 24d Compounds of the formula I.A1a in which the combination of $R^3$, $R^6$ and $R^7$ corresponds to line D3-24 of Table D3 and the meaning for the combination of $R^1$ and $R^2$ for each individual compound corresponds in each case to one line of Table B (compounds I.A1a.D3-24.B1 to I.A1a.D3-24.B550).

Table 25d Compounds of the formula I.A1a in which the combination of $R^3$, $R^6$ and $R^7$ corresponds to line D3-25 of Table D3 and the meaning for the combination of $R^1$ and $R^2$ for each individual compound corresponds in each case to one line of Table B (compounds I.A1a.D3-25.B1 to I.A1a.D3-25.B550).

Table 26d Compounds of the formula I.A1a in which the combination of $R^3$, $R^6$ and $R^7$ corresponds to line D3-26 of Table D3 and the meaning for the combination of $R^1$ and $R^2$ for each individual compound corresponds in each case to one line of Table B (compounds I.A1a.D3-26.B1 to I.A1a.D3-26.B550).

Table 27d Compounds of the formula I.A1a in which the combination of $R^3$, $R^6$ and $R^7$ corresponds to line D3-27 of Table D3 and the meaning for the combination of $R^1$ and $R^2$ for each individual compound corresponds in each case to one line of Table B (compounds I.A1a.D3-27.B1 to I.A1a.D3-27.B550).

Table 28d Compounds of the formula I.A1a in which the combination of $R^3$, $R^6$ and $R^7$ corresponds to line D3-28 of Table D3 and the meaning for the combination of $R^1$ and $R^2$ for each individual compound corresponds in each case to one line of Table B (compounds I.A1a.D3-28.B1 to I.A1a.D3-28.B550).

Table 29d Compounds of the formula I.A1a in which the combination of $R^3$, $R^6$ and $R^7$ corresponds to line D3-29 of Table D3 and the meaning for the combination of $R^1$ and $R^2$ for each individual compound corresponds in each case to one line of Table B (compounds I.A1a.D3-29.B1 to I.A1a.D3-29.B550).

Table 30d Compounds of the formula I.A1a in which the combination of $R^3$, $R^6$ and $R^7$ corresponds to line D3-30 of Table D3 and the meaning for the combination of $R^1$ and $R^2$ for each individual compound corresponds in each case to one line of Table B (compounds I.A1a.D3-30.B1 to I.A1a.D3-30.B550).

Table 31d Compounds of the formula I.A1a in which the combination of $R^3$, $R^6$ and $R^7$ corresponds to line D3-31 of Table D3 and the meaning for the combination of $R^1$ and $R^2$ for each individual compound corresponds in each case to one line of Table B (compounds I.A1a.D3-31.B1 to I.A1a.D3-31.B550).

Table 32d Compounds of the formula I.A1a in which the combination of $R^3$, $R^6$ and $R^7$ corresponds to line D3-32 of Table D3 and the meaning for the combination of $R^1$ and $R^2$ for each individual compound corresponds in each case to one line of Table B (compounds I.A1a.D3-32.B1 to I.A1a.D3-32.B550).

Table 33d Compounds of the formula I.A1a in which the combination of $R^3$, $R^6$ and $R^7$ corresponds to line D3-33 of Table D3 and the meaning for the combination of $R^1$ and $R^2$ for each individual compound corresponds in each case to one line of Table B (compounds I.A1a.D3-33.B1 to I.A1a.D3-33.B550).

Table 34d Compounds of the formula I.A1a in which the combination of $R^3$, $R^6$ and $R^7$ corresponds to line D3-34 of Table D3 and the meaning for the combination of $R^1$ and $R^2$ for each individual compound corresponds in each case to one line of Table B (compounds I.A1a.D3-34.B1 to I.A1a.D3-34.B550).

Table 35d Compounds of the formula I.A1a in which the combination of $R^3$, $R^6$ and $R^7$ corresponds to line D3-35 of Table D3 and the meaning for the combination of $R^1$ and $R^2$ for each individual compound corresponds in each case to one line of Table B (compounds I.A1a.D3-35.B1 to I.A1a.D3-35.B550).

Table 36d Compounds of the formula I.A1a in which the combination of $R^3$, $R^6$ and $R^7$ corresponds to line D3-36 of Table D3 and the meaning for the combination of $R^1$ and $R^2$ for each individual compound corresponds in each case to one line of Table B (compounds I.A1a.D3-36.B1 to I.A1a.D3-36.B550).

Table 37d Compounds of the formula I.A1a in which the combination of $R^3$, $R^6$ and $R^7$ corresponds to line D3-37 of Table D3 and the meaning for the combination of $R^1$ and $R^2$ for each individual compound corresponds in each case to one line of Table B (compounds I.A1a.D3-37.B1 to I.A1a.D3-37.B550).

Table 38d Compounds of the formula I.A1a in which the combination of $R^3$, $R^6$ and $R^7$ corresponds to line D3-38 of Table D3 and the meaning for the combination of $R^1$ and $R^2$ for each individual compound corresponds in each case to one line of Table B (compounds I.A1a.D3-38.B1 to I.A1a.D3-38.B550).

Table 39d Compounds of the formula I.A1a in which the combination of $R^3$, $R^6$ and $R^7$ corresponds to line D3-39 of Table D3 and the meaning for the combination of $R^1$ and $R^2$ for each individual compound corresponds in each case to one line of Table B (compounds I.A1a.D3-39.B1 to I.A1a.D3-39.B550).

Table 40d Compounds of the formula I.A1a in which the combination of $R^3$, $R^6$ and $R^7$ corresponds to line D3-40 of Table D3 and the meaning for the combination of $R^1$ and $R^2$ for each individual compound corresponds in each case to one line of Table B (compounds I.A1a.D3-40.B1 to I.A1a.D3-40.B550).

Table 41d Compounds of the formula I.A1a in which the combination of $R^3$, $R^6$ and $R^7$ corresponds to line D3-41 of Table D3 and the meaning for the combination of $R^1$ and $R^2$ for each individual compound corresponds in each case to one line of Table B (compounds I.A1a.D3-41.B1 to I.A1a.D3-41.B550).

Table 42d Compounds of the formula I.A1a in which the combination of $R^3$, $R^6$ and $R^7$ corresponds to line D3-42 of Table D3 and the meaning for the combination of $R^1$ and $R^2$ for each individual compound corresponds in each case to one line of Table B (compounds I.A1a.D3-42.B1 to I.A1a.D3-42.B550).

Table 43d Compounds of the formula I.A1a in which the combination of $R^3$, $R^6$ and $R^7$ corresponds to line D3-43 of Table D3 and the meaning for the combination of $R^1$ and $R^2$ for each individual compound corresponds in each case to one line of Table B (compounds I.A1a.D3-43.B1 to I.A1a.D3-43.B550).

Table 44d Compounds of the formula I.A1a in which the combination of $R^3$, $R^6$ and $R^7$ corresponds to line D3-44 of Table D3 and the meaning for the combination of $R^1$ and $R^2$ for each individual compound corresponds in each case to one line of Table B (compounds I.A1a.D3-44.B1 to I.A1a.D3-44.B550).

Table 45d Compounds of the formula I.A1a in which the combination of $R^3$, $R^6$ and $R^7$ corresponds to line D3-45 of Table D3 and the meaning for the combination of $R^1$ and $R^2$ for each individual compound corresponds in each case to one line of Table B (compounds I.A1a.D3-45.B1 to I.A1a.D3-45.B550).

Table 46d Compounds of the formula I.A1a in which the combination of $R^3$, $R^6$ and $R^7$ corresponds to line D3-46 of Table D3 and the meaning for the combination of $R^1$ and $R^2$ for each individual compound corresponds in each case to one line of Table B (compounds I.A1a.D3-46.B1 to I.A1a.D3-46.B550).

Table 47d Compounds of the formula I.A1a in which the combination of $R^3$, $R^6$ and $R^7$ corresponds to line D3-47 of Table D3 and the meaning for the combination of $R^1$ and $R^2$ for each individual compound corresponds in each case to one line of Table B (compounds I.A1a.D3-47.B1 to I.A1a.D3-47.B550).

Table 48d Compounds of the formula I.A1a in which the combination of $R^3$, $R^6$ and $R^7$ corresponds to line D3-48 of Table D3 and the meaning for the combination of $R^1$ and $R^2$ for each individual compound corresponds in each case to one line of Table B (compounds I.A1a.D3-48.B1 to I.A1a.D3-48.B550).

Table 49d Compounds of the formula I.A1a in which the combination of $R^3$, $R^6$ and $R^7$ corresponds to line D3-49 of Table D3 and the meaning for the combination of $R^1$ and $R^2$ for each individual compound corresponds in each case to one line of Table B (compounds I.A1a.D3-49.B1 to I.A1a.D3-49.B550).

Table 50d Compounds of the formula I.A1a in which the combination of $R^3$, $R^6$ and $R^7$ corresponds to line D3-50 of Table D3 and the meaning for the combination of $R^1$ and $R^2$ for each individual compound corresponds in each case to one line of Table B (compounds I.A1a.D3-50.B1 to I.A1a.D3-50.B550).

Table 51d Compounds of the formula I.A1a in which the combination of $R^3$, $R^6$ and $R^7$ corresponds to line D3-51 of Table D3 and the meaning for the combination of $R^1$ and $R^2$ for each individual compound corresponds in each case to one line of Table B (compounds I.A1a.D3-51.B1 to I.A1a.D3-51.B550).

Table 52d Compounds of the formula I.A1a in which the combination of $R^3$, $R^6$ and $R^7$ corresponds to line D3-52 of Table D3 and the meaning for the combination of $R^1$ and $R^2$ for each individual compound corresponds in each case to one line of Table B (compounds I.A1a.D3-52.B1 to I.A1a.D3-52.B550).

Table 53d Compounds of the formula I.A1a in which the combination of $R^3$, $R^6$ and $R^7$ corresponds to line D3-53 of Table D3 and the meaning for the combination of $R^1$ and $R^2$ for each individual compound corresponds in each case to one line of Table B (compounds I.A1a.D3-53.B1 to I.A1a.D3-53.B550).

Table 54d Compounds of the formula I.A1a in which the combination of $R^3$, $R^6$ and $R^7$ corresponds to line D3-54 of Table D3 and the meaning for the combination of $R^1$ and $R^2$ for each individual compound corresponds in each case to one line of Table B (compounds I.A1a.D3-54.B1 to I.A1a.D3-54.B550).

Table 55d Compounds of the formula I.A1a in which the combination of $R^3$, $R^6$ and $R^7$ corresponds to line D3-55 of Table D3 and the meaning for the combination of $R^1$ and $R^2$ for each individual compound corresponds in each case to one line of Table B (compounds I.A1a.D3-55.B1 to I.A1a.D3-55.B550).

Table 56d Compounds of the formula I.A1a in which the combination of $R^3$, $R^6$ and $R^7$ corresponds to line D3-56 of Table D3 and the meaning for the combination of $R^1$ and $R^2$ for each individual compound corresponds in each case to one line of Table B (compounds I.A1a.D3-56.B1 to I.A1a.D3-56.B550).

Table 57d Compounds of the formula I.A1a in which the combination of $R^3$, $R^6$ and $R^7$ corresponds to line D3-57 of Table D3 and the meaning for the combination of $R^1$ and $R^2$ for each individual compound corresponds in each case to one line of Table B (compounds I.A1a.D3-57.B1 to I.A1a.D3-57.B550).

Table 58d Compounds of the formula I.A1a in which the combination of $R^3$, $R^6$ and $R^7$ corresponds to line D3-58 of Table D3 and the meaning for the combination of $R^1$ and $R^2$ for each individual compound corresponds in each case to one line of Table B (compounds I.A1a.D3-58.B1 to I.A1a.D3-58.B550).

Table 59d Compounds of the formula I.A1a in which the combination of $R^3$, $R^6$ and $R^7$ corresponds to line D3-59 of Table D3 and the meaning for the combination of $R^1$ and $R^2$ for each individual compound corresponds in each case to one line of Table B (compounds I.A1a.D3-59.B1 to I.A1a.D3-59.B550).

Table 60d Compounds of the formula I.A1a in which the combination of $R^3$, $R^6$ and $R^7$ corresponds to line D3-60 of Table D3 and the meaning for the combination of $R^1$ and $R^2$ for each individual compound corresponds in each case to one line of Table B (compounds I.A1a.D3-60.B1 to I.A1a.D3-60.B550).

Table 61d Compounds of the formula I.A1a in which the combination of $R^3$, $R^6$ and $R^7$ corresponds to line D3-61 of Table D3 and the meaning for the combination of $R^1$ and $R^2$ for each individual compound corresponds in each case to one line of Table B (compounds I.A1a.D3-61.B1 to I.A1a.D3-61.B550).

Table 62d Compounds of the formula I.A1a in which the combination of $R^3$, $R^6$ and $R^7$ corresponds to line D3-62 of Table D3 and the meaning for the combination of $R^1$ and $R^2$ for each individual compound corresponds in each case to one line of Table B (compounds I.A1a.D3-62.B1 to I.A1a.D3-62.B550).

Table 63d Compounds of the formula I.A1a in which the combination of $R^3$, $R^6$ and $R^7$ corresponds to line D3-63 of Table D3 and the meaning for the combination of $R^1$ and $R^2$ for each individual compound corresponds in each case to one line of Table B (compounds I.A1a.D3-63.B1 to I.A1a.D3-63.B550).

Table 1e Compounds of the formula I.A4a in which the combination of $R^3$, $R^5$ and $R^7$ corresponds to line D4-1 of Table D4 and the meaning for the combination of $R^1$ and $R^2$ for each individual compound corresponds in each case to one line of Table B (compounds I.A4a.D4-1.B1 to I.A4a.D4-1.B550).

Table 2e Compounds of the formula I.A4a in which the combination of $R^3$, $R^5$ and $R^7$ corresponds to line D4-2 of Table D4 and the meaning for the combination of $R^1$ and $R^2$ for each individual compound corresponds in each case to one line of Table B (compounds I.A4a.D4-2.B1 to I.A4a.D4-2.B550).

Table 3e Compounds of the formula I.A4a in which the combination of $R^3$, $R^5$ and $R^7$ corresponds to line D4-3 of Table D4 and the meaning for the combination of $R^1$ and $R^2$ for each individual compound corresponds in each case to one line of Table B (compounds I.A4a.D4-3.B1 to I.A4a.D4-3.B550).

Table 4e Compounds of the formula I.A4a in which the combination of $R^3$, $R^5$ and $R^7$ corresponds to line D4-4 of Table D4 and the meaning for the combination of $R^1$ and $R^2$ for each individual compound corresponds in each case to one line of Table B (compounds I.A4a.D4-4.B1 to I.A4a.D4-4.B550).

Table 5e Compounds of the formula I.A4a in which the combination of $R^3$, $R^5$ and $R^7$ corresponds to line D4-5 of Table D4 and the meaning for the combination of $R^1$ and $R^2$ for each individual compound corresponds in each case to one line of Table B (compounds I.A4a.D4-5.B1 to I.A4a.D4-5.B550).

Table 6e Compounds of the formula I.A4a in which the combination of $R^3$, $R^5$ and $R^7$ corresponds to line D4-6 of Table D4 and the meaning for the combination of $R^1$ and $R^2$ for each individual compound corresponds in each case to one line of Table B (compounds I.A4a.D4-6.B1 to I.A4a.D4-6.B550).

Table 7e Compounds of the formula I.A4a in which the combination of $R^3$, $R^5$ and $R^7$ corresponds to line D4-7 of Table D4 and the meaning for the combination of $R^1$ and $R^2$ for each individual compound corresponds in each case to one line of Table B (compounds I.A4a.D4-7.B1 to I.A4a.D4-7.B550).

Table 8e Compounds of the formula I.A4a in which the combination of $R^3$, $R^5$ and $R^7$ corresponds to line D4-8 of Table D4 and the meaning for the combination of $R^1$ and $R^2$ for each individual compound corresponds in each case to one line of Table B (compounds I.A4a.D4-8.B1 to I.A4a.D4-8.B550).

Table 9e Compounds of the formula I.A4a in which the combination of $R^3$, $R^5$ and $R^7$ corresponds to line D4-9 of Table D4 and the meaning for the combination of $R^1$ and $R^2$ for each individual compound corresponds in each case to one line of Table B (compounds I.A4a.D4-9.B1 to I.A4a.D4-9.B550).

Table 10e Compounds of the formula I.A4a in which the combination of $R^3$, $R^5$ and $R^7$ corresponds to line D4-10 of Table D4 and the meaning for the combination of $R^1$ and $R^2$ for each individual compound corresponds in each case to one line of Table B (compounds I.A4a.D4-10.B1 to I.A4a.D4-10.B550).

Table 11e Compounds of the formula I.A4a in which the combination of $R^3$, $R^5$ and $R^7$ corresponds to line D4-11 of Table D4 and the meaning for the combination of $R^1$ and $R^2$ for each individual compound corresponds in each case to one line of Table B (compounds I.A4a.D4-11.B1 to I.A4a.D4-11.B550).

Table 12e Compounds of the formula I.A4a in which the combination of $R^3$, $R^5$ and $R^7$ corresponds to line D4-12 of Table D4 and the meaning for the combination of $R^1$ and $R^2$ for each individual compound corresponds in each case to one line of Table B (compounds I.A4a.D4-12.B1 to I.A4a.D4-12.B550).

Table 13e Compounds of the formula I.A4a in which the combination of $R^3$, $R^5$ and $R^7$ corresponds to line D4-13 of Table D4 and the meaning for the combination of $R^1$ and $R^2$ for each individual compound corresponds in each case to one line of Table B (compounds I.A4a.D4-13.B1 to I.A4a.D4-13.B550).

Table 14e Compounds of the formula I.A4a in which the combination of $R^3$, $R^5$ and $R^7$ corresponds to line D4-14 of Table D4 and the meaning for the combination of $R^1$ and $R^2$ for each individual compound corresponds in each case to one line of Table B (compounds I.A4a.D4-14.B1 to I.A4a.D4-14.B550).

Table 15e Compounds of the formula I.A4a in which the combination of $R^3$, $R^5$ and $R^7$ corresponds to line D4-15 of Table D4 and the meaning for the combination of $R^1$ and $R^2$ for each individual compound corresponds in each case to one line of Table B (compounds I.A4a.D4-15.B1 to I.A4a.D4-15.B550).

Table 16e Compounds of the formula I.A4a in which the combination of $R^3$, $R^5$ and $R^7$ corresponds to line D4-16 of Table D4 and the meaning for the combination of $R^1$ and $R^2$ for each individual compound corresponds in each case to one line of Table B (compounds I.A4a.D4-16.B1 to I.A4a.D4-16.B550).

Table 17e Compounds of the formula I.A4a in which the combination of $R^3$, $R^5$ and $R^7$ corresponds to line D4-17 of Table D4 and the meaning for the combination of $R^1$ and $R^2$ for each individual compound corresponds in each case to one line of Table B (compounds I.A4a.D4-17.B1 to I.A4a.D4-17.B550).

Table 18e Compounds of the formula I.A4a in which the combination of $R^3$, $R^5$ and $R^7$ corresponds to line D4-18 of Table D4 and the meaning for the combination of $R^1$ and $R^2$ for each individual compound corresponds in each case to one line of Table B (compounds I.A4a.D4-18.B1 to I.A4a.D4-18.B550).

Table 19e Compounds of the formula I.A4a in which the combination of $R^3$, $R^5$ and $R^7$ corresponds to line D4-19 of Table D4 and the meaning for the combination of $R^1$ and $R^2$ for each individual compound corresponds in each case to one line of Table B (compounds I.A4a.D4-19.B1 to I.A4a.D4-19.B550).

Table 20e Compounds of the formula I.A4a in which the combination of $R^3$, $R^5$ and $R^7$ corresponds to line D4-20 of Table D4 and the meaning for the combination of $R^1$ and $R^2$ for each individual compound corresponds in each case to one line of Table B (compounds I.A4a.D4-20.B1 to I.A4a.D4-20.B550).

Table 21e Compounds of the formula I.A4a in which the combination of $R^3$, $R^5$ and $R^7$ corresponds to line D4-21 of Table D4 and the meaning for the combination of $R^1$ and $R^2$ for each individual compound corresponds in each case to one line of Table B (compounds I.A4a.D4-21.B1 to I.A4a.D4-21.B550).

Table 22e Compounds of the formula I.A4a in which the combination of $R^3$, $R^5$ and $R^7$ corresponds to line D4-22 of Table D4 and the meaning for the combination of $R^1$ and $R^2$ for each individual compound corresponds in each case to one line of Table B (compounds I.A4a.D4-22.B1 to I.A4a.D4-22.B550).

Table 23e Compounds of the formula I.A4a in which the combination of $R^3$, $R^5$ and $R^7$ corresponds to line D4-23 of Table D4 and the meaning for the combination of $R^1$ and $R^2$ for each individual compound corresponds in each case to one line of Table B (compounds I.A4a.D4-23.B1 to I.A4a.D4-23.B550).

Table 24e Compounds of the formula I.A4a in which the combination of $R^3$, $R^5$ and $R^7$ corresponds to line D4-24 of Table D4 and the meaning for the combination of $R^1$ and $R^2$ for each individual compound corresponds in each case to one line of Table B (compounds I.A4a.D4-24.B1 to I.A4a.D4-24.B550).

Table 25e Compounds of the formula I.A4a in which the combination of $R^3$, $R^5$ and $R^7$ corresponds to line D4-25 of Table D4 and the meaning for the combination of $R^1$ and $R^2$ for each individual compound corresponds in each case to one line of Table B (compounds I.A4a.D4-25.B1 to I.A4a.D4-25.B550).

Table 26e Compounds of the formula I.A4a in which the combination of $R^3$, $R^5$ and $R^7$ corresponds to line D4-26 of Table D4 and the meaning for the combination of $R^1$ and $R^2$ for each individual compound corresponds in each case to one line of Table B (compounds I.A4a.D4-26.B1 to I.A4a.D4-26.B550).

Table 27e Compounds of the formula I.A4a in which the combination of $R^3$, $R^5$ and $R^7$ corresponds to line D4-27 of Table D4 and the meaning for the combination of $R^1$ and $R^2$ for each individual compound corresponds in each case to one line of Table B (compounds I.A4a.D4-27.B1 to I.A4a.D4-27.B550).

Table 28e Compounds of the formula I.A4a in which the combination of $R^3$, $R^5$ and $R^7$ corresponds to line D4-28 of Table D4 and the meaning for the combination of $R^1$ and $R^2$ for each individual compound corresponds in each case to one line of Table B (compounds I.A4a.D4-28.B1 to I.A4a.D4-28.B550).

Table 1f Compounds of the formula I.A4b in which the combination of $R^3$, $R^5$ and $R^7$ corresponds to line D4-1 of Table D4 and the meaning for the combination of $R^1$ and $R^2$ for each individual compound corresponds in each case to one line of Table B (compounds I.A4b.D4-1.B1 to I.A4b.D4-1.B550).

Table 2f Compounds of the formula I.A4b in which the combination of $R^3$, $R^5$ and $R^7$ corresponds to line D4-2 of Table D4 and the meaning for the combination of $R^1$ and $R^2$ for each individual compound corresponds in each case to one line of Table B (compounds I.A4b.D4-2.B1 to I.A4b.D4-2.B550).

Table 3f Compounds of the formula I.A4b in which the combination of $R^3$, $R^5$ and $R^7$ corresponds to line D4-3 of Table D4 and the meaning for the combination of $R^1$ and $R^2$ for each individual compound corresponds in each case to one line of Table B (compounds I.A4b.D4-3.B1 to I.A4b.D4-3.B550).

Table 4f Compounds of the formula I.A4b in which the combination of $R^3$, $R^5$ and $R^7$ corresponds to line D4-4 of Table D4 and the meaning for the combination of $R^1$ and $R^2$ for each individual compound corresponds in each case to one line of Table B (compounds I.A4b.D4-4.B1 to I.A4b.D4-4.B550).

Table 5f Compounds of the formula I.A4b in which the combination of $R^3$, $R^5$ and $R^7$ corresponds to line D4-5 of Table D4 and the meaning for the combination of $R^1$ and $R^2$ for each individual compound corresponds in each case to one line of Table B (compounds I.A4b.D4-5.B1 to I.A4b.D4-5.B550).

Table 6f Compounds of the formula I.A4b in which the combination of $R^3$, $R^5$ and $R^7$ corresponds to line D4-6 of Table D4 and the meaning for the combination of $R^1$ and $R^2$ for each individual compound corresponds in each case to one line of Table B (compounds I.A4b.D4-6.B1 to I.A4b.D4-6.B550).

Table 7f Compounds of the formula I.A4b in which the combination of $R^3$, $R^5$ and $R^7$ corresponds to line D4-7 of Table D4 and the meaning for the combination of $R^1$ and $R^2$ for each individual compound corresponds in each case to one line of Table B (compounds I.A4b.D4-7.B1 to I.A4b.D4-7.B550).

Table 8f Compounds of the formula I.A4b in which the combination of $R^3$, $R^5$ and $R^7$ corresponds to line D4-8 of Table D4 and the meaning for the combination of $R^1$ and $R^2$ for each individual compound corresponds in each case to one line of Table B (compounds I.A4b.D4-8.B1 to I.A4b.D4-8.B550).

Table 9f Compounds of the formula I.A4b in which the combination of $R^3$, $R^5$ and $R^7$ corresponds to line D4-9 of Table D4 and the meaning for the combination of $R^1$ and $R^2$ for each individual compound corresponds in each case to one line of Table B (compounds I.A4b.D4-9.B1 to I.A4b.D4-9.B550).

Table 10 Of Compounds of the formula I.A4b in which the combination of $R^3$, $R^5$ and $R^7$ corresponds to line D4-10 of Table D4 and the meaning for the combination of $R^1$ and $R^2$ for each individual compound corresponds in each case to one line of Table B (compounds I.A4b.D4-10.B1 to I.A4b.D4-10.B550).

Table 11f Compounds of the formula I.A4b in which the combination of $R^3$, $R^5$ and $R^7$ corresponds to line D4-11 of Table D4 and the meaning for the combination of $R^1$ and $R^2$ for each individual compound corresponds in each case to one line of Table B (compounds I.A4b.D4-11.B1 to I.A4b.D4-11.B550).

Table 12f Compounds of the formula I.A4b in which the combination of $R^3$, $R^5$ and $R^7$ corresponds to line D4-12 of Table D4 and the meaning for the combination of $R^1$ and $R^2$ for each individual compound corresponds in each case to one line of Table B (compounds I.A4b.D4-12.B1 to I.A4b.D4-12.B550).

Table 13f Compounds of the formula I.A4b in which the combination of $R^3$, $R^5$ and $R^7$ corresponds to line D4-13 of Table D4 and the meaning for the combination of $R^1$ and $R^2$ for each individual compound corresponds in each case to one line of Table B (compounds I.A4b.D4-13.B1 to I.A4b.D4-13.B550).

Table 14f Compounds of the formula I.A4b in which the combination of $R^3$, $R^5$ and $R^7$ corresponds to line D4-14 of Table D4 and the meaning for the combination of $R^1$ and $R^2$ for each individual compound corresponds in each case to one line of Table B (compounds I.A4b.D4-14.B1 to I.A4b.D4-14.B550).

Table 15f Compounds of the formula I.A4b in which the combination of $R^3$, $R^5$ and $R^7$ corresponds to line D4-15 of Table D4 and the meaning for the combination of $R^1$ and $R^2$ for each individual compound corresponds in each case to one line of Table B (compounds I.A4b.D4-15.B1 to I.A4b.D4-15.B550).

Table 16f Compounds of the formula I.A4b in which the combination of $R^3$, $R^5$ and $R^7$ corresponds to line D4-16 of Table D4 and the meaning for the combination of $R^1$ and $R^2$ for each individual compound corresponds in each case to one line of Table B (compounds I.A4b.D4-16.B1 to I.A4b.D4-16.B550).

Table 17f Compounds of the formula I.A4b in which the combination of $R^3$, $R^5$ and $R^7$ corresponds to line D4-17 of Table D4 and the meaning for the combination of $R^1$ and $R^2$ for each individual compound corresponds in each case to one line of Table B (compounds I.A4b.D4-17.B1 to I.A4b.D4-17.B550).

Table 18f Compounds of the formula I.A4b in which the combination of $R^3$, $R^5$ and $R^7$ corresponds to line D4-18 of Table D4 and the meaning for the combination of $R^1$ and $R^2$ for each individual compound corresponds in each case to one line of Table B (compounds I.A4b.D4-18.B1 to I.A4b.D4-18.B550).

Table 19f Compounds of the formula I.A4b in which the combination of $R^3$, $R^5$ and $R^7$ corresponds to line D4-19 of Table D4 and the meaning for the combination of $R^1$ and $R^2$ for each individual compound corresponds in each case to one line of Table B (compounds I.A4b.D4-19.B1 to I.A4b.D4-19.B550).

Table 20f Compounds of the formula I.A4b in which the combination of $R^3$, $R^5$ and $R^7$ corresponds to line D4-20 of Table D4 and the meaning for the combination of $R^1$ and $R^2$ for each individual compound corresponds in each case to one line of Table B (compounds I.A4b.D4-20.B1 to I.A4b.D4-20.B550).

Table 21f Compounds of the formula I.A4b in which the combination of $R^3$, $R^5$ and $R^7$ corresponds to line D4-21 of Table D4 and the meaning for the combination of $R^1$ and $R^2$ for each individual compound corresponds in each case to one line of Table B (compounds I.A4b.D4-21.B1 to I.A4b.D4-21.B550).

Table 22f Compounds of the formula I.A4b in which the combination of $R^3$, $R^5$ and $R^7$ corresponds to line D4-22 of Table D4 and the meaning for the combination of $R^1$ and $R^2$ for each individual compound corresponds in each case to one line of Table B (compounds I.A4b.D4-22.B1 to I.A4b.D4-22.B550).

Table 23f Compounds of the formula I.A4b in which the combination of $R^3$, $R^5$ and $R^7$ corresponds to line D4-23 of Table D4 and the meaning for the combination of $R^1$ and $R^2$ for each individual compound corresponds in each case to one line of Table B (compounds I.A4b.D4-23.B1 to I.A4b.D4-23.B550).

Table 24f Compounds of the formula I.A4b in which the combination of $R^3$, $R^5$ and $R^7$ corresponds to line D4-24 of Table D4 and the meaning for the combination of $R^1$ and $R^2$ for each individual compound corresponds in each case to one line of Table B (compounds I.A4b.D4-24.B1 to I.A4b.D4-24.B550).

Table 25f Compounds of the formula I.A4b in which the combination of $R^3$, $R^5$ and $R^7$ corresponds to line D4-25 of Table D4 and the meaning for the combination of $R^1$ and $R^2$ for each individual compound corresponds in each case to one line of Table B (compounds I.A4b.D4-25.B1 to I.A4b.D4-25.B550).

Table 26f Compounds of the formula I.A4b in which the combination of $R^3$, $R^5$ and $R^7$ corresponds to line D4-26 of Table D4 and the meaning for the combination of $R^1$ and $R^2$ for each individual compound corresponds in each case to one line of Table B (compounds I.A4b.D4-26.B1 to I.A4b.D4-26.B550).

Table 27f Compounds of the formula I.A4b in which the combination of $R^3$, $R^5$ and $R^7$ corresponds to line D4-27 of Table D4 and the meaning for the combination of $R^1$ and $R^2$ for each individual compound corresponds in each case to one line of Table B (compounds I.A4b.D4-27.B1 to I.A4b.D4-27.B550).

Table 28f Compounds of the formula I.A4b in which the combination of $R^3$, $R^5$ and $R^7$ corresponds to line D4-28 of Table D4 and the meaning for the combination of $R^1$ and $R^2$ for each individual compound corresponds in each case to one line of Table B (compounds I.A4b.D4-28.B1 to I.A4b.D4-28.B550).

Table 1 g Compounds of the formula I.Aa in which the combination of $R^3$, $R^5$, $R^6$ and $R^7$ corresponds to line D5-1 of Table D5 and the meaning for the combination of $R^1$ and $R^2$ for each individual compound corresponds in each case to one line of Table B (compounds I.Aa.D5-1.B1 to I.Aa.D5-1.B550).

Table 2g Compounds of the formula I.Aa in which the combination of $R^3$, $R^5$, $R^6$ and $R^7$ corresponds to line D5-2 of Table D5 and the meaning for the combination of $R^1$ and $R^2$ for each individual compound corresponds in each case to one line of Table B (compounds I.Aa.D5-2.B1 to I.Aa.D5-2.B550).

Table 3g Compounds of the formula I.Aa in which the combination of $R^3$, $R^5$, $R^6$ and $R^7$ corresponds to line D5-3 of Table D5 and the meaning for the combination of $R^1$ and $R^2$ for each individual compound corresponds in each case to one line of Table B (compounds I.Aa.D5-3.B1 to I.Aa.D5-3.B550).

Table 4g Compounds of the formula I.Aa in which the combination of $R^3$, $R^5$, $R^6$ and $R^7$ corresponds to line D5-4 of Table D5 and the meaning for the combination of $R^1$ and $R^2$ for each individual compound corresponds in each case to one line of Table B (compounds I.Aa.D5-4.B1 to I.Aa.D5-4.B550).

Table 5g Compounds of the formula I.Aa in which the combination of $R^3$, $R^5$, $R^6$ and $R^7$ corresponds to line D5-5 of Table D5 and the meaning for the combination of $R^1$ and $R^2$ for each individual compound corresponds in each case to one line of Table B (compounds I.Aa.D5-5.B1 to I.Aa.D5-5.B550).

Table 6g Compounds of the formula I.Aa in which the combination of $R^3$, $R^5$, $R^6$ and $R^7$ corresponds to line D5-6 of Table D5 and the meaning for the combination of $R^1$ and $R^2$ for each individual compound corresponds in each case to one line of Table B (compounds I.Aa.D5-6.B1 to I.Aa.D5-6.B550).

Table 7g Compounds of the formula I.Aa in which the combination of $R^3$, $R^5$, $R^6$ and $R^7$ corresponds to line D5-7 of Table D5 and the meaning for the combination of $R^1$ and $R^2$ for each individual compound corresponds in each case to one line of Table B (compounds I.Aa.D5-7.B1 to I.Aa.D5-7.B550).

Table 8g Compounds of the formula I.Aa in which the combination of $R^3$, $R^5$, $R^6$ and $R^7$ corresponds to line D5-8 of Table D5 and the meaning for the combination of $R^1$ and $R^2$ for each individual compound corresponds in each case to one line of Table B (compounds I.Aa.D5-8.B1 to I.Aa.D5-8.B550).

Table 9g Compounds of the formula I.Aa in which the combination of $R^3$, $R^5$, $R^6$ and $R^7$ corresponds to line D5-9 of Table D5 and the meaning for the combination of $R^1$ and $R^2$ for each individual compound corresponds in each case to one line of Table B (compounds I.Aa.D5-9.B1 to I.Aa.D5-9.B550).

Table 10g Compounds of the formula I.Aa in which the combination of $R^3$, $R^5$, $R^6$ and $R^7$ corresponds to line D5-10 of Table D5 and the meaning for the combination of $R^1$ and $R^2$ for each individual compound corresponds in each case to one line of Table B (compounds I.Aa.D5-10.B1 to I.Aa.D5-10.B550).

Table 11g Compounds of the formula I.Aa in which the combination of $R^3$, $R^5$, $R^6$ and $R^7$ corresponds to line D5-11 of Table D5 and the meaning for the combination of $R^1$ and $R^2$ for each individual compound corresponds in each case to one line of Table B (compounds I.Aa.D5-11.B1 to I.Aa.D5-11.B550).

Table 12g Compounds of the formula I.Aa in which the combination of $R^3$, $R^5$, $R^6$ and $R^7$ corresponds to line D5-12 of Table D5 and the meaning for the combination of $R^1$ and $R^2$ for each individual compound corresponds in each case to one line of Table B (compounds I.Aa.D5-12.B1 to I.Aa.D5-12.B550).

Table 13g Compounds of the formula I.Aa in which the combination of $R^3$, $R^5$, $R^6$ and $R^7$ corresponds to line D5-13 of Table D5 and the meaning for the combination of $R^1$ and $R^2$ for each individual compound corresponds in each case to one line of Table B (compounds I.Aa.D5-13.B1 to I.Aa.D5-13.B550).

Table 14g Compounds of the formula I.Aa in which the combination of $R^3$, $R^5$, $R^6$ and $R^7$ corresponds to line D5-14 of Table D5 and the meaning for the combination of $R^1$ and $R^2$ for each individual compound corresponds in each case to one line of Table B (compounds I.Aa.D5-14.B1 to I.Aa.D5-14.B550).

Table 15g Compounds of the formula I.Aa in which the combination of $R^3$, $R^5$, $R^6$ and $R^7$ corresponds to line D5-15 of Table D5 and the meaning for the combination of $R^1$ and $R^2$ for each individual compound corresponds in each case to one line of Table B (compounds I.Aa.D5-15.B1 to I.Aa.D5-15.B550).

Table 16g Compounds of the formula I.Aa in which the combination of $R^3$, $R^5$, $R^6$ and $R^7$ corresponds to line D5-16 of Table D5 and the meaning for the combination of $R^1$ and $R^2$ for each individual compound corresponds in each case to one line of Table B (compounds I.Aa.D5-16.B1 to I.Aa.D5-16.B550).

Table 17g Compounds of the formula I.Aa in which the combination of $R^3$, $R^5$, $R^6$ and $R^7$ corresponds to line D5-17 of Table D5 and the meaning for the combination of $R^1$ and $R^2$ for each individual compound corresponds in each case to one line of Table B (compounds I.Aa.D5-17.B1 to I.Aa.D5-17.B550).

Table 18g Compounds of the formula I.Aa in which the combination of $R^3$, $R^5$, $R^6$ and $R^7$ corresponds to line D5-18 of Table D5 and the meaning for the combination of $R^1$ and $R^2$ for each individual compound corresponds in each case to one line of Table B (compounds I.Aa.D5-18.B1 to I.Aa.D5-18.B550).

Table 19g Compounds of the formula I.Aa in which the combination of $R^3$, $R^5$, $R^6$ and $R^7$ corresponds to line D5-19 of Table D5 and the meaning for the combination of $R^1$ and $R^2$ for each individual compound corresponds in each case to one line of Table B (compounds I.Aa.D5-19.B1 to I.Aa.D5-19.B550).

Table 20g Compounds of the formula I.Aa in which the combination of $R^3$, $R^5$, $R^6$ and $R^7$ corresponds to line D5-20 of Table D5 and the meaning for the combination of $R^1$ and $R^2$ for each individual compound corresponds in each case to one line of Table B (compounds I.Aa.D5-20.B1 to I.Aa.D5-20.B550).

Table 21g Compounds of the formula I.Aa in which the combination of $R^3$, $R^5$, $R^6$ and $R^7$ corresponds to line D5-21 of Table D5 and the meaning for the combination of $R^1$ and $R^2$ for each individual compound corresponds in each case to one line of Table B (compounds I.Aa.D5-21.B1 to I.Aa.D5-21.B550).

Table 22g Compounds of the formula I.Aa in which the combination of $R^3$, $R^5$, $R^6$ and $R^7$ corresponds to line D5-22 of Table D5 and the meaning for the combination of $R^1$ and $R^2$ for each individual compound corresponds in each case to one line of Table B (compounds I.Aa.D5-22.B1 to I.Aa.D5-22.B550).

Table 23g Compounds of the formula I.Aa in which the combination of $R^3$, $R^5$, $R^6$ and $R^7$ corresponds to line D5-23 of Table D5 and the meaning for the combination of $R^1$ and $R^2$ for each individual compound corresponds in each case to one line of Table B (compounds I.Aa.D5-23.B1 to I.Aa.D5-23.B550).

Table 24g Compounds of the formula I.Aa in which the combination of $R^3$, $R^5$, $R^6$ and $R^7$ corresponds to line D5-24 of Table D5 and the meaning for the combination of $R^1$ and $R^2$ for each individual compound corresponds in each case to one line of Table B (compounds I.Aa.D5-24.B1 to I.Aa.D5-24.B550).

Table 25g Compounds of the formula I.Aa in which the combination of $R^3$, $R^5$, $R^6$ and $R^7$ corresponds to line D5-25 of Table D5 and the meaning for the combination of $R^1$ and $R^2$ for each individual compound corresponds in each case to one line of Table B (compounds I.Aa.D5-25.B1 to I.Aa.D5-25.B550).

Table 26g Compounds of the formula I.Aa in which the combination of $R^3$, $R^5$, $R^6$ and $R^7$ corresponds to line D5-26 of Table D5 and the meaning for the combination of $R^1$ and $R^2$ for each individual compound corresponds in each case to one line of Table B (compounds I.Aa.D5-26.B1 to I.Aa.D5-26.B550).

Table 27g Compounds of the formula I.Aa in which the combination of $R^3$, $R^5$, $R^6$ and $R^7$ corresponds to line D5-27 of Table D5 and the meaning for the combination of $R^1$ and $R^2$ for each individual compound corresponds in each case to one line of Table B (compounds I.Aa.D5-27.B1 to I.Aa.D5-27.B550).

Table 28g Compounds of the formula I.Aa in which the combination of $R^3$, $R^5$, $R^6$ and $R^7$ corresponds to line D5-28 of Table D5 and the meaning for the combination of $R^1$ and $R^2$ for each individual compound corresponds in each case to one line of Table B (compounds I.Aa.D5-28.B1 to I.Aa.D5-28.B550).

Table 29g Compounds of the formula I.Aa in which the combination of $R^3$, $R^5$, $R^6$ and $R^7$ corresponds to line D5-29 of Table D5 and the meaning for the combination of $R^1$ and $R^2$ for each individual compound corresponds in each case to one line of Table B (compounds I.Aa.D5-29.B1 to I.Aa.D5-29.B550).

Table 30g Compounds of the formula I.Aa in which the combination of $R^3$, $R^5$, $R^6$ and $R^7$ corresponds to line D5-30 of Table D5 and the meaning for the combination of $R^1$ and $R^2$ for each individual compound corresponds in each case to one line of Table B (compounds I.Aa.D5-30.B1 to I.Aa.D5-30.B550).

Table 31g Compounds of the formula I.Aa in which the combination of $R^3$, $R^5$, $R^6$ and $R^7$ corresponds to line D5-31 of Table D5 and the meaning for the combination of $R^1$ and $R^2$ for each individual compound corresponds in each case to one line of Table B (compounds I.Aa.D5-31.B1 to I.Aa.D5-31.B550).

Table 32g Compounds of the formula I.Aa in which the combination of $R^3$, $R^5$, $R^6$ and $R^7$ corresponds to line D5-32 of Table D5 and the meaning for the combination of $R^1$ and $R^2$ for each individual compound corresponds in each case to one line of Table B (compounds I.Aa.D5-32.B1 to I.Aa.D5-32.B550).

Table 33g Compounds of the formula I.Aa in which the combination of $R^3$, $R^5$, $R^6$ and $R^7$ corresponds to line D5-33 of Table D5 and the meaning for the combination of $R^1$ and $R^2$ for each individual compound corresponds in each case to one line of Table B (compounds I.Aa.D5-33.B1 to I.Aa.D5-33.B550).

Table 34g Compounds of the formula I.Aa in which the combination of $R^3$, $R^5$, $R^6$ and $R^7$ corresponds to line D5-34 of Table D5 and the meaning for the combination of $R^1$ and $R^2$ for each individual compound corresponds in each case to one line of Table B (compounds I.Aa.D5-34.B1 to I.Aa.D5-34.B550).

Table 35g Compounds of the formula I.Aa in which the combination of $R^3$, $R^5$, $R^6$ and $R^7$ corresponds to line D5-35 of Table D5 and the meaning for the combination of $R^1$ and $R^2$ for each individual compound corresponds in each case to one line of Table B (compounds I.Aa.D5-35.B1 to I.Aa.D5-35.B550).

Table 36g Compounds of the formula I.Aa in which the combination of $R^3$, $R^5$, $R^6$ and $R^7$ corresponds to line D5-36 of Table D5 and the meaning for the combination of $R^1$ and $R^2$ for each individual compound corresponds in each case to one line of Table B (compounds I.Aa.D5-36.B1 to I.Aa.D5-36.B550).

Table 37g Compounds of the formula I.Aa in which the combination of $R^3$, $R^5$, $R^6$ and $R^7$ corresponds to line D5-37 of Table D5 and the meaning for the combination of $R^1$ and $R^2$ for each individual compound corresponds in each case to one line of Table B (compounds I.Aa.D5-37.B1 to I.Aa.D5-37.B550).

Table 38g Compounds of the formula I.Aa in which the combination of $R^3$, $R^5$, $R^6$ and $R^7$ corresponds to line D5-38 of Table D5 and the meaning for the combination of $R^1$ and $R^2$ for each individual compound corresponds in each case to one line of Table B (compounds I.Aa.D5-38.B1 to I.Aa.D5-38.B550).

Table 39g Compounds of the formula I.Aa in which the combination of $R^3$, $R^5$, $R^6$ and $R^7$ corresponds to line D5-39 of Table D5 and the meaning for the combination of $R^1$ and $R^2$ for each individual compound corresponds in each case to one line of Table B (compounds I.Aa.D5-39.B1 to I.Aa.D5-39.B550).

Table 40g Compounds of the formula I.Aa in which the combination of $R^3$, $R^5$, $R^6$ and $R^7$ corresponds to line D5-40 of Table D5 and the meaning for the combination of $R^1$ and $R^2$ for each individual compound corresponds in each case to one line of Table B (compounds I.Aa.D5-40.B1 to I.Aa.D5-40.B550).

Table 41g Compounds of the formula I.Aa in which the combination of $R^3$, $R^5$, $R^6$ and $R^7$ corresponds to line D5-41 of Table D5 and the meaning for the combination of $R^1$ and $R^2$ for each individual compound corresponds in each case to one line of Table B (compounds I.Aa.D5-41.B1 to I.Aa.D5-41.B550).

Table 42g Compounds of the formula I.Aa in which the combination of $R^3$, $R^5$, $R^6$ and $R^7$ corresponds to line D5-42 of Table D5 and the meaning for the combination of $R^1$ and $R^2$ for each individual compound corresponds in each case to one line of Table B (compounds I.Aa.D5-42.B1 to I.Aa.D5-42.B550).

Table 43g Compounds of the formula I.Aa in which the combination of $R^3$, $R^5$, $R^6$ and $R^7$ corresponds to line D5-43 of Table D5 and the meaning for the combination of $R^1$ and $R^2$ for each individual compound corresponds in each case to one line of Table B (compounds I.Aa.D5-43.B1 to I.Aa.D5-43.B550).

Table 44g Compounds of the formula I.Aa in which the combination of $R^3$, $R^5$, $R^6$ and $R^7$ corresponds to line D5-44 of Table D5 and the meaning for the combination of $R^1$ and $R^2$ for each individual compound corresponds in each case to one line of Table B (compounds I.Aa.D5-44.B1 to I.Aa.D5-44.B550).

Table 45g Compounds of the formula I.Aa in which the combination of $R^3$, $R^5$, $R^6$ and $R^7$ corresponds to line D5-45 of Table D5 and the meaning for the combination of $R^1$ and $R^2$ for each individual compound corresponds in each case to one line of Table B (compounds I.Aa.D5-45.B1 to I.Aa.D5-45.B550).

Table 46g Compounds of the formula I.Aa in which the combination of $R^3$, $R^5$, $R^6$ and $R^7$ corresponds to line D5-46 of Table D5 and the meaning for the combination of $R^1$ and $R^2$ for each individual compound corresponds in each case to one line of Table B (compounds I.Aa.D5-46.B1 to I.Aa.D5-46.B550).

Table 47g Compounds of the formula I.Aa in which the combination of $R^3$, $R^5$, $R^6$ and $R^7$ corresponds to line D5-47 of Table D5 and the meaning for the combination of $R^1$ and $R^2$ for each individual compound corresponds in each case to one line of Table B (compounds I.Aa.D5-47.B1 to I.Aa.D5-47.B550).

Table 48g Compounds of the formula I.Aa in which the combination of $R^3$, $R^5$, $R^6$ and $R^7$ corresponds to line D5-48 of Table D5 and the meaning for the combination of $R^1$ and $R^2$ for each individual compound corresponds in each case to one line of Table B (compounds I.Aa.D5-48.B1 to I.Aa.D5-48.B550).

Table 49g Compounds of the formula I.Aa in which the combination of $R^3$, $R^5$, $R^6$ and $R^7$ corresponds to line D5-49 of Table D5 and the meaning for the combination of $R^1$ and $R^2$ for each individual compound corresponds in each case to one line of Table B (compounds I.Aa.D5-49.B1 to I.Aa.D5-49.B550).

Table 50g Compounds of the formula I.Aa in which the combination of $R^3$, $R^5$, $R^6$ and $R^7$ corresponds to line D5-50 of Table D5 and the meaning for the combination of $R^1$ and $R^2$ for each individual compound corresponds in each case to one line of Table B (compounds I.Aa.D5-50.B1 to I.Aa.D5-50.B550).

Table 51g Compounds of the formula I.Aa in which the combination of $R^3$, $R^5$, $R^6$ and $R^7$ corresponds to line D5-51 of Table D5 and the meaning for the combination of $R^1$ and $R^2$ for each individual compound corresponds in each case to one line of Table B (compounds I.Aa.D5-51.B1 to I.Aa.D5-51.B550).

Table 52g Compounds of the formula I.Aa in which the combination of $R^3$, $R^5$, $R^6$ and $R^7$ corresponds to line D5-52 of Table D5 and the meaning for the combination of $R^1$ and $R^2$ for each individual compound corresponds in each case to one line of Table B (compounds I.Aa.D5-52.B1 to I.Aa.D5-52.B550).

Table 53g Compounds of the formula I.Aa in which the combination of $R^3$, $R^5$, $R^6$ and $R^7$ corresponds to line D5-53 of Table D5 and the meaning for the combination of $R^1$ and $R^2$ for each individual compound corresponds in each case to one line of Table B (compounds I.Aa.D5-53.B1 to I.Aa.D5-53.B550).

Table 54g Compounds of the formula I.Aa in which the combination of $R^3$, $R^5$, $R^6$ and $R^7$ corresponds to line D5-54 of Table D5 and the meaning for the combination of $R^1$ and $R^2$ for each individual compound corresponds in each case to one line of Table B (compounds I.Aa.D5-54.B1 to I.Aa.D5-54.B550).

Table 55g Compounds of the formula I.Aa in which the combination of $R^3$, $R^5$, $R^6$ and $R^7$ corresponds to line D5-55 of Table D5 and the meaning for the combination of $R^1$ and $R^2$ for each individual compound corresponds in each case to one line of Table B (compounds I.Aa.D5-55.B1 to I.Aa.D5-55.B550).

Table 56g Compounds of the formula I.Aa in which the combination of $R^3$, $R^5$, $R^6$ and $R^7$ corresponds to line D5-56 of Table D5 and the meaning for the combination of $R^1$ and $R^2$ for each individual compound corresponds in each case to one line of Table B (compounds I.Aa.D5-56.B1 to I.Aa.D5-56.B550).

Table 1h Compounds of the formula I.A5-1a in which the combination of $R^3$, $(R^4)_m$, $R^5$ and $R^6$ corresponds to line D6-1 of Table D6 and the meaning for the combination of $R^1$ and $R^2$ for each individual compound corresponds in each case to one line of Table B (compounds I.A5-1a.D6-1.B1 to I.A5-1a.D6-1.B550).

Table 2h Compounds of the formula I.A5-1a in which the combination of $R^3$, $(R^4)_m$, $R^5$ and $R^6$ corresponds to line D6-2 of Table D6 and the meaning for the combination of $R^1$ and $R^2$ for each individual compound corresponds in each case to one line of Table B (compounds I.A5-1a.D6-2.B1 to I.A5-1a.D6-2.B550).

Table 3h Compounds of the formula I.A5-1a in which the combination of $R^3$, $(R^4)_m$, $R^5$ and $R^6$ corresponds to line D6-3 of Table D6 and the meaning for the combination of $R^1$ and $R^2$ for each individual compound corresponds in each case to one line of Table B (compounds I.A5-1a.D6-3.B1 to I.A5-1a.D6-3.B550).

Table 4h Compounds of the formula I.A5-1a in which the combination of $R^3$, $(R^4)_m$, $R^5$ and $R^6$ corresponds to line D6-4 of Table D6 and the meaning for the combination of $R^1$ and $R^2$ for each individual compound corresponds in each case to one line of Table B (compounds I.A5-1a.D6-4.B1 to I.A5-1a.D6-4.B550).

Table 5h Compounds of the formula I.A5-1a in which the combination of $R^3$, $(R^4)_m$, $R^5$ and $R^6$ corresponds to line D6-5 of Table D6 and the meaning for the combination of $R^1$ and $R^2$ for each individual compound corresponds in each case to one line of Table B (compounds I.A5-1a.D6-5.B1 to I.A5-1a.D6-5.B550).

Table 6h Compounds of the formula I.A5-1a in which the combination of $R^3$, $(R^4)_m$, $R^5$ and $R^6$ corresponds to line D6-6 of Table D6 and the meaning for the combination of $R^1$ and $R^2$ for each individual compound corresponds in each case to one line of Table B (compounds I.A5-1a.D6-6.B1 to I.A5-1a.D6-6.B550).

Table 7h Compounds of the formula I.A5-1a in which the combination of $R^3$, $(R^4)_m$, $R^5$ and $R^6$ corresponds to line D6-7 of Table D6 and the meaning for the combination of $R^1$ and $R^2$ for each individual compound corresponds in each case to one line of Table B (compounds I.A5-1a.D6-7.B1 to I.A5-1a.D6-7.B550).

Table 8h Compounds of the formula I.A5-1a in which the combination of $R^3$, $(R^4)_m$, $R^5$ and $R^6$ corresponds to line D6-8 of Table D6 and the meaning for the combination of $R^1$ and $R^2$ for each individual compound corresponds in each case to one line of Table B (compounds I.A5-1a.D6-8.B1 to I.A5-1a.D6-8.B550).

Table 9h Compounds of the formula I.A5-1a in which the combination of $R^3$, $(R^4)_m$, $R^5$ and $R^6$ corresponds to line D6-9 of Table D6 and the meaning for the combination of $R^1$ and $R^2$ for each individual compound corresponds in each case to one line of Table B (compounds I.A5-1a.D6-9.B1 to I.A5-1a.D6-9.B550).

Table 10h Compounds of the formula I.A5-1a in which the combination of $R^3$, $(R^4)_m$, $R^5$ and $R^6$ corresponds to line D6-10 of Table D6 and the meaning for the combination of $R^1$ and $R^2$ for each individual compound corresponds in each case to one line of Table B (compounds I.A5-1a.D6-10.B1 to I.A5-1a.D6-10.B550).

Table 11 h Compounds of the formula I.A5-1a in which the combination of $R^3$, $(R^4)_m$, $R^5$ and $R^6$ corresponds to line D6-11 of Table D6 and the meaning for the combination of $R^1$ and $R^2$ for each individual compound corresponds in each case to one line of Table B (compounds I.A5-1a.D6-11.B1 to I.A5-1a.D6-11.B550).

Table 12h Compounds of the formula I.A5-1a in which the combination of $R^3$, $(R^4)_m$, $R^5$ and $R^6$ corresponds to line D6-12 of Table D6 and the meaning for the combination of $R^1$ and $R^2$ for each individual compound corresponds in each case to one line of Table B (compounds I.A5-1a.D6-12.B1 to I.A5-1a.D6-12.B550).

Table 13h Compounds of the formula I.A5-1a in which the combination of $R^3$, $(R^4)_m$, $R^5$ and $R^6$ corresponds to line D6-13 of Table D6 and the meaning for the combination of $R^1$ and $R^2$ for each individual compound corresponds in each case to one line of Table B (compounds I.A5-1a.D6-13.B1 to I.A5-1a.D6-13.B550).

Table 14h Compounds of the formula I.A5-1a in which the combination of $R^3$, $(R^4)_m$, $R^5$ and $R^6$ corresponds to line D6-14 of Table D6 and the meaning for the combination of $R^1$ and $R^2$ for each individual compound corresponds in each case to one line of Table B (compounds I.A5-1a.D6-14.B1 to I.A5-1a.D6-14.B550).

Table 15h Compounds of the formula I.A5-1a in which the combination of $R^3$, $(R^4)_m$, $R^5$ and $R^6$ corresponds to line D6-15 of Table D6 and the meaning for the combination of $R^1$ and $R^2$ for each individual compound corresponds in each case to one line of Table B (compounds I.A5-1a.D6-15.B1 to I.A5-1a.D6-15.B550).

Table 16h Compounds of the formula I.A5-1a in which the combination of $R^3$, $(R^4)_m$, $R^5$ and $R^6$ corresponds to line D6-16 of Table D6 and the meaning for the combination of $R^1$ and $R^2$ for each individual compound corresponds in each case to one line of Table B (compounds I.A5-1a.D6-16.B1 to I.A5-1a.D6-16.B550).

Table 17h Compounds of the formula I.A5-1a in which the combination of $R^3$, $(R^4)_m$, $R^5$ and $R^6$ corresponds to line D6-17 of Table D6 and the meaning for the combination of $R^1$ and $R^2$ for each individual compound corresponds in each case to one line of Table B (compounds I.A5-1a.D6-17.B1 to I.A5-1a.D6-17.B550).

Table 18h Compounds of the formula I.A5-1a in which the combination of $R^3$, $(R^4)_m$, $R^5$ and $R^6$ corresponds to line D6-18 of Table D6 and the meaning for the combination of $R^1$ and $R^2$ for each individual compound corresponds in each case to one line of Table B (compounds I.A5-1a.D6-18.B1 to I.A5-1a.D6-18.B550).

Table 19h Compounds of the formula I.A5-1a in which the combination of $R^3$, $(R^4)_m$, $R^5$ and $R^6$ corresponds to line D6-19 of Table D6 and the meaning for the combination of $R^1$ and $R^2$ for each individual compound corresponds in each case to one line of Table B (compounds I.A5-1a.D6-19.B1 to I.A5-1a.D6-19.B550).

Table 20h Compounds of the formula I.A5-1a in which the combination of $R^3$, $(R^4)_m$, $R^5$ and $R^6$ corresponds to line D6-20 of Table D6 and the meaning for the combination of $R^1$ and $R^2$ for each individual compound corresponds in each case to one line of Table B (compounds I.A5-1a.D6-20.B1 to I.A5-1a.D6-20.B550).

Table 21h Compounds of the formula I.A5-1a in which the combination of $R^3$, $(R^4)_m$, $R^5$ and $R^6$ corresponds to line D6-21 of Table D6 and the meaning for the combination of $R^1$ and $R^2$ for each individual compound corresponds in each case to one line of Table B (compounds I.A5-1a.D6-21.B1 to I.A5-1a.D6-21.B550).

Table 22h Compounds of the formula I.A5-1a in which the combination of $R^3$, $(R^4)_m$, $R^5$ and $R^6$ corresponds to line D6-22 of Table D6 and the meaning for the combination of $R^1$ and $R^2$ for each individual compound corresponds in each case to one line of Table B (compounds I.A5-1a.D6-22.B1 to I.A5-1a.D6-22.B550).

Table 23h Compounds of the formula I.A5-1a in which the combination of $R^3$, $(R^4)_m$, $R^5$ and $R^6$ corresponds to line D6-23 of Table D6 and the meaning for the combination of $R^1$ and $R^2$ for each individual compound corresponds in each case to one line of Table B (compounds I.A5-1a.D6-23.B1 to I.A5-1a.D6-23.B550).

Table 24h Compounds of the formula I.A5-1a in which the combination of $R^3$, $(R^4)_m$, $R^5$ and $R^6$ corresponds to line D6-24 of Table D6 and the meaning for the combination of $R^1$ and $R^2$ for each individual compound corresponds in each case to one line of Table B (compounds I.A5-1a.D6-24.B1 to I.A5-1a.D6-24.B550).

Table 25h Compounds of the formula I.A5-1a in which the combination of $R^3$, $(R^4)_m$, $R^5$ and $R^6$ corresponds to line D6-25 of Table D6 and the meaning for the combination of $R^1$ and $R^2$ for each individual compound corresponds in each case to one line of Table B (compounds I.A5-1a.D6-25.B1 to I.A5-1a.D6-25.B550).

Table 26h Compounds of the formula I.A5-1a in which the combination of $R^3$, $(R^4)_m$, $R^5$ and $R^6$ corresponds to line D6-26 of Table D6 and the meaning for the combination of $R^1$ and $R^2$ for each individual compound corresponds in each case to one line of Table B (compounds I.A5-1a.D6-26.B1 to I.A5-1a.D6-26.B550).

Table 27h Compounds of the formula I.A5-1a in which the combination of $R^3$, $(R^4)_m$, $R^5$ and $R^6$ corresponds to line D6-27 of Table D6 and the meaning for the combination of $R^1$ and $R^2$ for each individual compound corresponds in each case to one line of Table B (compounds I.A5-1a.D6-27.B1 to I.A5-1a.D6-27.B550).

Table 28h Compounds of the formula I.A5-1a in which the combination of $R^3$, $(R^4)_m$, $R^5$ and $R^6$ corresponds to line D6-28 of Table D6 and the meaning for the combination of $R^1$ and $R^2$ for each individual compound corresponds in each case to one line of Table B (compounds I.A5-1a.D6-28.B1 to I.A5-1a.D6-28.B550).

Table 29h Compounds of the formula I.A5-1a in which the combination of $R^3$, $(R^4)_m$, $R^5$ and $R^6$ corresponds to line D6-29 of Table D6 and the meaning for the combination of $R^1$ and $R^2$ for each individual compound corresponds in each case to one line of Table B (compounds I.A5-1a.D6-29.B1 to I.A5-1a.D6-29.B550).

Table 30h Compounds of the formula I.A5-1a in which the combination of $R^3$, $(R^4)_m$, $R^5$ and $R^6$ corresponds to line D6-30 of Table D6 and the meaning for the combination of $R^1$ and $R^2$ for each individual compound corresponds in each case to one line of Table B (compounds I.A5-1a.D6-30.B1 to I.A5-1a.D6-30.B550).

Table 31h Compounds of the formula I.A5-1a in which the combination of $R^3$, $(R^4)_m$, $R^5$ and $R^6$ corresponds to line D6-31 of Table D6 and the meaning for the combination of $R^1$ and $R^2$ for each individual compound corresponds in each case to one line of Table B (compounds I.A5-1a.D6-31.B1 to I.A5-1a.D6-31.B550).

Table 32h Compounds of the formula I.A5-1a in which the combination of $R^3$, $(R^4)_m$, $R^5$ and $R^6$ corresponds to line D6-32 of Table D6 and the meaning for the combination of $R^1$ and $R^2$ for each individual compound corresponds in each case to one line of Table B (compounds I.A5-1a.D6-32.B1 to I.A5-1a.D6-32.B550).

Table 33h Compounds of the formula I.A5-1a in which the combination of $R^3$, $(R^4)_m$, $R^5$ and $R^6$ corresponds to line D6-33 of Table D6 and the meaning for the combination of $R^1$ and $R^2$ for each individual compound corresponds in each case to one line of Table B (compounds I.A5-1a.D6-33.B1 to I.A5-1a.D6-33.B550).

Table 34h Compounds of the formula I.A5-1a in which the combination of $R^3$, $(R^4)_m$, $R^5$ and $R^6$ corresponds to line D6-34 of Table D6 and the meaning for the combination of $R^1$ and $R^2$ for each individual compound corresponds in each case to one line of Table B (compounds I.A5-1a.D6-34.B1 to I.A5-1a.D6-34.B550).

Table 35h Compounds of the formula I.A5-1a in which the combination of $R^3$, $(R^4)_m$, $R^5$ and $R^6$ corresponds to line D6-35 of Table D6 and the meaning for the combination of $R^1$ and $R^2$ for each individual compound corresponds in each case to one line of Table B (compounds I.A5-1a.D6-35.B1 to I.A5-1a.D6-35.B550).

Table 36h Compounds of the formula I.A5-1a in which the combination of $R^3$, $(R^4)_m$, $R^5$ and $R^6$ corresponds to line D6-36 of Table D6 and the meaning for the combination of $R^1$ and $R^2$ for each individual compound corresponds in each case to one line of Table B (compounds I.A5-1a.D6-36.B1 to I.A5-1a.D6-36.B550).

Table 37h Compounds of the formula I.A5-1a in which the combination of $R^3$, $(R^4)_m$, $R^5$ and $R^6$ corresponds to line D6-37 of Table D6 and the meaning for the combination of $R^1$ and $R^2$ for each individual compound corresponds in each case to one line of Table B (compounds I.A5-1a.D6-37.B1 to I.A5-1a.D6-37.B550).

Table 38h Compounds of the formula I.A5-1a in which the combination of $R^3$, $(R^4)_m$, $R^5$ and $R^6$ corresponds to line D6-38 of Table D6 and the meaning for the combination of $R^1$ and $R^2$ for each individual compound corresponds in each case to one line of Table B (compounds I.A5-1a.D6-38.B1 to I.A5-1a.D6-38.B550).

Table 39h Compounds of the formula I.A5-1a in which the combination of $R^3$, $(R^4)_m$, $R^5$ and $R^6$ corresponds to line D6-39 of Table D6 and the meaning for the combination of $R^1$ and $R^2$ for each individual compound corresponds in each case to one line of Table B (compounds I.A5-1a.D6-39.B1 to I.A5-1a.D6-39.B550).

Table 40h Compounds of the formula I.A5-1a in which the combination of $R^3$, $(R^4)_m$, $R^5$ and $R^6$ corresponds to line D6-40 of Table D6 and the meaning for the combination of $R^1$ and $R^2$ for each individual compound corresponds in each case to one line of Table B (compounds I.A5-1a.D6-40.B1 to I.A5-1a.D6-40.B550).

Table 41h Compounds of the formula I.A5-1a in which the combination of $R^3$, $(R^4)_m$, $R^5$ and $R^6$ corresponds to line D6-41 of Table D6 and the meaning for the combination of $R^1$ and $R^2$ for each individual compound corresponds in each case to one line of Table B (compounds I.A5-1a.D6-41.B1 to I.A5-1a.D6-41.B550).

Table 42h Compounds of the formula I.A5-1a in which the combination of $R^3$, $(R^4)_m$, $R^5$ and $R^6$ corresponds to line D6-42 of Table D6 and the meaning for the combination of $R^1$ and $R^2$ for each individual compound corresponds in each case to one line of Table B (compounds I.A5-1a.D6-42.B1 to I.A5-1a.D6-42.B550).

Table 43h Compounds of the formula I.A5-1a in which the combination of $R^3$, $(R^4)_m$, $R^5$ and $R^6$ corresponds to line D6-43 of Table D6 and the meaning for the combination of $R^1$ and $R^2$ for each individual compound corresponds in each case to one line of Table B (compounds I.A5-1a.D6-43.B1 to I.A5-1a.D6-43.B550).

Table 44h Compounds of the formula I.A5-1a in which the combination of $R^3$, $(R^4)_m$, $R^5$ and $R^6$ corresponds to line D6-44 of Table D6 and the meaning for the combination of $R^1$ and $R^2$ for each individual compound corresponds in each case to one line of Table B (compounds I.A5-1a.D6-44.B1 to I.A5-1a.D6-44.B550).

Table 45h Compounds of the formula I.A5-1a in which the combination of $R^3$, $(R^4)_m$, $R^5$ and $R^6$ corresponds to line D6-45 of Table D6 and the meaning for the combination of $R^1$ and $R^2$ for each individual compound corresponds in each case to one line of Table B (compounds I.A5-1a.D6-45.B1 to I.A5-1a.D6-45.B550).

Table 46h Compounds of the formula I.A5-1a in which the combination of $R^3$, $(R^4)_m$, $R^5$ and $R^6$ corresponds to line D6-46 of Table D6 and the meaning for the combination of $R^1$ and $R^2$ for each individual compound corresponds in each case to one line of Table B (compounds I.A5-1a.D6-46.B1 to I.A5-1a.D6-46.B550).

Table 47h Compounds of the formula I.A5-1a in which the combination of $R^3$, $(R^4)_m$, $R^5$ and $R^6$ corresponds to line D6-47 of Table D6 and the meaning for the combination of $R^1$ and $R^2$ for each individual compound corresponds in each case to one line of Table B (compounds I.A5-1a.D6-47.B1 to I.A5-1a.D6-47.B550).

Table 48h Compounds of the formula I.A5-1a in which the combination of $R^3$, $(R^4)_m$, $R^5$ and $R^6$ corresponds to line D6-48 of Table D6 and the meaning for the combination of $R^1$ and $R^2$ for each individual compound corresponds in each case to one line of Table B (compounds I.A5-1a.D6-48.B1 to I.A5-1a.D6-48.B550).

Table 49h Compounds of the formula I.A5-1a in which the combination of $R^3$, $(R^4)_m$, $R^5$ and $R^6$ corresponds to line D6-49 of Table D6 and the meaning for the combination of $R^1$ and $R^2$ for each individual compound corresponds in each case to one line of Table B (compounds I.A5-1a.D6-49.B1 to I.A5-1a.D6-49.B550).

Table 50h Compounds of the formula I.A5-1a in which the combination of $R^3$, $(R^4)_m$, $R^5$ and $R^6$ corresponds to line D6-50 of Table D6 and the meaning for the combination of $R^1$ and $R^2$ for each individual compound corresponds in each case to one line of Table B (compounds I.A5-1a.D6-50.B1 to I.A5-1a.D6-50.B550).

Table 51h Compounds of the formula I.A5-1a in which the combination of $R^3$, $(R^4)_m$, $R^5$ and $R^6$ corresponds to line D6-51 of Table D6 and the meaning for the combination of $R^1$ and $R^2$ for each individual compound corresponds in each case to one line of Table B (compounds I.A5-1a.D6-51.B1 to I.A5-1a.D6-51.B550).

Table 52h Compounds of the formula I.A5-1a in which the combination of $R^3$, $(R^4)_m$, $R^5$ and $R^6$ corresponds to line D6-52 of Table D6 and the meaning for the combination of $R^1$ and $R^2$ for each individual compound corresponds in each case to one line of Table B (compounds I.A5-1a.D6-52.B1 to I.A5-1a.D6-52.B550).

Table 53h Compounds of the formula I.A5-1a in which the combination of $R^3$, $(R^4)_m$, $R^5$ and $R^6$ corresponds to line D6-53 of Table D6 and the meaning for the combination of $R^1$ and $R^2$ for each individual compound corresponds in each case to one line of Table B (compounds I.A5-1a.D6-53.B1 to I.A5-1a.D6-53.B550).

Table 54h Compounds of the formula I.A5-1a in which the combination of $R^3$, $(R^4)_m$, $R^5$ and $R^6$ corresponds to line D6-54 of Table D6 and the meaning for the combination of $R^1$ and $R^2$ for each individual compound corresponds in each case to one line of Table B (compounds I.A5-1a.D6-54.B1 to I.A5-1a.D6-54.B550).

Table 55h Compounds of the formula I.A5-1a in which the combination of $R^3$, $(R^4)_m$, $R^5$ and $R^6$ corresponds to line D6-55 of Table D6 and the meaning for the combination of $R^1$ and $R^2$ for each individual compound corresponds in each case to one line of Table B (compounds I.A5-1a.D6-55.B1 to I.A5-1a.D6-55.B550).

Table 56h Compounds of the formula I.A5-1a in which the combination of $R^3$, $(R^4)_m$, $R^5$ and $R^6$ corresponds to line D6-56 of Table D6 and the meaning for the combination of $R^1$ and $R^2$ for each individual compound corresponds in each case to one line of Table B (compounds I.A5-1a.D6-56.B1 to I.A5-1a.D6-56.B550).

Table 57h Compounds of the formula I.A5-1a in which the combination of $R^3$, $(R^4)_m$, $R^5$ and $R^6$ corresponds to line D6-57 of Table D6 and the meaning for the combination of $R^1$ and $R^2$ for each individual compound corresponds in each case to one line of Table B (compounds I.A5-1a.D6-57.B1 to I.A5-1a.D6-57.B550).

Table 58h Compounds of the formula I.A5-1a in which the combination of $R^3$, $(R^4)_m$, $R^5$ and $R^6$ corresponds to line D6-58 of Table D6 and the meaning for the combination of $R^1$ and $R^2$ for each individual compound corresponds in each case to one line of Table B (compounds I.A5-1a.D6-58.B1 to I.A5-1a.D6-58.B550).

Table 59h Compounds of the formula I.A5-1a in which the combination of $R^3$, $(R^4)_m$, $R^5$ and $R^6$ corresponds to line D6-59 of Table D6 and the meaning for the combination of $R^1$ and $R^2$ for each individual compound corresponds in each case to one line of Table B (compounds I.A5-1a.D6-59.B1 to I.A5-1a.D6-59.B550).

Table 60h Compounds of the formula I.A5-1a in which the combination of $R^3$, $(R^4)_m$, $R^5$ and $R^6$ corresponds to line D6-60 of Table D6 and the meaning for the combination of $R^1$ and $R^2$ for each individual compound corresponds in each case to one line of Table B (compounds I.A5-1a.D6-60.B1 to I.A5-1a.D6-60.B550).

Table 61h Compounds of the formula I.A5-1a in which the combination of $R^3$, $(R^4)_m$, $R^5$ and $R^6$ corresponds to line D6-61 of Table D6 and the meaning for the combination of $R^1$ and $R^2$ for each individual compound corresponds in each case to one line of Table B (compounds I.A5-1a.D6-61.B1 to I.A5-1a.D6-61.B550).

Table 62h Compounds of the formula I.A5-1a in which the combination of $R^3$, $(R^4)_m$, $R^5$ and $R^6$ corresponds to line D6-62 of Table D6 and the meaning for the combination of $R^1$ and $R^2$ for each individual compound corresponds in each case to one line of Table B (compounds I.A5-1a.D6-62.B1 to I.A5-1a.D6-62.B550).

Table 63h Compounds of the formula I.A5-1a in which the combination of $R^3$, $(R^4)_m$, $R^5$ and $R^6$ corresponds to line D6-63 of Table D6 and the meaning for the combination of $R^1$ and $R^2$ for each individual compound corresponds in each case to one line of Table B (compounds I.A5-1a.D6-63.B1 to I.A5-1a.D6-63.B550).

Table 64h Compounds of the formula I.A5-1a in which the combination of $R^3$, $(R^4)_m$, $R^5$ and $R^6$ corresponds to line D6-64 of Table D6 and the meaning for the combination of $R^1$ and $R^2$ for each individual compound corresponds in each case to one line of Table B (compounds I.A5-1a.D6-64.B1 to I.A5-1a.D6-64.B550).

Table 65h Compounds of the formula I.A5-1a in which the combination of $R^3$, $(R^4)_m$, $R^5$ and $R^6$ corresponds to line D6-65 of Table D6 and the meaning for the combination of $R^1$ and $R^2$ for each individual compound corresponds in each case to one line of Table B (compounds I.A5-1a.D6-65.B1 to I.A5-1a.D6-65.B550).

Table 66h Compounds of the formula I.A5-1a in which the combination of $R^3$, $(R^4)_m$, $R^5$ and $R^6$ corresponds to line D6-66 of Table D6 and the meaning for the combination of $R^1$ and $R^2$ for each individual compound corresponds in each case to one line of Table B (compounds I.A5-1a.D6-66.B1 to I.A5-1a.D6-66.B550).

Table 67h Compounds of the formula I.A5-1a in which the combination of $R^3$, $(R^4)_m$, $R^5$ and $R^6$ corresponds to line D6-67 of Table D6 and the meaning for the combination of $R^1$ and $R^2$ for each individual compound corresponds in each case to one line of Table B (compounds I.A5-1a.D6-67.B1 to I.A5-1a.D6-67.B550).

Table 68h Compounds of the formula I.A5-1a in which the combination of $R^3$, $(R^4)_m$, $R^5$ and $R^6$ corresponds to line D6-68 of Table D6 and the meaning for the combination of $R^1$ and $R^2$ for each individual compound corresponds in each case to one line of Table B (compounds I.A5-1a.D6-68.B1 to I.A5-1a.D6-68.B550).

Table 69h Compounds of the formula I.A5-1a in which the combination of $R^3$, $(R^4)_m$, $R^5$ and $R^6$ corresponds to line D6-69 of Table D6 and the meaning for the combination of $R^1$ and $R^2$ for each individual compound corresponds in each case to one line of Table B (compounds I.A5-1a.D6-69.B1 to I.A5-1a.D6-69.B550).

Table 70h Compounds of the formula I.A5-1a in which the combination of $R^3$, $(R^4)_m$, $R^5$ and $R^6$ corresponds to line D6-70 of Table D6 and the meaning for the combination of $R^1$ and $R^2$ for each individual compound corresponds in each case to one line of Table B (compounds I.A5-1a.D6-70.B1 to I.A5-1a.D6-70.B550).

Table 71h Compounds of the formula I.A5-1a in which the combination of $R^3$, $(R^4)_m$, $R^5$ and $R^6$ corresponds to line D6-71 of Table D6 and the meaning for the combination of $R^1$ and $R^2$ for each individual compound corresponds in each case to one line of Table B (compounds I.A5-1a.D6-71.B1 to I.A5-1a.D6-71.B550).

Table 72h Compounds of the formula I.A5-1a in which the combination of $R^3$, $(R^4)_m$, $R^5$ and $R^6$ corresponds to line D6-72 of Table D6 and the meaning for the combination of $R^1$ and $R^2$ for each individual compound corresponds in each case to one line of Table B (compounds I.A5-1a.D6-72.B1 to I.A5-1a.D6-72.B550).

Table 73h Compounds of the formula I.A5-1a in which the combination of $R^3$, $(R^4)_m$, $R^5$ and $R^6$ corresponds to line D6-73 of Table D6 and the meaning for the combination of $R^1$ and $R^2$ for each individual compound corresponds in each case to one line of Table B (compounds I.A5-1a.D6-73.B1 to I.A5-1a.D6-73.B550).

Table 74h Compounds of the formula I.A5-1a in which the combination of $R^3$, $(R^4)_m$, $R^5$ and $R^6$ corresponds to line D6-74 of Table D6 and the meaning for the combination of $R^1$ and $R^2$ for each individual compound corresponds in each case to one line of Table B (compounds I.A5-1a.D6-74.B1 to I.A5-1a.D6-74.B550).

Table 75h Compounds of the formula I.A5-1a in which the combination of $R^3$, $(R^4)_m$, $R^5$ and $R^6$ corresponds to line D6-75 of Table D6 and the meaning for the combination of $R^1$ and $R^2$ for each individual compound corresponds in each case to one line of Table B (compounds I.A5-1a.D6-75.B1 to I.A5-1a.D6-75.B550).

Table 76h Compounds of the formula I.A5-1a in which the combination of $R^3$, $(R^4)_m$, $R^5$ and $R^6$ corresponds to line D6-76 of Table D6 and the meaning for the combination of $R^1$ and $R^2$ for each individual compound corresponds in each case to one line of Table B (compounds I.A5-1a.D6-76.B1 to I.A5-1a.D6-76.B550).

Table 77h Compounds of the formula I.A5-1a in which the combination of $R^3$, $(R^4)_m$, $R^5$ and $R^6$ corresponds to line D6-77 of Table D6 and the meaning for the combination of $R^1$ and $R^2$ for each individual compound corresponds in each case to one line of Table B (compounds I.A5-1a.D6-77.B1 to I.A5-1a.D6-77.B550).

Table 78h Compounds of the formula I.A5-1a in which the combination of $R^3$, $(R^4)_m$, $R^5$ and $R^6$ corresponds to line D6-78 of Table D6 and the meaning for the combination of $R^1$ and $R^2$ for each individual compound corresponds in each case to one line of Table B (compounds I.A5-1a.D6-78.B1 to I.A5-1a.D6-78.B550).

Table 79h Compounds of the formula I.A5-1a in which the combination of $R^3$, $(R^4)_m$, $R^5$ and $R^6$ corresponds to line D6-79 of Table D6 and the meaning for the combination of $R^1$ and $R^2$ for each individual compound corresponds in each case to one line of Table B (compounds I.A5-1a.D6-79.B1 to I.A5-1a.D6-79.B550).

Table 80h Compounds of the formula I.A5-1a in which the combination of $R^3$, $(R^4)_m$, $R^5$ and $R^6$ corresponds to line D6-80 of Table D6 and the meaning for the combination of $R^1$ and $R^2$ for each individual compound corresponds in each case to one line of Table B (compounds I.A5-1a.D6-80.B1 to I.A5-1a.D6-80.B550).

Table 81h Compounds of the formula I.A5-1a in which the combination of $R^3$, $(R^4)_m$, $R^5$ and $R^6$ corresponds to line D6-81 of Table D6 and the meaning for the combination of $R^1$ and $R^2$ for each individual compound corresponds in each case to one line of Table B (compounds I.A5-1a.D6-81.B1 to I.A5-1a.D6-81.B550).

Table 82h Compounds of the formula I.A5-1a in which the combination of $R^3$, $(R^4)_m$, $R^5$ and $R^6$ corresponds to line D6-82 of Table D6 and the meaning for the combination of $R^1$ and $R^2$ for each individual compound corresponds in each case to one line of Table B (compounds I.A5-1a.D6-82.B1 to I.A5-1a.D6-82.B550).

Table 83h Compounds of the formula I.A5-1a in which the combination of $R^3$, $(R^4)_m$, $R^5$ and $R^6$ corresponds to line D6-83 of Table D6 and the meaning for the combination of $R^1$ and $R^2$ for each individual compound corresponds in each case to one line of Table B (compounds I.A5-1a.D6-83.B1 to I.A5-1a.D6-83.B550).

Table 84h Compounds of the formula I.A5-1a in which the combination of $R^3$, $(R^4)_m$, $R^5$ and $R^6$ corresponds to line D6-84 of Table D6 and the meaning for the combination of $R^1$ and $R^2$ for each individual compound corresponds in each case to one line of Table B (compounds I.A5-1a.D6-84.B1 to I.A5-1a.D6-84.B550).

Table 85h Compounds of the formula I.A5-1a in which the combination of $R^3$, $(R^4)_m$, $R^5$ and $R^6$ corresponds to line D6-85 of Table D6 and the meaning for the combination of $R^1$ and $R^2$ for each individual compound corresponds in each case to one line of Table B (compounds I.A5-1a.D6-85.B1 to I.A5-1a.D6-85.B550).

Table 86h Compounds of the formula I.A5-1a in which the combination of $R^3$, $(R^4)_m$, $R^5$ and $R^6$ corresponds to line D6-86 of Table D6 and the meaning for the combination of $R^1$ and $R^2$ for each individual compound corresponds in each case to one line of Table B (compounds I.A5-1a.D6-86.B1 to I.A5-1a.D6-86.B550).

Table 87h Compounds of the formula I.A5-1a in which the combination of $R^3$, $(R^4)_m$, $R^5$ and $R^6$ corresponds to line D6-87 of Table D6 and the meaning for the combination of $R^1$ and $R^2$ for each individual compound corresponds in each case to one line of Table B (compounds I.A5-1a.D6-87.B1 to I.A5-1a.D6-87.B550).

Table 88h Compounds of the formula I.A5-1a in which the combination of $R^3$, $(R^4)_m$, $R^5$ and $R^6$ corresponds to line D6-88 of Table D6 and the meaning for the combination of $R^1$ and $R^2$ for each individual compound corresponds in each case to one line of Table B (compounds I.A5-1a.D6-88.B1 to I.A5-1a.D6-88.B550).

Table 89h Compounds of the formula I.A5-1a in which the combination of $R^3$, $(R^4)_m$, $R^5$ and $R^6$ corresponds to line D6-89 of Table D6 and the meaning for the combination of $R^1$ and $R^2$ for each individual compound corresponds in each case to one line of Table B (compounds I.A5-1a.D6-89.B1 to I.A5-1a.D6-89.B550).

Table 90h Compounds of the formula I.A5-1a in which the combination of $R^3$, $(R^4)_m$, $R^5$ and $R^6$ corresponds to line D6-90 of Table D6 and the meaning for the combination of $R^1$ and $R^2$ for each individual compound corresponds in each case to one line of Table B (compounds I.A5-1a.D6-90.B1 to I.A5-1a.D6-90.B550).

Table 91h Compounds of the formula I.A5-1a in which the combination of $R^3$, $(R^4)_m$, $R^5$ and $R^6$ corresponds to line D6-91 of Table D6 and the meaning for the combination of $R^1$ and $R^2$ for each individual compound corresponds in each case to one line of Table B (compounds I.A5-1a.D6-91.B1 to I.A5-1a.D6-91.B550).

Table 92h Compounds of the formula I.A5-1a in which the combination of $R^3$, $(R^4)_m$, $R^5$ and $R^6$ corresponds to line D6-92 of Table D6 and the meaning for the combination of $R^1$ and $R^2$ for each individual compound corresponds in each case to one line of Table B (compounds I.A5-1a.D6-92.B1 to I.A5-1a.D6-92.B550).

Table 93h Compounds of the formula I.A5-1a in which the combination of $R^3$, $(R^4)_m$, $R^5$ and $R^6$ corresponds to line D6-93 of Table D6 and the meaning for the combination of $R^1$ and $R^2$ for each individual compound corresponds in each case to one line of Table B (compounds I.A5-1a.D6-93.B1 to I.A5-1a.D6-93.B550).

Table 94h Compounds of the formula I.A5-1a in which the combination of $R^3$, $(R^4)_m$, $R^5$ and $R^6$ corresponds to line D6-94 of Table D6 and the meaning for the combination of $R^1$ and $R^2$ for each individual compound corresponds in each case to one line of Table B (compounds I.A5-1a.D6-94.B1 to I.A5-1a.D6-94.B550).

Table 95h Compounds of the formula I.A5-1a in which the combination of $R^3$, $(R^4)_m$, $R^5$ and $R^6$ corresponds to line D6-95 of Table D6 and the meaning for the combination of $R^1$ and $R^2$ for each individual compound corresponds in each case to one line of Table B (compounds I.A5-1a.D6-95.B1 to I.A5-1a.D6-95.B550).

Table 96h Compounds of the formula I.A5-1a in which the combination of $R^3$, $(R^4)_m$, $R^5$ and $R^6$ corresponds to line D6-96 of Table D6 and the meaning for the combination of $R^1$ and $R^2$ for each individual compound corresponds in each case to one line of Table B (compounds I.A5-1a.D6-96.B1 to I.A5-1a.D6-96.B550).

Table 97h Compounds of the formula I.A5-1a in which the combination of $R^3$, $(R^4)_m$, $R^5$ and $R^6$ corresponds to line D6-97 of Table D6 and the meaning for the combination of $R^1$ and $R^2$ for each individual compound corresponds in each case to one line of Table B (compounds I.A5-1a.D6-97.B1 to I.A5-1a.D6-97.B550).

Table 98h Compounds of the formula I.A5-1a in which the combination of $R^3$, $(R^4)_m$, $R^5$ and $R^6$ corresponds to line D6-98 of Table D6 and the meaning for the combination of $R^1$ and $R^2$ for each individual compound corresponds in each case to one line of Table B (compounds I.A5-1a.D6-98.B1 to I.A5-1a.D6-98.B550).

Table 99h Compounds of the formula I.A5-1a in which the combination of $R^3$, $(R^4)_m$, $R^5$ and $R^6$ corresponds to line D6-99 of Table D6 and the meaning for the combination of $R^1$ and $R^2$ for each individual compound corresponds in each case to one line of Table B (compounds I.A5-1a.D6-99.B1 to I.A5-1a.D6-99.B550).

Table 100h Compounds of the formula I.A5-1a in which the combination of $R^3$, $(R^4)_m$, $R^5$ and $R^6$ corresponds to line D6-100 of Table D6 and the meaning for the combination of $R^1$ and $R^2$ for each individual compound corresponds in each case to one line of Table B (compounds I.A5-1a.D6-100.B1 to I.A5-1a.D6-100.B550).

Table 101h Compounds of the formula I.A5-1a in which the combination of $R^3$, $(R^4)_m$, $R^5$ and $R^6$ corresponds to line D6-101 of Table D6 and the meaning for the combination of $R^1$ and $R^2$ for each individual compound corresponds in each case to one line of Table B (compounds I.A5-1a.D6-101.B1 to I.A5-1a.D6-101.B550).

Table 102h Compounds of the formula I.A5-1a in which the combination of $R^3$, $(R^4)_m$, $R^5$ and $R^6$ corresponds to line D6-102 of Table D6 and the meaning for the combination of $R^1$ and $R^2$ for each individual compound corresponds in each case to one line of Table B (compounds I.A5-1a.D6-102.B1 to I.A5-1a.D6-102.B550).

Table 103h Compounds of the formula I.A5-1a in which the combination of $R^3$, $(R^4)_m$, $R^5$ and $R^6$ corresponds to line D6-103 of Table D6 and the meaning for the combination of $R^1$ and $R^2$ for each individual compound corresponds in each case to one line of Table B (compounds I.A5-1a.D6-103.B1 to I.A5-1a.D6-103.B550).

Table 104h Compounds of the formula I.A5-1a in which the combination of $R^3$, $(R^4)_m$, $R^5$ and $R^6$ corresponds to line D6-104 of Table D6 and the meaning for the combination of $R^1$ and $R^2$ for each individual compound corresponds in each case to one line of Table B (compounds I.A5-1a.D6-104.B1 to I.A5-1a.D6-104.B550).

Table 105h Compounds of the formula I.A5-1a in which the combination of $R^3$, $(R^4)_m$, $R^5$ and $R^6$ corresponds to line D6-105 of Table D6 and the meaning for the combination of $R^1$ and $R^2$ for each individual compound corresponds in each case to one line of Table B (compounds I.A5-1a.D6-105.B1 to I.A5-1a.D6-105.B550).

Table 106h Compounds of the formula I.A5-1a in which the combination of $R^3$, $(R^4)_m$, $R^5$ and $R^6$ corresponds to line D6-106 of Table D6 and the meaning for the combination of $R^1$ and $R^2$ for each individual compound corresponds in each case to one line of Table B (compounds I.A5-1a.D6-106.B1 to I.A5-1a.D6-106.B550).

Table 107h Compounds of the formula I.A5-1a in which the combination of $R^3$, $(R^4)_m$, $R^5$ and $R^6$ corresponds to line D6-107 of Table D6 and the meaning for the combination of $R^1$ and $R^2$ for each individual compound corresponds in each case to one line of Table B (compounds I.A5-1a.D6-107.B1 to I.A5-1a.D6-107.B550).

Table 108h Compounds of the formula I.A5-1a in which the combination of $R^3$, $(R^4)_m$, $R^5$ and $R^6$ corresponds to line D6-108 of Table D6 and the meaning for the combination of $R^1$ and $R^2$ for each individual compound corresponds in each case to one line of Table B (compounds I.A5-1a.D6-108.B1 to I.A5-1a.D6-108.B550).

Table 109h Compounds of the formula I.A5-1a in which the combination of $R^3$, $(R^4)_m$, $R^5$ and $R^6$ corresponds to line D6-109 of Table D6 and the meaning for the combination of $R^1$ and $R^2$ for each individual compound corresponds in each case to one line of Table B (compounds I.A5-1a.D6-109.B1 to I.A5-1a.D6-109.B550).

Table 110h Compounds of the formula I.A5-1a in which the combination of $R^3$, $(R^4)_m$, $R^5$ and $R^6$ corresponds to line D6-110 of Table D6 and the meaning for the combination of $R^1$ and $R^2$ for each individual compound corresponds in each case to one line of Table B (compounds I.A5-1a.D6-110.B1 to I.A5-1a.D6-110.B550).

Table 111h Compounds of the formula I.A5-1a in which the combination of $R^3$, $(R^4)_m$, $R^5$ and $R^6$ corresponds to line D6-111 of Table D6 and the meaning for the combination of $R^1$ and $R^2$ for each individual compound corresponds in each case to one line of Table B (compounds I.A5-1a.D6-111.B1 to I.A5-1a.D6-111.B550).

Table 112h Compounds of the formula I.A5-1a in which the combination of $R^3$, $(R^4)_m$, $R^5$ and $R^6$ corresponds to line D6-112 of Table D6 and the meaning for the combination of $R^1$ and $R^2$ for each individual compound corresponds in each case to one line of Table B (compounds I.A5-1a.D6-112.B1 to I.A5-1a.D6-112.B550).

Table 1i Compounds of the formula I.A5-1b in which the combination of $R^3$, $(R^4)_m$, $R^5$ and $R^6$ corresponds to line D6-1 of Table D6 and the meaning for the combination of $R^1$ and $R^2$ for each individual compound corresponds in each case to one line of Table B (compounds I.A5-1b.D6-1.B1 to I.A5-1b.D6-1.B550).

Table 2i Compounds of the formula I.A5-1b in which the combination of $R^3$, $(R^4)_m$, $R^5$ and $R^6$ corresponds to line D6-2 of Table D6 and the meaning for the combination of $R^1$ and $R^2$ for each individual compound corresponds in each case to one line of Table B (compounds I.A5-1b.D6-2.B1 to I.A5-1b.D6-2.B550).

Table 3i Compounds of the formula I.A5-1b in which the combination of $R^3$, $(R^4)_m$, $R^5$ and $R^6$ corresponds to line D6-3 of Table D6 and the meaning for the combination of $R^1$ and $R^2$ for each individual compound corresponds in each case to one line of Table B (compounds I.A5-1b.D6-3.B1 to I.A5-1b.D6-3.B550).

Table 4i Compounds of the formula I.A5-1b in which the combination of $R^3$, $(R^4)_m$, $R^5$ and $R^6$ corresponds to line D6-4 of Table D6 and the meaning for the combination of $R^1$ and $R^2$ for each individual compound corresponds in each case to one line of Table B (compounds I.A5-1b.D6-4.B1 to I.A5-1b.D6-4.B550).

Table 5i Compounds of the formula I.A5-1b in which the combination of $R^3$, $(R^4)_m$, $R^5$ and $R^6$ corresponds to line D6-5 of Table D6 and the meaning for the combination of $R^1$ and $R^2$ for each individual compound corresponds in each case to one line of Table B (compounds I.A5-1b.D6-5.B1 to I.A5-1b.D6-5.B550).

Table 6i Compounds of the formula I.A5-1b in which the combination of $R^3$, $(R^4)_m$, $R^5$ and $R^6$ corresponds to line D6-6 of Table D6 and the meaning for the combination of $R^1$ and $R^2$ for each individual compound corresponds in each case to one line of Table B (compounds I.A5-1b.D6-6.B1 to I.A5-1b.D6-6.B550).

Table 7i Compounds of the formula I.A5-1b in which the combination of $R^3$, $(R^4)_m$, $R^5$ and $R^6$ corresponds to line D6-7 of Table D6 and the meaning for the combination of $R^1$ and $R^2$ for each individual compound corresponds in each case to one line of Table B (compounds I.A5-1b.D6-7.B1 to I.A5-1b.D6-7.B550).

Table 8i Compounds of the formula I.A5-1b in which the combination of $R^3$, $(R^4)_m$, $R^5$ and $R^6$ corresponds to line D6-8 of Table D6 and the meaning for the combination of $R^1$ and $R^2$ for each individual compound corresponds in each case to one line of Table B (compounds I.A5-1b.D6-8.B1 to I.A5-1b.D6-8.B550).

Table 9i Compounds of the formula I.A5-1b in which the combination of $R^3$, $(R^4)_m$, $R^5$ and $R^6$ corresponds to line D6-9 of Table D6 and the meaning for the combination of $R^1$ and $R^2$ for each individual compound corresponds in each case to one line of Table B (compounds I.A5-1b.D6-9.B1 to I.A5-1b.D6-9.B550).

Table 10i Compounds of the formula I.A5-1b in which the combination of $R^3$, $(R^4)_m$, $R^5$ and $R^6$ corresponds to line D6-10 of Table D6 and the meaning for the combination of $R^1$ and $R^2$ for each individual compound corresponds in each case to one line of Table B (compounds I.A5-1b.D6-10.B1 to I.A5-1b.D6-10.B550).

Table 11i Compounds of the formula I.A5-1b in which the combination of $R^3$, $(R^4)_m$, $R^5$ and $R^6$ corresponds to line D6-11 of Table D6 and the meaning for the combination of $R^1$ and $R^2$ for each individual compound corresponds in each case to one line of Table B (compounds I.A5-1b.D6-11.B1 to I.A5-1b.D6-11.B550).

Table 12i Compounds of the formula I.A5-1b in which the combination of $R^3$, $(R^4)_m$, $R^5$ and $R^6$ corresponds to line D6-12 of Table D6 and the meaning for the combination of $R^1$ and $R^2$ for each individual compound corresponds in each case to one line of Table B (compounds I.A5-1b.D6-12.B1 to I.A5-1b.D6-12.B550).

Table 13i Compounds of the formula I.A5-1b in which the combination of $R^3$, $(R^4)_m$, $R^5$ and $R^6$ corresponds to line D6-13 of Table D6 and the meaning for the combination of $R^1$ and $R^2$ for each individual compound corresponds in each case to one line of Table B (compounds I.A5-1b.D6-13.B1 to I.A5-1b.D6-13.B550).

Table 14i Compounds of the formula I.A5-1b in which the combination of $R^3$, $(R^4)_m$, $R^5$ and $R^6$ corresponds to line D6-14 of Table D6 and the meaning for the combination of $R^1$ and $R^2$ for each individual compound corresponds in each case to one line of Table B (compounds I.A5-1b.D6-14.B1 to I.A5-1b.D6-14.B550).

Table 15i Compounds of the formula I.A5-1b in which the combination of $R^3$, $(R^4)_m$, $R^5$ and $R^6$ corresponds to line D6-15 of Table D6 and the meaning for the combination of $R^1$ and $R^2$ for each individual compound corresponds in each case to one line of Table B (compounds I.A5-1b.D6-15.B1 to I.A5-1b.D6-15.B550).

Table 16i Compounds of the formula I.A5-1b in which the combination of $R^3$, $(R^4)_m$, $R^5$ and $R^6$ corresponds to line D6-16 of Table D6 and the meaning for the combination of $R^1$ and $R^2$ for each individual compound corresponds in each case to one line of Table B (compounds I.A5-1b.D6-16.B1 to I.A5-1b.D6-16.B550).

Table 17i Compounds of the formula I.A5-1b in which the combination of $R^3$, $(R^4)_m$, $R^5$ and $R^6$ corresponds to line D6-17 of Table D6 and the meaning for the combination of $R^1$ and $R^2$ for each individual compound corresponds in each case to one line of Table B (compounds I.A5-1b.D6-17.B1 to I.A5-1b.D6-17.B550).

Table 18i Compounds of the formula I.A5-1b in which the combination of $R^3$, $(R^4)_m$, $R^5$ and $R^6$ corresponds to line D6-18 of Table D6 and the meaning for the combination of $R^1$ and $R^2$ for each individual compound corresponds in each case to one line of Table B (compounds I.A5-1b.D6-18.B1 to I.A5-1b.D6-18.B550).

Table 19i Compounds of the formula I.A5-1b in which the combination of $R^3$, $(R^4)_m$, $R^5$ and $R^6$ corresponds to line D6-19 of Table D6 and the meaning for the combination of $R^1$ and $R^2$ for each individual compound corresponds in each case to one line of Table B (compounds I.A5-1b.D6-19.B1 to I.A5-1b.D6-19.B550).

Table 20i Compounds of the formula I.A5-1b in which the combination of $R^3$, $(R^4)_m$, $R^5$ and $R^6$ corresponds to line D6-20 of Table D6 and the meaning for the combination of $R^1$ and $R^2$ for each individual compound corresponds in each case to one line of Table B (compounds I.A5-1b.D6-20.B1 to I.A5-1b.D6-20.B550).

Table 21i Compounds of the formula I.A5-1b in which the combination of $R^3$, $(R^4)_m$, $R^5$ and $R^6$ corresponds to line D6-21 of Table D6 and the meaning for the combination of $R^1$ and $R^2$ for each individual compound corresponds in each case to one line of Table B (compounds I.A5-1b.D6-21.B1 to I.A5-1b.D6-21.B550).

Table 22i Compounds of the formula I.A5-1b in which the combination of $R^3$, $(R^4)_m$, $R^5$ and $R^6$ corresponds to line D6-22 of Table D6 and the meaning for the combination of $R^1$ and $R^2$ for each individual compound corresponds in each case to one line of Table B (compounds I.A5-1b.D6-22.B1 to I.A5-1b.D6-22.B550).

Table 23i Compounds of the formula I.A5-1b in which the combination of $R^3$, $(R^4)_m$, $R^5$ and $R^6$ corresponds to line D6-23 of Table D6 and the meaning for the combination of $R^1$ and $R^2$ for each individual compound corresponds in each case to one line of Table B (compounds I.A5-1b.D6-23.B1 to I.A5-1b.D6-23.B550).

Table 24i Compounds of the formula I.A5-1b in which the combination of $R^3$, $(R^4)_m$, $R^5$ and $R^6$ corresponds to line D6-24 of Table D6 and the meaning for the combination of $R^1$ and $R^2$ for each individual compound corresponds in each case to one line of Table B (compounds I.A5-1b.D6-24.B1 to I.A5-1b.D6-24.B550).

Table 25i Compounds of the formula I.A5-1b in which the combination of $R^3$, $(R^4)_m$, $R^5$ and $R^6$ corresponds to line D6-25 of Table D6 and the meaning for the combination of $R^1$ and $R^2$ for each individual compound corresponds in each case to one line of Table B (compounds I.A5-1b.D6-25.B1 to I.A5-1b.D6-25.B550).

Table 26i Compounds of the formula I.A5-1b in which the combination of $R^3$, $(R^4)_m$, $R^5$ and $R^6$ corresponds to line D6-26 of Table D6 and the meaning for the combination of $R^1$ and $R^2$ for each individual compound corresponds in each case to one line of Table B (compounds I.A5-1b.D6-26.B1 to I.A5-1b.D6-26.B550).

Table 27i Compounds of the formula I.A5-1b in which the combination of $R^3$, $(R^4)_m$, $R^5$ and $R^6$ corresponds to line D6-27 of Table D6 and the meaning for the combination of $R^1$ and $R^2$ for each individual compound corresponds in each case to one line of Table B (compounds I.A5-1b.D6-27.B1 to I.A5-1b.D6-27.B550).

Table 28i Compounds of the formula I.A5-1b in which the combination of $R^3$, $(R^4)_m$, $R^5$ and $R^6$ corresponds to line D6-28 of Table D6 and the meaning for the combination of $R^1$ and $R^2$ for each individual compound corresponds in each case to one line of Table B (compounds I.A5-1b.D6-28.B1 to I.A5-1b.D6-28.B550).

Table 29i Compounds of the formula I.A5-1b in which the combination of $R^3$, $(R^4)_m$, $R^5$ and $R^6$ corresponds to line D6-29 of Table D6 and the meaning for the combination of $R^1$ and $R^2$ for each individual compound corresponds in each case to one line of Table B (compounds I.A5-1b.D6-29.B1 to I.A5-1b.D6-29.B550).

Table 30i Compounds of the formula I.A5-1b in which the combination of $R^3$, $(R^4)_m$, $R^5$ and $R^6$ corresponds to line D6-30 of Table D6 and the meaning for the combination of $R^1$ and $R^2$ for each individual compound corresponds in each case to one line of Table B (compounds I.A5-1b.D6-30.B1 to I.A5-1b.D6-30.B550).

Table 31i Compounds of the formula I.A5-1b in which the combination of $R^3$, $(R^4)_m$, $R^5$ and $R^6$ corresponds to line D6-31 of Table D6 and the meaning for the combination of $R^1$ and $R^2$ for each individual compound corresponds in each case to one line of Table B (compounds I.A5-1b.D6-31.B1 to I.A5-1b.D6-31.B550).

Table 32i Compounds of the formula I.A5-1b in which the combination of $R^3$, $(R^4)_m$, $R^5$ and $R^6$ corresponds to line D6-32 of Table D6 and the meaning for the combination of $R^1$ and $R^2$ for each individual compound corresponds in each case to one line of Table B (compounds I.A5-1b.D6-32.B1 to I.A5-1b.D6-32.B550).

Table 33i Compounds of the formula I.A5-1b in which the combination of $R^3$, $(R^4)_m$, $R^5$ and $R^6$ corresponds to line D6-33 of Table D6 and the meaning for the combination of $R^1$ and $R^2$ for each individual compound corresponds in each case to one line of Table B (compounds I.A5-1b.D6-33.B1 to I.A5-1b.D6-33.B550).

Table 34i Compounds of the formula I.A5-1b in which the combination of $R^3$, $(R^4)_m$, $R^5$ and $R^6$ corresponds to line D6-34 of Table D6 and the meaning for the combination of $R^1$ and $R^2$ for each individual compound corresponds in each case to one line of Table B (compounds I.A5-1b.D6-34.B1 to I.A5-1b.D6-34.B550).

Table 35i Compounds of the formula I.A5-1b in which the combination of $R^3$, $(R^4)_m$, $R^5$ and $R^6$ corresponds to line D6-35 of Table D6 and the meaning for the combination of $R^1$ and $R^2$ for each individual compound corresponds in each case to one line of Table B (compounds I.A5-1b.D6-35.B1 to I.A5-1b.D6-35.B550).

Table 36i Compounds of the formula I.A5-1b in which the combination of $R^3$, $(R^4)_m$, $R^5$ and $R^6$ corresponds to line D6-36 of Table D6 and the meaning for the combination of $R^1$ and $R^2$ for each individual compound corresponds in each case to one line of Table B (compounds I.A5-1b.D6-36.B1 to I.A5-1b.D6-36.B550).

Table 37i Compounds of the formula I.A5-1b in which the combination of $R^3$, $(R^4)_m$, $R^5$ and $R^6$ corresponds to line D6-37 of Table D6 and the meaning for the combination of $R^1$ and $R^2$ for each individual compound corresponds in each case to one line of Table B (compounds I.A5-1b.D6-37.B1 to I.A5-1b.D6-37.B550).

Table 38i Compounds of the formula I.A5-1b in which the combination of $R^3$, $(R^4)_m$, $R^5$ and $R^6$ corresponds to line D6-38 of Table D6 and the meaning for the combination of $R^1$ and $R^2$ for each individual compound corresponds in each case to one line of Table B (compounds I.A5-1b.D6-38.B1 to I.A5-1b.D6-38.B550).

Table 39i Compounds of the formula I.A5-1b in which the combination of $R^3$, $(R^4)_m$, $R^5$ and $R^6$ corresponds to line D6-39 of Table D6 and the meaning for the combination of $R^1$ and $R^2$ for each individual compound corresponds in each case to one line of Table B (compounds I.A5-1b.D6-39.B1 to I.A5-1b.D6-39.B550).

Table 40i Compounds of the formula I.A5-1b in which the combination of $R^3$, $(R^4)_m$, $R^5$ and $R^6$ corresponds to line D6-40 of Table D6 and the meaning for the combination of $R^1$ and $R^2$ for each individual compound corresponds in each case to one line of Table B (compounds I.A5-1b.D6-40.B1 to I.A5-1b.D6-40.B550).

Table 41i Compounds of the formula I.A5-1b in which the combination of $R^3$, $(R^4)_m$, $R^5$ and $R^6$ corresponds to line D6-41 of Table D6 and the meaning for the combination of $R^1$ and $R^2$ for each individual compound corresponds in each case to one line of Table B (compounds I.A5-1b.D6-41.B1 to I.A5-1b.D6-41.B550).

Table 42i Compounds of the formula I.A5-1b in which the combination of $R^3$, $(R^4)_m$, $R^5$ and $R^6$ corresponds to line D6-42 of Table D6 and the meaning for the combination of $R^1$ and $R^2$ for each individual compound corresponds in each case to one line of Table B (compounds I.A5-1b.D6-42.B1 to I.A5-1b.D6-42.B550).

Table 43i Compounds of the formula I.A5-1b in which the combination of $R^3$, $(R^4)_m$, $R^5$ and $R^6$ corresponds to line D6-43 of Table D6 and the meaning for the combination of $R^1$ and $R^2$ for each individual compound corresponds in each case to one line of Table B (compounds I.A5-1b.D6-43.B1 to I.A5-1b.D6-43.B550).

Table 44i Compounds of the formula I.A5-1b in which the combination of $R^3$, $(R^4)_m$, $R^5$ and $R^6$ corresponds to line D6-44 of Table D6 and the meaning for the combination of $R^1$ and $R^2$ for each individual compound corresponds in each case to one line of Table B (compounds I.A5-1b.D6-44.B1 to I.A5-1b.D6-44.B550).

Table 45i Compounds of the formula I.A5-1b in which the combination of $R^3$, $(R^4)_m$, $R^5$ and $R^6$ corresponds to line D6-45 of Table D6 and the meaning for the combination of $R^1$ and $R^2$ for each individual compound corresponds in each case to one line of Table B (compounds I.A5-1b.D6-45.B1 to I.A5-1b.D6-45.B550).

Table 46i Compounds of the formula I.A5-1b in which the combination of $R^3$, $(R^4)_m$, $R^5$ and $R^6$ corresponds to line D6-46 of Table D6 and the meaning for the combination of $R^1$ and $R^2$ for each individual compound corresponds in each case to one line of Table B (compounds I.A5-1b.D6-46.B1 to I.A5-1b.D6-46.B550).

Table 47i Compounds of the formula I.A5-1b in which the combination of $R^3$, $(R^4)_m$, $R^5$ and $R^6$ corresponds to line D6-47 of Table D6 and the meaning for the combination of $R^1$ and $R^2$ for each individual compound corresponds in each case to one line of Table B (compounds I.A5-1b.D6-47.B1 to I.A5-1b.D6-47.B550).

Table 48i Compounds of the formula I.A5-1b in which the combination of $R^3$, $(R^4)_m$, $R^5$ and $R^6$ corresponds to line D6-48 of Table D6 and the meaning for the combination of $R^1$ and $R^2$ for each individual compound corresponds in each case to one line of Table B (compounds I.A5-1b.D6-48.B1 to I.A5-1b.D6-48.B550).

Table 49i Compounds of the formula I.A5-1b in which the combination of $R^3$, $(R^4)_m$, $R^5$ and $R^6$ corresponds to line D6-49 of Table D6 and the meaning for the combination of $R^1$ and $R^2$ for each individual compound corresponds in each case to one line of Table B (compounds I.A5-1b.D6-49.B1 to I.A5-1b.D6-49.B550).

Table 50i Compounds of the formula I.A5-1b in which the combination of $R^3$, $(R^4)_m$, $R^5$ and $R^6$ corresponds to line D6-50 of Table D6 and the meaning for the combination of $R^1$ and $R^2$ for each individual compound corresponds in each case to one line of Table B (compounds I.A5-1b.D6-50.B1 to I.A5-1b.D6-50.B550).

Table 51i Compounds of the formula I.A5-1b in which the combination of $R^3$, $(R^4)_m$, $R^5$ and $R^6$ corresponds to line D6-51 of Table D6 and the meaning for the combination of $R^1$ and $R^2$ for each individual compound corresponds in each case to one line of Table B (compounds I.A5-1b.D6-51.B1 to I.A5-1b.D6-51.B550).

Table 52i Compounds of the formula I.A5-1b in which the combination of $R^3$, $(R^4)_m$, $R^5$ and $R^6$ corresponds to line D6-52 of Table D6 and the meaning for the combination of $R^1$ and $R^2$ for each individual compound corresponds in each case to one line of Table B (compounds I.A5-1b.D6-52.B1 to I.A5-1b.D6-52.B550).

Table 53i Compounds of the formula I.A5-1b in which the combination of $R^3$, $(R^4)_m$, $R^5$ and $R^6$ corresponds to line D6-53 of Table D6 and the meaning for the combination of $R^1$ and $R^2$ for each individual compound corresponds in each case to one line of Table B (compounds I.A5-1b.D6-53.B1 to I.A5-1b.D6-53.B550).

Table 54i Compounds of the formula I.A5-1b in which the combination of $R^3$, $(R^4)_m$, $R^5$ and $R^6$ corresponds to line D6-54 of Table D6 and the meaning for the combination of $R^1$ and $R^2$ for each individual compound corresponds in each case to one line of Table B (compounds I.A5-1b.D6-54.B1 to I.A5-1b.D6-54.B550).

Table 55i Compounds of the formula I.A5-1b in which the combination of $R^3$, $(R^4)_m$, $R^5$ and $R^6$ corresponds to line D6-55 of Table D6 and the meaning for the combination of $R^1$ and $R^2$ for each individual compound corresponds in each case to one line of Table B (compounds I.A5-1b.D6-55.B1 to I.A5-1b.D6-55.B550).

Table 56i Compounds of the formula I.A5-1b in which the combination of $R^3$, $(R^4)_m$, $R^5$ and $R^6$ corresponds to line D6-56 of Table D6 and the meaning for the combination of $R^1$ and $R^2$ for each individual compound corresponds in each case to one line of Table B (compounds I.A5-1b.D6-56.B1 to I.A5-1b.D6-56.B550).

Table 57i Compounds of the formula I.A5-1b in which the combination of $R^3$, $(R^4)_m$, $R^5$ and $R^6$ corresponds to line D6-57 of Table D6 and the meaning for the combination of $R^1$ and $R^2$ for each individual compound corresponds in each case to one line of Table B (compounds I.A5-1b.D6-57.B1 to I.A5-1b.D6-57.B550).

Table 58i Compounds of the formula I.A5-1b in which the combination of $R^3$, $(R^4)_m$, $R^5$ and $R^6$ corresponds to line D6-58 of Table D6 and the meaning for the combination of $R^1$ and $R^2$ for each individual compound corresponds in each case to one line of Table B (compounds I.A5-1b.D6-58.B1 to I.A5-1b.D6-58.B550).

Table 59i Compounds of the formula I.A5-1b in which the combination of $R^3$, $(R^4)_m$, $R^5$ and $R^6$ corresponds to line D6-59 of Table D6 and the meaning for the combination of $R^1$ and $R^2$ for each individual compound corresponds in each case to one line of Table B (compounds I.A5-1b.D6-59.B1 to I.A5-1b.D6-59.B550).

Table 60i Compounds of the formula I.A5-1b in which the combination of $R^3$, $(R^4)_m$, $R^5$ and $R^6$ corresponds to line D6-60 of Table D6 and the meaning for the combination of $R^1$ and $R^2$ for each individual compound corresponds in each case to one line of Table B (compounds I.A5-1b.D6-60.B1 to I.A5-1b.D6-60.B550).

Table 61i Compounds of the formula I.A5-1b in which the combination of $R^3$, $(R^4)_m$, $R^5$ and $R^6$ corresponds to line D6-61 of Table D6 and the meaning for the combination of $R^1$ and $R^2$ for each individual compound corresponds in each case to one line of Table B (compounds I.A5-1b.D6-61.B1 to I.A5-1b.D6-61.B550).

Table 62i Compounds of the formula I.A5-1b in which the combination of $R^3$, $(R^4)_m$, $R^5$ and $R^6$ corresponds to line D6-62 of Table D6 and the meaning for the combination of $R^1$ and $R^2$ for each individual compound corresponds in each case to one line of Table B (compounds I.A5-1b.D6-62.B1 to I.A5-1b.D6-62.B550).

Table 63i Compounds of the formula I.A5-1b in which the combination of $R^3$, $(R^4)_m$, $R^5$ and $R^6$ corresponds to line D6-63 of Table D6 and the meaning for the combination of $R^1$ and $R^2$ for each individual compound corresponds in each case to one line of Table B (compounds I.A5-1b.D6-63.B1 to I.A5-1b.D6-63.B550).

Table 64i Compounds of the formula I.A5-1b in which the combination of $R^3$, $(R^4)_m$, $R^5$ and $R^6$ corresponds to line D6-64 of Table D6 and the meaning for the combination of $R^1$ and $R^2$ for each individual compound corresponds in each case to one line of Table B (compounds I.A5-1b.D6-64.B1 to I.A5-1b.D6-64.B550).

Table 65i Compounds of the formula I.A5-1b in which the combination of $R^3$, $(R^4)_m$, $R^5$ and $R^6$ corresponds to line D6-65 of Table D6 and the meaning for the combination of $R^1$ and $R^2$ for each individual compound corresponds in each case to one line of Table B (compounds I.A5-1b.D6-65.B1 to I.A5-1b.D6-65.B550).

Table 66i Compounds of the formula I.A5-1b in which the combination of $R^3$, $(R^4)_m$, $R^5$ and $R^6$ corresponds to line D6-66 of Table D6 and the meaning for the combination of $R^1$ and $R^2$ for each individual compound corresponds in each case to one line of Table B (compounds I.A5-1b.D6-66.B1 to I.A5-1b.D6-66.B550).

Table 67i Compounds of the formula I.A5-1b in which the combination of $R^3$, $(R^4)_m$, $R^5$ and $R^6$ corresponds to line D6-67 of Table D6 and the meaning for the combination of $R^1$ and $R^2$ for each individual compound corresponds in each case to one line of Table B (compounds I.A5-1b.D6-67.B1 to I.A5-1b.D6-67.B550).

Table 68i Compounds of the formula I.A5-1b in which the combination of $R^3$, $(R^4)_m$, $R^5$ and $R^6$ corresponds to line D6-68 of Table D6 and the meaning for the combination of $R^1$ and $R^2$ for each individual compound corresponds in each case to one line of Table B (compounds I.A5-1b.D6-68.B1 to I.A5-1b.D6-68.B550).

Table 69i Compounds of the formula I.A5-1b in which the combination of $R^3$, $(R^4)_m$, $R^5$ and $R^6$ corresponds to line D6-69 of Table D6 and the meaning for the combination of $R^1$ and $R^2$ for each individual compound corresponds in each case to one line of Table B (compounds I.A5-1b.D6-69.B1 to I.A5-1b.D6-69.B550).

Table 70i Compounds of the formula I.A5-1b in which the combination of $R^3$, $(R^4)_m$, $R^5$ and $R^6$ corresponds to line D6-70 of Table D6 and the meaning for the combination of $R^1$ and $R^2$ for each individual compound corresponds in each case to one line of Table B (compounds I.A5-1b.D6-70.B1 to I.A5-1b.D6-70.B550).

Table 71i Compounds of the formula I.A5-1b in which the combination of $R^3$, $(R^4)_m$, $R^5$ and $R^6$ corresponds to line D6-71 of Table D6 and the meaning for the combination of $R^1$ and $R^2$ for each individual compound corresponds in each case to one line of Table B (compounds I.A5-1b.D6-71.B1 to I.A5-1b.D6-71.B550).

Table 72i Compounds of the formula I.A5-1b in which the combination of $R^3$, $(R^4)_m$, $R^5$ and $R^6$ corresponds to line D6-72 of Table D6 and the meaning for the combination of $R^1$ and $R^2$ for each individual compound corresponds in each case to one line of Table B (compounds I.A5-1b.D6-72.B1 to I.A5-1b.D6-72.B550).

Table 73i Compounds of the formula I.A5-1b in which the combination of $R^3$, $(R^4)_m$, $R^5$ and $R^6$ corresponds to line D6-73 of Table D6 and the meaning for the combination of $R^1$ and $R^2$ for each individual compound corresponds in each case to one line of Table B (compounds I.A5-1b.D6-73.B1 to I.A5-1b.D6-73.B550).

Table 74i Compounds of the formula I.A5-1b in which the combination of $R^3$, $(R^4)_m$, $R^5$ and $R^6$ corresponds to line D6-74 of Table D6 and the meaning for the combination of $R^1$ and $R^2$ for each individual compound corresponds in each case to one line of Table B (compounds I.A5-1b.D6-74.B1 to I.A5-1b.D6-74.B550).

Table 75i Compounds of the formula I.A5-1b in which the combination of $R^3$, $(R^4)_m$, $R^5$ and $R^6$ corresponds to line D6-75 of Table D6 and the meaning for the combination of $R^1$ and $R^2$ for each individual compound corresponds in each case to one line of Table B (compounds I.A5-1b.D6-75.B1 to I.A5-1b.D6-75.B550).

Table 76i Compounds of the formula I.A5-1b in which the combination of $R^3$, $(R^4)_m$, $R^5$ and $R^6$ corresponds to line D6-76 of Table D6 and the meaning for the combination of $R^1$ and $R^2$ for each individual compound corresponds in each case to one line of Table B (compounds I.A5-1b.D6-76.B1 to I.A5-1b.D6-76.B550).

Table 77i Compounds of the formula I.A5-1b in which the combination of $R^3$, $(R^4)_m$, $R^5$ and $R^6$ corresponds to line D6-77 of Table D6 and the meaning for the combination of $R^1$ and $R^2$ for each individual compound corresponds in each case to one line of Table B (compounds I.A5-1b.D6-77.B1 to I.A5-1b.D6-77.B550).

Table 78i Compounds of the formula I.A5-1b in which the combination of $R^3$, $(R^4)_m$, $R^5$ and $R^6$ corresponds to line D6-78 of Table D6 and the meaning for the combination of $R^1$ and $R^2$ for each individual compound corresponds in each case to one line of Table B (compounds I.A5-1b.D6-78.B1 to I.A5-1b.D6-78.B550).

Table 79i Compounds of the formula I.A5-1b in which the combination of $R^3$, $(R^4)_m$, $R^5$ and $R^6$ corresponds to line D6-79 of Table D6 and the meaning for the combination of $R^1$ and $R^2$ for each individual compound corresponds in each case to one line of Table B (compounds I.A5-1b.D6-79.B1 to I.A5-1b.D6-79.B550).

Table 80i Compounds of the formula I.A5-1b in which the combination of $R^3$, $(R^4)_m$, $R^5$ and $R^6$ corresponds to line D6-80 of Table D6 and the meaning for the combination of $R^1$ and $R^2$ for each individual compound corresponds in each case to one line of Table B (compounds I.A5-1b.D6-80.B1 to I.A5-1b.D6-80.B550).

Table 81i Compounds of the formula I.A5-1b in which the combination of $R^3$, $(R^4)_m$, $R^5$ and $R^6$ corresponds to line D6-81 of Table D6 and the meaning for the combination of $R^1$ and $R^2$ for each individual compound corresponds in each case to one line of Table B (compounds I.A5-1b.D6-81.B1 to I.A5-1b.D6-81.B550).

Table 82i Compounds of the formula I.A5-1b in which the combination of $R^3$, $(R^4)_m$, $R^5$ and $R^6$ corresponds to line D6-82 of Table D6 and the meaning for the combination of $R^1$ and $R^2$ for each individual compound corresponds in each case to one line of Table B (compounds I.A5-1b.D6-82.B1 to I.A5-1b.D6-82.B550).

Table 83i Compounds of the formula I.A5-1b in which the combination of $R^3$, $(R^4)_m$, $R^5$ and $R^6$ corresponds to line D6-83 of Table D6 and the meaning for the combination of $R^1$ and $R^2$ for each individual compound corresponds in each case to one line of Table B (compounds I.A5-1b.D6-83.B1 to I.A5-1b.D6-83.B550).

Table 84i Compounds of the formula I.A5-1b in which the combination of $R^3$, $(R^4)_m$, $R^5$ and $R^6$ corresponds to line D6-84 of Table D6 and the meaning for the combination of $R^1$ and $R^2$ for each individual compound corresponds in each case to one line of Table B (compounds I.A5-1b.D6-84.B1 to I.A5-1b.D6-84.B550).

Table 85i Compounds of the formula I.A5-1b in which the combination of $R^3$, $(R^4)_m$, $R^5$ and $R^6$ corresponds to line D6-85 of Table D6 and the meaning for the combination of $R^1$ and $R^2$ for each individual compound corresponds in each case to one line of Table B (compounds I.A5-1b.D6-85.B1 to I.A5-1b.D6-85.B550).

Table 86i Compounds of the formula I.A5-1b in which the combination of $R^3$, $(R^4)_m$, $R^5$ and $R^6$ corresponds to line D6-86 of Table D6 and the meaning for the combination of $R^1$ and $R^2$ for each individual compound corresponds in each case to one line of Table B (compounds I.A5-1b.D6-86.B1 to I.A5-1b.D6-86.B550).

Table 87i Compounds of the formula I.A5-1b in which the combination of $R^3$, $(R^4)_m$, $R^5$ and $R^6$ corresponds to line D6-87 of Table D6 and the meaning for the combination of $R^1$ and $R^2$ for each individual compound corresponds in each case to one line of Table B (compounds I.A5-1b.D6-87.B1 to I.A5-1b.D6-87.B550).

Table 88i Compounds of the formula I.A5-1b in which the combination of $R^3$, $(R^4)_m$, $R^5$ and $R^6$ corresponds to line D6-88 of Table D6 and the meaning for the combination of $R^1$ and $R^2$ for each individual compound corresponds in each case to one line of Table B (compounds I.A5-1b.D6-88.B1 to I.A5-1b.D6-88.B550).

Table 89i Compounds of the formula I.A5-1b in which the combination of $R^3$, $(R^4)_m$, $R^5$ and $R^6$ corresponds to line D6-89 of Table D6 and the meaning for the combination of $R^1$ and $R^2$ for each individual compound corresponds in each case to one line of Table B (compounds I.A5-1b.D6-89.B1 to I.A5-1b.D6-89.B550).

Table 90i Compounds of the formula I.A5-1b in which the combination of $R^3$, $(R^4)_m$, $R^5$ and $R^6$ corresponds to line D6-90 of Table D6 and the meaning for the combination of $R^1$ and $R^2$ for each individual compound corresponds in each case to one line of Table B (compounds I.A5-1b.D6-90.B1 to I.A5-1b.D6-90.B550).

Table 91i Compounds of the formula I.A5-1b in which the combination of $R^3$, $(R^4)_m$, $R^5$ and $R^6$ corresponds to line D6-91 of Table D6 and the meaning for the combination of $R^1$ and $R^2$ for each individual compound corresponds in each case to one line of Table B (compounds I.A5-1b.D6-91.B1 to I.A5-1b.D6-91.B550).

Table 92i Compounds of the formula I.A5-1b in which the combination of $R^3$, $(R^4)_m$, $R^5$ and $R^6$ corresponds to line D6-92 of Table D6 and the meaning for the combination of $R^1$ and $R^2$ for each individual compound corresponds in each case to one line of Table B (compounds I.A5-1b.D6-92.B1 to I.A5-1b.D6-92.B550).

Table 93i Compounds of the formula I.A5-1b in which the combination of $R^3$, $(R^4)_m$, $R^5$ and $R^6$ corresponds to line D6-93 of Table D6 and the meaning for the combination of $R^1$ and $R^2$ for each individual compound corresponds in each case to one line of Table B (compounds I.A5-1b.D6-93.B1 to I.A5-1b.D6-93.B550).

Table 94i Compounds of the formula I.A5-1b in which the combination of $R^3$, $(R^4)_m$, $R^5$ and $R^6$ corresponds to line D6-94 of Table D6 and the meaning for the combination of $R^1$ and $R^2$ for each individual compound corresponds in each case to one line of Table B (compounds I.A5-1b.D6-94.B1 to I.A5-1b.D6-94.B550).

Table 95i Compounds of the formula I.A5-1b in which the combination of $R^3$, $(R^4)_m$, $R^5$ and $R^6$ corresponds to line D6-95 of Table D6 and the meaning for the combination of $R^1$ and $R^2$ for each individual compound corresponds in each case to one line of Table B (compounds I.A5-1b.D6-95.B1 to I.A5-1b.D6-95.B550).

Table 96i Compounds of the formula I.A5-1b in which the combination of $R^3$, $(R^4)_m$, $R^5$ and $R^6$ corresponds to line D6-96 of Table D6 and the meaning for the combination of $R^1$ and $R^2$ for each individual compound corresponds in each case to one line of Table B (compounds I.A5-1b.D6-96.B1 to I.A5-1b.D6-96.B550).

Table 97i Compounds of the formula I.A5-1b in which the combination of $R^3$, $(R^4)_m$, $R^5$ and $R^6$ corresponds to line D6-97 of Table D6 and the meaning for the combination of $R^1$ and $R^2$ for each individual compound corresponds in each case to one line of Table B (compounds I.A5-1b.D6-97.B1 to I.A5-1b.D6-97.B550).

Table 98i Compounds of the formula I.A5-1b in which the combination of $R^3$, $(R^4)_m$, $R^5$ and $R^6$ corresponds to line D6-98 of Table D6 and the meaning for the combination of $R^1$ and $R^2$ for each individual compound corresponds in each case to one line of Table B (compounds I.A5-1b.D6-98.B1 to I.A5-1b.D6-98.B550).

Table 99i Compounds of the formula I.A5-1b in which the combination of $R^3$, $(R^4)_m$, $R^5$ and $R^6$ corresponds to line D6-99 of Table D6 and the meaning for the combination of $R^1$ and $R^2$ for each individual compound corresponds in each case to one line of Table B (compounds I.A5-1b.D6-99.B1 to I.A5-1b.D6-99.B550).

Table 100i Compounds of the formula I.A5-1b in which the combination of $R^3$, $(R^4)_m$, $R^5$ and $R^6$ corresponds to line D6-100 of Table D6 and the meaning for the combination of $R^1$ and $R^2$ for each individual compound corresponds in each case to one line of Table B (compounds I.A5-1b.D6-100.B1 to I.A5-1b.D6-100.B550).

Table 101i Compounds of the formula I.A5-1b in which the combination of $R^3$, $(R^4)_m$, $R^5$ and $R^6$ corresponds to line D6-101 of Table D6 and the meaning for the combination of $R^1$ and $R^2$ for each individual compound corresponds in each case to one line of Table B (compounds I.A5-1b.D6-101.B1 to I.A5-1b.D6-101.B550).

Table 102i Compounds of the formula I.A5-1b in which the combination of $R^3$, $(R^4)_m$, $R^5$ and $R^6$ corresponds to line D6-102 of Table D6 and the meaning for the combination of $R^1$ and $R^2$ for each individual compound corresponds in each case to one line of Table B (compounds I.A5-1b.D6-102.B1 to I.A5-1b.D6-102.B550).

Table 103i Compounds of the formula I.A5-1b in which the combination of $R^3$, $(R^4)_m$, $R^5$ and $R^6$ corresponds to line D6-103 of Table D6 and the meaning for the combination of $R^1$ and $R^2$ for each individual compound corresponds in each case to one line of Table B (compounds I.A5-1b.D6-103.B1 to I.A5-1b.D6-103.B550).

Table 104i Compounds of the formula I.A5-1b in which the combination of $R^3$, $(R^4)_m$, $R^5$ and $R^6$ corresponds to line D6-104 of Table D6 and the meaning for the combination of $R^1$ and $R^2$ for each individual compound corresponds in each case to one line of Table B (compounds I.A5-1b.D6-104.B1 to I.A5-1b.D6-104.B550).

Table 105i Compounds of the formula I.A5-1b in which the combination of $R^3$, $(R^4)_m$, $R^5$ and $R^6$ corresponds to line D6-105 of Table D6 and the meaning for the combination of $R^1$ and $R^2$ for each individual compound corresponds in each case to one line of Table B (compounds I.A5-1b.D6-105.B1 to I.A5-1b.D6-105.B550).

Table 106i Compounds of the formula I.A5-1b in which the combination of $R^3$, $(R^4)_m$, $R^5$ and $R^6$ corresponds to line D6-106 of Table D6 and the meaning for the combination of $R^1$ and $R^2$ for each individual compound corresponds in each case to one line of Table B (compounds I.A5-1b.D6-106.B1 to I.A5-1b.D6-106.B550).

Table 107i Compounds of the formula I.A5-1b in which the combination of $R^3$, $(R^4)_m$, $R^5$ and $R^6$ corresponds to line D6-107 of Table D6 and the meaning for the combination of $R^1$ and $R^2$ for each individual compound corresponds in each case to one line of Table B (compounds I.A5-1b.D6-107.B1 to I.A5-1b.D6-107.B550).

Table 108i Compounds of the formula I.A5-1b in which the combination of $R^3$, $(R^4)_m$, $R^5$ and $R^6$ corresponds to line D6-108 of Table D6 and the meaning for the combination of $R^1$ and $R^2$ for each individual compound corresponds in each case to one line of Table B (compounds I.A5-1b.D6-108.B1 to I.A5-1b.D6-108.B550).

Table 109i Compounds of the formula I.A5-1b in which the combination of $R^3$, $(R^4)_m$, $R^5$ and $R^6$ corresponds to line D6-109 of Table D6 and the meaning for the combination of $R^1$ and $R^2$ for each individual compound corresponds in each case to one line of Table B (compounds I.A5-1b.D6-109.B1 to I.A5-1b.D6-109.B550).

Table 110i Compounds of the formula I.A5-1b in which the combination of $R^3$, $(R^4)_m$, $R^5$ and $R^6$ corresponds to line D6-110 of Table D6 and the meaning for the combination of $R^1$ and $R^2$ for each individual compound corresponds in each case to one line of Table B (compounds I.A5-1b.D6-110.B1 to I.A5-1b.D6-110.B550).

Table 111i Compounds of the formula I.A5-1b in which the combination of $R^3$, $(R^4)_m$, $R^5$ and $R^6$ corresponds to line D6-111 of Table D6 and the meaning for the combination of $R^1$ and $R^2$ for each individual compound corresponds in each case to one line of Table B (compounds I.A5-1b.D6-111.B1 to I.A5-1b.D6-111.B550).

Table 112i Compounds of the formula I.A5-1b in which the combination of $R^3$, $(R^4)_m$, $R^5$ and $R^6$ corresponds to line D6-112 of Table D6 and the meaning for the combination of $R^1$ and $R^2$ for each individual compound corresponds in each case to one line of Table B (compounds I.A5-1b.D6-112.B1 to I.A5-1b.D6-112.B550).

Table 1j Compounds of the formula I.A10-1a in which the combination of $R^3$, $R^5$, $R^6$ and $R^{7a}$ corresponds to line D10-1 of Table D10 and the meaning for the combination of $R^1$ and $R^2$ for each individual compound corresponds in each case to one line of Table B (compounds I.A10-1a.D10-1.B1 to I.A10-1a.D10-1.B550).

Table 2j Compounds of the formula I.A10-1a in which the combination of $R^3$, $R^5$, $R^6$ and $R^{7a}$ corresponds to line D10-2 of Table D10 and the meaning for the combination of $R^1$ and $R^2$ for each individual compound corresponds in each case to one line of Table B (compounds I.A10-1a.D10-2.B1 to I.A10-1a.D10-2.B550).

Table 3j Compounds of the formula I.A10-1a in which the combination of $R^3$, $R^5$, $R^6$ and $R^{7a}$ corresponds to line D10-3 of Table D10 and the meaning for the combination of $R^1$ and $R^2$ for each individual compound corresponds in each case to one line of Table B (compounds I.A10-1a.D10-3.B1 to I.A10-1a.D10-3.B550).

Table 4j Compounds of the formula I.A10-1a in which the combination of $R^3$, $R^5$, $R^6$ and $R^{7a}$ corresponds to line D10-4 of Table D10 and the meaning for the combination of $R^1$ and $R^2$ for each individual compound corresponds in each case to one line of Table B (compounds I.A10-1a.D10-4.B1 to I.A10-1a.D10-4.B550).

Table 5j Compounds of the formula I.A10-1a in which the combination of $R^3$, $R^5$, $R^6$ and $R^{7a}$ corresponds to line D10-5 of Table D10 and the meaning for the combination of $R^1$ and $R^2$ for each individual compound corresponds in each case to one line of Table B (compounds I.A10-1a.D10-5.B1 to I.A10-1a.D10-5.B550).

Table 6j Compounds of the formula I.A10-1a in which the combination of $R^3$, $R^5$, $R^6$ and $R^{7a}$ corresponds to line D10-6 of Table D10 and the meaning for the combination of $R^1$ and $R^2$ for each individual compound corresponds in each case to one line of Table B (compounds I.A10-1a.D10-6.B1 to I.A10-1a.D10-6.B550).

Table 7j Compounds of the formula I.A10-1a in which the combination of $R^3$, $R^5$, $R^6$ and $R^{7a}$ corresponds to line D10-7 of Table D10 and the meaning for the combination of $R^1$ and $R^2$ for each individual compound corresponds in each case to one line of Table B (compounds I.A10-1a.D10-7.B1 to I.A10-1a.D10-7.B550).

Table 8j Compounds of the formula I.A10-1a in which the combination of $R^3$, $R^5$, $R^6$ and $R^{7a}$ corresponds to line D10-8 of Table D10 and the meaning for the combination of $R^1$ and $R^2$ for each individual compound corresponds in each case to one line of Table B (compounds I.A10-1a.D10-8.B1 to I.A10-1a.D10-8.B550).

Table 9j Compounds of the formula I.A10-1a in which the combination of $R^3$, $R^5$, $R^6$ and $R^{7a}$ corresponds to line D10-9 of Table D10 and the meaning for the combination of $R^1$ and $R^2$ for each individual compound corresponds in each case to one line of Table B (compounds I.A10-1a.D10-9.B1 to I.A10-1a.D10-9.B550).

Table 10j Compounds of the formula I.A10-1a in which the combination of $R^3$, $R^5$, $R^6$ and $R^{7a}$ corresponds to line D10-10 of Table D10 and the meaning for the combination of $R^1$ and $R^2$ for each individual compound corresponds in each case to one line of Table B (compounds I.A10-1a.D10-10.B1 to I.A10-1a.D10-10.B550).

Table 11j Compounds of the formula I.A10-1a in which the combination of $R^3$, $R^5$, $R^6$ and $R^{7a}$ corresponds to line D10-11 of Table D10 and the meaning for the combination of $R^1$ and $R^2$ for each individual compound corresponds in each case to one line of Table B (compounds I.A10-1a.D10-11.B1 to I.A10-1a.D10-11.B550).

Table 12j Compounds of the formula I.A10-1a in which the combination of $R^3$, $R^5$, $R^6$ and $R^{7a}$ corresponds to line D10-12 of Table D10 and the meaning for the combination of $R^1$ and $R^2$ for each individual compound corresponds in each case to one line of Table B (compounds I.A10-1a.D10-12.B1 to I.A10-1a.D10-12.B550).

Table 13j Compounds of the formula I.A10-1a in which the combination of $R^3$, $R^5$, $R^6$ and $R^{7a}$ corresponds to line D10-13 of Table D10 and the meaning for the combination of $R^1$ and $R^2$ for each individual compound corresponds in each case to one line of Table B (compounds I.A10-1a.D10-13.B1 to I.A10-1a.D10-13.B550).

Table 14j Compounds of the formula I.A10-1a in which the combination of $R^3$, $R^5$, $R^6$ and $R^{7a}$ corresponds to line D10-14 of Table D10 and the meaning for the combination of $R^1$ and $R^2$ for each individual compound corresponds in each case to one line of Table B (compounds I.A10-1a.D10-14.B1 to I.A10-1a.D10-14.B550).

Table 15j Compounds of the formula I.A10-1a in which the combination of $R^3$, $R^5$, $R^6$ and $R^{7a}$ corresponds to line D10-15 of Table D10 and the meaning for the combination of $R^1$ and $R^2$ for each individual compound corresponds in each case to one line of Table B (compounds I.A10-1a.D10-15.B1 to I.A10-1a.D10-15.B550).

Table 16j Compounds of the formula I.A10-1a in which the combination of $R^3$, $R^5$, $R^6$ and $R^{7a}$ corresponds to line D10-16 of Table D10 and the meaning for the combination of $R^1$ and $R^2$ for each individual compound corresponds in each case to one line of Table B (compounds I.A10-1a.D10-16.B1 to I.A10-1a.D10-16.B550).

Table 17j Compounds of the formula I.A10-1a in which the combination of $R^3$, $R^5$, $R^6$ and $R^{7a}$ corresponds to line D10-17 of Table D10 and the meaning for the combination of $R^1$ and $R^2$ for each individual compound corresponds in each case to one line of Table B (compounds I.A10-1a.D10-17.B1 to I.A10-1a.D10-17.B550).

Table 18j Compounds of the formula I.A10-1a in which the combination of $R^3$, $R^5$, $R^6$ and $R^{7a}$ corresponds to line D10-18 of Table D10 and the meaning for the combination of $R^1$ and $R^2$ for each individual compound corresponds in each case to one line of Table B (compounds I.A10-1a.D10-18.B1 to I.A10-1a.D10-18.B550).

Table 19j Compounds of the formula I.A10-1a in which the combination of $R^3$, $R^5$, $R^6$ and $R^{7a}$ corresponds to line D10-19 of Table D10 and the meaning for the combination of $R^1$ and $R^2$ for each individual compound corresponds in each case to one line of Table B (compounds I.A10-1a.D10-19.B1 to I.A10-1a.D10-19.B550).

Table 20j Compounds of the formula I.A10-1a in which the combination of $R^3$, $R^5$, $R^6$ and $R^{7a}$ corresponds to line D10-20 of Table D10 and the meaning for the combination of $R^1$ and $R^2$ for each individual compound corresponds in each case to one line of Table B (compounds I.A10-1a.D10-20.B1 to I.A10-1a.D10-20.B550).

Table 21j Compounds of the formula I.A10-1a in which the combination of $R^3$, $R^5$, $R^6$ and $R^{7a}$ corresponds to line D10-21 of Table D10 and the meaning for the combination of $R^1$ and $R^2$ for each individual compound corresponds in each case to one line of Table B (compounds I.A10-1a.D10-21.B1 to I.A10-1a.D10-21.B550).

Table 22j Compounds of the formula I.A10-1a in which the combination of $R^3$, $R^5$, $R^6$ and $R^{7a}$ corresponds to line D10-22 of Table D10 and the meaning for the combination of $R^1$ and $R^2$ for each individual compound corresponds in each case to one line of Table B (compounds I.A10-1a.D10-22.B1 to I.A10-1a.D10-22.B550).

Table 23j Compounds of the formula I.A10-1a in which the combination of $R^3$, $R^5$, $R^6$ and $R^{7a}$ corresponds to line D10-23 of Table D10 and the meaning for the combination of $R^1$ and $R^2$ for each individual compound corresponds in each case to one line of Table B (compounds I.A10-1a.D10-23.B1 to I.A10-1a.D10-23.B550).

Table 24j Compounds of the formula I.A10-1a in which the combination of $R^3$, $R^5$, $R^6$ and $R^{7a}$ corresponds to line D10-24 of Table D10 and the meaning for the combination of $R^1$ and $R^2$ for each individual compound corresponds in each case to one line of Table B (compounds I.A10-1a.D10-24.B1 to I.A10-1a.D10-24.B550).

Table 25j Compounds of the formula I.A10-1a in which the combination of $R^3$, $R^5$, $R^6$ and $R^{7a}$ corresponds to line D10-25 of Table D10 and the meaning for the combination of $R^1$ and $R^2$ for each individual compound corresponds in each case to one line of Table B (compounds I.A10-1a.D10-25.B1 to I.A10-1a.D10-25.B550).

Table 26j Compounds of the formula I.A10-1a in which the combination of $R^3$, $R^5$, $R^6$ and $R^{7a}$ corresponds to line D10-26 of Table D10 and the meaning for the combination of $R^1$ and $R^2$ for each individual compound corresponds in each case to one line of Table B (compounds I.A10-1a.D10-26.B1 to I.A10-1a.D10-26.B550).

Table 27j Compounds of the formula I.A10-1a in which the combination of $R^3$, $R^5$, $R^6$ and $R^{7a}$ corresponds to line D10-27 of Table D10 and the meaning for the combination of $R^1$ and $R^2$ for each individual compound corresponds in each case to one line of Table B (compounds I.A10-1a.D10-27.B1 to I.A10-1a.D10-27.B550).

Table 28j Compounds of the formula I.A10-1a in which the combination of $R^3$, $R^5$, $R^6$ and $R^{7a}$ corresponds to line D10-28 of Table D10 and the meaning for the combination of $R^1$ and $R^2$ for each individual compound corresponds in each case to one line of Table B (compounds I.A10-1a.D10-28.B1 to I.A10-1a.D10-28.B550).

Table 29j Compounds of the formula I.A10-1a in which the combination of $R^3$, $R^5$, $R^6$ and $R^{7a}$ corresponds to line D10-29 of Table D10 and the meaning for the combination of $R^1$ and $R^2$ for each individual compound corresponds in each case to one line of Table B (compounds I.A10-1a.D10-29.B1 to I.A10-1a.D10-29.B550).

Table 30j Compounds of the formula I.A10-1a in which the combination of $R^3$, $R^5$, $R^6$ and $R^{7a}$ corresponds to line D10-30 of Table D10 and the meaning for the combination of $R^1$ and $R^2$ for each individual compound corresponds in each case to one line of Table B (compounds I.A10-1a.D10-30.B1 to I.A10-1a.D10-30.B550).

Table 31j Compounds of the formula I.A10-1a in which the combination of $R^3$, $R^5$, $R^6$ and $R^{7a}$ corresponds to line D10-31 of Table D10 and the meaning for the combination of $R^1$ and $R^2$ for each individual compound corresponds in each case to one line of Table B (compounds I.A10-1a.D10-31.B1 to I.A10-1a.D10-31.B550).

Table 32j Compounds of the formula I.A10-1a in which the combination of $R^3$, $R^5$, $R^6$ and $R^{7a}$ corresponds to line D10-32 of Table D10 and the meaning for the combination of $R^1$ and $R^2$ for each individual compound corresponds in each case to one line of Table B (compounds I.A10-1a.D10-32.B1 to I.A10-1a.D10-32.B550).

Table 33j Compounds of the formula I.A10-1a in which the combination of $R^3$, $R^5$, $R^6$ and $R^{7a}$ corresponds to line D10-33 of Table D10 and the meaning for the combination of $R^1$ and $R^2$ for each individual compound corresponds in each case to one line of Table B (compounds I.A10-1a.D10-33.B1 to I.A10-1a.D10-33.B550).

Table 34j Compounds of the formula I.A10-1a in which the combination of $R^3$, $R^5$, $R^6$ and $R^{7a}$ corresponds to line D10-34 of Table D10 and the meaning for the combination of $R^1$ and $R^2$ for each individual compound corresponds in each case to one line of Table B (compounds I.A10-1a.D10-34.B1 to I.A10-1a.D10-34.B550).

Table 35j Compounds of the formula I.A10-1a in which the combination of $R^3$, $R^5$, $R^6$ and $R^{7a}$ corresponds to line D10-35 of Table D10 and the meaning for the combination of $R^1$ and $R^2$ for each individual compound corresponds in each case to one line of Table B (compounds I.A10-1a.D10-35.B1 to I.A10-1a.D10-35.B550).

Table 36j Compounds of the formula I.A10-1a in which the combination of $R^3$, $R^5$, $R^6$ and $R^{7a}$ corresponds to line D10-36 of Table D10 and the meaning for the combination of $R^1$ and $R^2$ for each individual compound corresponds in each case to one line of Table B (compounds I.A10-1a.D10-36.B1 to I.A10-1a.D10-36.B550).

Table 37j Compounds of the formula I.A10-1a in which the combination of $R^3$, $R^5$, $R^6$ and $R^{7a}$ corresponds to line D10-37 of Table D10 and the meaning for the combination of $R^1$ and $R^2$ for each individual compound corresponds in each case to one line of Table B (compounds I.A10-1a.D10-37.B1 to I.A10-1a.D10-37.B550).

Table 38j Compounds of the formula I.A10-1a in which the combination of $R^3$, $R^5$, $R^6$ and $R^{7a}$ corresponds to line D10-38 of Table D10 and the meaning for the combination of $R^1$ and $R^2$ for each individual compound corresponds in each case to one line of Table B (compounds I.A10-1a.D10-38.B1 to I.A10-1a.D10-38.B550).

Table 39j Compounds of the formula I.A10-1a in which the combination of $R^3$, $R^5$, $R^6$ and $R^{7a}$ corresponds to line D10-39 of Table D10 and the meaning for the combination of $R^1$ and $R^2$ for each individual compound corresponds in each case to one line of Table B (compounds I.A10-1a.D10-39.B1 to I.A10-1a.D10-39.B550).

Table 40j Compounds of the formula I.A10-1a in which the combination of $R^3$, $R^5$, $R^6$ and $R^{7a}$ corresponds to line D10-40 of Table D10 and the meaning for the combination of $R^1$ and $R^2$ for each individual compound corresponds in each case to one line of Table B (compounds I.A10-1a.D10-40.B1 to I.A10-1a.D10-40.B550).

Table 41j Compounds of the formula I.A10-1a in which the combination of $R^3$, $R^5$, $R^6$ and $R^{7a}$ corresponds to line D10-41 of Table D10 and the meaning for the combination of $R^1$ and $R^2$ for each individual compound corresponds in each case to one line of Table B (compounds I.A10-1a.D10-41.B1 to I.A10-1a.D10-41.B550).

Table 42j Compounds of the formula I.A10-1a in which the combination of $R^3$, $R^5$, $R^6$ and $R^{7a}$ corresponds to line D10-42 of Table D10 and the meaning for the combination of $R^1$ and $R^2$ for each individual compound corresponds in each case to one line of Table B (compounds I.A10-1a.D10-42.B1 to I.A10-1a.D10-42.B550).

Table 43j Compounds of the formula I.A10-1a in which the combination of $R^3$, $R^5$, $R^6$ and $R^{7a}$ corresponds to line D10-43 of Table D10 and the meaning for the combination of $R^1$ and $R^2$ for each individual compound corresponds in each case to one line of Table B (compounds I.A10-1a.D10-43.B1 to I.A10-1a.D10-43.B550).

Table 44j Compounds of the formula I.A10-1a in which the combination of $R^3$, $R^5$, $R^6$ and $R^{7a}$ corresponds to line D10-44 of Table D10 and the meaning for the combination of $R^1$ and $R^2$ for each individual compound corresponds in each case to one line of Table B (compounds I.A10-1a.D10-44.B1 to I.A10-1a.D10-44.B550).

Table 45j Compounds of the formula I.A10-1a in which the combination of $R^3$, $R^5$, $R^6$ and $R^{7a}$ corresponds to line D10-45 of Table D10 and the meaning for the combination of $R^1$ and $R^2$ for each individual compound corresponds in each case to one line of Table B (compounds I.A10-1a.D10-45.B1 to I.A10-1a.D10-45.B550).

Table 46j Compounds of the formula I.A10-1a in which the combination of $R^3$, $R^5$, $R^6$ and $R^{7a}$ corresponds to line D10-46 of Table D10 and the meaning for the combination of $R^1$ and $R^2$ for each individual compound corresponds in each case to one line of Table B (compounds I.A10-1a.D10-46.B1 to I.A10-1a.D10-46.B550).

Table 47j Compounds of the formula I.A10-1a in which the combination of $R^3$, $R^5$, $R^6$ and $R^{7a}$ corresponds to line D10-47 of Table D10 and the meaning for the combination of $R^1$ and $R^2$ for each individual compound corresponds in each case to one line of Table B (compounds I.A10-1a.D10-47.B1 to I.A10-1a.D10-47.B550).

Table 48j Compounds of the formula I.A10-1a in which the combination of $R^3$, $R^5$, $R^6$ and $R^{7a}$ corresponds to line D10-48 of Table D10 and the meaning for the combination of $R^1$ and $R^2$ for each individual compound corresponds in each case to one line of Table B (compounds I.A10-1a.D10-48.B1 to I.A10-1a.D10-48.B550).

Table 49j Compounds of the formula I.A10-1a in which the combination of $R^3$, $R^5$, $R^6$ and $R^{7a}$ corresponds to line D10-49 of Table D10 and the meaning for the combination of $R^1$ and $R^2$ for each individual compound corresponds in each case to one line of Table B (compounds I.A10-1a.D10-49.B1 to I.A10-1a.D10-49.B550).

Table 50j Compounds of the formula I.A10-1a in which the combination of $R^3$, $R^5$, $R^6$ and $R^{7a}$ corresponds to line D10-50 of Table D10 and the meaning for the combination of $R^1$ and $R^2$ for each individual compound corresponds in each case to one line of Table B (compounds I.A10-1a.D10-50.B1 to I.A10-1a.D10-50.B550).

Table 51j Compounds of the formula I.A10-1a in which the combination of $R^3$, $R^5$, $R^6$ and $R^{7a}$ corresponds to line D10-51 of Table D10 and the meaning for the combination of $R^1$ and $R^2$ for each individual compound corresponds in each case to one line of Table B (compounds I.A10-1a.D10-51.B1 to I.A10-1a.D10-51.B550).

Table 52j Compounds of the formula I.A10-1a in which the combination of $R^3$, $R^5$, $R^6$ and $R^{7a}$ corresponds to line D10-52 of Table D10 and the meaning for the combination of $R^1$ and $R^2$ for each individual compound corresponds in each case to one line of Table B (compounds I.A10-1a.D10-52.B1 to I.A10-1a.D10-52.B550).

Table 53j Compounds of the formula I.A10-1a in which the combination of $R^3$, $R^5$, $R^6$ and $R^{7a}$ corresponds to line D10-53 of Table D10 and the meaning for the combination of $R^1$ and $R^2$ for each individual compound corresponds in each case to one line of Table B (compounds I.A10-1a.D10-53.B1 to I.A10-1a.D10-53.B550).

Table 54j Compounds of the formula I.A10-1a in which the combination of $R^3$, $R^5$, $R^6$ and $R^{7a}$ corresponds to line D10-54 of Table D10 and the meaning for the combination of $R^1$ and $R^2$ for each individual compound corresponds in each case to one line of Table B (compounds I.A10-1a.D10-54.B1 to I.A10-1a.D10-54.B550).

Table 55j Compounds of the formula I.A10-1a in which the combination of $R^3$, $R^5$, $R^6$ and $R^{7a}$ corresponds to line D10-55 of Table D10 and the meaning for the combination of $R^1$ and $R^2$ for each individual compound corresponds in each case to one line of Table B (compounds I.A10-1a.D10-55.B1 to I.A10-1a.D10-55.B550).

Table 56j Compounds of the formula I.A10-1a in which the combination of $R^3$, $R^5$, $R^6$ and $R^{7a}$ corresponds to line D10-56 of Table D10 and the meaning for the combination of $R^1$ and $R^2$ for each individual compound corresponds in each case to one line of Table B (compounds I.A10-1a.D10-56.B1 to I.A10-1a.D10-56.B550).

Table 57j Compounds of the formula I.A10-1a in which the combination of $R^3$, $R^5$, $R^6$ and $R^{7a}$ corresponds to line D10-57 of Table D10 and the meaning for the combination of $R^1$ and $R^2$ for each individual compound corresponds in each case to one line of Table B (compounds I.A10-1a.D10-57.B1 to I.A10-1a.D10-57.B550).

Table 58j Compounds of the formula I.A10-1a in which the combination of $R^3$, $R^5$, $R^6$ and $R^{7a}$ corresponds to line D10-58 of Table D10 and the meaning for the combination of $R^1$ and $R^2$ for each individual compound corresponds in each case to one line of Table B (compounds I.A10-1a.D10-58.B1 to I.A10-1a.D10-58.B550).

Table 59j Compounds of the formula I.A10-1a in which the combination of $R^3$, $R^5$, $R^6$ and $R^{7a}$ corresponds to line D10-59 of Table D10 and the meaning for the combination of $R^1$ and $R^2$ for each individual compound corresponds in each case to one line of Table B (compounds I.A10-1a.D10-59.B1 to I.A10-1a.D10-59.B550).

Table 60j Compounds of the formula I.A10-1a in which the combination of $R^3$, $R^5$, $R^6$ and $R^{7a}$ corresponds to line D10-60 of Table D10 and the meaning for the combination of $R^1$ and $R^2$ for each individual compound corresponds in each case to one line of Table B (compounds I.A10-1a.D10-60.B1 to I.A10-1a.D10-60.B550).

Table 61j Compounds of the formula I.A10-1a in which the combination of $R^3$, $R^5$, $R^6$ and $R^{7a}$ corresponds to line D10-61 of Table D10 and the meaning for the combination of $R^1$ and $R^2$ for each individual compound corresponds in each case to one line of Table B (compounds I.A10-1a.D10-61.B1 to I.A10-1a.D10-61.B550).

Table 62j Compounds of the formula I.A10-1a in which the combination of $R^3$, $R^5$, $R^6$ and $R^{7a}$ corresponds to line D10-62 of Table D10 and the meaning for the combination of $R^1$ and $R^2$ for each individual compound corresponds in each case to one line of Table B (compounds I.A10-1a.D10-62.B1 to I.A10-1a.D10-62.B550).

Table 63j Compounds of the formula I.A10-1a in which the combination of $R^3$, $R^5$, $R^6$ and $R^{7a}$ corresponds to line D10-63 of Table D10 and the meaning for the combination of $R^1$ and $R^2$ for each individual compound corresponds in each case to one line of Table B (compounds I.A10-1a.D10-63.B1 to I.A10-1a.D10-63.B550).

Table 64j Compounds of the formula I.A10-1a in which the combination of $R^3$, $R^5$, $R^6$ and $R^{7a}$ corresponds to line D10-64 of Table D10 and the meaning for the combination of $R^1$ and $R^2$ for each individual compound corresponds in each case to one line of Table B (compounds I.A10-1a.D10-64.B1 to I.A10-1a.D10-64.B550).

Table 65j Compounds of the formula I.A10-1a in which the combination of $R^3$, $R^5$, $R^6$ and $R^{7a}$ corresponds to line D10-65 of Table D10 and the meaning for the combination of $R^1$ and $R^2$ for each individual compound corresponds in each case to one line of Table B (compounds I.A10-1a.D10-65.B1 to I.A10-1a.D10-65.B550).

Table 66j Compounds of the formula I.A10-1a in which the combination of $R^3$, $R^5$, $R^6$ and $R^{7a}$ corresponds to line D10-66 of Table D10 and the meaning for the combination of $R^1$ and $R^2$ for each individual compound corresponds in each case to one line of Table B (compounds I.A10-1a.D10-66.B1 to I.A10-1a.D10-66.B550).

Table 67j Compounds of the formula I.A10-1a in which the combination of $R^3$, $R^5$, $R^6$ and $R^{7a}$ corresponds to line D10-67 of Table D10 and the meaning for the combination of $R^1$ and $R^2$ for each individual compound corresponds in each case to one line of Table B (compounds I.A10-1a.D10-67.B1 to I.A10-1a.D10-67.B550).

Table 68j Compounds of the formula I.A10-1a in which the combination of $R^3$, $R^5$, $R^6$ and $R^{7a}$ corresponds to line D10-68 of Table D10 and the meaning for the combination of $R^1$ and $R^2$ for each individual compound corresponds in each case to one line of Table B (compounds I.A10-1a.D10-68.B1 to I.A10-1a.D10-68.B550).

Table 69j Compounds of the formula I.A10-1a in which the combination of $R^3$, $R^5$, $R^6$ and $R^{7a}$ corresponds to line D10-69 of Table D10 and the meaning for the combination of $R^1$ and $R^2$ for each individual compound corresponds in each case to one line of Table B (compounds I.A10-1a.D10-69.B1 to I.A10-1a.D10-69.B550).

Table 70j Compounds of the formula I.A10-1a in which the combination of $R^3$, $R^5$, $R^6$ and $R^{7a}$ corresponds to line D10-70 of Table D10 and the meaning for the combination of $R^1$ and $R^2$ for each individual compound corresponds in each case to one line of Table B (compounds I.A10-1a.D10-70.B1 to I.A10-1a.D10-70.B550).

Table 71j Compounds of the formula I.A10-1a in which the combination of $R^3$, $R^5$, $R^6$ and $R^{7a}$ corresponds to line D10-71 of Table D10 and the meaning for the combination of $R^1$ and $R^2$ for each individual compound corresponds in each case to one line of Table B (compounds I.A10-1a.D10-71. B1 to I.A10-1a.D10-71.B550).

Table 72j Compounds of the formula I.A10-1a in which the combination of $R^3$, $R^5$, $R^6$ and $R^{7a}$ corresponds to line D10-72 of Table D10 and the meaning for the combination of $R^1$ and $R^2$ for each individual compound corresponds in each case to one line of Table B (compounds I.A10-1a.D10-72.B1 to I.A10-1a.D10-72.B550).

Table 73j Compounds of the formula I.A10-1a in which the combination of $R^3$, $R^5$, $R^6$ and $R^{7a}$ corresponds to line D10-73 of Table D10 and the meaning for the combination of $R^1$ and $R^2$ for each individual compound corresponds in each case to one line of Table B (compounds I.A10-1a.D10-73.B1 to I.A10-1a.D10-73.B550).

Table 74j Compounds of the formula I.A10-1a in which the combination of $R^3$, $R^5$, $R^6$ and $R^{7a}$ corresponds to line D10-74 of Table D10 and the meaning for the combination of $R^1$ and $R^2$ for each individual compound corresponds in each case to one line of Table B (compounds I.A10-1a.D10-74.B1 to I.A10-1a.D10-74.B550).

Table 75j Compounds of the formula I.A10-1a in which the combination of $R^3$, $R^5$, $R^6$ and $R^{7a}$ corresponds to line D10-75 of Table D10 and the meaning for the combination of $R^1$ and $R^2$ for each individual compound corresponds in each case to one line of Table B (compounds I.A10-1a.D10-75.B1 to I.A10-1a.D10-75.B550).

Table 76j Compounds of the formula I.A10-1a in which the combination of $R^3$, $R^5$, $R^6$ and $R^{7a}$ corresponds to line D10-76 of Table D10 and the meaning for the combination of $R^1$ and $R^2$ for each individual compound corresponds in each case to one line of Table B (compounds I.A10-1a.D10-76.B1 to I.A10-1a.D10-76.B550).

Table 77j Compounds of the formula I.A10-1a in which the combination of $R^3$, $R^5$, $R^6$ and $R^{7a}$ corresponds to line D10-77 of Table D10 and the meaning for the combination of $R^1$ and $R^2$ for each individual compound corresponds in each case to one line of Table B (compounds I.A10-1a.D10-77.B1 to I.A10-1a.D10-77.B550).

Table 78j Compounds of the formula I.A10-1a in which the combination of $R^3$, $R^5$, $R^6$ and $R^{7a}$ corresponds to line D10-78 of Table D10 and the meaning for the combination of $R^1$ and $R^2$ for each individual compound corresponds in each case to one line of Table B (compounds I.A10-1a.D10-78.B1 to I.A10-1a.D10-78.B550).

Table 79j Compounds of the formula I.A10-1a in which the combination of $R^3$, $R^5$, $R^6$ and $R^{7a}$ corresponds to line D10-79 of Table D10 and the meaning for the combination of $R^1$ and $R^2$ for each individual compound corresponds in each case to one line of Table B (compounds I.A10-1a.D10-79.B1 to I.A10-1a.D10-79.B550).

Table 80j Compounds of the formula I.A10-1a in which the combination of $R^3$, $R^5$, $R^6$ and $R^{7a}$ corresponds to line D10-80 of Table D10 and the meaning for the combination of $R^1$ and $R^2$ for each individual compound corresponds in each case to one line of Table B (compounds I.A10-1a.D10-80.B1 to I.A10-1a.D10-80.B550).

Table 81j Compounds of the formula I.A10-1a in which the combination of $R^3$, $R^5$, $R^6$ and $R^{7a}$ corresponds to line D10-81 of Table D10 and the meaning for the combination of $R^1$ and $R^2$ for each individual compound corresponds in each case to one line of Table B (compounds I.A10-1a.D10-81. B1 to I.A10-1a.D10-81.B550).

Table 82j Compounds of the formula I.A10-1a in which the combination of $R^3$, $R^5$, $R^6$ and $R^{7a}$ corresponds to line D10-82 of Table D10 and the meaning for the combination of $R^1$ and $R^2$ for each individual compound corresponds in each case to one line of Table B (compounds I.A10-1a.D10-82.B1 to I.A10-1a.D10-82.B550).

Table 83j Compounds of the formula I.A10-1a in which the combination of $R^3$, $R^5$, $R^6$ and $R^{7a}$ corresponds to line D10-83 of Table D10 and the meaning for the combination of $R^1$ and $R^2$ for each individual compound corresponds in each case to one line of Table B (compounds I.A10-1a.D10-83.B1 to I.A10-1a.D10-83.B550).

Table 84j Compounds of the formula I.A10-1a in which the combination of $R^3$, $R^5$, $R^6$ and $R^{7a}$ corresponds to line D10-84 of Table D10 and the meaning for the combination of $R^1$ and $R^2$ for each individual compound corresponds in each case to one line of Table B (compounds I.A10-1a.D10-84.B1 to I.A10-1a.D10-84.B550).

Table 85j Compounds of the formula I.A10-1a in which the combination of $R^3$, $R^5$, $R^6$ and $R^{7a}$ corresponds to line D10-85 of Table D10 and the meaning for the combination of $R^1$ and $R^2$ for each individual compound corresponds in each case to one line of Table B (compounds I.A10-1a.D10-85.B1 to I.A10-1a.D10-85.B550).

Table 86j Compounds of the formula I.A10-1a in which the combination of $R^3$, $R^5$, $R^6$ and $R^{7a}$ corresponds to line D10-86 of Table D10 and the meaning for the combination of $R^1$ and $R^2$ for each individual compound corresponds in each case to one line of Table B (compounds I.A10-1a.D10-86.B1 to I.A10-1a.D10-86.B550).

Table 87j Compounds of the formula I.A10-1a in which the combination of $R^3$, $R^5$, $R^6$ and $R^{7a}$ corresponds to line D10-87 of Table D10 and the meaning for the combination of $R^1$ and $R^2$ for each individual compound corresponds in each case to one line of Table B (compounds I.A10-1a.D10-87.B1 to I.A10-1a.D10-87.B550).

Table 88j Compounds of the formula I.A10-1a in which the combination of $R^3$, $R^5$, $R^6$ and $R^{7a}$ corresponds to line D10-88 of Table D10 and the meaning for the combination of $R^1$ and $R^2$ for each individual compound corresponds in each case to one line of Table B (compounds I.A10-1a.D10-88.B1 to I.A10-1a.D10-88.B550).

Table 89j Compounds of the formula I.A10-1a in which the combination of $R^3$, $R^5$, $R^6$ and $R^{7a}$ corresponds to line D10-89 of Table D10 and the meaning for the combination of $R^1$ and $R^2$ for each individual compound corresponds in each case to one line of Table B (compounds I.A10-1a.D10-89.B1 to I.A10-1a.D10-89.B550).

Table 90j Compounds of the formula I.A10-1a in which the combination of $R^3$, $R^5$, $R^6$ and $R^{7a}$ corresponds to line D10-90 of Table D10 and the meaning for the combination of $R^1$ and $R^2$ for each individual compound corresponds in each case to one line of Table B (compounds I.A10-1a.D10-90.B1 to I.A10-1a.D10-90.B550).

Table 1k Compounds of the formula I.A10-1b in which the combination of $R^3$, $R^5$, $R^6$ and $R^{7a}$ corresponds to line D10-1 of Table D10 and the meaning for the combination of $R^1$ and $R^2$ for each individual compound corresponds in each case to one line of Table B (compounds I.A10-1b.D10-1.B1 to I.A10-1b.D10-1.B550).

Table 2k Compounds of the formula I.A10-1b in which the combination of $R^3$, $R^5$, $R^6$ and $R^{7a}$ corresponds to line D10-2 of Table D10 and the meaning for the combination of $R^1$ and $R^2$ for each individual compound corresponds in each case to one line of Table B (compounds I.A10-1b.D10-2.B1 to I.A10-1b.D10-2.B550).

Table 3k Compounds of the formula I.A10-1b in which the combination of $R^3$, $R^5$, $R^6$ and $R^{7a}$ corresponds to line D10-3 of Table D10 and the meaning for the combination of $R^1$ and $R^2$ for each individual compound corresponds in each case to one line of Table B (compounds I.A10-1b.D10-3.B1 to I.A10-1b.D10-3.B550).

Table 4k Compounds of the formula I.A10-1b in which the combination of $R^3$, $R^5$, $R^6$ and $R^{7a}$ corresponds to line D10-4 of Table D10 and the meaning for the combination of $R^1$ and $R^2$ for each individual compound corresponds in each case to one line of Table B (compounds I.A10-1b.D10-4.B1 to I.A10-1b.D10-4.B550).

Table 5k Compounds of the formula I.A10-1b in which the combination of $R^3$, $R^5$, $R^6$ and $R^{7a}$ corresponds to line D10-5 of Table D10 and the meaning for the combination of $R^1$ and $R^2$ for each individual compound corresponds in each case to one line of Table B (compounds I.A10-1b.D10-5.B1 to I.A10-1b.D10-5.B550).

Table 6k Compounds of the formula I.A10-1b in which the combination of $R^3$, $R^5$, $R^6$ and $R^{7a}$ corresponds to line D10-6 of Table D10 and the meaning for the combination of $R^1$ and $R^2$ for each individual compound corresponds in each case to one line of Table B (compounds I.A10-1b.D10-6.B1 to I.A10-1b.D10-6.B550).

Table 7k Compounds of the formula I.A10-1b in which the combination of $R^3$, $R^5$, $R^6$ and $R^{7a}$ corresponds to line D10-7 of Table D10 and the meaning for the combination of $R^1$ and $R^2$ for each individual compound corresponds in each case to one line of Table B (compounds I.A10-1b.D10-7.B1 to I.A10-1b.D10-7.B550).

Table 8k Compounds of the formula I.A10-1b in which the combination of $R^3$, $R^5$, $R^6$ and $R^{7a}$ corresponds to line D10-8 of Table D10 and the meaning for the combination of $R^1$ and $R^2$ for each individual compound corresponds in each case to one line of Table B (compounds I.A10-1b.D10-8.B1 to I.A10-1b.D10-8.B550).

Table 9k Compounds of the formula I.A10-1b in which the combination of $R^3$, $R^5$, $R^6$ and $R^{7a}$ corresponds to line D10-9 of Table D10 and the meaning for the combination of $R^1$ and $R^2$ for each individual compound corresponds in each case to one line of Table B (compounds I.A10-1b.D10-9.B1 to I.A10-1b.D10-9.B550).

Table 10k Compounds of the formula I.A10-1b in which the combination of $R^3$, $R^5$, $R^6$ and $R^{7a}$ corresponds to line D10-10 of Table D10 and the meaning for the combination of $R^1$ and $R^2$ for each individual compound corresponds in each case to one line of Table B (compounds I.A10-1b.D10-10.B1 to I.A10-1b.D10-10.B550).

Table 11k Compounds of the formula I.A10-1b in which the combination of $R^3$, $R^5$, $R^6$ and $R^{7a}$ corresponds to line D10-11 of Table D10 and the meaning for the combination of $R^1$ and $R^2$ for each individual compound corresponds in each case to one line of Table B (compounds I.A10-1b.D10-11.B1 to I.A10-1b.D10-11.B550).

Table 12k Compounds of the formula I.A10-1b in which the combination of $R^3$, $R^5$, $R^6$ and $R^{7a}$ corresponds to line D10-12 of Table D10 and the meaning for the combination of $R^1$ and $R^2$ for each individual compound corresponds in each case to one line of Table B (compounds I.A10-1b.D10-12.B1 to I.A10-1b.D10-12.B550).

Table 13k Compounds of the formula I.A10-1b in which the combination of $R^3$, $R^5$, $R^6$ and $R^{7a}$ corresponds to line D10-13 of Table D10 and the meaning for the combination of $R^1$ and $R^2$ for each individual compound corresponds in each case to one line of Table B (compounds I.A10-1b.D10-13.B1 to I.A10-1b.D10-13.B550).

Table 14k Compounds of the formula I.A10-1b in which the combination of $R^3$, $R^5$, $R^6$ and $R^{7a}$ corresponds to line D10-14 of Table D10 and the meaning for the combination of $R^1$ and $R^2$ for each individual compound corresponds in each case to one line of Table B (compounds I.A10-1b.D10-14.B1 to I.A10-1b.D10-14.B550).

Table 15k Compounds of the formula I.A10-1b in which the combination of $R^3$, $R^5$, $R^6$ and $R^{7a}$ corresponds to line D10-15 of Table D10 and the meaning for the combination of $R^1$ and $R^2$ for each individual compound corresponds in each case to one line of Table B (compounds I.A10-1b.D10-15.B1 to I.A10-1b.D10-15.B550).

Table 16k Compounds of the formula I.A10-1b in which the combination of $R^3$, $R^5$, $R^6$ and $R^{7a}$ corresponds to line D10-16 of Table D10 and the meaning for the combination of $R^1$ and $R^2$ for each individual compound corresponds in each case to one line of Table B (compounds I.A10-1b.D10-16.B1 to I.A10-1b.D10-16.B550).

Table 17k Compounds of the formula I.A10-1b in which the combination of $R^3$, $R^5$, $R^6$ and $R^{7a}$ corresponds to line D10-17 of Table D10 and the meaning for the combination of $R^1$ and $R^2$ for each individual compound corresponds in each case to one line of Table B (compounds I.A10-1b.D10-17.B1 to I.A10-1b.D10-17.B550).

Table 18k Compounds of the formula I.A10-1b in which the combination of $R^3$, $R^5$, $R^6$ and $R^{7a}$ corresponds to line D10-18 of Table D10 and the meaning for the combination of $R^1$ and $R^2$ for each individual compound corresponds in each case to one line of Table B (compounds I.A10-1b.D10-18.B1 to I.A10-1b.D10-18.B550).

Table 19k Compounds of the formula I.A10-1b in which the combination of $R^3$, $R^5$, $R^6$ and $R^{7a}$ corresponds to line D10-19 of Table D10 and the meaning for the combination of $R^1$ and $R^2$ for each individual compound corresponds in each case to one line of Table B (compounds I.A10-1b.D10-19.B1 to I.A10-1b.D10-19.B550).

Table 20k Compounds of the formula I.A10-1b in which the combination of $R^3$, $R^5$, $R^6$ and $R^{7a}$ corresponds to line D10-20 of Table D10 and the meaning for the combination of $R^1$ and $R^2$ for each individual compound corresponds in each case to one line of Table B (compounds I.A10-1b.D10-20.B1 to I.A10-1b.D10-20.B550).

Table 21k Compounds of the formula I.A10-1b in which the combination of $R^3$, $R^5$, $R^6$ and $R^{7a}$ corresponds to line D10-21 of Table D10 and the meaning for the combination of $R^1$ and $R^2$ for each individual compound corresponds in each case to one line of Table B (compounds I.A10-1b.D10-21.B1 to I.A10-1b.D10-21.B550).

Table 22k Compounds of the formula I.A10-1b in which the combination of $R^3$, $R^5$, $R^6$ and $R^{7a}$ corresponds to line D10-22 of Table D10 and the meaning for the combination of $R^1$ and $R^2$ for each individual compound corresponds in each case to one line of Table B (compounds I.A10-1b.D10-22.B1 to I.A10-1b.D10-22.B550).

Table 23k Compounds of the formula I.A10-1b in which the combination of $R^3$, $R^5$, $R^6$ and $R^{7a}$ corresponds to line D10-23 of Table D10 and the meaning for the combination of $R^1$ and $R^2$ for each individual compound corresponds in each case to one line of Table B (compounds I.A10-1b.D10-23.B1 to I.A10-1b.D10-23.B550).

Table 24k Compounds of the formula I.A10-1b in which the combination of $R^3$, $R^5$, $R^6$ and $R^{7a}$ corresponds to line D10-24 of Table D10 and the meaning for the combination of $R^1$ and $R^2$ for each individual compound corresponds in each case to one line of Table B (compounds I.A10-1b.D10-24.B1 to I.A10-1b.D10-24.B550).

Table 25k Compounds of the formula I.A10-1b in which the combination of $R^3$, $R^5$, $R^6$ and $R^{7a}$ corresponds to line D10-25 of Table D10 and the meaning for the combination of $R^1$ and $R^2$ for each individual compound corresponds in each case to one line of Table B (compounds I.A10-1b.D10-25.B1 to I.A10-1b.D10-25.B550).

Table 26k Compounds of the formula I.A10-1b in which the combination of $R^3$, $R^5$, $R^6$ and $R^{7a}$ corresponds to line D10-26 of Table D10 and the meaning for the combination of $R^1$ and $R^2$ for each individual compound corresponds in each case to one line of Table B (compounds I.A10-1b.D10-26.B1 to I.A10-1b.D10-26.B550).

Table 27k Compounds of the formula I.A10-1b in which the combination of $R^3$, $R^5$, $R^6$ and $R^{7a}$ corresponds to line D10-27 of Table D10 and the meaning for the combination of $R^1$ and $R^2$ for each individual compound corresponds in each case to one line of Table B (compounds I.A10-1b.D10-27.B1 to I.A10-1b.D10-27.B550).

Table 28k Compounds of the formula I.A10-1b in which the combination of $R^3$, $R^5$, $R^6$ and $R^{7a}$ corresponds to line D10-28 of Table D10 and the meaning for the combination of $R^1$ and $R^2$ for each individual compound corresponds in each case to one line of Table B (compounds I.A10-1b.D10-28.B1 to I.A10-1b.D10-28.B550).

Table 29k Compounds of the formula I.A10-1b in which the combination of $R^3$, $R^5$, $R^6$ and $R^{7a}$ corresponds to line D10-29 of Table D10 and the meaning for the combination of $R^1$ and $R^2$ for each individual compound corresponds in each case to one line of Table B (compounds I.A10-1b.D10-29.B1 to I.A10-1b.D10-29.B550).

Table 30k Compounds of the formula I.A10-1b in which the combination of $R^3$, $R^5$, $R^6$ and $R^{7a}$ corresponds to line D10-30 of Table D10 and the meaning for the combination of $R^1$ and $R^2$ for each individual compound corresponds in each case to one line of Table B (compounds I.A10-1b.D10-30.B1 to I.A10-1b.D10-30.B550).

Table 31k Compounds of the formula I.A10-1b in which the combination of $R^3$, $R^5$, $R^6$ and $R^{7a}$ corresponds to line D10-31 of Table D10 and the meaning for the combination of $R^1$ and $R^2$ for each individual compound corresponds in each case to one line of Table B (compounds I.A10-1b.D10-31.B1 to I.A10-1b.D10-31.B550).

Table 32k Compounds of the formula I.A10-1b in which the combination of $R^3$, $R^5$, $R^6$ and $R^{7a}$ corresponds to line D10-32 of Table D10 and the meaning for the combination of $R^1$ and $R^2$ for each individual compound corresponds in each case to one line of Table B (compounds I.A10-1b.D10-32.B1 to I.A10-1b.D10-32.B550).

Table 33k Compounds of the formula I.A10-1b in which the combination of $R^3$, $R^5$, $R^6$ and $R^{7a}$ corresponds to line D10-33 of Table D10 and the meaning for the combination of $R^1$ and $R^2$ for each individual compound corresponds in each case to one line of Table B (compounds I.A10-1b.D10-33.B1 to I.A10-1b.D10-33.B550).

Table 34k Compounds of the formula I.A10-1b in which the combination of $R^3$, $R^5$, $R^6$ and $R^{7a}$ corresponds to line D10-34 of Table D10 and the meaning for the combination of $R^1$ and $R^2$ for each individual compound corresponds in each case to one line of Table B (compounds I.A10-1b.D10-34.B1 to I.A10-1b.D10-34.B550).

Table 35k Compounds of the formula I.A10-1b in which the combination of $R^3$, $R^5$, $R^6$ and $R^{7a}$ corresponds to line D10-35 of Table D10 and the meaning for the combination of $R^1$ and $R^2$ for each individual compound corresponds in each case to one line of Table B (compounds I.A10-1b.D10-35.B1 to I.A10-1b.D10-35.B550).

Table 36k Compounds of the formula I.A10-1b in which the combination of $R^3$, $R^5$, $R^6$ and $R^{7a}$ corresponds to line D10-36 of Table D10 and the meaning for the combination of $R^1$ and $R^2$ for each individual compound corresponds in each case to one line of Table B (compounds I.A10-1b.D10-36.B1 to I.A10-1b.D10-36.B550).

Table 37k Compounds of the formula I.A10-1b in which the combination of $R^3$, $R^5$, $R^6$ and $R^{7a}$ corresponds to line D10-37 of Table D10 and the meaning for the combination of $R^1$ and $R^2$ for each individual compound corresponds in each case to one line of Table B (compounds I.A10-1b.D10-37.B1 to I.A10-1b.D10-37.B550).

Table 38k Compounds of the formula I.A10-1b in which the combination of $R^3$, $R^5$, $R^6$ and $R^{7a}$ corresponds to line D10-38 of Table D10 and the meaning for the combination of $R^1$ and $R^2$ for each individual compound corresponds in each case to one line of Table B (compounds I.A10-1b.D10-38.B1 to I.A10-1b.D10-38.B550).

Table 39k Compounds of the formula I.A10-1b in which the combination of $R^3$, $R^5$, $R^6$ and $R^{7a}$ corresponds to line D10-39 of Table D10 and the meaning for the combination of $R^1$ and $R^2$ for each individual compound corresponds in each case to one line of Table B (compounds I.A10-1b.D10-39.B1 to I.A10-1b.D10-39.B550).

Table 40k Compounds of the formula I.A10-1b in which the combination of $R^3$, $R^5$, $R^6$ and $R^{7a}$ corresponds to line D10-40 of Table D10 and the meaning for the combination of $R^1$ and $R^2$ for each individual compound corresponds in each case to one line of Table B (compounds I.A10-1b.D10-40.B1 to I.A10-1b.D10-40.B550).

Table 41k Compounds of the formula I.A10-1b in which the combination of $R^3$, $R^5$, $R^6$ and $R^{7a}$ corresponds to line D10-41 of Table D10 and the meaning for the combination of $R^1$ and $R^2$ for each individual compound corresponds in each case to one line of Table B (compounds I.A10-1b.D10-41.B1 to I.A10-1b.D10-41.B550).

Table 42k Compounds of the formula I.A10-1b in which the combination of $R^3$, $R^5$, $R^6$ and $R^{7a}$ corresponds to line D10-42 of Table D10 and the meaning for the combination of $R^1$ and $R^2$ for each individual compound corresponds in each case to one line of Table B (compounds I.A10-1b.D10-42.B1 to I.A10-1b.D10-42.B550).

Table 43k Compounds of the formula I.A10-1b in which the combination of $R^3$, $R^5$, $R^6$ and $R^{7a}$ corresponds to line D10-43 of Table D10 and the meaning for the combination of $R^1$ and $R^2$ for each individual compound corresponds in each case to one line of Table B (compounds I.A10-1b.D10-43.B1 to I.A10-1b.D10-43.B550).

Table 44k Compounds of the formula I.A10-1b in which the combination of $R^3$, $R^5$, $R^6$ and $R^{7a}$ corresponds to line D10-44 of Table D10 and the meaning for the combination of $R^1$ and $R^2$ for each individual compound corresponds in each case to one line of Table B (compounds I.A10-1b.D10-44.B1 to I.A10-1b.D10-44.B550).

Table 45k Compounds of the formula I.A10-1b in which the combination of $R^3$, $R^5$, $R^6$ and $R^{7a}$ corresponds to line D10-45 of Table D10 and the meaning for the combination of $R^1$ and $R^2$ for each individual compound corresponds in each case to one line of Table B (compounds I.A10-1b.D10-45.B1 to I.A10-1b.D10-45.B550).

Table 46k Compounds of the formula I.A10-1b in which the combination of $R^3$, $R^5$, $R^6$ and $R^{7a}$ corresponds to line D10-46 of Table D10 and the meaning for the combination of $R^1$ and $R^2$ for each individual compound corresponds in each case to one line of Table B (compounds I.A10-1b.D10-46.B1 to I.A10-1b.D10-46.B550).

Table 47k Compounds of the formula I.A10-1b in which the combination of $R^3$, $R^5$, $R^6$ and $R^{7a}$ corresponds to line D10-47 of Table D10 and the meaning for the combination of $R^1$ and $R^2$ for each individual compound corresponds in each case to one line of Table B (compounds I.A10-1b.D10-47.B1 to I.A10-1b.D10-47.B550).

Table 48k Compounds of the formula I.A10-1b in which the combination of $R^3$, $R^5$, $R^6$ and $R^{7a}$ corresponds to line D10-48 of Table D10 and the meaning for the combination of $R^1$ and $R^2$ for each individual compound corresponds in each case to one line of Table B (compounds I.A10-1b.D10-48.B1 to I.A10-1b.D10-48.B550).

Table 49k Compounds of the formula I.A10-1b in which the combination of $R^3$, $R^5$, $R^6$ and $R^{7a}$ corresponds to line D10-49 of Table D10 and the meaning for the combination of $R^1$ and $R^2$ for each individual compound corresponds in each case to one line of Table B (compounds I.A10-1b.D10-49.B1 to I.A10-1b.D10-49.B550).

Table 50k Compounds of the formula I.A10-1b in which the combination of $R^3$, $R^5$, $R^6$ and $R^{7a}$ corresponds to line D10-50 of Table D10 and the meaning for the combination of $R^1$ and $R^2$ for each individual compound corresponds in each case to one line of Table B (compounds I.A10-1b.D10-50.B1 to I.A10-1b.D10-50.B550).

Table 51k Compounds of the formula I.A10-1b in which the combination of $R^3$, $R^5$, $R^6$ and $R^{7a}$ corresponds to line D10-51 of Table D10 and the meaning for the combination of $R^1$ and $R^2$ for each individual compound corresponds in each case to one line of Table B (compounds I.A10-1b.D10-51.B1 to I.A10-1b.D10-51.B550).

Table 52k Compounds of the formula I.A10-1b in which the combination of $R^3$, $R^5$, $R^6$ and $R^{7a}$ corresponds to line D10-52 of Table D10 and the meaning for the combination of $R^1$ and $R^2$ for each individual compound corresponds in each case to one line of Table B (compounds I.A10-1b.D10-52.B1 to I.A10-1b.D10-52.B550).

Table 53k Compounds of the formula I.A10-1b in which the combination of $R^3$, $R^5$, $R^6$ and $R^{7a}$ corresponds to line D10-53 of Table D10 and the meaning for the combination of $R^1$ and $R^2$ for each individual compound corresponds in each case to one line of Table B (compounds I.A10-1b.D10-53.B1 to I.A10-1b.D10-53.B550).

Table 54k Compounds of the formula I.A10-1b in which the combination of $R^3$, $R^5$, $R^6$ and $R^{7a}$ corresponds to line D10-54 of Table D10 and the meaning for the combination of $R^1$ and $R^2$ for each individual compound corresponds in each case to one line of Table B (compounds I.A10-1b.D10-54.B1 to I.A10-1b.D10-54.B550).

Table 55k Compounds of the formula I.A10-1b in which the combination of $R^3$, $R^5$, $R^6$ and $R^{7a}$ corresponds to line D10-55 of Table D10 and the meaning for the combination of $R^1$ and $R^2$ for each individual compound corresponds in each case to one line of Table B (compounds I.A10-1b.D10-55.B1 to I.A10-1b.D10-55.B550).

Table 56k Compounds of the formula I.A10-1b in which the combination of $R^3$, $R^5$, $R^6$ and $R^{7a}$ corresponds to line D10-56 of Table D10 and the meaning for the combination of $R^1$ and $R^2$ for each individual compound corresponds in each case to one line of Table B (compounds I.A10-1b.D10-56.B1 to I.A10-1b.D10-56.B550).

Table 57k Compounds of the formula I.A10-1b in which the combination of $R^3$, $R^5$, $R^6$ and $R^{7a}$ corresponds to line D10-57 of Table D10 and the meaning for the combination of $R^1$ and $R^2$ for each individual compound corresponds in each case to one line of Table B (compounds I.A10-1b.D10-57.B1 to I.A10-1b.D10-57.B550).

Table 58k Compounds of the formula I.A10-1b in which the combination of $R^3$, $R^5$, $R^6$ and $R^{7a}$ corresponds to line D10-58 of Table D10 and the meaning for the combination of $R^1$ and $R^2$ for each individual compound corresponds in each case to one line of Table B (compounds I.A10-1b.D10-58.B1 to I.A10-1b.D10-58.B550).

Table 59k Compounds of the formula I.A10-1b in which the combination of $R^3$, $R^5$, $R^6$ and $R^{7a}$ corresponds to line D10-59 of Table D10 and the meaning for the combination of $R^1$ and $R^2$ for each individual compound corresponds in each case to one line of Table B (compounds I.A10-1b.D10-59.B1 to I.A10-1b.D10-59.B550).

Table 60k Compounds of the formula I.A10-1b in which the combination of $R^3$, $R^5$, $R^6$ and $R^{7a}$ corresponds to line D10-60 of Table D10 and the meaning for the combination of $R^1$ and $R^2$ for each individual compound corresponds in each case to one line of Table B (compounds I.A10-1b.D10-60.B1 to I.A10-1b.D10-60.B550).

Table 61k Compounds of the formula I.A10-1b in which the combination of $R^3$, $R^5$, $R^6$ and $R^{7a}$ corresponds to line D10-61 of Table D10 and the meaning for the combination of $R^1$ and $R^2$ for each individual compound corresponds in each case to one line of Table B (compounds I.A10-1b.D10-61.B1 to I.A10-1b.D10-61.B550).

Table 62k Compounds of the formula I.A10-1b in which the combination of $R^3$, $R^5$, $R^6$ and $R^{7a}$ corresponds to line D10-62 of Table D10 and the meaning for the combination of $R^1$ and $R^2$ for each individual compound corresponds in each case to one line of Table B (compounds I.A10-1b.D10-62.B1 to I.A10-1b.D10-62.B550).

Table 63k Compounds of the formula I.A10-1b in which the combination of $R^3$, $R^5$, $R^6$ and $R^{7a}$ corresponds to line D10-63 of Table D10 and the meaning for the combination of $R^1$ and $R^2$ for each individual compound corresponds in each case to one line of Table B (compounds I.A10-1b.D10-63.B1 to I.A10-1b.D10-63.B550).

Table 64k Compounds of the formula I.A10-1b in which the combination of $R^3$, $R^5$, $R^6$ and $R^{7a}$ corresponds to line D10-64 of Table D10 and the meaning for the combination of $R^1$ and $R^2$ for each individual compound corresponds in each case to one line of Table B (compounds I.A10-1b.D10-64.B1 to I.A10-1b.D10-64.B550).

Table 65k Compounds of the formula I.A10-1b in which the combination of $R^3$, $R^5$, $R^6$ and $R^{7a}$ corresponds to line D10-65 of Table D10 and the meaning for the combination of $R^1$ and $R^2$ for each individual compound corresponds in each case to one line of Table B (compounds I.A10-1b.D10-65.B1 to I.A10-1b.D10-65.B550).

Table 66k Compounds of the formula I.A10-1b in which the combination of $R^3$, $R^5$, $R^6$ and $R^{7a}$ corresponds to line D10-66 of Table D10 and the meaning for the combination of $R^1$ and $R^2$ for each individual compound corresponds in each case to one line of Table B (compounds I.A10-1b.D10-66.B1 to I.A10-1b.D10-66.B550).

Table 67k Compounds of the formula I.A10-1b in which the combination of $R^3$, $R^5$, $R^6$ and $R^{7a}$ corresponds to line D10-67 of Table D10 and the meaning for the combination of $R^1$ and $R^2$ for each individual compound corresponds in each case to one line of Table B (compounds I.A10-1b.D10-67.B1 to I.A10-1b.D10-67.B550).

Table 68k Compounds of the formula I.A10-1b in which the combination of $R^3$, $R^5$, $R^6$ and $R^{7a}$ corresponds to line D10-68 of Table D10 and the meaning for the combination of $R^1$ and $R^2$ for each individual compound corresponds in each case to one line of Table B (compounds I.A10-1b.D10-68.B1 to I.A10-1b.D10-68.B550).

Table 69k Compounds of the formula I.A10-1b in which the combination of $R^3$, $R^5$, $R^6$ and $R^{7a}$ corresponds to line D10-69 of Table D10 and the meaning for the combination of $R^1$ and $R^2$ for each individual compound corresponds in each case to one line of Table B (compounds I.A10-1b.D10-69.B1 to I.A10-1b.D10-69.B550).

Table 70k Compounds of the formula I.A10-1b in which the combination of $R^3$, $R^5$, $R^6$ and $R^{7a}$ corresponds to line D10-70 of Table D10 and the meaning for the combination of $R^1$ and $R^2$ for each individual compound corresponds in each case to one line of Table B (compounds I.A10-1b.D10-70.B1 to I.A10-1b.D10-70.B550).

Table 71k Compounds of the formula I.A10-1b in which the combination of $R^3$, $R^5$, $R^6$ and $R^{7a}$ corresponds to line D10-71 of Table D10 and the meaning for the combination of $R^1$ and $R^2$ for each individual compound corresponds in each case to one line of Table B (compounds I.A10-1b.D10-71.B1 to I.A10-1b.D10-71.B550).

Table 72k Compounds of the formula I.A10-1b in which the combination of $R^3$, $R^5$, $R^6$ and $R^{7a}$ corresponds to line D10-72 of Table D10 and the meaning for the combination of $R^1$ and $R^2$ for each individual compound corresponds in each case to one line of Table B (compounds I.A10-1b.D10-72.B1 to I.A10-1b.D10-72.B550).

Table 73k Compounds of the formula I.A10-1b in which the combination of $R^3$, $R^5$, $R^6$ and $R^{7a}$ corresponds to line D10-73 of Table D10 and the meaning for the combination of $R^1$ and $R^2$ for each individual compound corresponds in each case to one line of Table B (compounds I.A10-1b.D10-73.B1 to I.A10-1b.D10-73.B550).

Table 74k Compounds of the formula I.A10-1b in which the combination of $R^3$, $R^5$, $R^6$ and $R^{7a}$ corresponds to line D10-74 of Table D10 and the meaning for the combination of $R^1$ and $R^2$ for each individual compound corresponds in each case to one line of Table B (compounds I.A10-1b.D10-74.B1 to I.A10-1b.D10-74.B550).

Table 75k Compounds of the formula I.A10-1b in which the combination of $R^3$, $R^5$, $R^6$ and $R^{7a}$ corresponds to line D10-75 of Table D10 and the meaning for the combination of $R^1$ and $R^2$ for each individual compound corresponds in each case to one line of Table B (compounds I.A10-1b.D10-75.B1 to I.A10-1b.D10-75.B550).

Table 76k Compounds of the formula I.A10-1b in which the combination of $R^3$, $R^5$, $R^6$ and $R^{7a}$ corresponds to line D10-76 of Table D10 and the meaning for the combination of $R^1$ and $R^2$ for each individual compound corresponds in each case to one line of Table B (compounds I.A10-1b.D10-76.B1 to I.A10-1b.D10-76.B550).

Table 77k Compounds of the formula I.A10-1b in which the combination of $R^3$, $R^5$, $R^6$ and $R^{7a}$ corresponds to line D10-77 of Table D10 and the meaning for the combination of $R^1$ and $R^2$ for each individual compound corresponds in each case to one line of Table B (compounds I.A10-1b.D10-77.B1 to I.A10-1b.D10-77.B550).

Table 78k Compounds of the formula I.A10-1b in which the combination of $R^3$, $R^5$, $R^6$ and $R^{7a}$ corresponds to line D10-78 of Table D10 and the meaning for the combination of $R^1$ and $R^2$ for each individual compound corresponds in each case to one line of Table B (compounds I.A10-1b.D10-78.B1 to I.A10-1b.D10-78.B550).

Table 79k Compounds of the formula I.A10-1b in which the combination of $R^3$, $R^5$, $R^6$ and $R^{7a}$ corresponds to line D10-79 of Table D10 and the meaning for the combination of $R^1$ and $R^2$ for each individual compound corresponds in each case to one line of Table B (compounds I.A10-1b.D10-79.B1 to I.A10-1b.D10-79.B550).

Table 80k Compounds of the formula I.A10-1b in which the combination of $R^3$, $R^5$, $R^6$ and $R^{7a}$ corresponds to line D10-80 of Table D10 and the meaning for the combination of $R^1$ and $R^2$ for each individual compound corresponds in each case to one line of Table B (compounds I.A10-1b.D10-80.B1 to I.A10-1b.D10-80.B550).

Table 81k Compounds of the formula I.A10-1b in which the combination of $R^3$, $R^5$, $R^6$ and $R^{7a}$ corresponds to line D10-81 of Table D10 and the meaning for the combination of $R^1$ and $R^2$ for each individual compound corresponds in each case to one line of Table B (compounds I.A10-1b.D10-81.B1 to I.A10-1b.D10-81.B550).

Table 82k Compounds of the formula I.A10-1b in which the combination of $R^3$, $R^5$, $R^6$ and $R^{7a}$ corresponds to line D10-82 of Table D10 and the meaning for the combination of $R^1$ and $R^2$ for each individual compound corresponds in each case to one line of Table B (compounds I.A10-1b.D10-82.B1 to I.A10-1b.D10-82.B550).

Table 83k Compounds of the formula I.A10-1b in which the combination of $R^3$, $R^5$, $R^6$ and $R^{7a}$ corresponds to line D10-83 of Table D10 and the meaning for the combination of $R^1$ and $R^2$ for each individual compound corresponds in each case to one line of Table B (compounds I.A10-1b.D10-83.B1 to I.A10-1b.D10-83.B550).

Table 84k Compounds of the formula I.A10-1b in which the combination of $R^3$, $R^5$, $R^6$ and $R^{7a}$ corresponds to line D10-84 of Table D10 and the meaning for the combination of $R^1$ and $R^2$ for each individual compound corresponds in each case to one line of Table B (compounds I.A10-1b.D10-84.B1 to I.A10-1b.D10-84.B550).

Table 85k Compounds of the formula I.A10-1b in which the combination of $R^3$, $R^5$, $R^6$ and $R^{7a}$ corresponds to line D10-85 of Table D10 and the meaning for the combination of $R^1$ and $R^2$ for each individual compound corresponds in each case to one line of Table B (compounds I.A10-1b.D10-85.B1 to I.A10-1b.D10-85.B550).

Table 86k Compounds of the formula I.A10-1b in which the combination of $R^3$, $R^5$, $R^6$ and $R^{7a}$ corresponds to line D10-86 of Table D10 and the meaning for the combination of $R^1$ and $R^2$ for each individual compound corresponds in each case to one line of Table B (compounds I.A10-1b.D10-86.B1 to I.A10-1b.D10-86.B550).

Table 87k Compounds of the formula I.A10-1b in which the combination of $R^3$, $R^5$, $R^6$ and $R^{7a}$ corresponds to line D10-87 of Table D10 and the meaning for the combination of $R^1$ and $R^2$ for each individual compound corresponds in each case to one line of Table B (compounds I.A10-1b.D10-87.B1 to I.A10-1b.D10-87.B550).

Table 88k Compounds of the formula I.A10-1b in which the combination of $R^3$, $R^5$, $R^6$ and $R^{7a}$ corresponds to line D10-88 of Table D10 and the meaning for the combination of $R^1$ and $R^2$ for each individual compound corresponds in each case to one line of Table B (compounds I.A10-1b.D10-88.B1 to I.A10-1b.D10-88.B550).

Table 89k Compounds of the formula I.A10-1b in which the combination of $R^3$, $R^5$, $R^6$ and $R^{7a}$ corresponds to line D10-89 of Table D10 and the meaning for the combination of $R^1$ and $R^2$ for each individual compound corresponds in each case to one line of Table B (compounds I.A10-1b.D10-89.B1 to I.A10-1b.D10-89.B550).

Table 90k Compounds of the formula I.A10-1b in which the combination of $R^3$, $R^5$, $R^6$ and $R^{7a}$ corresponds to line D10-90 of Table D10 and the meaning for the combination of $R^1$ and $R^2$ for each individual compound corresponds in each case to one line of Table B (compounds I.A10-1b.D10-90.B1 to I.A10-1b.D10-90.B550).

Table 1l Compounds of the formula I.A2-1a in which the combination of $R^3$ and $(R^4)_m$ corresponds to line D7-1 of Table D7 and the meaning for the combination of $R^1$ and $R^2$ for each individual compound corresponds in each case to one line of Table B (compounds I.A2-1a.D7-1.B1 to I.A2-1a.D7-1.B550).

Table 2l Compounds of the formula I.A2-1a in which the combination of $R^3$ and $(R^4)_m$ corresponds to line D7-2 of Table D7 and the meaning for the combination of $R^1$ and $R^2$ for each individual compound corresponds in each case to one line of Table B (compounds I.A2-1a.D7-2.B1 to I.A2-1a.D7-2.B550).

Table 3l Compounds of the formula I.A2-1a in which the combination of $R^3$ and $(R^4)_m$ corresponds to line D7-3 of Table D7 and the meaning for the combination of $R^1$ and $R^2$ for each individual compound corresponds in each case to one line of Table B (compounds I.A2-1a.D7-3.B1 to I.A2-1a.D7-3.B550).

Table 4l Compounds of the formula I.A2-1a in which the combination of $R^3$ and $(R^4)_m$ corresponds to line D7-4 of Table D7 and the meaning for the combination of $R^1$ and $R^2$ for each individual compound corresponds in each case to one line of Table B (compounds I.A2-1a.D7-4.B1 to I.A2-1a.D7-4.B550).

Table 5l Compounds of the formula I.A2-1a in which the combination of $R^3$ and $(R^4)_m$ corresponds to line D7-5 of Table D7 and the meaning for the combination of $R^1$ and $R^2$ for each individual compound corresponds in each case to one line of Table B (compounds I.A2-1a.D7-5.B1 to I.A2-1a.D7-5.B550).

Table 6l Compounds of the formula I.A2-1a in which the combination of $R^3$ and $(R^4)_m$ corresponds to line D7-6 of Table D7 and the meaning for the combination of $R^1$ and $R^2$ for each individual compound corresponds in each case to one line of Table B (compounds I.A2-1a.D7-6.B1 to I.A2-1a.D7-6.B550).

Table 7l Compounds of the formula I.A2-1a in which the combination of $R^3$ and $(R^4)_m$ corresponds to line D7-7 of Table D7 and the meaning for the combination of $R^1$ and $R^2$ for each individual compound corresponds in each case to one line of Table B (compounds I.A2-1a.D7-7.B1 to I.A2-1a.D7-7.B550).

Table 8l Compounds of the formula I.A2-1a in which the combination of $R^3$ and $(R^4)_m$ corresponds to line D7-8 of Table D7 and the meaning for the combination of $R^1$ and $R^2$ for each individual compound corresponds in each case to one line of Table B (compounds I.A2-1a.D7-8.B1 to I.A2-1a.D7-8.B550).

Table 9l Compounds of the formula I.A2-1a in which the combination of $R^3$ and $(R^4)_m$ corresponds to line D7-9 of Table D7 and the meaning for the combination of $R^1$ and $R^2$ for each individual compound corresponds in each case to one line of Table B (compounds I.A2-1a.D7-9.B1 to I.A2-1a.D7-9.B550).

Table 10l Compounds of the formula I.A2-1a in which the combination of $R^3$ and $(R^4)_m$ corresponds to line D7-10 of Table D7 and the meaning for the combination of $R^1$ and $R^2$ for each individual compound corresponds in each case to one line of Table B (compounds I.A2-1a.D7-10.B1 to I.A2-1a.D7-10.B550).

Table 11l Compounds of the formula I.A2-1a in which the combination of $R^3$ and $(R^4)_m$ corresponds to line D7-11 of Table D7 and the meaning for the combination of $R^1$ and $R^2$ for each individual compound corresponds in each case to one line of Table B (compounds I.A2-1a.D7-11.B1 to I.A2-1a.D7-11.B550).

Table 12l Compounds of the formula I.A2-1a in which the combination of $R^3$ and $(R^4)_m$ corresponds to line D7-12 of Table D7 and the meaning for the combination of $R^1$ and $R^2$ for each individual compound corresponds in each case to one line of Table B (compounds I.A2-1a.D7-12.B1 to I.A2-1a.D7-12.B550).

Table 13l Compounds of the formula I.A2-1a in which the combination of $R^3$ and $(R^4)_m$ corresponds to line D7-13 of Table D7 and the meaning for the combination of $R^1$ and $R^2$ for each individual compound corresponds in each case to one line of Table B (compounds I.A2-1a.D7-13.B1 to I.A2-1a.D7-13.B550).

Table 14l Compounds of the formula I.A2-1a in which the combination of $R^3$ and $(R^4)_m$ corresponds to line D7-14 of Table D7 and the meaning for the combination of $R^1$ and $R^2$ for each individual compound corresponds in each case to one line of Table B (compounds I.A2-1a.D7-14.B1 to I.A2-1a.D7-14.B550).

Table 15l Compounds of the formula I.A2-1a in which the combination of $R^3$ and $(R^4)_m$ corresponds to line D7-15 of Table D7 and the meaning for the combination of $R^1$ and $R^2$ for each individual compound corresponds in each case to one line of Table B (compounds I.A2-1a.D7-15.B1 to I.A2-1a.D7-15.B550).

Table 16l Compounds of the formula I.A2-1a in which the combination of $R^3$ and $(R^4)_m$ corresponds to line D7-16 of Table D7 and the meaning for the combination of $R^1$ and $R^2$ for each individual compound corresponds in each case to one line of Table B (compounds I.A2-1a.D7-16.B1 to I.A2-1a.D7-16.B550).

Table 17l Compounds of the formula I.A2-1a in which the combination of $R^3$ and $(R^4)_m$ corresponds to line D7-17 of Table D7 and the meaning for the combination of $R^1$ and $R^2$ for each individual compound corresponds in each case to one line of Table B (compounds I.A2-1a.D7-17.B1 to I.A2-1a.D7-17.B550).

Table 18l Compounds of the formula I.A2-1a in which the combination of $R^3$ and $(R^4)_m$ corresponds to line D7-18 of Table D7 and the meaning for the combination of $R^1$ and $R^2$ for each individual compound corresponds in each case to one line of Table B (compounds I.A2-1a.D7-18.B1 to I.A2-1a.D7-18.B550).

Table 19l Compounds of the formula I.A2-1a in which the combination of $R^3$ and $(R^4)_m$ corresponds to line D7-19 of Table D7 and the meaning for the combination of $R^1$ and $R^2$ for each individual compound corresponds in each case to one line of Table B (compounds I.A2-1a.D7-19.B1 to I.A2-1a.D7-19.B550).

Table 20l Compounds of the formula I.A2-1a in which the combination of $R^3$ and $(R^4)_m$ corresponds to line D7-20 of Table D7 and the meaning for the combination of $R^1$ and $R^2$ for each individual compound corresponds in each case to one line of Table B (compounds I.A2-1a.D7-20.B1 to I.A2-1a.D7-20.B550).

Table 21l Compounds of the formula I.A2-1a in which the combination of $R^3$ and $(R^4)_m$ corresponds to line D7-21 of Table D7 and the meaning for the combination of $R^1$ and $R^2$ for each individual compound corresponds in each case to one line of Table B (compounds I.A2-1a.D7-21.B1 to I.A2-1a.D7-21.B550).

Table 22l Compounds of the formula I.A2-1a in which the combination of $R^3$ and $(R^4)_m$ corresponds to line D7-22 of Table D7 and the meaning for the combination of $R^1$ and $R^2$ for each individual compound corresponds in each case to one line of Table B (compounds I.A2-1a.D7-22.B1 to I.A2-1a.D7-22.B550).

Table 23l Compounds of the formula I.A2-1a in which the combination of $R^3$ and $(R^4)_m$ corresponds to line D7-23 of Table D7 and the meaning for the combination of $R^1$ and $R^2$ for each individual compound corresponds in each case to one line of Table B (compounds I.A2-1a.D7-23.B1 to I.A2-1a.D7-23.B550).

Table 24l Compounds of the formula I.A2-1a in which the combination of $R^3$ and $(R^4)_m$ corresponds to line D7-24 of Table D7 and the meaning for the combination of $R^1$ and $R^2$ for each individual compound corresponds in each case to one line of Table B (compounds I.A2-1a.D7-24.B1 to I.A2-1a.D7-24.B550).

Table 25l Compounds of the formula I.A2-1a in which the combination of $R^3$ and $(R^4)_m$ corresponds to line D7-25 of Table D7 and the meaning for the combination of $R^1$ and $R^2$ for each individual compound corresponds in each case to one line of Table B (compounds I.A2-1a.D7-25.B1 to I.A2-1a.D7-25.B550).

Table 26l Compounds of the formula I.A2-1a in which the combination of $R^3$ and $(R^4)_m$ corresponds to line D7-26 of Table D7 and the meaning for the combination of $R^1$ and $R^2$ for each individual compound corresponds in each case to one line of Table B (compounds I.A2-1a.D7-26.B1 to I.A2-1a.D7-26.B550).

Table 27l Compounds of the formula I.A2-1a in which the combination of $R^3$ and $(R^4)_m$ corresponds to line D7-27 of Table D7 and the meaning for the combination of $R^1$ and $R^2$ for each individual compound corresponds in each case to one line of Table B (compounds I.A2-1a.D7-27.B1 to I.A2-1a.D7-27.B550).

Table 28l Compounds of the formula I.A2-1a in which the combination of $R^3$ and $(R^4)_m$ corresponds to line D7-28 of Table D7 and the meaning for the combination of $R^1$ and $R^2$ for each individual compound corresponds in each case to one line of Table B (compounds I.A2-1a.D7-28.B1 to I.A2-1a.D7-28.B550).

Table 1m Compounds of the formula I.A11-1 in which the combination of $R^3$, $R^5$ and $R^6$ corresponds to line D11-1 of Table D11 and the meaning for the combination of $R^1$ and $R^2$ for each individual compound corresponds in each case to one line of Table B (compounds I.A11-1.D11-1.B1 to I.A11-1.D11-1.B550).

Table 2m Compounds of the formula I.A11-1 in which the combination of $R^3$, $R^5$ and $R^6$ corresponds to line D11-2 of Table D11 and the meaning for the combination of $R^1$ and $R^2$ for each individual compound corresponds in each case to one line of Table B (compounds I.A11-1.D11-2.B1 to I.A11-1.D11-2.B550).

Table 3m Compounds of the formula I.A11-1 in which the combination of $R^3$, $R^5$ and $R^6$ corresponds to line D11-3 of Table D11 and the meaning for the combination of $R^1$ and $R^2$ for each individual compound corresponds in each case to one line of Table B (compounds I.A11-1.D11-3.B1 to I.A11-1.D11-3.B550).

Table 4m Compounds of the formula I.A11-1 in which the combination of $R^3$, $R^5$ and $R^6$ corresponds to line D11-4 of Table D11 and the meaning for the combination of $R^1$ and $R^2$ for each individual compound corresponds in each case to one line of Table B (compounds I.A11-1.D11-4.B1 to I.A11-1.D11-4.B550).

Table 5m Compounds of the formula I.A11-1 in which the combination of $R^3$, $R^5$ and $R^6$ corresponds to line D11-5 of Table D11 and the meaning for the combination of $R^1$ and $R^2$ for each individual compound corresponds in each case to one line of Table B (compounds I.A11-1.D11-5.B1 to I.A11-1.D11-5.B550).

Table 6m Compounds of the formula I.A11-1 in which the combination of $R^3$, $R^5$ and $R^6$ corresponds to line D11-6 of Table D11 and the meaning for the combination of $R^1$ and $R^2$ for each individual compound corresponds in each case to one line of Table B (compounds I.A11-1.D11-6.B1 to I.A11-1.D11-6.B550).

Table 7m Compounds of the formula I.A11-1 in which the combination of $R^3$, $R^5$ and $R^6$ corresponds to line D11-7 of Table D11 and the meaning for the combination of $R^1$ and $R^2$ for each individual compound corresponds in each case to one line of Table B (compounds I.A11-1.D11-7.B1 to I.A11-1.D11-7.B550).

Table 8m Compounds of the formula I.A11-1 in which the combination of $R^3$, $R^5$ and $R^6$ corresponds to line D11-8 of Table D11 and the meaning for the combination of $R^1$ and $R^2$ for each individual compound corresponds in each case to one line of Table B (compounds I.A11-1.D11-8.B1 to I.A11-1.D11-8.B550). Table 9m Compounds of the formula I.A11-1 in which the combination of $R^3$, $R^5$ and $R^6$ corresponds to line D11-9 of Table D11 and the meaning for the combination of $R^1$ and $R^2$ for each individual compound corresponds in each case to one line of Table B (compounds I.A11-1.D11-9.B1 to I.A11-1.D11-9.B550).

Table 10m Compounds of the formula I.A11-1 in which the combination of $R^3$, $R^5$ and $R^6$ corresponds to line D11-10 of Table D11 and the meaning for the combination of $R^1$ and $R^2$ for each individual compound corresponds in each case to one line of Table B (compounds I.A11-1.D11-10.B1 to I.A11-1.D11-10.B550).

Table 11m Compounds of the formula I.A11-1 in which the combination of $R^3$, $R^5$ and $R^6$ corresponds to line D11-11 of Table D11 and the meaning for the combination of $R^1$ and $R^2$ for each individual compound corresponds in each case to one line of Table B (compounds I.A11-1.D11-11.B1 to I.A11-1.D11-11.B550).

Table 12m Compounds of the formula I.A11-1 in which the combination of $R^3$, $R^5$ and $R^6$ corresponds to line D11-12 of Table D11 and the meaning for the combination of $R^1$ and $R^2$ for each individual compound corresponds in each case to one line of Table B (compounds I.A11-1.D11-12.B1 to I.A11-1.D11-12.B550).

Table 13m Compounds of the formula I.A11-1 in which the combination of $R^3$, $R^5$ and $R^6$ corresponds to line D11-13 of Table D11 and the meaning for the combination of $R^1$ and $R^2$ for each individual compound corresponds in each case to one line of Table B (compounds I.A11-1.D11-13.B1 to I.A11-1.D11-13.B550).

Table 14m Compounds of the formula I.A11-1 in which the combination of $R^3$, $R^5$ and $R^6$ corresponds to line D11-14 of Table D11 and the meaning for the combination of $R^1$ and $R^2$ for each individual compound corresponds in each case to one line of Table B (compounds I.A11-1.D11-14.B1 to I.A11-1.D11-14.B550).

Table 15m Compounds of the formula I.A11-1 in which the combination of $R^3$, $R^5$ and $R^6$ corresponds to line D11-15 of Table D11 and the meaning for the combination of $R^1$ and $R^2$ for each individual compound corresponds in each case to one line of Table B (compounds I.A11-1.D11-15.B1 to I.A11-1.D11-15.B550).

Table 16m Compounds of the formula I.A11-1 in which the combination of $R^3$, $R^5$ and $R^6$ corresponds to line D11-16 of Table D11 and the meaning for the combination of $R^1$ and $R^2$ for each individual compound corresponds in each case to one line of Table B (compounds I.A11-1.D11-16.B1 to I.A11-1.D11-16.B550).

Table 17m Compounds of the formula I.A11-1 in which the combination of $R^3$, $R^5$ and $R^6$ corresponds to line D11-17 of Table D11 and the meaning for the combination of $R^1$ and $R^2$ for each individual compound corresponds in each case to one line of Table B (compounds I.A11-1.D11-17.B1 to I.A11-1.D11-17.B550).

Table 18m Compounds of the formula I.A11-1 in which the combination of $R^3$, $R^5$ and $R^6$ corresponds to line D11-1 of Table D11 and the meaning for the combination of $R^1$ and $R^2$ for each individual compound corresponds in each case to one line of Table B (compounds I.A11-1.D11-1.B1 to I.A11-1.D11-1.B550).

Table 1ma Compounds of the formula I.A11-2 in which the combination of $R^3$, $R^5$ and $R^6$ corresponds to line D11-2 of Table D11 and the meaning for the combination of $R^1$ and $R^2$ for each individual compound corresponds in each case to one line of Table B (compounds I.A11-2.D11-2.B1 to I.A11-2.D11-2.B550).

Table 2ma Compounds of the formula I.A11-2 in which the combination of $R^3$, $R^5$ and $R^6$ corresponds to line D11-3 of Table D11 and the meaning for the combination of $R^1$ and $R^2$ for each individual compound corresponds in each case to one line of Table B (compounds I.A11-2.D11-3.B1 to I.A11-2.D11-3.B550).

Table 3ma Compounds of the formula I.A11-2 in which the combination of $R^3$, $R^5$ and $R^6$ corresponds to line D11-4 of Table D11 and the meaning for the combination of $R^1$ and $R^2$ for each individual compound corresponds in each case to one line of Table B (compounds I.A11-2.D11-4.B1 to I.A11-2.D11-4.B550).

Table 4ma Compounds of the formula I.A11-2 in which the combination of $R^3$, $R^5$ and $R^6$ corresponds to line D11-5 of Table D11 and the meaning for the combination of $R^1$ and $R^2$ for each individual compound corresponds in each case to one line of Table B (compounds I.A11-2.D11-5.B1 to I.A11-2.D11-5.B550).

Table 5ma Compounds of the formula I.A11-2 in which the combination of $R^3$, $R^5$ and $R^6$ corresponds to line D11-6 of Table D11 and the meaning for the combination of $R^1$ and $R^2$ for each individual compound corresponds in each case to one line of Table B (compounds I.A11-2.D11-6.B1 to I.A11-2.D11-6.B550).

Table 6ma Compounds of the formula I.A11-2 in which the combination of $R^3$, $R^5$ and $R^6$ corresponds to line D11-7 of Table D11 and the meaning for the combination of $R^1$ and $R^2$ for each individual compound corresponds in each case to one line of Table B (compounds I.A11-2.D11-7.B1 to I.A11-2.D11-7.B550).

Table 7ma Compounds of the formula I.A11-2 in which the combination of $R^3$, $R^5$ and $R^6$ corresponds to line D11-8 of Table D11 and the meaning for the combination of $R^1$ and $R^2$ for each individual compound corresponds in each case to one line of Table B (compounds I.A11-2.D11-8.B1 to I.A11-2.D11-8.B550).

Table 8ma Compounds of the formula I.A11-2 in which the combination of $R^3$, $R^5$ and $R^6$ corresponds to line D11-9 of Table D11 and the meaning for the combination of $R^1$ and $R^2$ for each individual compound corresponds in each case to one line of Table B (compounds I.A11-2.D11-9.B1 to I.A11-2.D11-9.B550).

Table 9ma Compounds of the formula I.A11-2 in which the combination of $R^3$, $R^5$ and $R^6$ corresponds to line D11-10 of Table D11 and the meaning for the combination of $R^1$ and $R^2$ for each individual compound corresponds in each case to one line of Table B (compounds I.A11-2.D11-10.B1 to I.A11-2.D11-10.B550).

Table 10ma Compounds of the formula I.A11-2 in which the combination of $R^3$, $R^5$ and $R^6$ corresponds to line D11-11 of Table D11 and the meaning for the combination of $R^1$ and $R^2$ for each individual compound corresponds in each case to one line of Table B (compounds I.A11-2.D11-11.B1 to I.A11-2.D11-11.B550).

Table 11 ma Compounds of the formula I.A11-2 in which the combination of $R^3$, $R^5$ and $R^6$ corresponds to line D11-12 of Table D11 and the meaning for the combination of $R^1$ and $R^2$ for each individual compound corresponds in each case to one line of Table B (compounds I.A11-2.D11-12.B1 to I.A11-2.D11-12.B550).

Table 12ma Compounds of the formula I.A11-2 in which the combination of $R^3$, $R^5$ and $R^6$ corresponds to line D11-13 of Table D11 and the meaning for the combination of $R^1$ and $R^2$ for each individual compound corresponds in each case to one line of Table B (compounds I.A11-2.D11-13.B1 to I.A11-2.D11-13.B550).

Table 13ma Compounds of the formula I.A11-2 in which the combination of $R^3$, $R^5$ and $R^6$ corresponds to line D11-14 of Table D11 and the meaning for the combination of $R^1$ and $R^2$ for each individual compound corresponds in each case to one line of Table B (compounds I.A11-2.D11-14.B1 to I.A11-2.D11-14.B550).

Table 14ma Compounds of the formula I.A11-2 in which the combination of $R^3$, $R^5$ and $R^6$ corresponds to line D11-15 of Table D11 and the meaning for the combination of $R^1$ and $R^2$ for each individual compound corresponds in each case to one line of Table B (compounds I.A11-2.D11-15.B1 to I.A11-2.D11-15.B550).

Table 15ma Compounds of the formula I.A11-2 in which the combination of $R^3$, $R^5$ and $R^6$ corresponds to line D11-16 of Table D11 and the meaning for the combination of $R^1$ and $R^2$ for each individual compound corresponds in each case to one line of Table B (compounds I.A11-2.D11-16.B1 to I.A11-2.D11-16.B550).

Table 16ma Compounds of the formula I.A11-2 in which the combination of $R^3$, $R^5$ and $R^6$ corresponds to line D11-17 of Table D11 and the meaning for the combination of $R^1$ and $R^2$ for each individual compound corresponds in each case to one line of Table B (compounds I.A11-2.D11-17.B1 to I.A11-2.D11-17.B550).

Table 17ma Compounds of the formula I.A11-2 in which the combination of $R^3$, $R^5$ and $R^6$ corresponds to line D11-17 of Table D11 and the meaning for the combination of $R^1$ and $R^2$ for each individual compound corresponds in each case to one line of Table B (compounds I.A11-2.D11-17.B1 to I.A11-2.D11-17.B550).

Table 18ma Compounds of the formula I.A11-2 in which the combination of $R^3$, $R^5$ and $R^6$ corresponds to line D11-1 of Table D11 and the meaning for the combination of $R^1$ and $R^2$ for each individual compound corresponds in each case to one line of Table B (compounds I.A11-2.D11-1.B1 to I.A11-2.D11-1.B550).

Table 1n Compounds of the formula I.A9-1 in which n in $(R^8)_n$ is 0, the combination of $R^3$ and $R^5$ corresponds to line D8-1 of Table D8 and the meaning for the combination of $R^1$ and $R^2$ for each individual compound corresponds in each case to one line of Table B (compounds I.A9-1.D8-1.B1 to I.A9-1.D8-1.B550).

Table 2n Compounds of the formula I.A9-1 in which n in $(R^8)_n$ is 0, the combination of $R^3$ and $R^5$ corresponds to line D8-2 of Table D8 and the meaning for the combination of $R^1$ and $R^2$ for each individual compound corresponds in each case to one line of Table B (compounds I.A9-1.D8-2.B1 to I.A9-1.D8-2.B550).

Table 3n Compounds of the formula I.A9-1 in which n in $(R^8)_n$ is 0, the combination of $R^3$ and $R^5$ corresponds to line D8-3 of Table D8 and the meaning for the combination of $R^1$ and $R^2$ for each individual compound corresponds in each case to one line of Table B (compounds I.A9-1.D8-3.B1 to I.A9-1.D8-3.B550).

Table 4n Compounds of the formula I.A9-1 in which n in $(R^8)_n$ is 0, the combination of $R^3$ and $R^5$ corresponds to line D8-4 of Table D8 and the meaning for the combination of $R^1$ and $R^2$ for each individual compound corresponds in each case to one line of Table B (compounds I.A9-1.D8-4.B1 to I.A9-1.D8-4.B550).

Table 5n Compounds of the formula I.A9-1 in which n in $(R^8)_n$ is 0, the combination of $R^3$ and $R^5$ corresponds to line D8-5 of Table D8 and the meaning for the combination of $R^1$ and $R^2$ for each individual compound corresponds in each case to one line of Table B (compounds I.A9-1.D8-5.B1 to I.A9-1.D8-5.B550).

Table 6n Compounds of the formula I.A9-1 in which n in $(R^8)_n$ is 0, the combination of $R^3$ and $R^5$ corresponds to line D8-6 of Table D8 and the meaning for the combination of $R^1$ and $R^2$ for each individual compound corresponds in each case to one line of Table B (compounds I.A9-1.D8-6.B1 to I.A9-1.D8-6.B550).

Table 7n Compounds of the formula I.A9-1 in which n in $(R^8)_n$ is 0, the combination of $R^3$ and $R^5$ corresponds to line D8-7 of Table D8 and the meaning for the combination of $R^1$ and $R^2$ for each individual compound corresponds in each case to one line of Table B (compounds I.A9-1.D8-7.B1 to I.A9-1.D8-7.B550).

Table 1o Compounds of the formula I.A9-2 in which n in $(R^8)_n$ is 0, the combination of $R^3$ and $R^5$ corresponds to line D8-1 of Table D8 and the meaning for the combination of $R^1$ and $R^2$ for each individual compound corresponds in each case to one line of Table B (compounds I.A9-2.D8-1.B1 to I.A9-2.D8-1.B550).

Table 2o Compounds of the formula I.A9-2 in which n in $(R^8)_n$ is 0, the combination of $R^3$ and $R^5$ corresponds to line D8-2 of Table D8 and the meaning for the combination of $R^1$ and $R^2$ for each individual compound corresponds in each case to one line of Table B (compounds I.A9-2.D8-2.B1 to I.A9-2.D8-2.B550).

Table 3o Compounds of the formula I.A9-2 in which n in $(R^8)_n$ is 0, the combination of $R^3$ and $R^5$ corresponds to line D8-3 of Table D8 and the meaning for the combination of $R^1$ and $R^2$ for each individual compound corresponds in each case to one line of Table B (compounds I.A9-2.D8-3.B1 to I.A9-2.D8-3.B550).

Table 4o Compounds of the formula I.A9-2 in which n in $(R^8)_n$ is 0, the combination of $R^3$ and $R^5$ corresponds to line D8-4 of Table D8 and the meaning for the combination of $R^1$ and $R^2$ for each individual compound corresponds in each case to one line of Table B (compounds I.A9-2.D8-4.B1 to I.A9-2.D8-4.B550).

Table 5o Compounds of the formula I.A9-2 in which n in $(R^8)_n$ is 0, the combination of $R^3$ and $R^5$ corresponds to line D8-5 of Table D8 and the meaning for the combination of $R^1$ and $R^2$ for each individual compound corresponds in each case to one line of Table B (compounds I.A9-2.D8-5.B1 to I.A9-2.D8-5.B550).

Table 6o Compounds of the formula I.A9-2 in which n in $(R^8)_n$ is 0, the combination of $R^3$ and $R^5$ corresponds to line D8-6 of Table D8 and the meaning for the combination of $R^1$ and $R^2$ for each individual compound corresponds in each case to one line of Table B (compounds I.A9-2.D8-6.B1 to I.A9-2.D8-6.B550).

Table 7o Compounds of the formula I.A9-2 in which n in $(R^8)_n$ is 0, the combination of $R^3$ and $R^5$ corresponds to line D8-7 of Table D8 and the meaning for the combination of $R^1$ and $R^2$ for each individual compound corresponds in each case to one line of Table B (compounds I.A9-2.D8-7.B1 to I.A9-2.D8-7.B550).

Table 1p Compounds of the formula I.A8-1 in which n in $(R^8)_n$ is 0, the combination of $R^3$ and $R^6$ corresponds to line D9-1 of Table D9 and the meaning for the combination of $R^1$ and $R^2$ for each individual compound corresponds in each case to one line of Table B (compounds I.A8-1.D9-1.B1 to I.A8-1.D9-1.B550).

Table 2p Compounds of the formula I.A8-1 in which n in $(R^8)_n$ is 0, the combination of $R^3$ and $R^6$ corresponds to line D9-2 of Table D9 and the meaning for the combination of $R^1$ and $R^2$ for each individual compound corresponds in each case to one line of Table B (compounds I.A8-1.D9-2.B1 to I.A8-1.D9-2.B550).

Table 3p Compounds of the formula I.A8-1 in which n in $(R^8)_n$ is 0, the combination of $R^3$ and $R^6$ corresponds to line D9-3 of Table D9 and the meaning for the combination of $R^1$ and $R^2$ for each individual compound corresponds in each case to one line of Table B (compounds I.A8-1.D9-3.B1 to I.A8-1.D9-3.B550).

Table 4p Compounds of the formula I.A8-1 in which n in $(R^8)_n$ is 0, the combination of $R^3$ and $R^6$ corresponds to line D9-4 of Table D9 and the meaning for the combination of $R^1$ and $R^2$ for each individual compound corresponds in each case to one line of Table B (compounds I.A8-1.D9-4.B1 to I.A8-1.D9-4.B550).

Table 5p Compounds of the formula I.A8-1 in which n in $(R^8)_n$ is 0, the combination of $R^3$ and $R^6$ corresponds to line D9-5 of Table D9 and the meaning for the combination of $R^1$ and $R^2$ for each individual compound corresponds in each case to one line of Table B (compounds I.A8-1.D9-5.B1 to I.A8-1.D9-5.B550).

Table 6p Compounds of the formula I.A8-1 in which n in $(R^8)_n$ is 0, the combination of $R^3$ and $R^6$ corresponds to line D9-6 of Table D9 and the meaning for the combination of $R^1$ and $R^2$ for each individual compound corresponds in each case to one line of Table B (compounds I.A8-1.D9-6.B1 to I.A8-1.D9-6.B550).

Table 7p Compounds of the formula I.A8-1 in which n in $(R^8)_n$ is 0, the combination of $R^3$ and $R^6$ corresponds to line D9-7 of Table D9 and the meaning for the combination of $R^1$ and $R^2$ for each individual compound corresponds in each case to one line of Table B (compounds I.A8-1.D9-7.B1 to I.A8-1.D9-7.B550).

Table 8p Compounds of the formula I.A8-1 in which n in $(R^8)_n$ is 0, the combination of $R^3$ and $R^6$ corresponds to line D9-8 of Table D9 and the meaning for the combination of $R^1$ and $R^2$ for each individual compound corresponds in each case to one line of Table B (compounds I.A8-1.D9-8.B1 to I.A8-1.D9-8.B550).

Table 9p Compounds of the formula I.A8-1 in which n in $(R^8)_n$ is 0, the combination of $R^3$ and $R^6$ corresponds to line D9-9 of Table D9 and the meaning for the combination of $R^1$ and $R^2$ for each individual compound corresponds in each case to one line of Table B (compounds I.A8-1.D9-9.B1 to I.A8-1.D9-9.B550).

Table 10p Compounds of the formula I.A8-1 in which n in $(R^8)_n$ is 0, the combination of $R^3$ and $R^6$ corresponds to line D9-10 of Table D9 and the meaning for the combination of $R^1$ and $R^2$ for each individual compound corresponds in each case to one line of Table B (compounds I.A8-1.D9-10.B1 to I.A8-1.D9-10.B550).

Table 11p Compounds of the formula I.A8-1 in which n in $(R^8)_n$ is 0, the combination of $R^3$ and $R^6$ corresponds to line D9-11 of Table D9 and the meaning for the combination of $R^1$ and $R^2$ for each individual compound corresponds in each case to one line of Table B (compounds I.A8-1.D9-11.B1 to I.A8-1.D9-11.B550).

Table 12p Compounds of the formula I.A8-1 in which n in $(R^8)_n$ is 0, the combination of $R^3$ and $R^6$ corresponds to line D9-12 of Table D9 and the meaning for the combination of $R^1$ and $R^2$ for each individual compound corresponds in each case to one line of Table B (compounds I.A8-1.D9-12.B1 to I.A8-1.D9-12.B550).

Table 13p Compounds of the formula I.A8-1 in which n in $(R^8)_n$ is 0, the combination of $R^3$ and $R^6$ corresponds to line D9-13 of Table D9 and the meaning for the combination of $R^1$ and $R^2$ for each individual compound corresponds in each case to one line of Table B (compounds I.A8-1.D9-13.B1 to I.A8-1.D9-13.B550).

Table 14p Compounds of the formula I.A8-1 in which n in $(R^8)_n$ is 0, the combination of $R^3$ and $R^6$ corresponds to line D9-14 of Table D9 and the meaning for the combination of $R^1$ and $R^2$ for each individual compound corresponds in each case to one line of Table B (compounds I.A8-1.D9-14.B1 to I.A8-1.D9-14.B550).

Table 15p Compounds of the formula I.A8-1 in which n in $(R^8)_n$ is 0, the combination of $R^3$ and $R^6$ corresponds to line D9-15 of Table D9 and the meaning for the combination of $R^1$ and $R^2$ for each individual compound corresponds in each case to one line of Table B (compounds I.A8-1.D9-15.B1 to I.A8-1.D9-15.B550).

Table 16p Compounds of the formula I.A8-1 in which n in $(R^8)_n$ is 0, the combination of $R^3$ and $R^6$ corresponds to line D9-16 of Table D9 and the meaning for the combination of $R^1$ and $R^2$ for each individual compound corresponds in each case to one line of Table B (compounds I.A8-1.D9-16.B1 to I.A8-1.D9-16.B550).

Table 17p Compounds of the formula I.A8-1 in which n in $(R^8)_n$ is 0, the combination of $R^3$ and $R^6$ corresponds to line D9-17 of Table D9 and the meaning for the combination of $R^1$ and $R^2$ for each individual compound corresponds in Table 18p Compounds of the formula I.A8-1 in which n in $(R^8)_n$ is 0, the combination of $R^3$ and $R^6$ corresponds to line D9-18 of Table D9 and the meaning for the combination of $R^1$ and $R^2$ for each individual compound corresponds in each case to one line of Table B (compounds I.A8-1.D9-18.B1 to I.A8-1.D9-18.B550).

Table 19p Compounds of the formula I.A8-1 in which n in $(R^8)_n$ is 0, the combination of $R^3$ and $R^6$ corresponds to line D9-19 of Table D9 and the meaning for the combination of $R^1$ and $R^2$ for each individual compound corresponds in each case to one line of Table B (compounds I.A8-1.D9-19.B1 to I.A8-1.D9-19.B550).

Table 20p Compounds of the formula I.A8-1 in which n in $(R^8)_n$ is 0, the combination of $R^3$ and $R^6$ corresponds to line D9-20 of Table D9 and the meaning for the combination of $R^1$ and $R^2$ for each individual compound corresponds in each case to one line of Table B (compounds I.A8-1.D9-20.B1 to I.A8-1.D9-20.B550).

Table 21p Compounds of the formula I.A8-1 in which n in $(R^8)_n$ is 0, the combination of $R^3$ and $R^6$ corresponds to line D9-21 of Table D9 and the meaning for the combination of $R^1$ and $R^2$ for each individual compound corresponds in each case to one line of Table B (compounds I.A8-1.D9-21.B1 to I.A8-1.D9-21.B550).

Table 1q Compounds of the formula I.A8-2 in which n in $(R^8)_n$ is 0, the combination of $R^3$ and $R^6$ corresponds to line D9-1 of Table D9 and the meaning for the combination of $R^1$ and $R^2$ for each individual compound corresponds in each case to one line of Table B (compounds I.A8-2.D9-1.B1 to I.A8-2.D9-1.B550).

Table 2q Compounds of the formula I.A8-2 in which n in $(R^8)_n$ is 0, the combination of $R^3$ and $R^6$ corresponds to line D9-2 of Table D9 and the meaning for the combination of $R^1$ and $R^2$ for each individual compound corresponds in each case to one line of Table B (compounds I.A8-2.D9-2.B1 to I.A8-2.D9-2.B550).

Table 3q Compounds of the formula I.A8-2 in which n in $(R^8)_n$ is 0, the combination of $R^3$ and $R^6$ corresponds to line D9-3 of Table D9 and the meaning for the combination of $R^1$ and $R^2$ for each individual compound corresponds in each case to one line of Table B (compounds I.A8-2.D9-3.B1 to I.A8-2.D9-3.B550).

Table 4q Compounds of the formula I.A8-2 in which n in $(R^8)_n$ is 0, the combination of $R^3$ and $R^6$ corresponds to line D9-4 of Table D9 and the meaning for the combination of $R^1$ and $R^2$ for each individual compound corresponds in each case to one line of Table B (compounds I.A8-2.D9-4.B1 to I.A8-2.D9-4.B550).

Table 5q Compounds of the formula I.A8-2 in which n in $(R^8)_n$ is 0, the combination of $R^3$ and $R^6$ corresponds to line D9-5 of Table D9 and the meaning for the combination of $R^1$ and $R^2$ for each individual compound corresponds in each case to one line of Table B (compounds I.A8-2.D9-5.B1 to I.A8-2.D9-5.B550).

Table 6q Compounds of the formula I.A8-2 in which n in $(R^8)_n$ is 0, the combination of $R^3$ and $R^6$ corresponds to line D9-6 of Table D9 and the meaning for the combination of $R^1$ and $R^2$ for each individual compound corresponds in each case to one line of Table B (compounds I.A8-2.D9-6.B1 to I.A8-2.D9-6.B550).

Table 7q Compounds of the formula I.A8-2 in which n in $(R^8)_n$ is 0, the combination of $R^3$ and $R^6$ corresponds to line D9-7 of Table D9 and the meaning for the combination of $R^1$ and $R^2$ for each individual compound corresponds in each case to one line of Table B (compounds I.A8-2.D9-7.B1 to I.A8-2.D9-7.B550).

Table 8q Compounds of the formula I.A8-2 in which n in $(R^8)_n$ is 0, the combination of $R^3$ and $R^6$ corresponds to line D9-8 of Table D9 and the meaning for the combination of $R^1$ and $R^2$ for each individual compound corresponds in each case to one line of Table B (compounds I.A8-2.D9-8.B1 to I.A8-2.D9-8.B550).

Table 9q Compounds of the formula I.A8-2 in which n in $(R^8)_n$ is 0, the combination of $R^3$ and $R^6$ corresponds to line D9-9 of Table D9 and the meaning for the combination of $R^1$ and $R^2$ for each individual compound corresponds in each case to one line of Table B (compounds I.A8-2.D9-9.B1 to I.A8-2.D9-9.B550).

Table 10q Compounds of the formula I.A8-2 in which n in $(R^8)_n$ is 0, the combination of $R^3$ and $R^6$ corresponds to line D9-10 of Table D9 and the meaning for the combination of $R^1$ and $R^2$ for each individual compound corresponds in each case to one line of Table B (compounds I.A8-2.D9-10.B1 to I.A8-2.D9-10.B550).

Table 11q Compounds of the formula I.A8-2 in which n in $(R^8)_n$ is 0, the combination of $R^3$ and $R^6$ corresponds to line D9-11 of Table D9 and the meaning for the combination of $R^1$ and $R^2$ for each individual compound corresponds in each case to one line of Table B (compounds I.A8-2.D9-11.B1 to I.A8-2.D9-11.B550).

Table 12q Compounds of the formula I.A8-2 in which n in $(R^8)_n$ is 0, the combination of $R^3$ and $R^6$ corresponds to line D9-12 of Table D9 and the meaning for the combination of $R^1$ and $R^2$ for each individual compound corresponds in each case to one line of Table B (compounds I.A8-2.D9-12.B1 to I.A8-2.D9-12.B550).

Table 13q Compounds of the formula I.A8-2 in which n in $(R^8)_n$ is 0, the combination of $R^3$ and $R^6$ corresponds to line D9-13 of Table D9 and the meaning for the combination of $R^1$ and $R^2$ for each individual compound corresponds in each case to one line of Table B (compounds I.A8-2.D9-13.B1 to I.A8-2.D9-13.B550).

Table 14q Compounds of the formula I.A8-2 in which n in $(R^8)_n$ is 0, the combination of $R^3$ and $R^6$ corresponds to line D9-14 of Table D9 and the meaning for the combination of $R^1$ and $R^2$ for each individual compound corresponds in each case to one line of Table B (compounds I.A8-2.D9-14.B1 to I.A8-2.D9-14.B550).

Table 15q Compounds of the formula I.A8-2 in which n in $(R^8)_n$ is 0, the combination of $R^3$ and $R^6$ corresponds to line D9-15 of Table D9 and the meaning for the combination of $R^1$ and $R^2$ for each individual compound corresponds in each case to one line of Table B (compounds I.A8-2.D9-15.B1 to I.A8-2.D9-15.B550).

Table 16q Compounds of the formula I.A8-2 in which n in $(R^8)_n$ is 0, the combination of $R^3$ and $R^6$ corresponds to line D9-16 of Table D9 and the meaning for the combination of $R^1$ and $R^2$ for each individual compound corresponds in each case to one line of Table B (compounds I.A8-2.D9-16.B1 to I.A8-2.D9-16.B550).

Table 17q Compounds of the formula I.A8-2 in which n in $(R^8)_n$ is 0, the combination of $R^3$ and $R^6$ corresponds to line D9-17 of Table D9 and the meaning for the combination of $R^1$ and $R^2$ for each individual compound corresponds in each case to one line of Table B (compounds I.A8-2.D9-17.B1 to I.A8-2.D9-17.B550).

Table 18q Compounds of the formula I.A8-2 in which n in $(R^8)_n$ is 0, the combination of $R^3$ and $R^6$ corresponds to line D9-18 of Table D9 and the meaning for the combination of $R^1$ and $R^2$ for each individual compound corresponds in each case to one line of Table B (compounds I.A8-2.D9-18.B1 to I.A8-2.D9-18.B550).

Table 19q Compounds of the formula I.A8-2 in which n in $(R^8)_n$ is 0, the combination of $R^3$ and $R^6$ corresponds to line D9-19 of Table D9 and the meaning for the combination of $R^1$ and $R^2$ for each individual compound corresponds in each case to one line of Table B (compounds I.A8-2.D9-19.B1 to I.A8-2.D9-19.B550).

Table 20q Compounds of the formula I.A8-2 in which n in $(R^8)_n$ is 0, the combination of $R^3$ and $R^6$ corresponds to line D9-20 of Table D9 and the meaning for the combination of $R^1$ and $R^2$ for each individual compound corresponds in each case to one line of Table B (compounds I.A8-2.D9-20.B1 to I.A8-2.D9-20.B550).

Table 21q Compounds of the formula I.A8-2 in which n in $(R^8)_n$ is 0, the combination of $R^3$ and $R^6$ corresponds to line D9-21 of Table D9 and the meaning for the combination of $R^1$ and $R^2$ for each individual compound corresponds in each case to one line of Table B (compounds I.A8-2.D9-21.B1 to I.A8-2.D9-21.B550).

TABLE D1

| line | $R^3$ | $R^7$ |
|---|---|---|
| D1-1 | H | H |
| D1-2 | Cl | H |
| D1-3 | F | H |
| D1-4 | Br | H |
| D1-5 | $CF_3$ | H |
| D1-6 | $CH_3$ | H |
| D1-7 | $OCH_3$ | H |
| D1-8 | H | Cl |
| D1-9 | Cl | Cl |
| D1-10 | F | Cl |
| D1-11 | Br | Cl |
| D1-12 | $CF_3$ | Cl |
| D1-13 | $CH_3$ | Cl |
| D1-14 | $OCH_3$ | Cl |
| D1-15 | H | Br |
| D1-16 | Cl | Br |
| D1-17 | F | Br |
| D1-18 | Br | Br |
| D1-19 | $CF_3$ | Br |
| D1-20 | $CH_3$ | Br |
| D1-21 | $OCH_3$ | Br |
| D1-22 | H | $CH_3$ |
| D1-23 | Cl | $CH_3$ |
| D1-24 | F | $CH_3$ |
| D1-25 | Br | $CH_3$ |
| D1-26 | $CF_3$ | $CH_3$ |
| D1-27 | $CH_3$ | $CH_3$ |
| D1-28 | $OCH_3$ | $CH_3$ |
| D1-29 | H | $CF_3$ |
| D1-30 | Cl | $CF_3$ |
| D1-31 | F | $CF_3$ |
| D1-32 | Br | $CF_3$ |
| D1-33 | $CF_3$ | $CF_3$ |
| D1-34 | $CH_3$ | $CF_3$ |
| D1-35 | $OCH_3$ | $CF_3$ |
| D1-36 | H | $CH(CH_3)_2$ |
| D1-37 | Cl | $CH(CH_3)_2$ |
| D1-38 | F | $CH(CH_3)_2$ |
| D1-39 | Br | $CH(CH_3)_2$ |
| D1-40 | $CF_3$ | $CH(CH_3)_2$ |
| D1-41 | $CH_3$ | $CH(CH_3)_2$ |
| D1-42 | $OCH_3$ | $CH(CH_3)_2$ |
| D1-43 | H | $C(CH_3)_3$ |
| D1-44 | Cl | $C(CH_3)_3$ |
| D1-45 | F | $C(CH_3)_3$ |
| D1-46 | Br | $C(CH_3)_3$ |
| D1-47 | $CF_3$ | $C(CH_3)_3$ |
| D1-48 | $CH_3$ | $C(CH_3)_3$ |
| D1-49 | $OCH_3$ | $C(CH_3)_3$ |

TABLE D2

| line | $R^3$ | $R^5$ |
|---|---|---|
| D2-1 | H | Cl |
| D2-2 | Cl | Cl |
| D2-3 | F | Cl |
| D2-4 | Br | Cl |
| D2-5 | $CF_3$ | Cl |
| D2-6 | $CH_3$ | Cl |
| D2-7 | $OCH_3$ | Cl |
| D2-8 | H | Br |
| D2-9 | Cl | Br |
| D2-10 | F | Br |
| D2-11 | Br | Br |
| D2-12 | $CF_3$ | Br |
| D2-13 | $CH_3$ | Br |
| D2-14 | $OCH_3$ | Br |
| D2-15 | H | $CH_3$ |
| D2-16 | Cl | $CH_3$ |
| D2-17 | F | $CH_3$ |
| D2-18 | Br | $CH_3$ |
| D2-19 | $CF_3$ | $CH_3$ |
| D2-20 | $CH_3$ | $CH_3$ |
| D2-21 | $OCH_3$ | $CH_3$ |
| D2-22 | H | $CF_3$ |
| D2-23 | Cl | $CF_3$ |
| D2-24 | F | $CF_3$ |
| D2-25 | Br | $CF_3$ |
| D2-26 | $CF_3$ | $CF_3$ |
| D2-27 | $CH_3$ | $CF_3$ |
| D2-28 | $OCH_3$ | $CF_3$ |
| D2-29 | H | $CH(CH_3)_2$ |
| D2-30 | Cl | $CH(CH_3)_2$ |
| D2-31 | F | $CH(CH_3)_2$ |
| D2-32 | Br | $CH(CH_3)_2$ |
| D2-33 | $CF_3$ | $CH(CH_3)_2$ |
| D2-34 | $CH_3$ | $CH(CH_3)_2$ |
| D2-35 | $OCH_3$ | $CH(CH_3)_2$ |
| D2-36 | H | $C(CH_3)_3$ |
| D2-37 | Cl | $C(CH_3)_3$ |
| D2-38 | F | $C(CH_3)_3$ |
| D2-39 | Br | $C(CH_3)_3$ |
| D2-40 | $CF_3$ | $C(CH_3)_3$ |
| D2-41 | $CH_3$ | $C(CH_3)_3$ |
| D2-42 | $OCH_3$ | $C(CH_3)_3$ |

TABLE D3

| line | $R^3$ | $R^6$ | $R^7$ |
|---|---|---|---|
| D3-1 | H | Cl | Cl |
| D3-2 | Cl | Cl | Cl |
| D3-3 | F | Cl | Cl |
| D3-4 | Br | Cl | Cl |
| D3-5 | $CF_3$ | Cl | Cl |
| D3-6 | $CH_3$ | Cl | Cl |
| D3-7 | $OCH_3$ | Cl | Cl |
| D3-8 | H | Br | Cl |
| D3-9 | Cl | Br | Cl |
| D3-10 | F | Br | Cl |
| D3-11 | Br | Br | Cl |
| D3-12 | $CF_3$ | Br | Cl |
| D3-13 | $CH_3$ | Br | Cl |
| D3-14 | $OCH_3$ | Br | Cl |
| D3-15 | H | $CH_3$ | Cl |
| D3-16 | Cl | $CH_3$ | Cl |
| D3-17 | F | $CH_3$ | Cl |
| D3-18 | Br | $CH_3$ | Cl |
| D3-19 | $CF_3$ | $CH_3$ | Cl |
| D3-20 | $CH_3$ | $CH_3$ | Cl |
| D3-21 | $OCH_3$ | $CH_3$ | Cl |
| D3-22 | H | Cl | Br |
| D3-23 | Cl | Cl | Br |
| D3-24 | F | Cl | Br |
| D3-25 | Br | Cl | Br |
| D3-26 | $CF_3$ | Cl | Br |
| D3-27 | $CH_3$ | Cl | Br |
| D3-28 | $OCH_3$ | Cl | Br |

TABLE D3-continued

| line | R³ | R⁶ | R⁷ |
|---|---|---|---|
| D3-29 | H | Br | Br |
| D3-30 | Cl | Br | Br |
| D3-31 | F | Br | Br |
| D3-32 | Br | Br | Br |
| D3-33 | CF₃ | Br | Br |
| D3-34 | CH₃ | Br | Br |
| D3-35 | OCH₃ | Br | Br |
| D3-36 | H | CH₃ | Br |
| D3-37 | Cl | CH₃ | Br |
| D3-38 | F | CH₃ | Br |
| D3-39 | Br | CH₃ | Br |
| D3-40 | CF₃ | CH₃ | Br |
| D3-41 | CH₃ | CH₃ | Br |
| D3-42 | OCH₃ | CH₃ | Br |
| D3-43 | H | Cl | CH₃ |
| D3-44 | Cl | Cl | CH₃ |
| D3-45 | F | Cl | CH₃ |
| D3-46 | Br | Cl | CH₃ |
| D3-47 | CF₃ | Cl | CH₃ |
| D3-48 | CH₃ | Cl | CH₃ |
| D3-49 | OCH₃ | Cl | CH₃ |
| D3-50 | H | Br | CH₃ |
| D3-51 | Cl | Br | CH₃ |
| D3-52 | F | Br | CH₃ |
| D3-53 | Br | Br | CH₃ |
| D3-54 | CF₃ | Br | CH₃ |
| D3-55 | CH₃ | Br | CH₃ |
| D3-56 | OCH₃ | Br | CH₃ |
| D3-57 | H | CF₃ | Cl |
| D3-58 | Cl | CF₃ | Cl |
| D3-59 | F | CF₃ | Cl |
| D3-60 | Br | CF₃ | Cl |
| D3-61 | CF₃ | CF₃ | Cl |
| D3-62 | CH₃ | CF₃ | Cl |
| D3-63 | OCH₃ | CF₃ | Cl |

TABLE D4

| line | R³ | R⁵ | R⁷ |
|---|---|---|---|
| D4-1 | H | Cl | Cl |
| D4-2 | Cl | Cl | Cl |
| D4-3 | F | Cl | Cl |
| D4-4 | Br | Cl | Cl |
| D4-5 | CF₃ | Cl | Cl |
| D4-6 | CH₃ | Cl | Cl |
| D4-7 | OCH₃ | Cl | Cl |
| D4-8 | H | CH₃ | Cl |
| D4-9 | Cl | CH₃ | Cl |
| D4-10 | F | CH₃ | Cl |
| D4-11 | Br | CH₃ | Cl |
| D4-12 | CF₃ | CH₃ | Cl |
| D4-13 | CH₃ | CH₃ | Cl |
| D4-14 | OCH₃ | CH₃ | Cl |
| D4-15 | H | Cl | CH₃ |
| D4-16 | Cl | Cl | CH₃ |
| D4-17 | F | Cl | CH₃ |
| D4-18 | Br | Cl | CH₃ |
| D4-19 | CF₃ | Cl | CH₃ |
| D4-20 | CH₃ | Cl | CH₃ |
| D4-21 | OCH₃ | Cl | CH₃ |
| D4-22 | H | CF₃ | Cl |
| D4-23 | Cl | CF₃ | Cl |
| D4-24 | F | CF₃ | Cl |
| D4-25 | Br | CF₃ | Cl |
| D4-26 | CF₃ | CF₃ | Cl |
| D4-27 | CH₃ | CF₃ | Cl |
| D4-28 | OCH₃ | CF₃ | Cl |

TABLE D5

| line | R³ | R⁵ | R⁶ | R⁷ |
|---|---|---|---|---|
| D5-1 | H | Cl | Cl | Cl |
| D5-2 | Cl | Cl | Cl | Cl |
| D5-3 | F | Cl | Cl | Cl |
| D5-4 | Br | Cl | Cl | Cl |
| D5-5 | CF₃ | Cl | Cl | Cl |
| D5-6 | CH₃ | Cl | Cl | Cl |
| D5-7 | OCH₃ | Cl | Cl | Cl |
| D5-8 | H | CH₃ | Cl | Cl |
| D5-9 | Cl | CH₃ | Cl | Cl |
| D5-10 | F | CH₃ | Cl | Cl |
| D5-11 | Br | CH₃ | Cl | Cl |
| D5-12 | CF₃ | CH₃ | Cl | Cl |
| D5-13 | CH₃ | CH₃ | Cl | Cl |
| D5-14 | OCH₃ | CH₃ | Cl | Cl |
| D5-15 | H | Cl | CH₃ | Cl |
| D5-16 | Cl | Cl | CH₃ | Cl |
| D5-17 | F | Cl | CH₃ | Cl |
| D5-18 | Br | Cl | CH₃ | Cl |
| D5-19 | CF₃ | Cl | CH₃ | Cl |
| D5-20 | CH₃ | Cl | CH₃ | Cl |
| D5-21 | OCH₃ | Cl | CH₃ | Cl |
| D5-22 | H | Cl | CF₃ | Cl |
| D5-23 | Cl | Cl | CF₃ | Cl |
| D5-24 | F | Cl | CF₃ | Cl |
| D5-25 | Br | Cl | CF₃ | Cl |
| D5-26 | CF₃ | Cl | CF₃ | Cl |
| D5-27 | CH₃ | Cl | CF₃ | Cl |
| D5-28 | OCH₃ | Cl | CF₃ | Cl |
| D5-29 | H | Cl | Cl | CH₃ |
| D5-30 | Cl | Cl | Cl | CH₃ |
| D5-31 | F | Cl | Cl | CH₃ |
| D5-32 | Br | Cl | Cl | CH₃ |
| D5-33 | CF₃ | Cl | Cl | CH₃ |
| D5-34 | CH₃ | Cl | Cl | CH₃ |
| D5-35 | OCH₃ | Cl | Cl | CH₃ |
| D5-36 | H | CH₃ | Cl | CH₃ |
| D5-37 | Cl | CH₃ | Cl | CH₃ |
| D5-38 | F | CH₃ | Cl | CH₃ |
| D5-39 | Br | CH₃ | Cl | CH₃ |
| D5-40 | CF₃ | CH₃ | Cl | CH₃ |
| D5-41 | CH₃ | CH₃ | Cl | CH₃ |
| D5-42 | OCH₃ | CH₃ | Cl | CH₃ |
| D5-43 | H | Cl | CH₃ | CH₃ |
| D5-44 | Cl | Cl | CH₃ | CH₃ |
| D5-45 | F | Cl | CH₃ | CH₃ |
| D5-46 | Br | Cl | CH₃ | CH₃ |
| D5-47 | CF₃ | Cl | CH₃ | CH₃ |
| D5-48 | CH₃ | Cl | CH₃ | CH₃ |
| D5-49 | OCH₃ | Cl | CH₃ | CH₃ |
| D5-50 | H | CF₃ | Cl | Cl |
| D5-51 | Cl | CF₃ | Cl | Cl |
| D5-52 | F | CF₃ | Cl | Cl |
| D5-53 | Br | CF₃ | Cl | Cl |
| D5-54 | CF₃ | CF₃ | Cl | Cl |
| D5-55 | CH₃ | CF₃ | Cl | Cl |
| D5-56 | OCH₃ | CF₃ | Cl | Cl |

TABLE D6

| Line | R³ | (R⁴)ₘ | R⁵ | R⁶ |
|---|---|---|---|---|
| D6-1 | H | m = 0 | H | H |
| D6-2 | Cl | m = 0 | H | H |
| D6-3 | F | m = 0 | H | H |
| D6-4 | Br | m = 0 | H | H |
| D6-5 | CF₃ | m = 0 | H | H |
| D6-6 | CH₃ | m = 0 | H | H |
| D6-7 | OCH₃ | m = 0 | H | H |
| D6-8 | H | 1-Cl | H | H |
| D6-9 | Cl | 1-Cl | H | H |
| D6-10 | F | 1-Cl | H | H |
| D6-11 | Br | 1-Cl | H | H |
| D6-12 | CF₃ | 1-Cl | H | H |
| D6-13 | CH₃ | 1-Cl | H | H |
| D6-14 | OCH₃ | 1-Cl | H | H |

TABLE D6-continued

| Line | R³ | (R⁴)ₘ | R⁵ | R⁶ |
|---|---|---|---|---|
| D6-15 | H | 1-F | H | H |
| D6-16 | Cl | 1-F | H | H |
| D6-17 | F | 1-F | H | H |
| D6-18 | Br | 1-F | H | H |
| D6-19 | CF₃ | 1-F | H | H |
| D6-20 | CH₃ | 1-F | H | H |
| D6-21 | OCH₃ | 1-F | H | H |
| D6-22 | H | 1-CH₃ | H | H |
| D6-23 | Cl | 1-CH₃ | H | H |
| D6-24 | F | 1-CH₃ | H | H |
| D6-25 | Br | 1-CH₃ | H | H |
| D6-26 | CF₃ | 1-CH₃ | H | H |
| D6-27 | CH₃ | 1-CH₃ | H | H |
| D6-28 | OCH₃ | 1-CH₃ | H | H |
| D6-29 | H | m = 0 | CH₃ | H |
| D6-30 | Cl | m = 0 | CH₃ | H |
| D6-31 | F | m = 0 | CH₃ | H |
| D6-32 | Br | m = 0 | CH₃ | H |
| D6-33 | CF₃ | m = 0 | CH₃ | H |
| D6-34 | CH₃ | m = 0 | CH₃ | H |
| D6-35 | OCH₃ | m = 0 | CH₃ | H |
| D6-36 | H | 1-Cl | CH₃ | H |
| D6-37 | Cl | 1-Cl | CH₃ | H |
| D6-38 | F | 1-Cl | CH₃ | H |
| D6-39 | Br | 1-Cl | CH₃ | H |
| D6-40 | CF₃ | 1-Cl | CH₃ | H |
| D6-41 | CH₃ | 1-Cl | CH₃ | H |
| D6-42 | OCH₃ | 1-Cl | CH₃ | H |
| D6-43 | H | 1-F | CH₃ | H |
| D6-44 | Cl | 1-F | CH₃ | H |
| D6-45 | F | 1-F | CH₃ | H |
| D6-46 | Br | 1-F | CH₃ | H |
| D6-47 | CF₃ | 1-F | CH₃ | H |
| D6-48 | CH₃ | 1-F | CH₃ | H |
| D6-49 | OCH₃ | 1-F | CH₃ | H |
| D6-50 | H | 1-CH₃ | CH₃ | H |
| D6-51 | Cl | 1-CH₃ | CH₃ | H |
| D6-52 | F | 1-CH₃ | CH₃ | H |
| D6-53 | Br | 1-CH₃ | CH₃ | H |
| D6-54 | CF₃ | 1-CH₃ | CH₃ | H |
| D6-55 | CH₃ | 1-CH₃ | CH₃ | H |
| D6-56 | OCH₃ | 1-CH₃ | CH₃ | H |
| D6-57 | H | m = 0 | H | CH₃ |
| D6-58 | Cl | m = 0 | H | CH₃ |
| D6-59 | F | m = 0 | H | CH₃ |
| D6-60 | Br | m = 0 | H | CH₃ |
| D6-61 | CF₃ | m = 0 | H | CH₃ |
| D6-62 | CH₃ | m = 0 | H | CH₃ |
| D6-63 | OCH₃ | m = 0 | H | CH₃ |
| D6-64 | H | 1-Cl | H | CH₃ |
| D6-65 | Cl | 1-Cl | H | CH₃ |
| D6-66 | F | 1-Cl | H | CH₃ |
| D6-67 | Br | 1-Cl | H | CH₃ |
| D6-68 | CF₃ | 1-Cl | H | CH₃ |
| D6-69 | CH₃ | 1-Cl | H | CH₃ |
| D6-70 | OCH₃ | 1-Cl | H | CH₃ |
| D6-71 | H | 1-F | H | CH₃ |
| D6-72 | Cl | 1-F | H | CH₃ |
| D6-73 | F | 1-F | H | CH₃ |
| D6-74 | Br | 1-F | H | CH₃ |
| D6-75 | CF₃ | 1-F | H | CH₃ |
| D6-76 | CH₃ | 1-F | H | CH₃ |
| D6-77 | OCH₃ | 1-F | H | CH₃ |
| D6-78 | H | 1-CH₃ | H | CH₃ |
| D6-79 | Cl | 1-CH₃ | H | CH₃ |
| D6-80 | F | 1-CH₃ | H | CH₃ |
| D6-81 | Br | 1-CH₃ | H | CH₃ |
| D6-82 | CF₃ | 1-CH₃ | H | CH₃ |
| D6-83 | CH₃ | 1-CH₃ | H | CH₃ |
| D6-84 | OCH₃ | 1-CH₃ | H | CH₃ |
| D6-85 | H | m = 0 | CH₃ | CH₃ |
| D6-86 | Cl | m = 0 | CH₃ | CH₃ |
| D6-87 | F | m = 0 | CH₃ | CH₃ |
| D6-88 | Br | m = 0 | CH₃ | CH₃ |
| D6-89 | CF₃ | m = 0 | CH₃ | CH₃ |
| D6-90 | CH₃ | m = 0 | CH₃ | CH₃ |
| D6-91 | OCH₃ | m = 0 | CH₃ | CH₃ |
| D6-92 | H | 1-Cl | CH₃ | CH₃ |
| D6-93 | Cl | 1-Cl | CH₃ | CH₃ |
| D6-94 | F | 1-Cl | CH₃ | CH₃ |
| D6-95 | Br | 1-Cl | CH₃ | CH₃ |
| D6-96 | CF₃ | 1-Cl | CH₃ | CH₃ |
| D6-97 | CH₃ | 1-Cl | CH₃ | CH₃ |
| D6-98 | OCH₃ | 1-Cl | CH₃ | CH₃ |
| D6-99 | H | 1-F | CH₃ | CH₃ |
| D6-100 | Cl | 1-F | CH₃ | CH₃ |
| D6-101 | F | 1-F | CH₃ | CH₃ |
| D6-102 | Br | 1-F | CH₃ | CH₃ |
| D6-103 | CF₃ | 1-F | CH₃ | CH₃ |
| D6-104 | CH₃ | 1-F | CH₃ | CH₃ |
| D6-105 | OCH₃ | 1-F | CH₃ | CH₃ |
| D6-106 | H | 1-CH₃ | CH₃ | CH₃ |
| D6-107 | Cl | 1-CH₃ | CH₃ | CH₃ |
| D6-108 | F | 1-CH₃ | CH₃ | CH₃ |
| D6-109 | Br | 1-CH₃ | CH₃ | CH₃ |
| D6-110 | CF₃ | 1-CH₃ | CH₃ | CH₃ |
| D6-111 | CH₃ | 1-CH₃ | CH₃ | CH₃ |
| D6-112 | OCH₃ | 1-CH₃ | CH₃ | CH₃ |

TABLE D7

| line | R³ | (R⁴)ₘ |
|---|---|---|
| D7-1 | H | m = 0 |
| D7-2 | Cl | m = 0 |
| D7-3 | F | m = 0 |
| D7-4 | Br | m = 0 |
| D7-5 | CF₃ | m = 0 |
| D7-6 | CH₃ | m = 0 |
| D7-7 | OCH₃ | m = 0 |
| D7-8 | H | 1-Cl |
| D7-9 | Cl | 1-Cl |
| D7-10 | F | 1-Cl |
| D7-11 | Br | 1-Cl |
| D7-12 | CF₃ | 1-Cl |
| D7-13 | CH₃ | 1-Cl |
| D7-14 | OCH₃ | 1-Cl |
| D7-15 | H | 1-F |
| D7-16 | Cl | 1-F |
| D7-17 | F | 1-F |
| D7-18 | Br | 1-F |
| D7-19 | CF₃ | 1-F |
| D7-20 | CH₃ | 1-F |
| D7-21 | OCH₃ | 1-F |
| D7-22 | H | 1-CH₃ |
| D7-23 | Cl | 1-CH₃ |
| D7-24 | F | 1-CH₃ |
| D7-25 | Br | 1-CH₃ |
| D7-26 | CF₃ | 1-CH₃ |
| D7-27 | CH₃ | 1-CH₃ |
| D7-28 | OCH₃ | 1-CH₃ |

TABLE D8

| Line | R³ | R⁵ |
|---|---|---|
| D8-1 | H | H |
| D8-2 | Cl | H |
| D8-3 | F | H |
| D8-4 | Br | H |
| D8-5 | CF₃ | H |
| D8-6 | CH₃ | H |
| D8-7 | OCH₃ | H |

TABLE D9

| line | $R^3$ | $R^6$ |
|---|---|---|
| D9-1 | H | H |
| D9-2 | Cl | H |
| D9-3 | F | H |
| D9-4 | Br | H |
| D9-5 | $CF_3$ | H |
| D9-6 | $CH_3$ | H |
| D9-7 | $OCH_3$ | H |
| D9-8 | H | Cl |
| D9-9 | Cl | Cl |
| D9-10 | F | Cl |
| D9-11 | Br | Cl |
| D9-12 | $CF_3$ | Cl |
| D9-13 | $CH_3$ | Cl |
| D9-14 | $OCH_3$ | Cl |
| D9-15 | H | $CH_3$ |
| D9-16 | Cl | $CH_3$ |
| D9-17 | F | $CH_3$ |
| D9-18 | Br | $CH_3$ |
| D9-19 | $CF_3$ | $CH_3$ |
| D9-20 | $CH_3$ | $CH_3$ |
| D9-21 | $OCH_3$ | $CH_3$ |

TABLE D10

| line | $R^3$ | $R^5$ | $R^6$ | $R^{7a}$ |
|---|---|---|---|---|
| D10-1 | H | H | H | $CH_3$ |
| D10-2 | Cl | H | H | $CH_3$ |
| D10-3 | $CF_3$ | H | H | $CH_3$ |
| D10-4 | H | $CH_3$ | H | $CH_3$ |
| D10-5 | Cl | $CH_3$ | H | $CH_3$ |
| D10-6 | $CF_3$ | $CH_3$ | H | $CH_3$ |
| D10-7 | H | Cl | H | $CH_3$ |
| D10-8 | Cl | Cl | H | $CH_3$ |
| D10-9 | $CF_3$ | Cl | H | $CH_3$ |
| D10-10 | H | H | $CH_3$ | $CH_3$ |
| D10-11 | Cl | H | $CH_3$ | $CH_3$ |
| D10-12 | $CF_3$ | H | $CH_3$ | $CH_3$ |
| D10-13 | H | $CH_3$ | $CH_3$ | $CH_3$ |
| D10-14 | Cl | $CH_3$ | $CH_3$ | $CH_3$ |
| D10-15 | $CF_3$ | $CH_3$ | $CH_3$ | $CH_3$ |
| D10-16 | H | Cl | $CH_3$ | $CH_3$ |
| D10-17 | Cl | Cl | $CH_3$ | $CH_3$ |
| D10-18 | $CF_3$ | Cl | $CH_3$ | $CH_3$ |
| D10-19 | H | H | H | Cl |
| D10-20 | Cl | H | H | Cl |
| D10-21 | $CF_3$ | H | H | Cl |
| D10-22 | H | $CH_3$ | H | Cl |
| D10-23 | Cl | $CH_3$ | H | Cl |
| D10-24 | $CF_3$ | $CH_3$ | H | Cl |
| D10-25 | H | Cl | H | Cl |
| D10-26 | Cl | Cl | H | Cl |
| D10-27 | $CF_3$ | Cl | H | Cl |
| D10-28 | H | H | $CH_3$ | Cl |
| D10-29 | Cl | H | $CH_3$ | Cl |
| D10-30 | $CF_3$ | H | $CH_3$ | Cl |
| D10-31 | H | $CH_3$ | $CH_3$ | Cl |
| D10-32 | Cl | $CH_3$ | $CH_3$ | Cl |
| D10-33 | $CF_3$ | $CH_3$ | $CH_3$ | Cl |
| D10-34 | H | Cl | $CH_3$ | Cl |
| D10-35 | Cl | Cl | $CH_3$ | Cl |
| D10-36 | $CF_3$ | Cl | $CH_3$ | Cl |
| D10-37 | H | H | H | Br |
| D10-38 | Cl | H | H | Br |
| D10-39 | $CF_3$ | H | H | Br |
| D10-40 | H | $CH_3$ | H | Br |
| D10-41 | Cl | $CH_3$ | H | Br |
| D10-42 | $CF_3$ | $CH_3$ | H | Br |
| D10-43 | H | Cl | H | Br |
| D10-44 | Cl | Cl | H | Br |
| D10-45 | $CF_3$ | Cl | H | Br |
| D10-46 | H | H | $CH_3$ | Br |
| D10-47 | Cl | H | $CH_3$ | Br |
| D10-48 | $CF_3$ | H | $CH_3$ | Br |
| D10-49 | H | $CH_3$ | $CH_3$ | Br |
| D10-50 | Cl | $CH_3$ | $CH_3$ | Br |
| D10-51 | $CF_3$ | $CH_3$ | $CH_3$ | Br |
| D10-52 | H | Cl | $CH_3$ | Br |
| D10-53 | Cl | Cl | $CH_3$ | Br |
| D10-54 | $CF_3$ | Cl | $CH_3$ | Br |
| D10-55 | H | H | H | $CF_3$ |
| D10-56 | Cl | H | H | $CF_3$ |
| D10-57 | $CF_3$ | H | H | $CF_3$ |
| D10-58 | H | $CH_3$ | H | $CF_3$ |
| D10-59 | Cl | $CH_3$ | H | $CF_3$ |
| D10-60 | $CF_3$ | $CH_3$ | H | $CF_3$ |
| D10-61 | H | Cl | H | $CF_3$ |
| D10-62 | Cl | Cl | H | $CF_3$ |
| D10-63 | $CF_3$ | Cl | H | $CF_3$ |
| D10-64 | H | H | $CH_3$ | $CF_3$ |
| D10-65 | Cl | H | $CH_3$ | $CF_3$ |
| D10-66 | $CF_3$ | H | $CH_3$ | $CF_3$ |
| D10-67 | H | $CH_3$ | $CH_3$ | $CF_3$ |
| D10-68 | Cl | $CH_3$ | $CH_3$ | $CF_3$ |
| D10-69 | $CF_3$ | $CH_3$ | $CH_3$ | $CF_3$ |
| D10-70 | H | Cl | $CH_3$ | $CF_3$ |
| D10-71 | Cl | Cl | $CH_3$ | $CF_3$ |
| D10-72 | $CF_3$ | Cl | $CH_3$ | $CF_3$ |
| D10-73 | H | H | H | $Si(CH_3)_3$ |
| D10-74 | Cl | H | H | $Si(CH_3)_3$ |
| D10-75 | $CF_3$ | H | H | $Si(CH_3)_3$ |
| D10-76 | H | $CH_3$ | H | $Si(CH_3)_3$ |
| D10-77 | Cl | $CH_3$ | H | $Si(CH_3)_3$ |
| D10-78 | $CF_3$ | $CH_3$ | H | $Si(CH_3)_3$ |
| D10-79 | H | Cl | H | $Si(CH_3)_3$ |
| D10-80 | Cl | Cl | H | $Si(CH_3)_3$ |
| D10-81 | $CF_3$ | Cl | H | $Si(CH_3)_3$ |
| D10-82 | H | H | $CH_3$ | $Si(CH_3)_3$ |
| D10-83 | Cl | H | $CH_3$ | $Si(CH_3)_3$ |
| D10-84 | $CF_3$ | H | $CH_3$ | $Si(CH_3)_3$ |
| D10-85 | H | $CH_3$ | $CH_3$ | $Si(CH_3)_3$ |
| D10-86 | Cl | $CH_3$ | $CH_3$ | $Si(CH_3)_3$ |
| D10-87 | $CF_3$ | $CH_3$ | $CH_3$ | $Si(CH_3)_3$ |
| D10-88 | H | Cl | $CH_3$ | $Si(CH_3)_3$ |
| D10-89 | Cl | Cl | $CH_3$ | $Si(CH_3)_3$ |
| D10-90 | $CF_3$ | Cl | $CH_3$ | $Si(CH_3)_3$ |

TABLE D11

| line | $R^3$ | $R^5$ | $R^6$ |
|---|---|---|---|
| D11-1 | H | H | H |
| D11-2 | Cl | H | H |
| D11-3 | $CF_3$ | H | H |
| D11-4 | H | $CH_3$ | H |
| D11-5 | Cl | $CH_3$ | H |
| D11-6 | $CF_3$ | $CH_3$ | H |
| D11-7 | H | Cl | H |
| D11-8 | Cl | Cl | H |
| D11-9 | $CF_3$ | Cl | H |
| D11-10 | H | H | $CH_3$ |
| D11-11 | Cl | H | $CH_3$ |
| D11-12 | $CF_3$ | H | $CH_3$ |
| D11-13 | H | $CH_3$ | $CH_3$ |
| D11-14 | Cl | $CH_3$ | $CH_3$ |
| D11-15 | $CF_3$ | $CH_3$ | $CH_3$ |
| D11-16 | H | Cl | $CH_3$ |
| D11-17 | Cl | Cl | $CH_3$ |
| D11-18 | $CF_3$ | Cl | $CH_3$ |

TABLE B

| line | $R^1$ | $R^2$ |
|---|---|---|
| B-1 | $CH_3$ | H |
| B-2 | $CH_2CH_3$ | H |
| B-3 | $CH_2CH_2CH_3$ | H |
| B-4 | $CH(CH_3)_2$ | H |

TABLE B-continued

| line | R¹ | R² |
|---|---|---|
| B-5 | C(CH₃)₃ | H |
| B-6 | CH(CH₃)CH₂CH₃ | H |
| B-7 | CH₂CH(CH₃)₂ | H |
| B-8 | CH₂CH₂CH₂CH₃ | H |
| B-9 | CF₃ | H |
| B-10 | CHF₂ | H |
| B-11 | CH₂F | H |
| B-12 | CHCl₂ | H |
| B-13 | CH₂Cl | H |
| B-14 | CH₂OH | H |
| B-15 | CF₂CH₃ | H |
| B-16 | CH₂CF₃ | H |
| B-17 | CF₂CF₃ | H |
| B-18 | CH₂CH₂OH | H |
| B-19 | CH₂CH₂CH₂OH | H |
| B-20 | CH(CH₃)CH₂OH | H |
| B-21 | CH₂CH(CH₃)OH | H |
| B-22 | n-C₄H₈OH | H |
| B-23 | CH₂OCH₃ | H |
| B-24 | CH₂OCH₂CH₃ | H |
| B-25 | CH(CH₃)OCH₃ | H |
| B-26 | CH₂OCF₃ | H |
| B-27 | CH₂CH₂OCF₃ | H |
| B-28 | CH₂OCCl₃ | H |
| B-29 | CH₂CH₂OCCl₃ | H |
| B-30 | CH=CH₂ | H |
| B-31 | CH₂CH=CH₂ | H |
| B-32 | CH₂CH=CHCH₃ | H |
| B-33 | CH₂C(CH₃)=CH₂ | H |
| B-34 | CH=CHCH₃ | H |
| B-35 | C(CH₃)=CH₂ | H |
| B-36 | CH=C(CH₃)₂ | H |
| B-37 | C(CH₃)=C(CH₃)₂ | H |
| B-38 | C(CH₃)=CH(CH₃) | H |
| B-39 | C(Cl)=CH₂ | H |
| B-40 | C(H)=CHCl | H |
| B-41 | C(Cl)=CHCl | H |
| B-42 | CH=CCl₂ | H |
| B-43 | C(Cl)=CCl₂ | H |
| B-44 | C(H)=CH(F) | H |
| B-45 | C(H)=CF₂ | H |
| B-46 | C(F)=CF₂ | H |
| B-47 | C(F)=CHF | H |
| B-48 | CH=CHCH₂OH | H |
| B-49 | CH=CHOCH₃ | H |
| B-50 | CH=CHCH₂OCH₃ | H |
| B-51 | CH=CHCH₂OCF₃ | H |
| B-52 | CH=CH(C₃H₅) | H |
| B-53 | C≡CH | H |
| B-54 | C≡CCH₃ | H |
| B-55 | CH₂C≡CCH₃ | H |
| B-56 | CH₂C≡CH | H |
| B-57 | CH₂C≡CCH₂CH₃ | H |
| B-58 | C≡CCH(CH₃)₂ | H |
| B-59 | C≡CC(CH₃)₃ | H |
| B-60 | C≡C(C₃H₅) | H |
| B-61 | C≡C(C₄H₇) | H |
| B-62 | C≡C(1-Cl—C₃H₄) | H |
| B-63 | C≡C(1-Cl—C₄H₆) | H |
| B-64 | C≡C—Cl | H |
| B-65 | C≡C—Br | H |
| B-66 | C≡C—I | H |
| B-67 | CH₂C≡C—Cl | H |
| B-68 | CH₂C≡C—Br | H |
| B-69 | CH₂C≡C—I | H |
| B-70 | C≡CCH₂OCH₃ | H |
| B-71 | C≡CCH(OH)CH₃ | H |
| B-72 | C≡COCH₃ | H |
| B-73 | CH₂C≡COCH₃ | H |
| B-74 | C≡CCH₂OCCl₃ | H |
| B-75 | C≡CCH₂OCF₃ | H |
| B-76 | C≡CCH₂(C₃H₅) | H |
| B-77 | C≡C(1-Cl—C₃H₄) | H |
| B-78 | C≡C(1-F—C₃H₄) | H |
| B-79 | C₃H₅ (cyclopropyl) | H |
| B-80 | CH(CH₃)—C₃H₅ | H |
| B-81 | CH₂—C₃H₅ | H |
| B-82 | 1-(Cl)—C₃H₅ | H |
| B-83 | 1-(F)—C₃H₅ | H |
| B-84 | 1-(CH₃)—C₃H₅ | H |
| B-85 | 1-(CN)—C₃H₅ | H |
| B-86 | 2-(Cl)—C₃H₅ | H |
| B-87 | 2-(F)—C₃H₅ | H |
| B-88 | 1-C₃H₅—C₃H₅ | H |
| B-89 | 2-C₃H₅—C₃H₅ | H |
| B-90 | CH₂-(1-Cl—C₃H₅) | H |
| B-91 | CH₂-(1-F—C₃H₅) | H |
| B-92 | CH₃ | CH₃ |
| B-93 | CH₂CH₃ | CH₃ |
| B-94 | CH₂CH₂CH₃ | CH₃ |
| B-95 | CH(CH₃)₂ | CH₃ |
| B-96 | C(CH₃)₃ | CH₃ |
| B-97 | CH(CH₃)CH₂CH₃ | CH₃ |
| B-98 | CH₂CH(CH₃)₂ | CH₃ |
| B-99 | CH₂CH₂CH₂CH₃ | CH₃ |
| B-100 | CF₃ | CH₃ |
| B-101 | CHF₂ | CH₃ |
| B-102 | CH₂F | CH₃ |
| B-103 | CHCl₂ | CH₃ |
| B-104 | CH₂Cl | CH₃ |
| B-105 | CF₂CH₃ | CH₃ |
| B-106 | CH₂CF₃ | CH₃ |
| B-107 | CF₂CF₃ | CH₃ |
| B-108 | CH₂OH | CH₃ |
| B-109 | CH₂CH₂OH | CH₃ |
| B-110 | CH₂CH₂CH₂OH | CH₃ |
| B-111 | CH(CH₃)CH₂OH | CH₃ |
| B-112 | CH₂CH(CH₃)OH | CH₃ |
| B-113 | n-C₄H₈OH | CH₃ |
| B-114 | CH₂OCH₃ | CH₃ |
| B-115 | CH₂OCH₂CH₃ | CH₃ |
| B-116 | CH(CH₃)OCH₃ | CH₃ |
| B-117 | CH₂OCF₃ | CH₃ |
| B-118 | CH₂CH₂OCF₃ | CH₃ |
| B-119 | CH₂OCCl₃ | CH₃ |
| B-120 | CH₂CH₂OCCl₃ | CH₃ |
| B-121 | CH=CH₂ | CH₃ |
| B-122 | CH₂CH=CH₂ | CH₃ |
| B-123 | CH₂CH=CHCH₃ | CH₃ |
| B-124 | CH₂C(CH₃)=CH₂ | CH₃ |
| B-125 | CH=CHCH₃ | CH₃ |
| B-126 | C(CH₃)=CH₂ | CH₃ |
| B-127 | CH=C(CH₃)₂ | CH₃ |
| B-128 | C(CH₃)=C(CH₃)₂ | CH₃ |
| B-129 | C(CH₃)=CH(CH₃) | CH₃ |
| B-130 | C(Cl)=CH₂ | CH₃ |
| B-131 | C(H)=CHCl | CH₃ |
| B-132 | C(Cl)=CHCl | CH₃ |
| B-133 | CH=CCl₂ | CH₃ |
| B-134 | C(Cl)=CCl₂ | CH₃ |
| B-135 | C(H)=CH(F) | CH₃ |
| B-136 | C(H)=CF₂ | CH₃ |
| B-137 | C(F)=CF₂ | CH₃ |
| B-138 | C(F)=CHF | CH₃ |
| B-139 | CH=CHCH₂OH | CH₃ |
| B-140 | CH=CHOCH₃ | CH₃ |
| B-141 | CH=CHCH₂OCH₃ | CH₃ |
| B-142 | CH=CHCH₂OCF₃ | CH₃ |
| B-143 | CH=CH(C₃H₅) | CH₃ |
| B-144 | C≡CH | CH₃ |
| B-145 | C≡CCH₃ | CH₃ |
| B-146 | CH₂C≡CCH₃ | CH₃ |
| B-147 | CH₂C≡CH | CH₃ |
| B-148 | CH₂C≡CCH₂CH₃ | CH₃ |
| B-149 | C≡CCH(CH₃)₂ | CH₃ |
| B-150 | C≡CC(CH₃)₃ | CH₃ |
| B-151 | C≡C(C₃H₅) | CH₃ |
| B-152 | C≡C(C₄H₇) | CH₃ |
| B-153 | C≡C(1-Cl—C₃H₄) | CH₃ |
| B-154 | C≡C(1-Cl—C₄H₆) | CH₃ |
| B-155 | C≡CCl | CH₃ |
| B-156 | C≡CBr | CH₃ |
| B-157 | C≡C—I | CH₃ |
| B-158 | CH₂C≡CCl | CH₃ |
| B-159 | CH₂C≡CBr | CH₃ |
| B-160 | CH₂C≡C—I | CH₃ |

TABLE B-continued

| line | R¹ | R² |
|---|---|---|
| B-161 | C≡CCH₂OCH₃ | CH₃ |
| B-162 | C≡CCH(OH)CH₃ | CH₃ |
| B-163 | C≡COCH₃ | CH₃ |
| B-164 | CH₂C≡COCH₃ | CH₃ |
| B-165 | C≡CCH₂OCCl₃ | CH₃ |
| B-166 | C≡CCH₂OCF₃ | CH₃ |
| B-167 | C≡CCH₂(C₃H₅) | CH₃ |
| B-168 | C≡C(1-Cl—C₃H₄) | CH₃ |
| B-169 | C≡C(1-F—C₃H₄) | CH₃ |
| B-170 | C₃H₅ (cyclopropyl) | CH₃ |
| B-171 | CH(CH₃)—C₃H₅ | CH₃ |
| B-172 | CH₂—C₃H₅ | CH₃ |
| B-173 | 1-(Cl)—C₃H₅ | CH₃ |
| B-174 | 1-(F)—C₃H₅ | CH₃ |
| B-175 | 1-(CH₃)—C₃H₅ | CH₃ |
| B-176 | 1-(CN)—C₃H₅ | CH₃ |
| B-177 | 2-(Cl)—C₃H₅ | CH₃ |
| B-178 | 2-(F)—C₃H₅ | CH₃ |
| B-179 | 1-C₃H₅—C₃H₅ | CH₃ |
| B-180 | 2-C₃H₅—C₃H₅ | CH₃ |
| B-181 | CH₂-(1-Cl—C₃H₅) | CH₃ |
| B-182 | CH₂-(1-F—C₃H₅) | CH₃ |
| B-183 | CH₃ | C₂H₅ |
| B-184 | CH₂CH₃ | C₂H₅ |
| B-185 | CH₂CH₂CH₃ | C₂H₅ |
| B-186 | CH(CH₃)₂ | C₂H₅ |
| B-187 | C(CH₃)₃ | C₂H₅ |
| B-188 | CH(CH₃)CH₂CH₃ | C₂H₅ |
| B-189 | CH₂CH(CH₃)₂ | C₂H₅ |
| B-190 | CH₂CH₂CH₂CH₃ | C₂H₅ |
| B-191 | CF₃ | C₂H₅ |
| B-192 | CHF₂ | C₂H₅ |
| B-193 | CH₂F | C₂H₅ |
| B-194 | CHCl₂ | C₂H₅ |
| B-195 | CH₂Cl | C₂H₅ |
| B-196 | CF₂CH₃ | C₂H₅ |
| B-197 | CH₂CF₃ | C₂H₅ |
| B-198 | CF₂CF₃ | C₂H₅ |
| B-199 | CH₂OH | C₂H₅ |
| B-200 | CH₂CH₂OH | C₂H₅ |
| B-201 | CH₂CH₂CH₂OH | C₂H₅ |
| B-202 | CH(CH₃)CH₂OH | C₂H₅ |
| B-203 | CH₂CH(CH₃)OH | C₂H₅ |
| B-204 | n-C₄H₈OH | C₂H₅ |
| B-205 | CH₂OCH₃ | C₂H₅ |
| B-206 | CH₂OCH₂CH₃ | C₂H₅ |
| B-207 | CH(CH₃)OCH₃ | C₂H₅ |
| B-208 | CH₂OCF₃ | C₂H₅ |
| B-209 | CH₂CH₂OCF₃ | C₂H₅ |
| B-210 | CH₂OCCl₃ | C₂H₅ |
| B-211 | CH₂CH₂OCCl₃ | C₂H₅ |
| B-212 | CH=CH₂ | C₂H₅ |
| B-213 | CH₂CH=CH₂ | C₂H₅ |
| B-214 | CH₂CH=CHCH₃ | C₂H₅ |
| B-215 | CH₂C(CH₃)=CH₂ | C₂H₅ |
| B-216 | CH=CHCH₃ | C₂H₅ |
| B-217 | C(CH₃)=CH₂ | C₂H₅ |
| B-218 | CH=C(CH₃)₂ | C₂H₅ |
| B-219 | C(CH₃)=C(CH₃)₂ | C₂H₅ |
| B-220 | C(CH₃)=CH(CH₃) | C₂H₅ |
| B-221 | C(Cl)=CH₂ | C₂H₅ |
| B-222 | C(H)=CHCl | C₂H₅ |
| B-223 | C(Cl)=CHCl | C₂H₅ |
| B-224 | CH=CCl₂ | C₂H₅ |
| B-225 | C(Cl)=CCl₂ | C₂H₅ |
| B-226 | C(H)=CH(F) | C₂H₅ |
| B-227 | C(H)=CF₂ | C₂H₅ |
| B-228 | C(F)=CF₂ | C₂H₅ |
| B-229 | C(F)=CHF | C₂H₅ |
| B-230 | CH=CHCH₂OH | C₂H₅ |
| B-231 | CH=CHOCH₃ | C₂H₅ |
| B-232 | CH=CHCH₂OCH₃ | C₂H₅ |
| B-233 | CH=CHCH₂OCF₃ | C₂H₅ |
| B-234 | CH=CH(C₃H₅) | C₂H₅ |
| B-235 | C≡CH | C₂H₅ |
| B-236 | C≡CCH₃ | C₂H₅ |
| B-237 | CH₂C≡CCH₃ | C₂H₅ |
| B-238 | CH₂C≡CH | C₂H₅ |
| B-239 | CH₂C≡CCH₂CH₃ | C₂H₅ |
| B-240 | C≡CCH(CH₃)₂ | C₂H₅ |
| B-241 | C≡CC(CH₃)₃ | C₂H₅ |
| B-242 | C≡C(C₃H₅) | C₂H₅ |
| B-243 | C≡C(C₄H₇) | C₂H₅ |
| B-244 | C≡C(1-Cl—C₃H₄) | C₂H₅ |
| B-245 | C≡C(1-Cl—C₄H₆) | C₂H₅ |
| B-246 | C≡CCl | C₂H₅ |
| B-247 | C≡CBr | C₂H₅ |
| B-248 | C≡C—I | C₂H₅ |
| B-249 | CH₂C≡CCl | C₂H₅ |
| B-250 | CH₂C≡CBr | C₂H₅ |
| B-251 | CH₂C≡C—I | C₂H₅ |
| B-252 | C≡CCH₂OCH₃ | C₂H₅ |
| B-253 | C≡CCH(OH)CH₃ | C₂H₅ |
| B-254 | C≡COCH₃ | C₂H₅ |
| B-255 | CH₂C≡COCH₃ | C₂H₅ |
| B-256 | C≡CCH₂OCCl₃ | C₂H₅ |
| B-257 | C≡CCH₂OCF₃ | C₂H₅ |
| B-258 | C≡CCH₂(C₃H₅) | C₂H₅ |
| B-259 | C≡C(1-Cl—C₃H₄) | C₂H₅ |
| B-260 | C≡C(1-F—C₃H₄) | C₂H₅ |
| B-261 | C₃H₅ (cyclopropyl) | C₂H₅ |
| B-262 | CH(CH₃)—C₃H₅ | C₂H₅ |
| B-263 | CH₂—C₃H₅ | C₂H₅ |
| B-264 | 1-(Cl)—C₃H₅ | C₂H₅ |
| B-265 | 1-(F)—C₃H₅ | C₂H₅ |
| B-266 | 1-(CH₃)—C₃H 5 | C₂H₅ |
| B-267 | 1-(CN)—C₃H₅ | C₂H₅ |
| B-268 | 2-(Cl)—C₃H₅ | C₂H₅ |
| B-269 | 2-(F)—C₃H₅ | C₂H₅ |
| B-270 | 1-C₃H₅—C₃H₅ | C₂H₅ |
| B-271 | 2-C₃H₅—C₃H₅ | C₂H₅ |
| B-272 | CH₂-(1-Cl—C₃H₅) | C₂H₅ |
| B-273 | CH₂-(1-F—C₃H₅) | C₂H₅ |
| B-274 | CH₃ | CH₂CH=CH₂ |
| B-275 | CH₂CH₃ | CH₂CH=CH₂ |
| B-276 | CH₂CH₂CH₃ | CH₂CH=CH₂ |
| B-277 | CH(CH₃)₂ | CH₂CH=CH₂ |
| B-278 | C(CH₃)₃ | CH₂CH=CH₂ |
| B-279 | CH(CH₃)CH₂CH₃ | CH₂CH=CH₂ |
| B-280 | CH₂CH(CH₃)₂ | CH₂CH=CH₂ |
| B-281 | CH₂CH₂CH₂CH₃ | CH₂CH=CH₂ |
| B-282 | CF₃ | CH₂CH=CH₂ |
| B-283 | CHF₂ | CH₂CH=CH₂ |
| B-284 | CH₂F | CH₂CH=CH₂ |
| B-285 | CHCl₂ | CH₂CH=CH₂ |
| B-286 | CH₂Cl | CH₂CH=CH₂ |
| B-287 | CF₂CH₃ | CH₂CH=CH₂ |
| B-288 | CH₂CF₃ | CH₂CH=CH₂ |
| B-289 | CF₂CF₃ | CH₂CH=CH₂ |
| B-290 | CH₂OH | CH₂CH=CH₂ |
| B-291 | CH₂CH₂OH | CH₂CH=CH₂ |
| B-292 | CH₂CH₂CH₂OH | CH₂CH=CH₂ |
| B-293 | CH(CH₃)CH₂OH | CH₂CH=CH₂ |
| B-294 | CH₂CH(CH₃)OH | CH₂CH=CH₂ |
| B-295 | n-C₄H₈OH | CH₂CH=CH₂ |
| B-296 | CH₂OCH₃ | CH₂CH=CH₂ |
| B-297 | CH₂OCH₂CH₃ | CH₂CH=CH₂ |
| B-298 | CH(CH₃)OCH₃ | CH₂CH=CH₂ |
| B-299 | CH₂OCF₃ | CH₂CH=CH₂ |
| B-300 | CH₂CH₂OCF₃ | CH₂CH=CH₂ |
| B-301 | CH₂OCCl₃ | CH₂CH=CH₂ |
| B-302 | CH₂CH₂OCCl₃ | CH₂CH=CH₂ |
| B-303 | CH=CH₂ | CH₂CH=CH₂ |
| B-304 | CH₂CH=CH₂ | CH₂CH=CH₂ |
| B-305 | CH₂CH=CHCH₃ | CH₂CH=CH₂ |
| B-306 | CH₂C(CH₃)=CH₂ | CH₂CH=CH₂ |
| B-307 | CH=CHCH₃ | CH₂CH=CH₂ |
| B-308 | C(CH₃)=CH₂ | CH₂CH=CH₂ |
| B-309 | CH=C(CH₃)₂ | CH₂CH=CH₂ |
| B-310 | C(CH₃)=C(CH₃)₂ | CH₂CH=CH₂ |
| B-311 | C(CH₃)=CH(CH₃) | CH₂CH=CH₂ |
| B-312 | C(Cl)=CH₂ | CH₂CH=CH₂ |
| B-313 | C(H)=CHCl | CH₂CH=CH₂ |
| B-314 | C(Cl)=CHCl | CH₂CH=CH₂ |
| B-315 | CH=CCl₂ | CH₂CH=CH₂ |
| B-316 | C(Cl)=CCl₂ | CH₂CH=CH₂ |

TABLE B-continued

| line | R$^1$ | R$^2$ |
|---|---|---|
| B-317 | C(H)=CH(F) | CH$_2$CH=CH$_2$ |
| B-318 | C(H)=CF$_2$ | CH$_2$CH=CH$_2$ |
| B-319 | C(F)=CF$_2$ | CH$_2$CH=CH$_2$ |
| B-320 | C(F)=CHF | CH$_2$CH=CH$_2$ |
| B-321 | CH=CHCH$_2$OH | CH$_2$CH=CH$_2$ |
| B-322 | CH=CHOCH$_3$ | CH$_2$CH=CH$_2$ |
| B-323 | CH=CHCH$_2$OCH$_3$ | CH$_2$CH=CH$_2$ |
| B-324 | CH=CHCH$_2$OCF$_3$ | CH$_2$CH=CH$_2$ |
| B-325 | CH=CH(C$_3$H$_5$) | CH$_2$CH=CH$_2$ |
| B-326 | C≡CH | CH$_2$CH=CH$_2$ |
| B-327 | C≡CCH$_3$ | CH$_2$CH=CH$_2$ |
| B-328 | CH$_2$C≡CCH$_3$ | CH$_2$CH=CH$_2$ |
| B-329 | CH$_2$C≡CH | CH$_2$CH=CH$_2$ |
| B-330 | CH$_2$C≡CCH$_2$CH$_3$ | CH$_2$CH=CH$_2$ |
| B-331 | C≡CCH(CH$_3$)$_2$ | CH$_2$CH=CH$_2$ |
| B-332 | C≡CC(CH$_3$)$_3$ | CH$_2$CH=CH$_2$ |
| B-333 | C≡C(C$_3$H$_5$) | CH$_2$CH=CH$_2$ |
| B-334 | C≡C(C$_4$H$_7$) | CH$_2$CH=CH$_2$ |
| B-335 | C≡C(1-Cl—C$_3$H$_4$) | CH$_2$CH=CH$_2$ |
| B-336 | C≡C(1-Cl—C$_4$H$_6$) | CH$_2$CH=CH$_2$ |
| B-337 | C≡CCl | CH$_2$CH=CH$_2$ |
| B-338 | C≡CBr | CH$_2$CH=CH$_2$ |
| B-339 | C≡C—I | CH$_2$CH=CH$_2$ |
| B-340 | CH$_2$C≡CCl | CH$_2$CH=CH$_2$ |
| B-341 | CH$_2$C≡CBr | CH$_2$CH=CH$_2$ |
| B-342 | CH$_2$C≡C—I | CH$_2$CH=CH$_2$ |
| B-343 | C≡CCH$_2$OCH$_3$ | CH$_2$CH=CH$_2$ |
| B-344 | C≡CCH(OH)CH$_3$ | CH$_2$CH=CH$_2$ |
| B-345 | C≡COCH$_3$ | CH$_2$CH=CH$_2$ |
| B-346 | CH$_2$C≡COCH$_3$ | CH$_2$CH=CH$_2$ |
| B-347 | C≡CCH$_2$OCCl$_3$ | CH$_2$CH=CH$_2$ |
| B-348 | C≡CCH$_2$OCF$_3$ | CH$_2$CH=CH$_2$ |
| B-349 | C≡CCH$_2$(C$_3$H$_5$) | CH$_2$CH=CH$_2$ |
| B-350 | C≡C(1-Cl—C$_3$H$_4$) | CH$_2$CH=CH$_2$ |
| B-351 | C≡C(1-F—C$_3$H$_4$) | CH$_2$CH=CH$_2$ |
| B-352 | C$_3$H$_5$ (cyclopropyl) | CH$_2$CH=CH$_2$ |
| B-353 | CH(CH$_3$)—C$_3$H$_5$ | CH$_2$CH=CH$_2$ |
| B-354 | CH$_2$—C$_3$H$_5$ | CH$_2$CH=CH$_2$ |
| B-355 | 1-(Cl)—C$_3$H$_5$ | CH$_2$CH=CH$_2$ |
| B-356 | 1-(F)—C$_3$H$_5$ | CH$_2$CH=CH$_2$ |
| B-357 | 1-(CH$_3$)—C$_3$H$_5$ | CH$_2$CH=CH$_2$ |
| B-358 | 1-(CN)—C$_3$H$_5$ | CH$_2$CH=CH$_2$ |
| B-359 | 2-(Cl)—C$_3$H$_5$ | CH$_2$CH=CH$_2$ |
| B-360 | 2-(F)—C$_3$H$_5$ | CH$_2$CH=CH$_2$ |
| B-361 | 1-C$_3$H$_5$—C$_3$H$_5$ | CH$_2$CH=CH$_2$ |
| B-362 | 2-C$_3$H$_5$—C$_3$H$_5$ | CH$_2$CH=CH$_2$ |
| B-363 | CH$_2$-(1-Cl—C$_3$H$_5$) | CH$_2$CH=CH$_2$ |
| B-364 | CH$_2$-(1-F—C$_3$H$_5$) | CH$_2$CH=CH$_2$ |
| B-365 | CH$_3$ | CH$_2$C≡CH |
| B-366 | CH$_2$CH$_3$ | CH$_2$C≡CH |
| B-367 | CH$_2$CH$_2$CH$_3$ | CH$_2$C≡CH |
| B-368 | CH(CH$_3$)$_2$ | CH$_2$C≡CH |
| B-369 | C(CH$_3$)$_3$ | CH$_2$C≡CH |
| B-370 | CH(CH$_3$)CH$_2$CH$_3$ | CH$_2$C≡CH |
| B-371 | CH$_2$CH(CH$_3$)$_2$ | CH$_2$C≡CH |
| B-372 | CH$_2$CH$_2$CH$_2$CH$_3$ | CH$_2$C≡CH |
| B-373 | CF$_3$ | CH$_2$C≡CH |
| B-374 | CHF$_2$ | CH$_2$C≡CH |
| B-375 | CH$_2$F | CH$_2$C≡CH |
| B-376 | CHCl$_2$ | CH$_2$C≡CH |
| B-377 | CH$_2$Cl | CH$_2$C≡CH |
| B-378 | CF$_2$CH$_3$ | CH$_2$C≡CH |
| B-379 | CH$_2$CF$_3$ | CH$_2$C≡CH |
| B-380 | CF$_2$CF$_3$ | CH$_2$C≡CH |
| B-381 | CH$_2$OH | CH$_2$C≡CH |
| B-382 | CH$_2$CH$_2$OH | CH$_2$C≡CH |
| B-383 | CH$_2$CH$_2$CH$_2$OH | CH$_2$C≡CH |
| B-384 | CH(CH$_3$)CH$_2$OH | CH$_2$C≡CH |
| B-385 | CH$_2$CH(CH$_3$)OH | CH$_2$C≡CH |
| B-386 | n-C$_4$H$_8$OH | CH$_2$C≡CH |
| B-387 | CH$_2$OCH$_3$ | CH$_2$C≡CH |
| B-388 | CH$_2$OCH$_2$CH$_3$ | CH$_2$C≡CH |
| B-389 | CH(CH$_3$)OCH$_3$ | CH$_2$C≡CH |
| B-390 | CH$_2$OCF$_3$ | CH$_2$C≡CH |
| B-391 | CH$_2$CH$_2$OCF$_3$ | CH$_2$C≡CH |
| B-392 | CH$_2$OCCl$_3$ | CH$_2$C≡CH |
| B-393 | CH$_2$CH$_2$OCCl$_3$ | CH$_2$C≡CH |
| B-394 | CH=CH$_2$ | CH$_2$C≡CH |
| B-395 | CH$_2$CH=CH$_2$ | CH$_2$C≡CH |
| B-396 | CH$_2$CH=CHCH$_3$ | CH$_2$C≡CH |
| B-397 | CH$_2$C(CH$_3$)=CH$_2$ | CH$_2$C≡CH |
| B-398 | CH=CHCH$_3$ | CH$_2$C≡CH |
| B-399 | C(CH$_3$)=CH$_2$ | CH$_2$C≡CH |
| B-400 | CH=C(CH$_3$)$_2$ | CH$_2$C≡CH |
| B-401 | C(CH$_3$)=C(CH$_3$)$_2$ | CH$_2$C≡CH |
| B-402 | C(CH$_3$)=CH(CH$_3$) | CH$_2$C≡CH |
| B-403 | C(Cl)=CH$_2$ | CH$_2$C≡CH |
| B-404 | C(H)=CHCl | CH$_2$C≡CH |
| B-405 | C(Cl)=CHCl | CH$_2$C≡CH |
| B-406 | CH=CCl$_2$ | CH$_2$C≡CH |
| B-407 | C(Cl)=CCl$_2$ | CH$_2$C≡CH |
| B-408 | C(H)=CH(F) | CH$_2$C≡CH |
| B-409 | C(H)=CF$_2$ | CH$_2$C≡CH |
| B-410 | C(F)=CF$_2$ | CH$_2$C≡CH |
| B-411 | C(F)=CHF | CH$_2$C≡CH |
| B-412 | CH=CHCH$_2$OH | CH$_2$C≡CH |
| B-413 | CH=CHOCH$_3$ | CH$_2$C≡CH |
| B-414 | CH=CHCH$_2$OCH$_3$ | CH$_2$C≡CH |
| B-415 | CH=CHCH$_2$OCF$_3$ | CH$_2$C≡CH |
| B-416 | CH=CH(C$_3$H$_5$) | CH$_2$C≡CH |
| B-417 | C≡CH | CH$_2$C≡CH |
| B-418 | C≡CCH$_3$ | CH$_2$C≡CH |
| B-419 | CH$_2$C≡CCH$_3$ | CH$_2$C≡CH |
| B-420 | CH$_2$C≡CH | CH$_2$C≡CH |
| B-421 | CH$_2$C≡CCH$_2$CH$_3$ | CH$_2$C≡CH |
| B-422 | C≡CCH(CH$_3$)$_2$ | CH$_2$C≡CH |
| B-423 | C≡CC(CH$_3$)$_3$ | CH$_2$C≡CH |
| B-424 | C≡C(C$_3$H$_5$) | CH$_2$C≡CH |
| B-425 | C≡C(C$_4$H$_7$) | CH$_2$C≡CH |
| B-426 | C≡C(1-Cl—C$_3$H$_4$) | CH$_2$C≡CH |
| B-427 | C≡C(1-Cl—C$_4$H$_6$) | CH$_2$C≡CH |
| B-428 | C≡CCl | CH$_2$C≡CH |
| B-429 | C≡CBr | CH$_2$C≡CH |
| B-430 | C≡C—I | CH$_2$C≡CH |
| B-431 | CH$_2$C≡CCl | CH$_2$C≡CH |
| B-432 | CH$_2$C≡CBr | CH$_2$C≡CH |
| B-433 | CH$_2$C≡C—I | CH$_2$C≡CH |
| B-434 | C≡CCH$_2$OCH$_3$ | CH$_2$C≡CH |
| B-435 | C≡CCH(OH)CH$_3$ | CH$_2$C≡CH |
| B-436 | C≡COCH$_3$ | CH$_2$C≡CH |
| B-437 | CH$_2$C≡COCH$_3$ | CH$_2$C≡CH |
| B-438 | C≡CCH$_2$OCCl$_3$ | CH$_2$C≡CH |
| B-439 | C≡CCH$_2$OCF$_3$ | CH$_2$C≡CH |
| B-440 | C≡CCH$_2$(C$_3$H$_5$) | CH$_2$C≡CH |
| B-441 | C≡C(1-Cl—C$_3$H$_4$) | CH$_2$C≡CH |
| B-442 | C≡C(1-F—C$_3$H$_4$) | CH$_2$C≡CH |
| B-443 | C$_3$H$_5$ (cyclopropyl) | CH$_2$C≡CH |
| B-444 | CH(CH$_3$)—C$_3$H$_5$ | CH$_2$C≡CH |
| B-445 | CH$_2$—C$_3$H$_5$ | CH$_2$C≡CH |
| B-446 | 1-(Cl)—C$_3$H$_5$ | CH$_2$C≡CH |
| B-447 | 1-(F)—C$_3$H$_5$ | CH$_2$C≡CH |
| B-448 | 1-(CH$_3$)—C$_3$H$_5$ | CH$_2$C≡CH |
| B-449 | 1-(CN)—C$_3$H$_5$ | CH$_2$C≡CH |
| B-450 | 2-(Cl)—C$_3$H$_5$ | CH$_2$C≡CH |
| B-451 | 2-(F)—C$_3$H$_5$ | CH$_2$C≡CH |
| B-452 | 1-C$_3$H$_5$—C$_3$H$_5$ | CH$_2$C≡CH |
| B-453 | 2-C$_3$H$_5$—C$_3$H$_5$ | CH$_2$C≡CH |
| B-454 | CH$_2$-(1-Cl—C$_3$H$_5$) | CH$_2$C≡CH |
| B-455 | CH$_2$-(1-F—C$_3$H$_5$) | CH$_2$C≡CH |

The compounds I and the compositions according to the invention, respectively, are suitable as fungicides.

Consequently, according to a further aspect, the present invention relates to the use of compounds of formula I, the N-oxides and the agriculturally acceptable salts thereof or of the compositions of the invention for combating phytopathogenic fungi.

Accordingly, the present invention also encompasses a method for combating harmful fungi, comprising treating the fungi or the materials, plants, the soil or seeds to be protected against fungal attack with an effective amount of at least one compound of formula I or with a composition comprising according to the invention.

The compounds I and the compositions according to the invention, respectively, are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti ). Some are systemically effective and they can be used in crop protection as foliar fungicides, fungicides for seed dressing and soil fungicides. Moreover, they are suitable for controlling harmful fungi, which inter alia occur in wood or roots of plants.

The compounds I and the compositions according to the invention are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e. g. conifers; and on the plant propagation material, such as seeds, and the crop material of these plants.

Preferably, compounds I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://cera-gmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxylphenylpyruvate dioxy-genase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus Bacillus, particularly from Bacillus thuringiensis, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. Photorhabdus spp. or Xenorhabdus spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase;

diuretic hormone receptors (helicokinin receptors); stilbene synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme phosphinothricin-N-acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the Mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The compounds I and compositions thereof, respectively, are particularly suitable for controlling the following plant diseases:

*Albugo* spp. (white rust) on ornamentals, vegetables (e. g. *A. candida*) and sunflowers (e. g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. alternata*), tomatoes (e. g. *A. solani* or *A. alternata*) and wheat; *Aphanomyces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.), e. g. Southern leaf blight (*D. maydis*) or Northern leaf blight (*B. zeicola*) on corn, e. g. spot blotch (*B. sorokiniana*) on cereals and e. g. *B. oryzae* on rice and turfs; *Blumeria* (formerly *Erysiphe*) *graminis* (powdery mildew) on cereals (e. g. on wheat or barley); *Botrytis cinerea* (teleomorph: *Botryotinia fuckeliana*: grey mold) on fruits and berries (e. g. strawberries), vegetables (e. g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn (e. g. Gray leaf spot: *C. zeae-maydis*), rice, sugar beets (e. g. *C. beticola*), sugar cane, vegetables, coffee, soybeans (e. g. *C. sojina* or *C. kikuchii*) and rice; *Cladosporium* spp. on tomatoes (e. g. *C. fulvum*: leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypi*), corn (e. g. *C. graminicola*: Anthracnose stalk rot), soft fruits, potatoes (e. g. *C. coccodes*: black dot), beans (e. g. *C. lindemuthianum*) and soybeans (e. g. *C. truncatum* or *C. gloeosporioides*); *Corticium* spp., e. g. *C. sasakii* (sheath blight) on rice; *Corynespora cassiicola* (leaf spots) on soybeans and ornamentals; *Cycloconium* spp., e. g. *C. oleaginum* on olive trees; *Cylindrocarpon* spp. (e. g. fruit tree canker or young vine decline, teleomorph: *Nectria* or *Neonectria* spp.) on fruit trees, vines (e. g. *C. liriodendri*, teleomorph: *Neonectria liriodendri*: Black Foot Disease) and ornamentals; *Dematophora* (teleomorph: *Rosellinia*) *necatrix* (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici-repentis*: tan spot), rice and turf; Esca (dieback, apoplexy) on vines, caused by *Formitiporia* (syn. *Phellinus*) *punctata*, *F. mediterranea*, *Phaeomoniella chlamydospora* (earlier *Phaeoacremonium chlamydosporum*), *Phaeoacremonium aleophi-*

*lum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e. g. *E. pisi*), such as cucurbits (e. g. *E. cichoracearum*), cabbages, rape (e. g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* (f. sp. *glycines* now syn. *F. virguliforme*) and *F. tucumaniae* and *F. brasiliense* each causing sudden death syndrome on soybeans, and *F. verticillioides* on corn; *Gaeumannomyces graminis* (take-all) on cereals (e. g. wheat or barley) and corn; *Gibberella* spp. on cereals (e. g. *G. zeae*) and rice (e. g. *G. fujikuroi*: Bakanae disease); *Glomerella cingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochliobolus*) on corn, cereals and rice; *Hemileia* spp., e. g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monilinia* spp., e. g. *M. laxa*, *M. fructicola* and *M. fructigena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria tritici*, *Septoria* blotch) on wheat or *M. fijiensis* (black Sigatoka disease) on bananas; *Peronospora* spp. (downy mildew) on cabbage (e. g. *P. brassicae*), rape (e. g. *P. parasitica*), onions (e. g. *P. destructor*), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e. g. *P. tracheiphila* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticola*: can and leaf spot) and soybeans (e. g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e. g. *P. capsici*), soybeans (e. g. *P. megasperma*, syn. *P. sojae*), potatoes and tomatoes (e. g. *P. infestans*: late blight) and broad-leaved trees (e. g. *P. ramorum*: sudden oak death); *Plasmodiophora brassicae* (club root) on cabbage, rape, radish and other plants; *Plasmopara* spp., e. g. *P. viticola* (grapevine downy mildew) on vines and *P. halstedii* on sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e. g. wheat or barley; *Pseudoperonospora* (downy mildew) on various plants, e. g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, *P. kuehnii* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyricularia* spp., e. g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphanidermatum*); *Ramularia* spp., e. g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. sclerotiorum*) and soybeans (e. g. *S. rolfsii* or *S. sclerotiorum*); *Septoria* spp. on various plants, e. g. *S. glycines* (brown spot) on soybeans, *S. tritici* (*Septoria* blotch) on wheat and *S.* (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setospaeria* spp. (leaf blight) on corn (e. g. *S. turcicum*, syn. *Helminthosporium turcicum*) and turf; *Sphacelotheca* spp. (smut) on corn, (e. g. *S. reiliana*: head smut), sorghum und sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. *T. caries*, wheat bunt) and *T. controversa* (dwarf bunt) on wheat; *Typhula incarnata* (grey snow mold) on barley or wheat; *Urocystis* spp., e. g. *U. occulta* (stem smut) on rye; *Uromyces* spp. (rust) on vegetables, such as beans (e. g. *U. appendiculatus*, syn. *U. phaseoli*) and sugar beets (e. g. *U. betae*); *Ustilago* spp. (loose smut) on cereals (e. g. *U. nuda* and *U. avaenae*), corn (e. g. *U. maydis*: corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e. g. *V. dahliae* on strawberries, rape, potatoes and tomatoes.

The compounds I and compositions thereof, respectively, are also suitable for controlling harmful fungi in the protection of stored products or harvest and in the protection of materials.

The term "protection of materials" is to be understood to denote the protection of technical and non-living materials, such as adhesives, glues, wood, paper and paperboard, textiles, leather, paint dispersions, plastics, cooling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichoderma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae*.

The method of treatment according to the invention can also be used in the field of protecting stored products or harvest against attack of fungi and microorganisms. According to the present invention, the term "stored products" is understood to denote natural substances of plant or animal origin and their processed forms, which have been taken from the natural life cycle and for which long-term protection is desired. Stored products of crop plant origin, such as plants or parts thereof, for example stalks, leafs, tubers, seeds, fruits or grains, can be protected in the freshly harvested state or in processed form, such as pre-dried, moistened, comminuted, ground, pressed or roasted, which process is also known as post-harvest treatment. Also falling under the definition of stored products is timber, whether in the form of crude timber, such as construction timber, electricity pylons and barriers, or in the form of finished articles, such as furniture or objects made from wood. Stored products of animal origin are hides, leather, furs, hairs and the like. The combinations according the present invention can prevent disadvantageous effects such as decay, discoloration or mold. Preferably "stored products" is understood to denote natural substances of plant origin and their processed forms, more preferably fruits and their processed forms, such as pomes, stone fruits, soft fruits and citrus fruits and their processed forms.

The compounds I and compositions thereof, respectively, may be used for improving the health of a plant. The invention also relates to a method for improving plant health by treating a plant, its propagation material and/or the locus where the plant is growing or is to grow with an effective amount of compounds I and compositions thereof, respectively.

The term "plant health" is to be understood to denote a condition of the plant and/or its products which is determined by several indicators alone or in combination with each other such as yield (e. g. increased biomass and/or increased content of valuable ingredients), plant vigor (e. g. improved plant growth and/or greener leaves ("greening effect")), quality (e. g. improved content or composition of certain ingredients) and tolerance to abiotic and/or biotic stress. The above identified indicators for the health condition of a plant may be interdependent or may result from each other.

The compounds of formula I can be present in different crystal modifications whose biological activity may differ. They are likewise subject matter of the present invention.

The compounds I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds I as such or a composition comprising at least one compound I prophylactically either at or before planting or transplanting.

The invention also relates to agrochemical compositions comprising an auxiliary and at least one compound I according to the invention.

An agrochemical composition comprises a fungicidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compounds I, their N-oxides and salts can be converted into customary types of agrochemical compositions, e. g. solutions, emulsions, suspensions, dusts, powders, pastes, granules, pressings, capsules, and mixtures thereof. Examples for composition types are suspensions (e. g. SC, OD, FS), emulsifiable concentrates (e. g. EC), emulsions (e. g. EW, EO, ES, ME), capsules (e. g. CS, ZC), pastes, pastilles, wettable powders or dusts (e. g. WP, SP, WS, DP, DS), pressings (e. g. BR, TB, DT), granules (e. g. WG, SG, GR, FG, GG, MG), insecticidal articles (e. g. LN), as well as gel formulations for the treatment of plant propagation materials such as seeds (e. g. GF). These and further compositions types are defined in the "Catalogue of pesticide formulation types and international coding system", Technical Monograph No. 2, 6$^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e. g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e. g. ethanol, propanol, butanol, benzyl alcohol, cyclohexanol; glycols; DMSO; ketones, e. g. cyclohexanone; esters, e. g. lactates, carbonates, fatty acid esters, gamma-butyrolactone; fatty acids; phosphonates; amines; amides, e. g. N-methyl pyrrolidone, fatty acid dimethyl amides; and mixtures thereof.

Suitable solid carriers or fillers are mineral earths, e. g. silicates, silica gels, talc, kaolins, limestone, lime, chalk, clays, dolomite, diatomaceous earth, bentonite, calcium sulfate, magnesium sulfate, magnesium oxide; polysaccharides, e. g. cellulose, starch; fertilizers, e. g. ammonium sulfate, ammonium phosphate, ammonium nitrate, ureas; products of vegetable origin, e. g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof.

Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl sulfonates, diphenyl sulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinyl pyrrolidone, vinyl alcohols, or vinyl acetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B—C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinyl amines or polyethylene amines.

Suitable adjuvants are compounds, which have a negligible or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e. g. xanthan gum, carboxymethyl cellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e. g. in red, blue, or green) are pigments of low water solubility and water-soluble dyes. Examples are inorganic colorants (e. g. iron oxide, titan oxide, iron hexacyanoferrate) and organic colorants (e. g. alizarin-, azo- and phthalocyanine colorants).

Suitable tackifiers or binders are polyvinyl pyrrolidones, polyvinyl acetates, polyvinyl alcohols, polyacrylates, biological or synthetic waxes, and cellulose ethers.

Examples for composition types and their preparation are:
i) Water-Soluble Concentrates (SL, LS)

10-60 wt % of a compound I and 5-15 wt % wetting agent (e. g. alcohol alkoxylates) are dissolved in water and/or in a water-soluble solvent (e. g. alcohols) ad 100 wt %. The active substance dissolves upon dilution with water.

ii) Dispersible Concentrates (DC)

5-25 wt % of a compound I and 1-10 wt % dispersant (e. g. polyvinyl pyrrolidone) are dissolved in organic solvent (e. g. cyclohexanone) ad 100 wt %. Dilution with water gives a dispersion.

iii) Emulsifiable Concentrates (EC)

15-70 wt % of a compound I and 5-10 wt % emulsifiers (e. g. calcium dodecylbenzenesulfonate and castor oil ethoxylate) are dissolved in water-insoluble organic solvent (e. g. aromatic hydrocarbon) ad 100 wt %. Dilution with water gives an emulsion.

iv) Emulsions (EW, EO, ES)

5-40 wt % of a compound I and 1-10 wt % emulsifiers (e. g. calcium dodecylbenzenesulfonate and castor oil ethoxylate) are dissolved in 20-40 wt % water-insoluble organic solvent (e. g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound I are comminuted with addition of 2-10 wt % dispersants and wetting agents (e. g. sodium lignosulfonate and alcohol ethoxylate), 0.1-2 wt % thickener (e. g. xanthan gum) and water ad 100 wt % to give a fine active substance suspension.

Dilution with water gives a stable suspension of the active substance. For FS type composition up to 40 wt % binder (e. g. polyvinyl alcohol) is added.

vi) Water-Dispersible Granules and Water-Soluble Granules (WG, SG)

50-80 wt % of a compound I are ground finely with addition of dispersants and wetting agents (e. g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I are ground in a rotor-stator mill with addition of 1-5 wt % dispersants (e. g. sodium lignosulfonate), 1-3 wt % wetting agents (e. g. alcohol ethoxylate) and solid carrier (e. g. silica gel) ad 100 wt %. Dilution with water gives a stable dispersion or solution of the active substance.

viii) Gel (GW, GF)

In an agitated ball mill, 5-25 wt % of a compound I are comminuted with addition of 3-10 wt % dispersants (e. g. sodium lignosulfonate), 1-5 wt % thickener (e. g. carboxymethyl cellulose) and water ad 100 wt % to give a fine suspension of the active substance. Dilution with water gives a stable suspension of the active substance.

ix) Microemulsion (ME)

5-20 wt % of a compound I are added to 5-30 wt % organic solvent blend (e. g. fatty acid dimethyl amide and cyclohexanone), 10-25 wt % surfactant blend (e. g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a compound I, 0-40 wt % water insoluble organic solvent (e. g. aromatic hydrocarbon), 2-15 wt % acrylic monomers (e. g. methylmethacrylate, methacrylic acid and a di- or triacrylate) are dispersed into an aqueous solution of a protective colloid (e. g. polyvinyl alcohol). Radical polymerization results in the formation of poly(meth)acrylate microcapsules. Alternatively, an oil phase comprising 5-50 wt % of a compound I according to the invention, 0-40 wt % water insoluble organic solvent (e. g. aromatic hydrocarbon), and an isocyanate monomer (e. g. diphenylmethene-4,4'-diisocyanatae) are dispersed into an aqueous solution of a protective colloid (e. g. polyvinyl alcohol). The addition of a polyamine (e. g. hexamethylenediamine) results in the formation of polyurea microcapsules. The monomers amount to 1-10 wt %. The wt % relate to the total CS composition.

xi) Dustable Powders (DP, DS)

1-10 wt % of a compound I are ground finely and mixed intimately with solid carrier (e. g. finely divided kaolin) ad 100 wt %.

xii) Granules (GR, FG)

0.5-30 wt % of a compound I is ground finely and associated with solid carrier (e. g. silicate) ad 100 wt %. Granulation is achieved by extrusion, spray-drying or fluidized bed.

xiii) Ultra-Low Volume Liquids (UL)

1-50 wt % of a compound I are dissolved in organic solvent (e. g. aromatic hydrocarbon) ad 100 wt %.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

For the purposes of treatment of plant propagation materials, particularly seeds, solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC), and gels (GF) are usually employed. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying compound I and compositions thereof, respectively, onto plant propagation material, especially seeds, include dressing, coating, pelleting, dusting, and soaking as well as in-furrow application methods. Preferably, compound I or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e. g. herbicides, insecticides, fungicides, growth regulators, safeners, biopesticides) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

A pesticide is generally a chemical or biological agent (such as pestidal active ingredient, compound, composition, virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease. The term pesticides includes also plant growth regulators that alter the expected growth, flowering, or reproduction rate of plants; defoliants that cause leaves or other foliage to drop from a plant, usually to facilitate harvest; desiccants that promote drying of living tissues, such as unwanted plant tops; plant activators that activate plant physiology for defense of against certain pests; safeners that reduce unwanted herbicidal action of pesticides on crop plants; and plant growth promoters that affect plant physiology to increase plant growth, biomass, yield or any other quality parameter of the harvestable goods of a crop plant.

Biopesticides have been defined as a form of pesticides based on micro-organisms (bacteria, fungi, viruses, nematodes, etc.) or natural products (compounds, such as metabolites, proteins, or extracts from biological or other natural sources) (U.S. Environmental Protection Agency: http://www.epa.gov/pesticides/biopesticides/).

Biopesticides are typically created by growing and concentrating naturally occurring organisms and/or their metabolites including bacteria and other microbes, fungi, viruses, nematodes, proteins, etc. They are often considered to be important components of integrated pest management (IPM) programs.

Biopesticides fall into two major classes, microbial and biochemical pesticides:

(1) Microbial pesticides consist of bacteria, fungi or viruses (and often include the metabolites that bacteria and fungi produce). Entomopathogenic nematodes are also classed as microbial pesticides, even though they are multi-cellular.

(2) Biochemical pesticides are naturally occurring substances that control pests or provide other crop protection uses as defined below, but are relatively non-toxic to mammals.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank or any other kind of vessel used for applications (e. g. seed treater drums, seed pelleting machinery, knapsack sprayer) and further auxiliaries may be added, if appropriate.

When living microorganisms, such as pesticides from groups L1), L3) and L5), form part of such kit, it must be taken care that choice and amounts of the components (e. g. chemical pesticidal agents) and of the further auxiliaries should not influence the viability of the microbial pesticides in the composition mixed by the user. Especially for bactericides and solvents, compatibility with the respective microbial pesticide has to be taken into account.

Consequently, one embodiment of the invention is a kit for preparing a usable pesticidal composition, the kit comprising a) a composition comprising component 1) as defined herein and at least one auxiliary; and b) a composition comprising component 2) as defined herein and at least one auxiliary; and optionally c) a composition comprising at least one auxiliary and optionally a further active component 3) as defined herein.

Mixing the compounds I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of pesticides II (e. g. pesticidally-active substances and biopesticides), in con-junction with which the compounds I can be used, is intended to illustrate the possible combinations but does not limit them:

A) Respiration Inhibitors

Inhibitors of complex III at $Q_o$ site (e. g. strobilurins): azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxystrobin (A.1.13), pyraclostrobin (A.1.14), pyrametostrobin (A.1.15), pyraoxystrobin (A.1.16), trifloxystrobin (A.1.17) and 2-(2-(3-(2,6-dichlorophenyl)-1-methyl-allylidene-aminooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21); methyl-N-[2-[(1,4-dimethyl-5-phenyl-pyrazol-3-yl)oxylmethyl]phenyl]-N-methoxy-carbamate (A.1.22), 1-[3-chloro-2-[[1-(4-chlorophenyl)-1H-pyrazol-3-yl]oxymethyl]phenyl]-4-methyl-tetrazol-5-one (A.1.23), 1-[3-bromo-2-[[1-(4-chlorophenyl)pyrazol-3-yl]oxymethyl]phenyl]-4-methyl-tetrazol-5-one (A.1.24), 1-[2-[[1-(4-chlorophenyl)pyrazol-3-yl]oxymethyl]-3-methyl-phenyl]-4-methyl-tetrazol-5-one (A.1.25), 1-[2-[[1-(4-chlorophenyl)pyrazol-3-yl]oxymethyl]-3-fluoro-phenyl]-4-methyl-tetrazol-5-one (A.1.26), 1-[2-[[1-(2,4-dichlorophenyl)pyrazol-3-yl]oxymethyl]-3-fluoro-phenyl]-4-methyl-tetrazol-5-one (A.1.27), 1-[2-[[4-(4-chlorophenyl)thiazol-2-yl]oxymethyl]-3-methyl-phenyl]-4-methyl-tetrazol-5-one (A.1.28), 1-[3-chloro-2-[[4-(p-tolyl)thiazol-2-yl]oxymethyl]phenyl]-4-methyl-tetrazo-5-one (A.1.29), 1-[3-cyclopropyl-2-[[2-methyl-4-(1-methylpyrazol-3-yl)phenoxy]methyl]phenyl]-4-methyl-tetrazol-5-one (A.1.30), 1-[3-(difluoromethoxy)-2-[[2-methyl-4-(1-methylpyrazol-3-yl)phenoxy]methyl]phenyl]-4-methyl-tetrazol-5-one (A.1.31), 1-methyl-4-[3-methyl-2-[[2-methyl-4-(1-methylpyrazol-3-yl)phenoxy]methyl]phenyl]tetrazol-5-one (A.1.32), 1-methyl-4-[3-methyl-2-[[1-[3-(trifluoromethyl)phenyl]-ethylideneamino]oxymethyl]phenyl]tetrazol-5-one (A.1.33), (Z,2E)-5-[1-(2,4-dichlorophenyl)pyrazol-3-yl]-oxy-2-methoxyimino-N,3-dimethyl-pent-3-enamide (A.1.34), (Z,2E)-5-[1-(4-chlorophenyl)pyrazol-3-yl]oxy-2-methoxyimino-N,3-dimethyl-pent-3-enamide (A. 1.35), (Z,2E)-5-[1-(4-chloro-2-fluoro-phenyl)pyrazol-3-yl]oxy-2-methoxyimino-N,3-dimethyl-pent-3-enamide (A.1.36);

inhibitors of complex III at $Q_i$ site: cyazofamid (A.2.1), amisulbrom (A.2.2), [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate (A.2.3), [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate (A.2.4), [(3S,6S,7R,8R)-8-benzyl-3-[(3-isobutoxycarbonyloxy-4-meth-oxy-pyridine-2-carbonyl)amino]-6-methyl-4,9-dioxo-1,5-dioxonan-7-yl] 2-methylpropanoate (A.2.5), [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate (A.2.6); (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate (A.2.7); (3S,6S7R,8R)-8-benzyl-3-[3-[(isobutyryloxy)methoxy]-4-methoxypicolinamido]-6-methyl-4,9-dioxo-1,5-dioxonan-7-yl isobutyrate (A.2.8);

inhibitors of complex II (e. g. carboxamides): benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.14), penthiopyrad (A.3.15), sedaxane (A.3.16), tecloftalam (A.3.17), thifluzamide (A.3.18), N-(4'-trifluoromethylthiobiphenyl-2-yl)-3-difluoromethyl-1-methyl-1H-pyrazole-4-carboxamide (A.3.19), N-(2-(1,3,3-trimethyl-butyl)-phenyl)-1,3-dimethyl-5-fluoro-1H-pyrazole-4-carboxamide (A.3.20), 3-(difluoromethyl)-1-methyl-N-(1,1,3-trimethylindan-4-yl)pyrazole-4-carboxamide (A.3.21), 3-(trifluoromethyl)-1-methyl-N-(1,1,3-trimethylindan-4-yl)pyrazole-4-carboxamide (A.3.22), 1,3-dimethyl-N-(1,1,3-trimethylindan-4-yl)pyrazole-4-carboxamide (A.3.23), 3-(trifluoromethyl)-1,5-dimethyl-N-(1,1,3-trimethylindan-4-yl)pyrazole-4-carboxamide (A.3.24), 1,3,5-trimethyl-N-(1,1,3-trimethylindan-4-yl)pyrazole-4-carboxamide (A.3.25), N-(7-fluoro-1,1,3-trimethyl-indan-4-yl)-1,3-dimethyl-pyrazole-4-carboxamide (A.3.26), N-[2-(2,4-dichlorophenyl)-2-methoxy-1-methyl-ethyl]-3-(difluoromethyl)-1-methyl-pyrazole-4-carboxamide (A.3.27);

other respiration inhibitors (e. g. complex I, uncouplers): diflumetorim (A.4.1), (5,8-difluoro-quinazolin-4-yl)-{2-[2-fluoro-4-(4-trifluoromethyl pyridin-2-yloxy)-phenyl]-ethyl}-amine (A.4.2); nitrophenyl derivates: binapacryl (A.4.3), dinobuton (A.4.4), dinocap (A.4.5), fluazinam (A.4.6); ferimzone (A.4.7); organometal compounds: fentin salts, such as fentin-acetate (A.4.8), fentin chloride (A.4.9) or fentin hydroxide (A.4.10); ametoctradin (A.4.11); and silthiofam (A.4.12);

B) Sterol Biosynthesis Inhibitors (SBI Fungicides)

C14 demethylase inhibitors (DMI fungicides): triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), 1-[rel-(2S;3R)-3-(2-chlorophenyl)-2-(2,4-difluorophenyl)-oxiranylmethyl]-5-thiocyanato-1H-[1,2,4]triazolo (B.1.31), 2-[rel-(2S;3R)-3-(2-chlorophenyl)-2-(2,4-difluorophenyl)-oxiranylmethyl]-2H-[1,2,4]triazole-3-thiol (B.1.32), 2-[2-chloro-4-(4-chlorophenoxy)phenyl]-1-(1,2,4-triazol-1-yl)pentan-2-ol (B.1.33), 1-[4-(4-chlorophenoxy)-2-(trifluoromethyl)phenyl]-1-cyclopropyl-2-(1,2,4-triazol-1-yl)ethanol (B.1.34), 2-[4-(4-chlorophenoxy)-2-(trifluoromethyl)phenyl]-1-(1,2,4-triazol-1-yl)butan-2-ol (B.1.35), 2-[2-chloro-4-(4-chlorophenoxy)phenyl]-1-(1,2,4-triazol-1-yl)butan-2-ol (B.1.36), 2-[4-(4-chlorophenoxy)-2-(trifluoromethyl)phenyl]-3-methyl-1-(1,2,4-triazol-1-yl)butan-2-ol (B.1.37), 2-[4-(4-chlorophenoxy)-2-(trifluoromethyl)phenyl]-1-(1,2,4-triazol-1-yl)propan-2-ol (B.1.38), 2-[2-chloro-4-(4-chlorophenoxy)phenyl]-3-methyl-1-(1,2,4-triazol-1-yl)butan-2-ol (B.1.39), 2-[4-(4-chlorophenoxy)-2-(trifluoromethyl)phenyl]-1-(1,2,4-triazol-1-yl)pentan-2-ol (B.1.40), 2-[4-(4-fluorophenoxy)-2-(trifluoromethyl)phenyl]-1-(1,2,4-triazol-1-yl)propan-2-ol (B.1.41); imidazoles: imazalil (B.1.42), pefurazoate (B.1.43), prochloraz (B.1.44), triflumizol (B.1.45); pyrimidines, pyridines and piperazines: fenarimol (B.1.46), nuarimol (B.1.47), pyrifenox (B.1.48), triforine (B.1.49), [3-(4-chloro-2-fluoro-phenyl)-5-(2,4-difluorophenyl)isoxazol-4-yl]-(3-pyridyl)methanol (B.1.50), 2-[2-chloro-4-(4-chlorophenoxy)phenyl]-1-(1,2,4-triazol-1-yl)pent-3-yn-2-ol (B.1.51);

Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8);

Inhibitors of 3-keto reductase: fenhexamid (B.3.1);

C) Nucleic Acid Synthesis Inhibitors phenylamides or acyl amino acid fungicides: benalaxyl (C.1.1), benalaxyl-M (C.1.2), kiralaxyl (C.1.3), metalaxyl (C.1.4), metalaxyl-M (mefenoxam, C.1.5), ofurace (C.1.6), oxadixyl (C.1.7);

others: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluorophenylmethoxy)pyrimidin-4-amine (C.2.7);

D) Inhibitors of Cell Division and Cytoskeleton tubulin inhibitors, such as benzimidazoles, thiophanates: benomyl (D1.1), carbendazim (D1.2), fuberidazole (D1.3), thiabendazole (D1.4), thiophanate-methyl (D1.5); triazolopyrimidines: 5-chloro-7-(4-methylpiperidin-1-yl)-6-(2,4,6-trifluorophenyl)-[1,2,4]triazolo[1,5-a]pyrimidine (D1.6);

other cell division inhibitors: diethofencarb (D2.1), ethaboxam (D2.2), pencycuron (D2.3), fluopicolide (D2.4), zoxamide (D2.5), metrafenone (D2.6), pyriofenone (D2.7);

E) Inhibitors of Amino Acid and Protein Synthesis methionine synthesis inhibitors (anilino-pyrimidines): cyprodinil (E.1.1), mepanipyrim (E.1.2), pyrimethanil (E.1.3);

protein synthesis inhibitors: blasticidin-S (E.2.1), kasugamycin (E.2.2), kasugamycin hydrochloride-hydrate (E.2.3), mildiomycin (E.2.4), streptomycin (E.2.5), oxytetracyclin (E.2.6), polyoxine (E.2.7), validamycin A (E.2.8);

F) Signal Transduction Inhibitors

MAP/histidine kinase inhibitors: fluoroimid (F.1.1), iprodione (F.1.2), procymidone (F.1.3), vinclozolin (F.1.4), fenpiclonil (F.1.5), fludioxonil (F.1.6);

G protein inhibitors: quinoxyfen (F.2.1);

G) Lipid and Membrane Synthesis Inhibitors

Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofos-methyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7) and N-(1-(1-(4-cyano-phenyl)ethanesulfonyl)-but-2-yl) carbamic acid-(4-fluorophenyl) ester (G.3.8);

compounds affecting cell membrane permeability and fatty acides: propamocarb (G.4.1);

fatty acid amide hydrolase inhibitors: oxathiapiprolin (G.5.1), 2-{3-[2-(1-{[3,5-bis(di-fluoromethyl-1 H-pyrazol-1-yl]acetyl}piperidin-4-yl)-1,3-thiazol-4-yl]-4,5-dihydro-1,2-oxazol-5-yl]phenyl methanesulfonate (G.5.2), 2-{3-[2-(1-{[3,5-bis(difluoromethyl)-1H-pyrazol-1-yl]acetyl}piperidin-4-yl) 1,3-thiazol-4-yl]-4,5-dihydro-1,2-oxazol-5-yl}-3-chlorophenyl methanesulfonate (G.5.3);

H) Inhibitors with Multi Site Action inorganic active substances: Bordeaux mixture (H.1.1), copper acetate (H.1.2), copper hydroxide (H.1.3), copper oxychloride (H.1.4), basic copper sulfate (H.1.5), sulfur (H.1.6);

thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);

organochlorine compounds (e. g. phthalimides, sulfamides, chloronitriles): anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9)

and its salts, phthalide (H.3.10), tolylfluanid (H.3.11), N-(4-chloro-2-nitro-phenyl)-N-ethyl-4-methyl-benzenesulfonamide (H.3.12);

guanidines and others: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1H,5H-[1,4]dithiino[2,3-c:5,6-c']dipyrrole-1,3,5,7(2H,6H)-tetraone (H.4.10);

I) Cell Wall Synthesis Inhibitors inhibitors of glucan synthesis: validamycin (I.1.1), polyoxin B (I.1.2);

melanin synthesis inhibitors: pyroquilon (I.2.1), tricyclazole (I.2.2), carpropamid (I.2.3), dicyclomet (I.2.4), fenoxanil (I.2.5);

J) Plant Defence Inducers acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), potassium or sodium bicarbonate (J.1.9);

K) Unknown Mode of Action bronopol (K.1.1), chinomethionat (K.1.2), cyflufenamid (K.1.3), cymoxanil (K.1.4), dazomet (K.1.5), debacarb (K.1.6), diclomezine (K.1.7), difenzoquat (K.1.8), difenzoquat-methylsulfate (K.1.9), diphenylamin (K.1.10), fenpyrazamine (K.1.11), flumetover (K.1.12), flusulfamide (K.1.13), flutianil (K.1.14), methasulfocarb (K.1.15), nitrapyrin (K.1.16), nitrothal-isopropyl (K.1.18), oxathiapiprolin (K.1.19), tolprocarb (K.1.20), oxin-copper (K.1.21), pro-quinazid (K.1.22), tebufloquin (K.1.23), tecloftalam (K.1.24), triazoxide (K.1.25), 2-butoxy-6-iodo-3-propylchromen-4-one (K.1.26), 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone (K.1.27), 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone (K.1.28), 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone (K.1.29), N-(cyclo-propylmethoxyimino-(6-difluoromethoxy-2,3-difluoro-phenyl)-methyl)-2-phenyl acetamide (K.1.30), N'-(4-(4-chloro-3-trifluoromethyl-phenoxy)-2,5-dimethyl-phenyl)-N-ethyl-N-methyl formamidine (K.1.31), N'-(4-(4-fluoro-3-trifluoromethyl-phenoxy)-2,5-dimethyl-phenyl)-N-ethyl-N-methyl formamidine (K.1.32), N'-(2-methyl-5-trifluoromethyl-4-(3-trimethylsilanyl-propoxy)-phenyl)-N-ethyl-N-methyl formamidine (K.1.33), N'-(5-difluoromethyl-2-methyl-4-(3-trimethylsilanyl-propoxy)-phenyl)-N-ethyl-N-methyl formamidine (K.1.34), methoxy-acetic acid 6-tert-butyl-8-fluoro-2,3-dimethyl-quinolin-4-yl ester (K.1.35), 3-[5-(4-methylphenyl)-2,3-dimethyl-isoxazolidin-3-yl]-pyridine (K.1.36), 3-[5-(4-chloro-phenyl)-2,3-dimethyl-isoxazolidin-3-yl]-pyridine (pyrisoxazole) (K.1.37), N-(6-methoxy-pyridin-3-yl) cyclopropanecarboxylic acid amide (K.1.38), 5-chloro-1-(4,6-dimethoxy-pyrimidin-2-yl)-2-methyl-1H-benzoimidazole (K.1.39), 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate (K.1.40), picarbutrazox (K.1.41), pentyl N-[6-[[(Z)-[(1-methyl-tetrazol-5-yl)-phenyl-methylene]amino]oxymethyl]-2-pyridyl]carbamate (K.1.42), 2-[2-[(7,8-difluoro-2-methyl-3-quinolyl)oxy]-6-fluoro-phenyl]propan-2-ol (K.1.43), 2-[2-fluoro-6-[(8-fluoro-2-methyl-3-quinolyl)oxy]phen-yl]propan-2-ol (K.1.44), 3-(5-fluoro-3,3,4,4-tetramethyl-3,4-dihydroisoquinolin-1-yl)quinoline (K.1.45), 3-(4,4-difluoro-3,3-dimethyl-3,4-dihydroisoquinolin-1-yl)quinoline (K.1.46), 3-(4,4,5-trifluoro-3,3-dimethyl-3,4-dihydroisoquinolin-1-yl)quinoline (K.1.47), 9-fluoro-2,2-dimethyl-5-(3-quinolyl)-3H-1,4-benzoxazepine (K.1.48);

M) Growth Regulators abscisic acid (M.1.1), amidochlor, ancymidol, 6-benzylaminopurine, brassinolide, butralin, chlormequat, chlormequat chloride, choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat, mepiquat chloride, naphthaleneacetic acid, N-6-benzyladenine, paclobutrazol, prohexadione, prohexadione-calcium, prohydrojasmon, thidiazuron, triapenthenol, tributyl phosphorotrithioate, 2,3,5-tri-iodobenzoic acid, trinexapac-ethyl and uniconazole;

N) Herbicides acetamides: acetochlor (N.1.1), alachlor, butachlor, dimethachlor, dimethenamid (N.1.2), flufenacet (N.1.3), mefenacet (N.1.4), metolachlor (N.1.5), metazachlor (N.1.6), napropamide, naproanilide, pethoxamid, pretilachlor, propachlor, thenylchlor;

amino acid derivatives: bilanafos, glyphosate (N.2.1), glufosinate (N.2.2), sulfosate (N.2.3);

aryloxyphenoxypropionates: clodinafop (N.3.1), cyhalofop-butyl, fenoxaprop (N.3.2), fluazifop (N.3.3), haloxyfop (N.3.4), metamifop, propaquizafop, quizalofop, quizalofop-P-tefuryl;

Bipyridyls: diquat, paraquat (N.4.1);

(thio)carbamates: asulam, butylate, carbetamide, desmedipham, dimepiperate, eptam (EPTC), esprocarb, molinate, orbencarb, phenmedipham (N.5.1), prosulfocarb, pyributicarb, thiobencarb, triallate;

cyclohexanediones: butroxydim, clethodim (N.6.1), cycloxydim (N.6.2), profoxydim (N.6.3), sethoxydim (N.6.4), tepraloxydim (N.6.5), tralkoxydim;

dinitroanilines: benfluralin, ethalfluralin, oryzalin, pendimethalin (N.7.1), prodiamine (N.7.2), trifluralin (N.7.3);

diphenyl ethers: acifluorfen (N.8.1), aclonifen, bifenox, diclofop, ethoxyfen, fomesafen, lactofen, oxyfluorfen;

hydroxybenzonitriles: bromoxynil (N.9.1), dichlobenil, ioxynil;

imidazolinones: imazamethabenz, imazamox (N.10.1), imazapic (N.10.2), imazapyr (N.10.3), imazaquin (N.10.4), imazethapyr (N.10.5);

phenoxy acetic acids: clomeprop, 2,4-dichlorophenoxyacetic acid (2,4-D) (N.11.1), 2,4-DB, dichlorprop, MCPA, MCPA-thioethyl, MCPB, Mecoprop;

pyrazines: chloridazon (N.11.1), flufenpyr-ethyl, fluthiacet, norflurazon, pyridate;

pyridines: aminopyralid, clopyralid (N.12.1), diflufenican, dithiopyr, fluridone, fluroxypyr (N.12.2), picloram (N.12.3), picolinafen (N.12.4), thiazopyr;

sulfonyl ureas: amidosulfuron, azimsulfuron, bensulfuron (N.13.1), chlorimuron-ethyl (N.13.2), chlorsulfuron, cinosulfuron, cyclosulfamuron (N.13.3), ethoxysulfuron, flazasulfuron, flucetosulfuron, flupyrsulfuron, foramsulfuron, halosulfuron, imazosulfuron, iodosulfuron (N.13.4), mesosulfuron (N.13.5), metazosulfuron, metsulfuron-methyl (N.13.6), nicosulfuron (N.13.7), oxasulfuron, primisulfuron, prosulfuron, pyrazosulfuron, rimsulfuron (N.13.8), sulfometuron, sulfosulfuron, thifensulfuron, triasulfuron, tribenuron, trifloxysulfuron, triflusulfuron (N.13.9), tritosulfuron, 1-((2-chloro-6-propyl-imidazo[1,2-b]pyridazin-3-yl) sulfonyl)-3-(4,6-dimethoxy-pyrimidin-2-yl)urea;

triazines: ametryn, atrazine (N.14.1), cyanazine, dimethametryn, ethiozin, hexazinone (N.14.2), metamitron, metribuzin, prometryn, simazine, terbuthylazine, terbutryn, triaziflam;

ureas: chlorotoluron, daimuron, diuron (N.15.1), fluometuron, isoproturon, linuron, methabenzthiazuron, tebuthiuron;

other acetolactate synthase inhibitors: bispyribac-sodium, cloransulam-methyl, diclosulam, florasulam (N.16.1), flucarbazone, flumetsulam, metosulam, ortho-sulfamuron, penoxsulam, propoxycarbazone, pyribambenzpropyl, pyribenzoxim, pyriftalid, pyriminobac-methyl, pyri-misulfan, pyrithiobac, pyroxasulfone (N.16.2), pyroxsulam;

others: amicarbazone, aminotriazole, anilofos, beflubutamid, benazolin, bencarbazone, benfluresate, benzofenap, bentazone (N.17.1), benzobicyclon, bicyclopyrone, bromacil, bromobutide, butafenacil, butamifos, cafenstrole, carfentrazone, cinidon-ethyl (N.17.2), chlorthal, cinmethylin (N.17.3), clomazone (N.17.4), cumyluron, cyprosulfamide, dicamba (N.17.5), difenzoquat, diflufenzopyr (N.17.6), *Drechslera monoceras*, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac (N.17.7), quinmerac (N.17.8), mesotrione (N.17.9), methyl arsonic acid, naptalam, oxadiargyl, oxadiazon, oxaziclomefone, pentoxazone, pinoxaden, pyraclonil, pyraflufenethyl, pyrasulfotole, pyrazoxyfen, pyrazolynate, quinoclamine, saflufenacil (N.17.10), sulcotrione (N.17.11), sulfentrazone, terbacil, tefuryltrione, tembotrione, thiencarbazone, topramezone (N.17.12), (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester;

O) Insecticides organo(thio)phosphates: acephate (O.1.1), azamethiphos (O.1.2), azinphos-methyl (O.1.3), chlorpyrifos (O.1.4), chlorpyrifos-methyl (O.1.5), chlorfenvinphos (O.1.6), diazinon (O.1.7), dichlorvos (O.1.8), dicrotophos (O.1.9), dimethoate (O.1.10), disulfoton (O.1.11), ethion (O.1.12), fenitrothion (O.1.13), fenthion (O.1.14), isoxathion (O.1.15), malathion (O.1.16), methamidophos (O.1.17), methidathion (O.1.18), methyl-parathion (O.1.19), mevinphos (O.1.20), monocrotophos (O.1.21), oxydemeton-methyl (O.1.22), paraoxon (O.1.23), parathion (O.1.24), phenthoate (O.1.25), phosalone (O.1.26), phosmet (O.1.27), phosphamidon (O.1.28), phorate (O.1.29), phoxim (O.1.30), pirimiphos-methyl (O.1.31), profenofos (O.1.32), prothiofos (O.1.33), sulprophos (O.1.34), tetrachlorvinphos (O.1.35), terbufos (O.1.36), triazophos (O.1.37), trichlorfon (O.1.38);

carbamates: alanycarb (O.2.1), aldicarb (O.2.2), bendiocarb (O.2.3), benfuracarb (O.2.4), carbaryl (O.2.5), carbofuran (O.2.6), carbosulfan (O.2.7), fenoxycarb (O.2.8), furathiocarb (O.2.9), methiocarb (O.2.10), methomyl (O.2.11), oxamyl (O.2.12), pirimicarb (O.2.13), propoxur (O.2.14), thiodicarb (O.2.15), triazamate (O.2.16);

pyrethroids: allethrin (O.3.1), bifenthrin (O.3.2), cyfluthrin (O.3.3), cyhalothrin (O.3.4), cyphenothrin (O.3.5), cypermethrin (O.3.6), alpha-cypermethrin (O.3.7), beta-cypermethrin (O.3.8), zeta-cypermethrin (O.3.9), deltamethrin (O.3.10), esfenvalerate (O.3.11), etofenprox (O.3.11), fenpropathrin (O.3.12), fenvalerate (O.3.13), imiprothrin (O.3.14), lambda-cyhalothrin (O.3.15), permethrin (O.3.16), prallethrin (O.3.17), pyrethrin I and II (O.3.18), resmethrin (O.3.19), silafluofen (O.3.20), tau-fluvalinate (O.3.21), tefluthrin (O.3.22), tetramethrin (O.3.23), tralomethrin (O.3.24), transfluthrin (O.3.25), profluthrin (O.3.26), dimeflúthrin (O.3.27);

insect growth regulators: a) chitin synthesis inhibitors: benzoylureas: chlorfluazuron (O.4.1), cyramazin (O.4.2), diflubenzuron (O.4.3), flucycloxuron (O.4.4), flufenoxuron (O.4.5), hexaflumuron (O.4.6), lufenuron (O.4.7), novaluron (O.4.8), teflubenzuron (O.4.9), triflumuron (O.4.10); buprofezin (O.4.11), diofenolan (O.4.12), hexythiazox (O.4.13), etoxazole (O.4.14), clofentazine (O.4.15); b) ecdysone antagonists: halofenozide (O.4.16), methoxyfenozide (O.4.17), tebufenozide (O.4.18), azadirachtin (O.4.19); c) juvenoids: pyriproxyfen (O.4.20), methoprene (O.4.21), fenoxycarb (O.4.22); d) lipid biosynthesis inhibitors: spirodiclofen (O.4.23), spiromesifen (O.4.24), spirotetramat (O.4.24);

nicotinic receptor agonists/antagonists compounds: clothianidin (O.5.1), dinotefuran (O.5.2), flupyradifurone (O.5.3), imidacloprid (O.5.4), thiamethoxam (O.5.5), nitenpyram (O.5.6), acetamiprid (O.5.7), thiacloprid (O.5.8), 1-2-chloro-thiazol-5-ylmethyl)-2-nitrimino-3,5-dimethyl-[1,3,5]triazinane (O.5.9);

GABA antagonist compounds: endosulfan (O.6.19, ethiprole (O.6.2), fipronil (O.6.3), vaniliprole (O.6.4), pyrafluprole (O.6.5), pyriprole (O.6.6), 5-amino-1-(2,6-dichloro-4-methyl-phenyl)-4-sulfinamoyl-1H-pyrazole-3-carbothioic acid amide (O.6.7);

macrocyclic lactone insecticides: abamectin (O.7.1), emamectin (O.7.2), milbemectin (O.7.3), lepimectin (O.7.4), spinosad (O.7.5), spinetoram (O.7.6);

mitochondrial electron transport inhibitor (METI) I acaricides: fenazaquin (O.8.1), pyridaben (O.8.2), tebufenpyrad (O.8.3), tolfenpyrad (O.8.4), flufenerim (O.8.5);

METI II and III compounds: acequinocyl (O.9.1), fluacyprim (O.9.2), hydramethylnon (O.9.3);

Uncouplers: chlorfenapyr (O.10.1);

oxidative phosphorylation inhibitors: cyhexatin (O.11.1), diafenthiuron (O.11.2), fenbutatin oxide (O.11.3), propargite (O.11.4);

moulting disruptor compounds: cryomazine (O.12.1);

mixed function oxidase inhibitors: piperonyl butoxide (O.13.1);

sodium channel blockers: indoxacarb (O.14.1), metaflumizone (O.14.2);

ryanodine receptor inhibitors: chlorantraniliprole (O.15.1), cyantraniliprole (O.15.2), flubendiamide (O.15.3), N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide (O.15.4); N-[4-chloro-2-[(di-ethyl-lambda-4-sulfanylidene)carbamoyl]-6-methyl-phenyl]-2-(3-chloro-2-pyridyl)-5-(trifluoromethyl) pyrazole-3-carboxamide (O.15.5); N-[4-chloro-2-[(di-2-propyl-lambda-4-sulfanylidene) carbamoyl]-6-methyl-phenyl]-2-(3-chloro-2-pyridyl)-5-(trifluoromethyl)pyrazole-3-carboxamide (O.15.6); N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide (O.15.7); N-[4,6-dichloro-2-[(diethyl-lambda-4-sulfanylidene) carbamoyl]-phenyl]-2-(3-chloro-2-pyridyl)-5-(di-fluoromethyl)pyrazole-3-carboxamide (O.15.8); N-[4,6-dibromo-2-[(di-2-propyl-lambda-4-sulfanylidene) carbamoyl]-phenyl]-2-(3-chloro-2-pyridyl)-5-(trifluoromethyl)pyrazole-3-carboxamide (O.15.9); N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide (O.15.10); N-[4,6-dibromo-2-[(diethyl-lambda-4-sulfanylidene) carbamoyl]-phenyl]-2-(3-chloro-2-pyridyl)-5-(tri-fluoromethyl)pyrazole-3-carboxamide (O.15.11);

others: benclothiaz (O.16.1), bifenazate (O.16.2), artap (O.16.3), flonicamid (O.16.4), pyridalyl (O.16.5), pymetrozine (O.16.6), sulfur (O.16.7), thiocyclam (O.16.8), cyenopyrafen (O.16.9), flupyrazofos (O.16.10), cyflumetofen (O.16.11), amidoflumet (O.16.12), imicyafos (O.16.13), bistifluron (O.16.14), pyrifluquinazon (O.16.15) and 1,1'-[(3S,4R,4aR,6S, 6aS,12R, 12aS, 12bS)-4-[[(2-cyclopropylacetyl)oxy] methyl]-1,3,4,4a,5,6,6a,12,12a,12b-decahydro-12-hydroxy-4,6a, 12b-trimethyl-11-oxo-9-(3-pyridinyl)-2H, 11H-naphtho[2,1-b]pyrano[3,4-e]pyran-3,6-diyl] cyclopropaneacetic acid ester (O.16.16); tioxazafen (O.16.17). The active substances referred to as component 2, their preparation and their activity e. g. against harmful fungi is known (cf.: http://www.alan-wood.net/pesticides/); these substances are commercially available. The compounds described by IUPAC nomenclature, their preparation and their pesticidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 2011/77514; WO13/047749, WO 10/069882, WO 13/047441, WO 03/16303, WO 09/90181, WO 13/007767, WO 13/010862, WO 13/127704, WO 13/024009, WO 13/024010 and WO 13/047441, WO 13/162072, WO 13/092224, WO 11/135833).

The present invention furthermore relates to agrochemical compositions comprising a mixture of at least one compound I (component 1) and at least one further active substance useful for plant protection, e. g. selected from the groups A) to O) (component 2), in particular one further fungicide, e. g. one or more fungicide from the groups A) to K), as described above, and if desired one suitable solvent or solid carrier. Those mixtures are of particular interest, since many of them at the same application rate show higher efficiencies against harmful fungi. Furthermore, combating harmful fungi with a mixture of compounds I and at least one fungicide from groups A) to K), as described above, is more efficient than combating those fungi with individual compounds I or individual fungicides from groups A) to K).

By applying compounds I together with at least one active substance from groups A) to O) a synergistic effect can be obtained, i.e. more then simple addition of the individual effects is obtained (synergistic mixtures).

This can be obtained by applying the compounds I and at least one further active substance simultaneously, either jointly (e. g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

When applying compound I and a pesticide II sequentially the time between both applications may vary e. g. between 2 hours to 7 days. Also a broader range is possible ranging from 0.25 hour to 30 days, preferably from 0.5 hour to 14 days, particularly from 1 hour to 7 days or from 1.5 hours to 5 days, even more preferred from 2 hours to 1 day. In the binary mixtures and compositions according to the invention the weight ratio of the component 1) and the component 2) generally depends from the properties of the active components used, usually it is in the range of from 1:100 to 100:1, regularly in the range of from 1:50 to 50:1, preferably in the range of from 1:20 to 20:1, more preferably in the range of from 1:10 to 10:1, even more preferably in the range of from 1:4 to 4:1 and in particular in the range of from 1:2 to 2:1.

According to a further embodiments of the binary mixtures and compositions, the weight ratio of the component 1) and the component 2) usually is in the range of from 1000:1 to 1:1, often in the range of from 100:1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

According to a further embodiments of the binary mixtures and compositions, the weight ratio of the component 1) and the component 2) usually is in the range of from 1:1 to 1:1000, often in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

In the ternary mixtures, i.e. compositions according to the invention comprising the component 1) and component 2) and a compound III (component 3), the weight ratio of component 1) and component 2) depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1, and the weight ratio of component 1) and component 3) usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1.

Any further active components are, if desired, added in a ratio of from 20:1 to 1:20 to the component 1).

These ratios are also suitable for inventive mixtures applied by seed treatment.

Preference is also given to mixtures comprising as component 2) at least one active substance selected from group A), which is particularly selected from (A.1.1), (A.1.4), (A.1.8), (A.1.9), (A.1.12), (A.1.13), (A.1.14), (A.1.17), (A.1.19), (A.1.21), (A.2.1), (A.2.2), (A.3.2), (A.3.3), (A.3.4), (A.3.7), (A.3.8), (A.3.9), (A.3.12), (A.3.14), (A.3.15), (A.3.16), (A.3.19), (A.3.20), (A.3.21), (A.3.22), (A.3.23), (A.3.24), (A.3.25), (A.3.26), (A.3.27); (A.4.5), (A.4.6), (A.4.8), (A.4.9) and (A.4.11).

Preference is given to mixtures as component 2) at least one active substance selected from group B), which is particularly selected from (B.1.4), (B.1.5), diniconazole (B.1.6), (B.1.8), (B.1.10), (B.1.11), (B.1.12), (B.1.17), (B.1.18), (B.1.21), (B.1.22), (B.1.23), (B.1.25), (B.1.26), (B.1.27), (B.1.28), (B.1.29), uni (B.1.31), (B.1.32), (B.1.33), (B.1.34), (B.1.35), (B.1.36), (B.1.37), (B.1.38), (B.1.39), (B.1.40), (B.1.41), (B.1.42), (B.1.44), (B.1.46), (B.1.49) and (B.1.50; (B.2.2), (B.2.4), (B.2.5), (B.2.6), piperalin (B.2.7), (B.2.8); and (B.3.1).

Preference is given to mixtures comprising as component 2) at least one active substance selected from group C), which is particularly selected from (C.1.4), C.1.5), (C.1.6), and (C.2.4).

Preference is given to mixtures comprising as component 2) at least one active substance selected from group D), which is particularly selected from (D1.1), (D1.2), (D1.4), (D1.5); (D2.2), (D2.4), (D2.5), (D2.6) and (D2.7); Preference is also given to mixtures comprising as component 2) at least one active substance selected from group E), which is particularly selected from (E.1.1), (E.1.2), and (E.1.3); Preference is also given to mixtures comprising as component 2) at least one active substance selected from group F), which is particularly selected from (F.1.2), (F.1.4), (F.1.5), (F.1.6) and (F.2.1).

Preference is also given to mixtures as component 2) at least one active substance selected from group G), which is particularly selected from (G.3.1), (G.3.2), (G.3.3), (G.3.4), (G.3.5), (G.3.6), (G.4.1) and (G.5.1).

Preference is also given to mixtures comprising as component 2) at least one active substance selected from group H), which is and particularly selected from (H.1.2), (H.1.3), copper oxychloride (H.1.4), (H.1.5), (H.1.6); (H.2.2), (H.2.5), (H.2.7), (H.3.2), (H.3.3), (H.3.4), (H.3.5), (H.3.6), (H.3.12); (H.4.2), (H.4.6), dithianon (H.4.9) and (H.4.10).

Preference is also given to mixtures comprising as component 2) at least one active substance selected from group I), which is particularly selected from (I.2.3) and (I.2.5).

Preference is also given to mixtures comprising as component 2) at least one active substance selected from group J), which is particularly selected from (J.1.1), (J.1.2), (J.1.3), (J.1.4), (J.1.6), (J.1.7), (J.1.8) and (J.1.9).

Preference is also given to mixtures comprising as component 2) at least one active substance selected from group K), which is particularly selected from (K.1.4), (K.1.5), (K.1.8), (K.1.12), (K.1.14), (K.1.15), (K.1.19) and (K.1.22).

Accordingly, the present invention furthermore relates to compositions comprising one compound I (component 1) and one pesticide II (component 2), which pesticide II is selected from the column "Co. 2" of the lines C-1 to C-593 of Table C.

A further embodiment relates to the compositions C-1 to C-593 listed in Table C, where a row of Table C corresponds in each case to a fungicidal composition comprising as active components one of the in the present specification individualized compounds of formula I (component 1) and the respective pesticide II from groups A) to O) (component 2) stated in the row in question. Preferably, the compositions described comprise the active components in synergistically effective amounts.

TABLE C

Compositions comprising as active components one individualized compound I (I) (in Column Co. 1) and as component 2) (in Column Co. 2) one pesticide from groups A) to O) [which is coded e.g. as (A.1.1) for azoxystrobin as defined above].

| Mixt. | Co. 1 | Co. 2 |
| --- | --- | --- |
| C-1 | (I) | (A.1.1) |
| C-2 | (I) | (A.1.2) |
| C-3 | (I) | (A.1.3) |
| C-4 | (I) | (A.1.4) |
| C-5 | (I) | (A.1.5) |
| C-6 | (I) | (A.1.6) |
| C-7 | (I) | (A.1.7) |
| C-8 | (I) | (A.1.8) |
| C-9 | (I) | (A.1.9) |
| C-10 | (I) | (A.1.10) |
| C-11 | (I) | (A.1.11) |
| C-12 | (I) | (A.1.12) |
| C-13 | (I) | (A.1.13) |
| C-14 | (I) | (A.1.14) |
| C-15 | (I) | (A.1.15) |
| C-16 | (I) | (A.1.16) |
| C-17 | (I) | (A.1.17) |
| C-18 | (I) | (A.1.18) |
| C-19 | (I) | (A.1.19) |
| C-20 | (I) | (A.1.20) |
| C-21 | (I) | (A.1.21) |
| C-22 | (I) | (A.1.22) |
| C-23 | (I) | (A.1.23) |
| C-24 | (I) | (A.1.24) |
| C-25 | (I) | (A.1.25) |
| C-26 | (I) | (A.1.26) |
| C-27 | (I) | (A.1.27) |
| C-28 | (I) | (A.1.28) |
| C-29 | (I) | (A.1.29) |
| C-30 | (I) | (A.1.30) |
| C-31 | (I) | (A.1.31) |
| C-32 | (I) | (A.1.32) |
| C-33 | (I) | (A.1.33) |
| C-34 | (I) | (A.1.34) |
| C-35 | (I) | (A.1.35) |
| C-36 | (I) | (A.1.36) |
| C-37 | (I) | (A.2.1) |
| C-38 | (I) | (A.2.2) |
| C-39 | (I) | (A.2.3) |
| C-40 | (I) | (A.2.4) |
| C-41 | (I) | (A.2.5) |
| C-42 | (I) | (A.2.6) |
| C-43 | (I) | (A.2.7) |
| C-44 | (I) | (A.2.8) |
| C-45 | (I) | (A.3.1) |
| C-46 | (I) | (A.3.2) |
| C-47 | (I) | (A.3.3) |
| C-48 | (I) | (A.3.4) |
| C-49 | (I) | (A.3.5) |
| C-50 | (I) | (A.3.6) |
| C-51 | (I) | (A.3.7) |
| C-52 | (I) | (A.3.8) |
| C-53 | (I) | (A.3.9) |
| C-54 | (I) | (A.3.10) |
| C-55 | (I) | (A.3.11) |
| C-56 | (I) | (A.3.12) |
| C-57 | (I) | (A.3.13) |

TABLE C-continued

Compositions comprising as active components one individualized compound I (I) (in Column Co. 1) and as component 2) (in Column Co. 2) one pesticide from groups A) to O) [which is coded e.g. as (A.1.1) for azoxystrobin as defined above].

| Mixt. | Co. 1 | Co. 2 |
|---|---|---|
| C-58 | (I) | (A.3.14) |
| C-59 | (I) | (A.3.15) |
| C-60 | (I) | (A.3.16) |
| C-61 | (I) | (A.3.17) |
| C-62 | (I) | (A.3.18) |
| C-63 | (I) | (A.3.19) |
| C-64 | (I) | (A.3.20) |
| C-65 | (I) | (A.3.21) |
| C-66 | (I) | (A.3.22) |
| C-67 | (I) | (A.3.23) |
| C-68 | (I) | (A.3.24) |
| C-69 | (I) | (A.3.25) |
| C-70 | (I) | (A.3.26) |
| C-71 | (I) | (A.3.27) |
| C-72 | (I) | (A.4.1) |
| C-73 | (I) | (A.4.2) |
| C-74 | (I) | (A.4.3) |
| C-75 | (I) | (A.4.4) |
| C-76 | (I) | (A.4.5) |
| C-77 | (I) | (A.4.6) |
| C-78 | (I) | (A.4.7) |
| C-79 | (I) | (A.4.8) |
| C-80 | (I) | (A.4.9) |
| C-81 | (I) | (A.4.10) |
| C-82 | (I) | (A.4.11) |
| C-83 | (I) | (A.4.12) |
| C-84 | (I) | (B.1.1) |
| C-85 | (I) | (B.1.2) |
| C-86 | (I) | (B.1.3) |
| C-87 | (I) | (B.1.4) |
| C-88 | (I) | (B.1.5) |
| C-89 | (I) | (B.1.6) |
| C-90 | (I) | (B.1.7) |
| C-91 | (I) | (B.1.8) |
| C-92 | (I) | (B.1.9) |
| C-93 | (I) | (B.1.10) |
| C-94 | (I) | (B.1.11) |
| C-95 | (I) | (B.1.12) |
| C-96 | (I) | (B.1.13) |
| C-97 | (I) | (B.1.14) |
| C-98 | (I) | (B.1.15) |
| C-99 | (I) | (B.1.16) |
| C-100 | (I) | (B.1.17) |
| C-101 | (I) | (B.1.18) |
| C-102 | (I) | (B.1.19) |
| C-103 | (I) | (B.1.20) |
| C-104 | (I) | (B.1.21) |
| C-105 | (I) | (B.1.22) |
| C-106 | (I) | (B.1.23) |
| C-107 | (I) | (B.1.24) |
| C-108 | (I) | (B.1.25) |
| C-109 | (I) | (B.1.26) |
| C-110 | (I) | (B.1.27) |
| C-111 | (I) | (B.1.28) |
| C-112 | (I) | (B.1.29) |
| C-113 | (I) | (B.1.30) |
| C-114 | (I) | (B.1.31) |
| C-115 | (I) | (B.1.32) |
| C-116 | (I) | (B.1.33) |
| C-117 | (I) | (B.1.34) |
| C-118 | (I) | (B.1.35) |
| C-119 | (I) | (B.1.36) |
| C-120 | (I) | (B.1.37) |
| C-121 | (I) | (B.1.38) |
| C-122 | (I) | (B.1.39) |
| C-123 | (I) | (B.1.40) |
| C-124 | (I) | (B.1.41) |
| C-125 | (I) | (B.1.42) |
| C-126 | (I) | (B.1.43) |
| C-127 | (I) | (B.1.44) |
| C-128 | (I) | (B.1.45) |
| C-129 | (I) | (B.1.46) |
| C-130 | (I) | (B.1.47) |
| C-131 | (I) | (B.1.48) |
| C-132 | (I) | (B.1.49) |
| C-133 | (I) | (B.1.50) |
| C-134 | (I) | (B.1.51) |
| C-135 | (I) | (B.2.1) |
| C-136 | (I) | (B.2.2) |
| C-137 | (I) | (B.2.3) |
| C-138 | (I) | (B.2.4) |
| C-139 | (I) | (B.2.5) |
| C-140 | (I) | (B.2.6) |
| C-141 | (I) | (B.2.7) |
| C-142 | (I) | (B.2.8) |
| C-143 | (I) | (B.3.1) |
| C-144 | (I) | (C.1.1) |
| C-145 | (I) | (C.1.2) |
| C-146 | (I) | (C.1.3) |
| C-147 | (I) | (C.1.4) |
| C-148 | (I) | (C.1.5) |
| C-149 | (I) | (C.1.6) |
| C-150 | (I) | (C.1.7) |
| C-151 | (I) | (C.2.1) |
| C-152 | (I) | (C.2.2) |
| C-153 | (I) | (C.2.3) |
| C-154 | (I) | (C.2.4) |
| C-155 | (I) | (C.2.5) |
| C-156 | (I) | (C.2.6) |
| C-157 | (I) | (C.2.7) |
| C-158 | (I) | (D.1.1) |
| C-159 | (I) | (D.1.2) |
| C-160 | (I) | (D.1.3) |
| C-161 | (I) | (D.1.4) |
| C-162 | (I) | (D.1.5) |
| C-163 | (I) | (D.1.6) |
| C-164 | (I) | (D.2.1) |
| C-165 | (I) | (D.2.2) |
| C-166 | (I) | (D.2.3) |
| C-167 | (I) | (D.2.4) |
| C-168 | (I) | (D.2.5) |
| C-169 | (I) | (D.2.6) |
| C-170 | (I) | (D.2.7) |
| C-171 | (I) | (E.1.1) |
| C-172 | (I) | (E.1.2) |
| C-173 | (I) | (E.1.3) |
| C-174 | (I) | (E.2.1) |
| C-175 | (I) | (E.2.2) |
| C-176 | (I) | (E.2.3) |
| C-177 | (I) | (E.2.4) |
| C-178 | (I) | (E.2.5) |
| C-179 | (I) | (E.2.6) |
| C-180 | (I) | (E.2.7) |
| C-181 | (I) | (E.2.8) |
| C-182 | (I) | (F.1.1) |
| C-183 | (I) | (F.1.2) |
| C-184 | (I) | (F.1.3) |
| C-185 | (I) | (F.1.4) |
| C-186 | (I) | (F.1.5) |
| C-187 | (I) | (F.1.6) |
| C-188 | (I) | (F.2.1) |
| C-189 | (I) | (G.1.1) |
| C-190 | (I) | (G.1.2) |
| C-191 | (I) | (G.1.3) |
| C-192 | (I) | (G.1.4) |
| C-193 | (I) | (G.2.1) |
| C-194 | (I) | (G.2.2) |
| C-195 | (I) | (G.2.3) |
| C-196 | (I) | (G.2.4) |
| C-197 | (I) | (G.2.5) |
| C-198 | (I) | (G.2.6) |
| C-199 | (I) | (G.2.7) |
| C-200 | (I) | (G.3.1) |
| C-201 | (I) | (G.3.2) |
| C-202 | (I) | (G.3.3) |
| C-203 | (I) | (G.3.4) |

TABLE C-continued

Compositions comprising as active components one individualized compound I (I) (in Column Co. 1) and as component 2) (in Column Co. 2) one pesticide from groups A) to O) [which is coded e.g. as (A.1.1) for azoxystrobin as defined above].

| Mixt. | Co. 1 | Co. 2 |
|---|---|---|
| C-204 | (I) | (G.3.5) |
| C-205 | (I) | (G.3.6) |
| C-206 | (I) | (G.3.7) |
| C-207 | (I) | (G.3.8) |
| C-208 | (I) | (G.4.1) |
| C-209 | (I) | (G.5.1) |
| C-210 | (I) | (G.5.2) |
| C-211 | (I) | (G.5.3) |
| C-212 | (I) | (H.1.1) |
| C-213 | (I) | (H.1.2) |
| C-214 | (I) | (H.1.3) |
| C-215 | (I) | (H.1.4) |
| C-216 | (I) | (H.1.5) |
| C-217 | (I) | (H.1.6) |
| C-218 | (I) | (H.2.1) |
| C-219 | (I) | (H.2.2) |
| C-220 | (I) | (H.2.3) |
| C-221 | (I) | (H.2.4) |
| C-222 | (I) | (H.2.5) |
| C-223 | (I) | (H.2.6) |
| C-224 | (I) | (H.2.7) |
| C-225 | (I) | (H.2.8) |
| C-226 | (I) | (H.2.9) |
| C-227 | (I) | (H.3.1) |
| C-228 | (I) | (H.3.2) |
| C-229 | (I) | (H.3.3) |
| C-230 | (I) | (H.3.4) |
| C-231 | (I) | (H.3.5) |
| C-232 | (I) | (H.3.6) |
| C-233 | (I) | (H.3.7) |
| C-234 | (I) | (H.3.8) |
| C-235 | (I) | (H.3.9) |
| C-236 | (I) | (H.3.10) |
| C-237 | (I) | (H.3.11) |
| C-238 | (I) | (H.4.1) |
| C-239 | (I) | (H.4.2) |
| C-240 | (I) | (H.4.3) |
| C-241 | (I) | (H.4.4) |
| C-242 | (I) | (H.4.5) |
| C-243 | (I) | (H.4.6) |
| C-244 | (I) | (H.4.7) |
| C-245 | (I) | (H.4.8) |
| C-246 | (I) | (H.4.9) |
| C-247 | (I) | (H.4.10) |
| C-248 | (I) | (I.1.1) |
| C-249 | (I) | (I.1.2) |
| C-250 | (I) | (I.2.1) |
| C-251 | (I) | (I.2.2) |
| C-252 | (I) | (I.2.3) |
| C-253 | (I) | (I.2.4) |
| C-254 | (I) | (I.2.5) |
| C-255 | (I) | (J.1.1) |
| C-256 | (I) | (J.1.2) |
| C-257 | (I) | (J.1.3) |
| C-258 | (I) | (J.1.4) |
| C-259 | (I) | (J.1.5) |
| C-260 | (I) | (J.1.6) |
| C-261 | (I) | (J.1.7) |
| C-262 | (I) | (J.1.8) |
| C-263 | (I) | (J.1.9) |
| C-264 | (I) | (K.1.1) |
| C-265 | (I) | (K.1.2) |
| C-266 | (I) | (K.1.3) |
| C-267 | (I) | (K.1.4) |
| C-268 | (I) | (K.1.5) |
| C-269 | (I) | (K.1.6) |
| C-270 | (I) | (K.1.7) |
| C-271 | (I) | (K.1.8) |
| C-272 | (I) | (K.1.9) |
| C-273 | (I) | (K.1.10) |
| C-274 | (I) | (K.1.11) |
| C-275 | (I) | (K.1.12) |
| C-276 | (I) | (K.1.13) |
| C-277 | (I) | (K.1.14) |
| C-278 | (I) | (K.1.15) |
| C-279 | (I) | (K.1.16) |
| C-280 | (I) | (K.1.17) |
| C-281 | (I) | (K.1.18) |
| C-282 | (I) | (K.1.19) |
| C-283 | (I) | (K.1.20) |
| C-284 | (I) | (K.1.21) |
| C-285 | (I) | (K.1.22) |
| C-286 | (I) | (K.1.23) |
| C-287 | (I) | (K.1.24) |
| C-288 | (I) | (K.1.25) |
| C-289 | (I) | (K.1.26) |
| C-290 | (I) | (K.1.27) |
| C-291 | (I) | (K.1.28) |
| C-292 | (I) | (K.1.29) |
| C-293 | (I) | (K.1.30) |
| C-294 | (I) | (K.1.31) |
| C-295 | (I) | (K.1.32) |
| C-296 | (I) | (K.1.33) |
| C-297 | (I) | (K.1.34) |
| C-298 | (I) | (K.1.35) |
| C-299 | (I) | (K.1.36) |
| C-300 | (I) | (K.1.37) |
| C-301 | (I) | (K.1.38) |
| C-302 | (I) | (K.1.39) |
| C-303 | (I) | (K.1.40) |
| C-304 | (I) | (K.1.41) |
| C-305 | (I) | (K.1.42) |
| C-306 | (I) | (K.1.43) |
| C-307 | (I) | (K.1.44) |
| C-308 | (I) | (K.1.45) |
| C-309 | (I) | (K.1.46) |
| C-310 | (I) | (K.1.47) |
| C-311 | (I) | (K.1.48) |
| C-312 | (I) | (M.1.1) |
| C-313 | (I) | (M.1.2) |
| C-314 | (I) | (M.1.3) |
| C-315 | (I) | (M.1.4) |
| C-316 | (I) | (M.1.5) |
| C-317 | (I) | (M.1.6) |
| C-318 | (I) | (M.1.7) |
| C-319 | (I) | (M.1.8) |
| C-320 | (I) | (M.1.9) |
| C-321 | (I) | (M.1.10) |
| C-322 | (I) | (M.1.11) |
| C-323 | (I) | (M.1.12) |
| C-324 | (I) | (M.1.13) |
| C-325 | (I) | (M.1.14) |
| C-326 | (I) | (M.1.15) |
| C-327 | (I) | (M.1.16) |
| C-328 | (I) | (M.1.17) |
| C-329 | (I) | (M.1.18) |
| C-330 | (I) | (M.1.19) |
| C-331 | (I) | (M.1.20) |
| C-332 | (I) | (M.1.21) |
| C-333 | (I) | (M.1.22) |
| C-334 | (I) | (M.1.23) |
| C-335 | (I) | (M.1.24) |
| C-336 | (I) | (M.1.25) |
| C-337 | (I) | (M.1.26) |
| C-338 | (I) | (M.1.27) |
| C-339 | (I) | (M.1.28) |
| C-340 | (I) | (M.1.29) |
| C-341 | (I) | (M.1.30) |
| C-342 | (I) | (M.1.31) |
| C-343 | (I) | (M.1.32) |
| C-344 | (I) | (M.1.33) |
| C-345 | (I) | (M.1.34) |
| C-346 | (I) | (M.1.35) |
| C-347 | (I) | (M.1.36) |
| C-348 | (I) | (M.1.37) |
| C-349 | (I) | (M.1.38) |

TABLE C-continued

Compositions comprising as active components one individualized compound I (I) (in Column Co. 1) and as component 2) (in Column Co. 2) one pesticide from groups A) to O) [which is coded e.g. as (A.1.1) for azoxystrobin as defined above].

| Mixt. | Co. 1 | Co. 2 |
|---|---|---|
| C-350 | (I) | (M.1.39) |
| C-351 | (I) | (M.1.40) |
| C-352 | (I) | (M.1.41) |
| C-353 | (I) | (M.1.42) |
| C-354 | (I) | (M.1.43) |
| C-355 | (I) | (M.1.44) |
| C-356 | (I) | (M.1.45) |
| C-357 | (I) | (M.1.46) |
| C-358 | (I) | (M.1.47) |
| C-359 | (I) | (M.1.48) |
| C-360 | (I) | (M.1.49) |
| C-361 | (I) | (M.1.50) |
| C-362 | (I) | (N.1.1) |
| C-363 | (I) | (N.1.2) |
| C-364 | (I) | (N.1.3) |
| C-365 | (I) | (N.1.4) |
| C-366 | (I) | (N.1.5) |
| C-367 | (I) | (N.2.1) |
| C-368 | (I) | (N.2.2) |
| C-369 | (I) | (N.2.3) |
| C-370 | (I) | (N.3.1) |
| C-371 | (I) | (N.3.2) |
| C-372 | (I) | (N.3.3) |
| C-373 | (I) | (N.3.4) |
| C-374 | (I) | (N.4.1) |
| C-375 | (I) | (N.5.1) |
| C-376 | (I) | (N.6.1) |
| C-377 | (I) | (N.6.2) |
| C-378 | (I) | (N.6.3) |
| C-379 | (I) | (N.6.4) |
| C-380 | (I) | (N.6.5) |
| C-381 | (I) | (N.7.1) |
| C-382 | (I) | (N.7.2) |
| C-383 | (I) | (N.7.3) |
| C-384 | (I) | (N.8.1) |
| C-385 | (I) | (N.9.1) |
| C-386 | (I) | (N.10.1) |
| C-387 | (I) | (N.10.2) |
| C-388 | (I) | (N.10.3) |
| C-389 | (I) | (N.10.4) |
| C-390 | (I) | (N.10.5) |
| C-391 | (I) | (N.11.1) |
| C-392 | (I) | (N.12.1) |
| C-393 | (I) | (N.12.2) |
| C-394 | (I) | (N.12.3) |
| C-395 | (I) | (N.12.4) |
| C-396 | (I) | (N.13.1) |
| C-397 | (I) | (N.13.2) |
| C-398 | (I) | (N.13.3) |
| C-399 | (I) | (N.13.4) |
| C-400 | (I) | (N.13.5) |
| C-401 | (I) | (N.13.6) |
| C-402 | (I) | (N.13.7) |
| C-403 | (I) | (N.13.8) |
| C-404 | (I) | (N.13.9) |
| C-405 | (I) | (N.14.1) |
| C-406 | (I) | (N.14.2) |
| C-407 | (I) | (N.15.1) |
| C-408 | (I) | (N.16.1) |
| C-409 | (I) | (N.16.2) |
| C-410 | (I) | (N.17.1) |
| C-411 | (I) | (N.17.2) |
| C-412 | (I) | (N.17.3) |
| C-413 | (I) | (N.17.4) |
| C-414 | (I) | (N.17.5) |
| C-415 | (I) | (N.17.6) |
| C-416 | (I) | (N.17.7) |
| C-417 | (I) | (N.17.8) |
| C-418 | (I) | (N.17.9) |
| C-419 | (I) | (N.17.10) |
| C-420 | (I) | (N.17.11) |
| C-421 | (I) | (N.17.12) |
| C-422 | (I) | (O.1.1) |
| C-423 | (I) | (O.1.2) |
| C-424 | (I) | (O.1.3) |
| C-425 | (I) | (O.1.4) |
| C-426 | (I) | (O.1.5) |
| C-427 | (I) | (O.1.6) |
| C-428 | (I) | (O.1.7) |
| C-429 | (I) | (O.1.8) |
| C-430 | (I) | (O.1.9) |
| C-431 | (I) | (O.1.10) |
| C-432 | (I) | (O.1.11) |
| C-433 | (I) | (O.1.12) |
| C-434 | (I) | (O.1.13) |
| C-435 | (I) | (O.1.14) |
| C-436 | (I) | (O.1.15) |
| C-437 | (I) | (O.1.16) |
| C-438 | (I) | (O.1.17) |
| C-439 | (I) | (O.1.18) |
| C-440 | (I) | (O.1.19) |
| C-441 | (I) | (O.1.20) |
| C-442 | (I) | (O.1.21) |
| C-443 | (I) | (O.1.22) |
| C-444 | (I) | (O.1.23) |
| C-445 | (I) | (O.1.24) |
| C-446 | (I) | (O.1.25) |
| C-447 | (I) | (O.1.26) |
| C-448 | (I) | (O.1.27) |
| C-449 | (I) | (O.1.28) |
| C-450 | (I) | (O.1.29) |
| C-451 | (I) | (O.1.30) |
| C-452 | (I) | (O.1.31) |
| C-453 | (I) | (O.1.32) |
| C-454 | (I) | (O.1.33) |
| C-455 | (I) | (O.1.34) |
| C-456 | (I) | (O.1.35) |
| C-457 | (I) | (O.1.36) |
| C-458 | (I) | (O.1.37) |
| C-459 | (I) | (O.1.38) |
| C-460 | (I) | (O.2.1) |
| C-461 | (I) | (O.2.2) |
| C-462 | (I) | (O.2.3) |
| C-463 | (I) | (O.2.4) |
| C-464 | (I) | (O.2.5) |
| C-465 | (I) | (O.2.6) |
| C-466 | (I) | (O.2.7) |
| C-467 | (I) | (O.2.8) |
| C-468 | (I) | (O.2.9) |
| C-469 | (I) | (O.2.10) |
| C-470 | (I) | (O.2.11) |
| C-471 | (I) | (O.2.12) |
| C-472 | (I) | (O.2.13) |
| C-473 | (I) | (O.2.14) |
| C-474 | (I) | (O.2.15) |
| C-475 | (I) | (O.2.16) |
| C-476 | (I) | (O.3.1) |
| C-477 | (I) | (O.3.2) |
| C-478 | (I) | (O.3.3) |
| C-479 | (I) | (O.3.4) |
| C-480 | (I) | (O.3.5) |
| C-481 | (I) | (O.3.6) |
| C-482 | (I) | (O.3.7) |
| C-483 | (I) | (O.3.8) |
| C-484 | (I) | (O.3.9) |
| C-485 | (I) | (O.3.10) |
| C-486 | (I) | (O.3.11) |
| C-487 | (I) | (O.3.12) |
| C-488 | (I) | (O.3.13) |
| C-489 | (I) | (O.3.14) |
| C-490 | (I) | (O.3.15) |
| C-491 | (I) | (O.3.16) |
| C-492 | (I) | (O.3.17) |
| C-493 | (I) | (O.3.18) |
| C-494 | (I) | (O.3.19) |
| C-495 | (I) | (O.3.20) |

TABLE C-continued

Compositions comprising as active components one individualized compound I (I) (in Column Co. 1) and as component 2) (in Column Co. 2) one pesticide from groups A) to O) [which is coded e.g. as (A.1.1) for azoxystrobin as defined above].

| Mixt. | Co. 1 | Co. 2 |
|---|---|---|
| C-496 | (I) | (O.3.21) |
| C-497 | (I) | (O.3.22) |
| C-498 | (I) | (O.3.23) |
| C-499 | (I) | (O.3.24) |
| C-500 | (I) | (O.3.25) |
| C-501 | (I) | (O.3.26) |
| C-502 | (I) | (O.3.27) |
| C-503 | (I) | (O.4.1) |
| C-504 | (I) | (O.4.2) |
| C-505 | (I) | (O.4.3) |
| C-506 | (I) | (O.4.4) |
| C-507 | (I) | (O.4.5) |
| C-508 | (I) | (O.4.6) |
| C-509 | (I) | (O.4.7) |
| C-510 | (I) | (O.4.8) |
| C-511 | (I) | (O.4.9) |
| C-512 | (I) | (O.4.10) |
| C-513 | (I) | (O.4.11) |
| C-514 | (I) | (O.4.12) |
| C-515 | (I) | (O.4.13) |
| C-516 | (I) | (O.4.14) |
| C-517 | (I) | (O.4.15) |
| C-518 | (I) | (O.4.16) |
| C-519 | (I) | (O.4.17) |
| C-520 | (I) | (O.4.18) |
| C-521 | (I) | (O.4.19) |
| C-522 | (I) | (O.4.20) |
| C-523 | (I) | (O.4.21) |
| C-524 | (I) | (O.4.22) |
| C-525 | (I) | (O.4.23) |
| C-526 | (I) | (O.4.24) |
| C-527 | (I) | (O.5.1) |
| C-528 | (I) | (O.5.2) |
| C-529 | (I) | (O.5.3) |
| C-530 | (I) | (O.5.4) |
| C-531 | (I) | (O.5.5) |
| C-532 | (I) | (O.5.6) |
| C-533 | (I) | (O.5.7) |
| C-534 | (I) | (O.5.8) |
| C-535 | (I) | (O.5.9) |
| C-536 | (I) | (O.6.1) |
| C-537 | (I) | (O.6.2) |
| C-538 | (I) | (O.6.3) |
| C-539 | (I) | (O.6.4) |
| C-540 | (I) | (O.6.5) |
| C-541 | (I) | (O.6.6) |
| C-542 | (I) | (O.6.7) |
| C-543 | (I) | (O.7.1) |
| C-544 | (I) | (O.7.2) |
| C-545 | (I) | (O.7.3) |
| C-546 | (I) | (O.7.4) |
| C-547 | (I) | (O.7.5) |
| C-548 | (I) | (O.7.6) |
| C-549 | (I) | (O.8.1) |
| C-550 | (I) | (O.8.2) |
| C-551 | (I) | (O.8.3) |
| C-552 | (I) | (O.8.4) |
| C-553 | (I) | (O.8.5) |
| C-554 | (I) | (O.9.1) |
| C-555 | (I) | (O.9.2) |
| C-556 | (I) | (O.9.3) |
| C-557 | (I) | (O.10.1) |
| C-558 | (I) | (O.11.1) |
| C-559 | (I) | (O.11.2) |
| C-560 | (I) | (O.11.3) |
| C-561 | (I) | (O.11.4) |
| C-562 | (I) | (O.12.1) |
| C-563 | (I) | (O.13.1) |
| C-564 | (I) | (O.14.1) |
| C-565 | (I) | (O.14.2) |
| C-566 | (I) | (O.15.1) |
| C-567 | (I) | (O.15.2) |
| C-568 | (I) | (O.15.3) |
| C-569 | (I) | (O.15.4) |
| C-570 | (I) | (O.15.5) |
| C-571 | (I) | (O.15.6) |
| C-572 | (I) | (O.15.7) |
| C-573 | (I) | (O.15.8) |
| C-574 | (I) | (O.15.9) |
| C-575 | (I) | (O.15.10) |
| C-576 | (I) | (O.15.11) |
| C-577 | (I) | (O.16.1) |
| C-578 | (I) | (O.16.2) |
| C-579 | (I) | (O.16.3) |
| C-580 | (I) | (O.16.4) |
| C-581 | (I) | (O.16.5) |
| C-582 | (I) | (O.16.6) |
| C-583 | (I) | (O.16.7) |
| C-584 | (I) | (O.16.8) |
| C-585 | (I) | (O.16.9) |
| C-586 | (I) | (O.16.10) |
| C-587 | (I) | (O.16.11) |
| C-588 | (I) | (O.16.12) |
| C-589 | (I) | (O.16.13) |
| C-590 | (I) | (O.16.14) |
| C-591 | (I) | (O.16.15) |
| C-592 | (I) | (O.16.16) |
| C-593 | (I) | (O.16.17) |

The mixtures of active substances can be prepared as compositions comprising besides the active ingredients at least one inert ingredient (auxiliary) by usual means, e. g. by the means given for the compositions of compounds I.

Concerning usual ingredients of such compositions reference is made to the explanations given for the compositions containing compounds I.

The mixtures of active substances according to the present invention are suitable as fungicides, as are the compounds of formula I. They are distinguished by an outstanding effectiveness against a broad spectrum of phytopathogenic fungi, especially from the classes of the Ascomycetes, Basidiomycetes, Deuteromycetes and Peronosporomycetes (syn. Oomycetes). In addition, it is referred to the explanations regarding the fungicidal activity of the compounds and the compositions containing compounds I, respectively.

I. Synthesis Examples

EXAMPLE 1

Synthesis of I-1

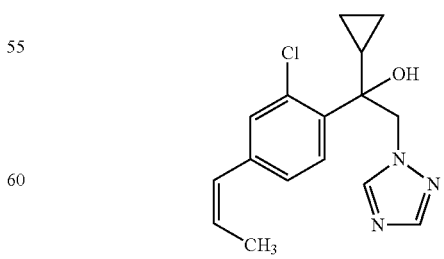

A flask was charged with Pd(dppf)Cl$_2$ (12.0 mg, 1 mol %) and Pd(PPh$_3$)$_4$ (101 mg, 6 mol %) before solutions of the respective arylbromide (500 mg, 1.0 eq) and Z-propen-1-yl boronic acid (188 mg, 1.5 eq) in 1,2-dimethoxyethane (5 mL each) were added. The resulting mixture was treated with a solution of Na₂CO₃ (387 mg, 2.5 eq) in water (2 mL), the vessel was tightly sealed and warmed to 100° C. for 4 h after which HPLC showed complete consumption of the starting material. The reaction was cooled to room temperature, poured into a saturated solution of NH₄Cl and extracted with EtOAc. The combined organic extracts were dried over Na₂SO₄, filtered and concentrated under reduced pressure. Purification of the residual crude product afforded the title compound as oil. HPLC**: $t_R$=1.138 min, ¹H NMR (298 K, CDCl₃): δ [ppm]=0.20-0.30 (1H), 0.40-0.50 (2H), 0.60-0.70 (1H), 1.75-1.90 (1H), 1.90-1.95 (3H), 4.43-4.45 (1H), 4.55-4.65 (1H), 5.35-5.45 (1H), 5.80-5.90 (1H), 6.20-6.30 (1H), 7.10 (1H), 7.45-7.50 (1H), 7.55-7.60 (1H), 7.90 (1H), 8.10 (1H).

EXAMPLE 2

Synthesis of I-2

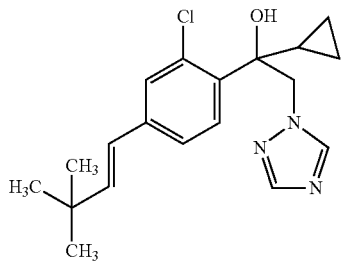 [SMILES: CC(C)(C)/C=C/c1ccc(C(O)(Cn2cncn2)C2CC2)c(Cl)c1]

A flask was charged with Pd(dppf)Cl₂ (36.0 mg, 5 mol %) and Pd(PPh₃)₄ (60.7 mg, 6 mol %) before solutions of the respective arylbromide (300 mg, 1.0 eq) and the respective pinacol boronate (281 mg, 1.5 eq) in 1,2-dimethoxyethane (4 mL each) were added. The resulting mixture was treated with a solution of Na₂CO₃ (228 mg, 2.5 eq) in water (2 mL), the vessel was tightly sealed and warmed to 90° C. overnight. The reaction was cooled to room temperature, stripped onto silica gel and purified by column chromatography to yield the olefin (263 mg, 87%) as yellow oil. HPLC**: $t_R$=1.519 min, ¹H NMR (298 K, CDCl₃): δ [ppm]=0.20-0.30 (1H), 0.35-0.50 (2H), 0.60-0.70 (1H), 1.10 (9H), 1.80-1.90 (1H), 4.40 (1H), 4.60 (1H), 5.40 (1H), 6.15 (1H), 6.25 (1H), 7.15 (1H), 7.35 (1H), 7.50 (1H), 7.85 (1H), 8.05 (1H).

EXAMPLE 15

I-15

Step 15.1: Synthesis of

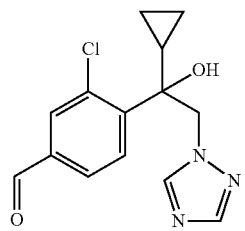 [SMILES: O=Cc1ccc(C(O)(Cn2cncn2)C2CC2)c(Cl)c1]

A solution of the respective arylbromide (10.0 g, 1.0 eq) in dry THF (200 mL) was cooled to −78° C. and n-BuLi (73.0 mL, 1.6 M solution in hexanes, 4.0 eq) was added dropwise. After complete addition, the yellow solution was stirred for 15 minutes before DMF (4.27 g, 4.50 mL, 2.0 eq) was added dropwise and the mixture was stirred for another 30 minutes. The reaction was quenched by the addition of a saturated solution of NH₄Cl and subsequently warmed to ambient temperature. The product was extracted into MTBE, the combined organic extracts were dried over MgSO₄ and freed from solvent under reduced pressure. The crude product (1.60 g, 19%) was sufficiently pure to be engaged directly in the next step. HPLC**: $t_R$=0.905 min, ¹H NMR (298 K, CDCl₃): δ [ppm]=0.15-0.30 (1H), 0.40-0.55 (2H), 0.65-0.80 (1H), 1.80-1.90 (1H), 4.65 (1H), 5.40 (1H), 7.65 (1H), 7.75-7.95 (2H), 8.00 (2H), 9.95 (1H).

Step 15.2: Synthesis of I-15

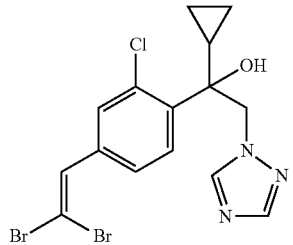

To a solution of CBr₄ (841 mg, 2.0 eq) in CH₂Cl₂ (10 mL) was added PPh₃ (1.33 g, 4.0 eq) under nitrogen and the mixture was stirred for 15 minutes at room temperature before a solution of the aldehyde obtained from Step 15.1 (370 mg, 1.0 eq) in CH₂Cl₂ (5 mL) was added. After 1 h, HPLC showed complete consumption of the starting material and the mixture was diluted with EtOAc. The organic layer was washed with a saturated solution of NaHCO₃ and the aqueous phase back-extracted with EtOAc. The combined organic extracts were washed with brine, dried over Na₂SO₄ and concentrated under reduced pressure. Further purification of the crude product by column chromatography furnished the title compound as oil. ¹H NMR (298 K, CDCl₃): δ [ppm]=0.20-0.30 (1H), 0.35-0.45 (2H), 0.50-0.65 (1H), 1.70-1.90 (1H), 4.60 (1H), 5.35 (1H), 7.30-7.45 (2H), 7.55 (1H), 7.65 (1H), 7.85 (1H), 8.00 (1H).

EXAMPLE 16

Synthesis of: I-16

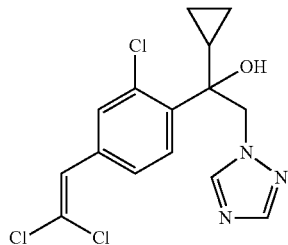 [SMILES: OC(Cn1cncn1)(c1ccc(C=C(Cl)Cl)cc1Cl)C1CC1]

To a solution of PPh₃ (1.08 g, 3.0 eq) in THF was added a solution of the aldehyde obtained from step 15.1 (400 mg, 1.0 eq) in THF (5 mL) and the mixture was warmed to 60° C. before CCl₄ (2.11 g, 10 eq) was added dropwise. After 6 h at this temperature, the reaction was judged to be complete, hence cooled to room temperature and diluted with EtOAc. The organic layer was washed with a saturated solution of NaHCO$_3$ and the aqueous phase back-extracted with EtOAc. The combined organic extracts were washed with brine, dried over Na$_2$SO$_4$ and concentrated under reduced pressure. Further purification of the crude product by column chromatography furnished the title compound as oil. HPLC**: $t_R$=1.197 min

EXAMPLE 17

Synthesis of I-17

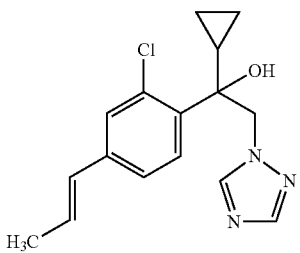 [SMILES: C/C=C/c1ccc(C(O)(Cn2cncn2)C2CC2)c(Cl)c1]

To a suspension of ethyl triphenylphosphonium bromide (1.02 g, 2.0 eq) in THF (20 mL) was added potassium tert-butoxide (312 mg, 2.0 eq) at room temperature. After 15 minutes, a solution of the aldehyde from step 15.1 (400 mg, 1.0 eq) in THF (5 mL) was added to the dark-red solution and the mixture was stirred overnight at ambient temperature before it was quenched with a saturated solution of NH$_4$Cl. The product was extracted into MTBE and the combined organic layers were dried over Na$_2$SO$_4$ and freed from solvent under reduced pressure. The residue was purified by column chromatography to yield the title compound as mixture of isomers (Z/E=65/35) (190 mg, 46%). HPLC**: $t_R$=1.134 min (E-Isomer), 1.138 (Z-Isomer). The pure Z-isomer was prepared via a Suzuki coupling (see above).

EXAMPLE 18

Synthesis of I-18

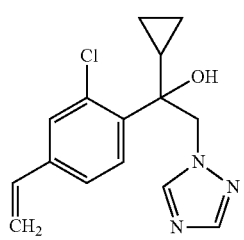 [SMILES: C=Cc1ccc(C(O)(Cn2cncn2)C2CC2)c(Cl)c1]

In an analogous manner as described above, the title compound was prepared as solid in 46% yield. Mp: 89° C., HPLC**: $t_R$=1.090 min, $^1$H NMR (298 K, CDCl$_3$): δ [ppm]=0.20-0.30 (1H), 0.40-0.50 (2H), 0.55-0.70 (1H), 1.75-1.85 (1H), 4.45 (1H), 4.55 (1H), 5.30 (1H), 5.70 (1H), 6.40-6.55 (2H), 7.20 (1H), 7.35 (1H), 7.55 (1H), 7.85 (1H), 8.00 (1H).

According to the general procedure above, the following inventive compounds I (R$^2$=H and A=N) were also prepared:

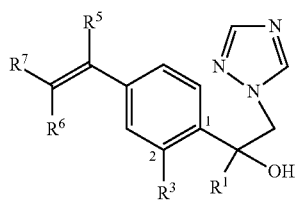

| Example No. | R$^1$ | R$^3$ | R$^5$ | R$^6$ | R$^7$ | HPLC** $t_R$/min |
|---|---|---|---|---|---|---|
| I-3 | cyclopropyl (C$_3$H$_5$) | Cl | H | CH$_3$ | CH$_3$ | 1.359 |
| I-4 | cyclopropyl (C$_3$H$_5$) | Cl | H | H | cyclopropyl (C$_3$H$_5$) | 1.376 |
| I-5 | cyclopropyl (C$_3$H$_5$) | CF$_3$ | H | H | cyclopropyl (C$_3$H$_5$) | 1.205 |
| I-6 | cyclopropyl (C$_3$H$_5$) | H | H | H | cyclopropyl (C$_3$H$_5$) | 1.071 |
| I-7 | CH$_3$ | Cl | H | H | cyclopropyl (C$_3$H$_5$) | 1.081 |
| I-8 | CH$_3$ | CF$_3$ | H | H | cyclopropyl (C$_3$H$_5$) | 1.104 |
| I-9 | CH$_3$ | H | H | H | cyclopropyl (C$_3$H$_5$) | 0.984 |
| I-10 | cyclopropyl (C$_3$H$_5$) | H | H | H | C(CH$_3$)$_3$ | 1.201 |
| I-11 | cyclopropyl (C$_3$H$_5$) | CF$_3$ | H | H | C(CH$_3$)$_3$ | 1.329 |
| I-12 | CH$_3$ | H | H | H | C(CH$_3$)$_3$ | 1.113 |
| I-13 | CH$_3$ | Cl | H | H | C(CH$_3$)$_3$ | 1.214 |
| I-14 | CH$_3$ | CF$_3$ | H | H | C(CH$_3$)$_3$ | 1.230 |
| I-19 | cyclopropyl (C$_3$H$_5$) | Cl | H | H | C(=O)OCH$_3$ | 1.025 |
| I-20 | cyclopropyl (C$_3$H$_5$) | Cl | H | H | Cl | 1.118 |
| I-21 | cyclopropyl (C$_3$H$_5$) | Cl | H | H | CH(CH$_3$)$_2$ | 1.262 |
| I-22 | CF$_2$(CH$_3$) | Cl | H | H | cyclopropyl (C$_3$H$_5$) | 1.163 |
| I-23 | cyclopropyl (C$_3$H$_5$) | Cl | H | cyclopropyl (C$_3$H$_4$) | | 1.147 |
| I-24 | cyclopropyl (C$_3$H$_5$) | Cl | H | cyclobutyl (C$_4$H$_6$) | | 1.222 |
| I-25 | cyclopropyl (C$_3$H$_5$) | Cl | H | cyclopentyl (C$_5$H$_8$) | | 1.286 |
| I-26 | C(CH$_3$)$_3$ | Cl | H | H | cyclopropyl (C$_3$H$_5$) | 1.342 |
| I-27 | C(CH$_3$)$_3$ | CF$_3$ | H | H | cyclopropyl (C$_3$H$_5$) | 1.330 |
| I-28 | C(CH$_3$)$_3$ | H | H | H | cyclopropyl (C$_3$H$_5$) | 1.224 |
| I-29 | CH$_2$CH$_3$ | Cl | H | H | cyclopropyl (C$_3$H$_5$) | 1.153 |
| I-30 | CH$_2$CH$_3$ | H | H | H | cyclopropyl (C$_3$H$_5$) | 1.050 |
| I-31 | cyclopropyl (C$_3$H$_5$) | Cl | H | H | CH$_3$ | 1.126 |
| I-32 | cyclopropyl (C$_3$H$_5$) | Cl | CH$_3$ | H | H | 1.153 |
| I-33 | cyclopropyl (C$_3$H$_5$) | Cl | CH$_3$ | CH$_3$ | CH$_3$ | 1.247 |
| I-34 | cyclopropyl (C$_3$H$_5$) | CF$_3$ | H | H | | 1.142 |
| I-35 | cyclopropyl (C$_3$H$_5$) | Cl | R$^5$ and R$^7$ form cyclohexenyl, R$^6$ is H | | | 1.281 |
| I-36 | cyclopropyl (C$_3$H$_5$) | Cl | R$^5$ and R$^7$ form cyclopentenyl, R$^6$ is H | | | 1.227 |

-continued

| Example No. | $R^1$ | $R^3$ | $R^5$ | $R^6$ | $R^7$ | HPLC** $t_R$/min |
|---|---|---|---|---|---|---|
| I-37 | cyclopropyl ($C_3H_5$) | Cl | H | H | Si(CH$_3$)$_3$ | 1.364 |
| I-38 | cyclopropyl ($C_3H_5$) | Cl | CH$_3$ | H | CH$_3$ | 1.183 |
| I-39 | cyclopropyl ($C_3H_5$) | Cl | CH$_3$ | CH$_3$ | H | 1.183 |
| I-40 | cyclopropyl ($C_3H_5$) | Cl | H | H | CH$_3$ | 1.120 |
| I-41 | C(CH$_3$)$_3$ | H | H | H | CH$_3$ | 1.163 |
| I-42 | CH$_3$ | CF$_3$ | H | H | CH$_3$ | 1.038 |
| I-43 | cyclopropyl ($C_3H_5$) | Cl | H | H | C≡CH | 1.075 |
| I-44 | cyclopropyl ($C_3H_5$) | Cl | H | H | CH=CBr$_2$ | 1.298 |
| I-45 | cyclopropyl ($C_3H_5$) | Cl | H | H | F | 1.269 |
| I-46 | CH$_2$CH$_3$ | Cl | H | H | CH$_3$ | 1.082 |
| I-47 | cyclopropyl ($C_3H_5$) | Cl | H | H | CF$_3$ | 1.166 |
| I-48 | C(CH$_3$)$_3$ | H | H | H | CF$_3$ | 1.216 |
| I-49 | CH$_3$ | CF$_3$ | H | H | CF$_3$ | 1.081 |
| I-50 | CH$_3$ | CF$_3$ | CH$_3$ | CH$_3$ | CH$_3$ | 1.156 |
| I-51 | CH$_2$CH$_3$ | Cl | H | H | CF$_3$ | 1.112 |
| I-52 | cyclopropyl ($C_3H_5$) | Cl | H | H | Br | 1.132 |

**HPLC method Data:

Mobile Phase: A: Wasser+0.1% T FA; B: acetonitrile; Gradient: 5% B to 100% B in 1.5 min; Temperature: 60° C.; MS-Method: ESI positive; mass area (m/z): 100-700; Flow: 0.8 ml/min to 1.0 ml/min in 1.5 min; Column: Kinetex XB C18 1.7μ 50×2.1 mm; Aparatus: Shimadzu Nexera LC-30 LCMS-2020.

II. Examples of the Action Against Harmful Fungi

The fungicidal action of the compounds of the formula I was demonstrated by the following experiments:

Microtest

The active compounds were formulated separately as a stock solution having a concentration of 10000 ppm in dimethyl sulfoxide.

1. Activity Against the Grey Mold *Botrytis cinerea* in the Microtiterplate Test (*Botrci*)

The stock solutions were mixed according to the ratio, pipetted onto a micro titer plate (MTP) and diluted with water to the stated concentrations. A spore suspension of *Botrci cinerea* in an aqueous biomalt or yeast-bactopeptone-sodiumacetate solution was then added. The plates were placed in a water vapor-saturated chamber at a temperature of 18° C. Using an absorption photometer, the MTPs were measured at 405 nm 7 days after the inoculation.

Compounds I-2, I-3, I-4, I-18, I-19, I-1, I-6, I-7, I-8, I-9, I-10, I-12, I-20, I-21, I-5, I-13, I-15, I-17, I-22, I-23, I-24, I-25, I-26, I-28, I-31, I-32, I-33, I-34, I-35, I-36, I-38, I-39, I-40, I-41, I-42, I-43, I-44, I-45, I-46, I-47, I-48, I-49, I-51 and I-52, respectively, showed a growth of 12% or less at 31 ppm.

2. Activity Against Rice Blast *Pyricularia Oryzae* in the Microtiterplate Test (*Pyrior*)

The stock solutions were mixed according to the ratio, pipetted onto a micro titer plate (MTP) and diluted with water to the stated concentrations. A spore suspension of *Pyricularia oryzae* in an aqueous biomalt or yeast-bacto-peptone-glycerine solution was then added. The plates were placed in a water vapor-saturated chamber at a temperature of 18° C. Using an absorption photometer, the MTPs were measured at 405 nm 7 days after the inoculation.

Compounds I-2, I-3, I-4, I-18, I-19, I-1, I-6, I-7, I-8, I-10, I-11, I-12, I-14, I-20, I-21, I-5, I-13, I-15, I-17, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, I-46, I-47, I-48, I-49, I-51 and I-52, respectively, showed a growth of 19% or less at 31 ppm.

3. Activity Against Leaf Blotch on Wheat Caused by *Septoria tritici* (Septtr)

The stock solutions were mixed according to the ratio, pipetted onto a micro titer plate (MTP) and diluted with water to the stated concentrations. A spore suspension of *Septoria tritici* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation. Compounds I-3, I-4, I-18, I-19, I-1, I-6, I-7, I-8, I-9, I-10, I-11, I-12, I-14, I-20, I-21, I-5, I-13, I-15, I-17, I-22, I-23, I-24, I-27, I-28, I-31, I-32, I-33, I-34, I-36, I-38, I-39, I-40, I-41, I-42, I-43, I-45, I-46, I-47, I-48, I-49, I-51 and I-52, respectively, showed a growth of 20% or less at 31 ppm.

The measured parameters were compared to the growth of the active compound-free control variant (100%) and the fungus-free and active compound-free blank value to determine the relative growth in % of the pathogens in the respective active compounds.

Green House

The spray solutions were prepared in several steps:

The stock solution were prepared: a mixture of acetone and/or dimethylsulfoxide and the wetting agent/emulsifier Wettol, which is based on ethoxylated alkylphenoles, in a relation (volume) solvent-emulsifier of 99 to 1 was added to 25 mg of the compound to give a total of 5 ml.

Water was then added to total volume of 100 ml.

This stock solution was diluted with the described solvent-emulsifier-water mixture to the given concentration.

1. Preventative Fungicidal Control of Early Blight on Tomatoes (*Alternaria Solani*) (Alteso P1)

Young seedlings of tomato plants were grown in pots. These plants were sprayed to run-off with an aqueous suspension, containing the concentration of active ingredient or mixture mentioned in the table below. The next day, the treated plants were inoculated with an aqueous suspension of *Alternaria solani*. Then the trial plants were immediately transferred to a humid chamber. After 5 days at 18 to 20° C. and a relative humidity close to 100%, the extent of fungal attack on the leaves was visually assessed as % diseased leaf area. In this test, the plants which had been treated with 125 ppm of the active substance I-3, I-4, I-18, I-1, I-8, I-20, I-21, I-5, I-13, I-15, I-17, I-22, I-24, I-25, I-28, I-29, I-30, I-31, I-35, I-38, I-40, I-41, I-43, I-44, I-45, I-46, I-47, I-49, I-51 or I-52, respectively, showed an infection of 16% or less whereas the untreated plants were 80% infected.

2. Protective Control of Soy Bean Rust on Soy Beans Caused by *Phakopsora pachyrhizi* (Phakpa P2)

Leaves of pot-grown soy bean seedlings were sprayed to run-off with an aqueous suspension, containing the concentration of active ingredient or their mixture as described below. The plants were allowed to air-dry. The trial plants were cultivated for 2 days in a greenhouse chamber at 23-27° C. and a relative humidity between 60 and 80%. Then the plants were inoculated with spores of *Phakopsora pachyrhizi*. To ensure the success the artificial inoculation, the plants were transferred to a humid chamber with a relative humidity of about 95% and 20 to 24 ☐ C for 24 h. The trial plants were cultivated for fourteen days in a greenhouse chamber at 23-27° C. and a relative humidity between 60 and 80%. The extent of fungal attack on the leaves was visually assessed as % diseased leaf area. In this test, the plants which had been treated with 16 ppm of the active substance I-2, I-1, I-7, I-10, I-11, I-20, I-21, I-5, I-13, I-15, I-17, I-26, I-28, I-29, I-31, I-32, I-33, I-34, I-37, I-46, I-47, I-48, I-51 or I-52, respectively, showed an infection of 15% or less whereas the untreated plants were 80% infected.

The invention claimed is:

1. A compound of the formula I

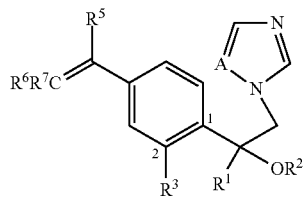

wherein
A is CH or N;
$R^1$ is selected from the group consisting of $C_1$-$C_6$-alkyl, $C_2$-$C_6$-alkenyl, $C_2$-$C_6$-alkynyl and $C_3$-$C_6$-cycloalkyl;
wherein the aliphatic moieties of $R^1$ are not further substituted or carry one, two, three or up to the maximum possible number of identical or different groups $R^{1a}$ which independently of one another are selected from:
$R^{1a}$ is selected from the group consisting of halogen, OH, CN, $C_1$-$C_4$-alkoxy, $C_3$-$C_6$-cycloalkyl, $C_3$-$C_6$-halogencycloalkyl and $C_1$-$C_4$-halogenalkoxy;
wherein the cycloalkyl moieties of $R^1$ are not further substituted or carry one, two, three, four, five or up to the maximum number of identical or different groups $R^{1b}$ which independently of one another are selected from:
$R^{1b}$ is selected from the group consisting of halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl and $C_1$-$C_4$-halogenalkoxy;
$R^2$ is selected from the group consisting of hydrogen, $C_1$-$C_4$-alkyl, $C_2$-$C_4$-alkenyl and $C_2$-$C_4$-alkynyl;
wherein the aliphatic moieties of $R^2$ are not further substituted or carry one, two, three or up to the maximum possible number of identical or different groups $R^{2a}$ which independently of one another are selected from:
$R^{2a}$ is selected from the group consisting of halogen, OH, CN, $C_1$-$C_4$-alkoxy, $C_3$-$C_6$-cycloalkyl, $C_3$-$C_6$-halogencycloalkyl and $C_1$-$C_4$-halogenalkoxy;
$R^3$ is selected from the group consisting of hydrogen, halogen, CN, $C_1$-$C_4$-alkyl, $C_1$-$C_4$-alkoxy, $C_2$-$C_4$-alkenyl, $C_2$-$C_4$-alkynyl, $C_3$-$C_6$-cycloalkyl and $S(O)_p(C_1$-$C_4$-alkyl), wherein p is 0, 1 or 2, and wherein each of $R^3$ is unsubstituted or further substituted by one, two, three or four $R^{3a}$; wherein
$R^{3a}$ is independently selected from the group consisting of halogen, CN, OH, $C_1$-$C_4$-alkyl, $C_1$-$C_4$-halogenalkyl, $C_3$-$C_6$-cycloalkyl, $C_3$-$C_6$-halogencycloalkyl, $C_1$-$C_4$-alkoxy and $C_1$-$C_4$-halogenalkoxy;
$R^5$ is selected from the group consisting of hydrogen, halogen, CN, $C_1$-$C_6$-alkyl, $C_1$-$C_6$-halogenalkyl, $C_1$-$C_6$-alkoxy, $C_1$-$C_6$-halogenalkoxy, C(=O)—O—($C_1$-$C_6$-alkyl), $C_3$-$C_6$-cycloalkyl or saturated or partially unsaturated three-, four-, five-, six- or seven-membered heterocyclyl, wherein the heterocyclyl contains 1, 2, 3 or 4 heteroatoms selected from the group consisting of O, N and S, and wherein the cycloalkyl and heterocyclyl is unsubstituted (m=0) or substituted by $(R^4)_m$;
$R^6$ is selected from the group consisting of hydrogen, halogen, CN, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy and $C_1$-$C_6$-halogenalkoxy; wherein the alkenyl and alkynyl moieties are not further substituted or carry one, two, three, four, five or up to the maximum number of identical or different groups $R^{6a}$ which independently of one another are selected from:
$R^{6a}$ is selected from the group consisting of halogen, $C_1$-$C_4$-alkyl, $C_1$-$C_4$-halogenalkyl, and Si(CH$_3$)$_3$;
$R^7$ is selected from the group consisting of hydrogen, halogen, CN, $C_1$-$C_6$-alkyl, $C_1$-$C_6$-halogenalkyl, $C_2$-$C_6$-alkenyl, $C_2$-$C_6$-alkynyl, $C_1$-$C_6$-alkoxy, $C_1$-$C_6$-halogenalkoxy, C(=O)—O—($C_1$-$C_6$-alkyl), Si(CH$_3$)$_3$, $C_3$-$C_6$-cycloalkyl or saturated or partially unsaturated three-, four-, five-, six- or seven-membered heterocyclyl, wherein the heterocyclyl contains 1, 2, 3 or 4 heteroatoms selected from the group consisting of O, N and S, and wherein the cycloalkyl and heterocyclyl is unsubstituted (m=0) or substituted by $(R^4)_m$; and wherein the alkenyl and alkynyl moieties are not further substituted or carry one, two, three, four, five or up to the maximum number of identical or different groups $R^{7a}$ which independently of one another are selected from:
$R^{7a}$ is selected from the group consisting of halogen, $C_1$-$C_4$-alkyl, $C_1$-$C_4$-halogenalkyl, and Si(CH$_3$)$_3$;
wherein zero or one of $R^5$ and $R^7$ is selected from cycloalkyl and heterocycyl;
or $R^5$ and $R^7$ together with the carbon atoms to which they are bound form a $C_3$-$C_6$-cycloalkenyl, that is unsubstituted at the saturated chain or substituted by $(R^8)_n$; and $R^6$ is as defined above;
or $R^6$ and $R^7$ together with the carbon atoms to which they are bound form a $C_3$-$C_6$-cycloalkyl, that is unsubstituted or substituted by $(R^8)_n$; and $R^5$ is selected from the group consisting of hydrogen, halogen, CN, $C_1$-$C_6$-alkyl, $C_1$-$C_6$-halogenalkyl, $C_1$-$C_6$-alkoxy, $C_1$-$C_6$-halogenalkoxy and C(=O)—O—($C_1$-$C_6$-alkyl);
wherein
m is 0, 1, 2, 3, 4 or 5;
$R^4$ is in each case independently selected from the group consisting of halogen, CN, NO$_2$, OH, SH, $C_1$-$C_6$-alkyl, $C_1$-$C_6$-alkoxy, $C_2$-$C_6$-alkenyl, $C_2$-$C_6$-alkynyl and $C_3$-$C_6$-cycloalkyl, wherein each of $R^4$ is unsubstituted or further substituted by one, two, three or four $R^{4a}$
wherein
$R_{4a}$ is independently selected from halogen;
n is 0, 1, 2, 3, 4 or 5 ;
$R^8$ is in each case independently selected from the substituents as defined for $R^4$;
wherein each of $R^8$ is unsubstituted or further substituted by one, two, three or four $R^{8a}$ that is in each case independently selected from the substituents as defined for $R^{4a}$;
and an N-oxide and/or an agriculturally acceptable salt thereof.

2. The compound of claim 1, wherein A is N.
3. The compound of claim 1, wherein $R^5$ is H.
4. The compound of claim 1, wherein $R^6$ is H.
5. The compound of claim 1, wherein $R^7$ is H.

6. The compound of claim 1, wherein $R^7$ is $C_3$-$C_6$-cycloalkyl, that is unsubstituted (m=0) or substituted by $(R^4)_m$.

7. The compound of claim 6, wherein $R^7$ is cyclopropyl and m is 0 or 1.

8. The compound of claim 1, wherein $R^3$ is selected from the group consisting of F, Cl, Br, CN, $C_1$-$C_4$-alkyl, $C_1$-$C_4$-halogenalkyl, $C_1$-$C_4$-alkoxy and $S(C_1$-$C_4$-alkyl).

9. The compound of claim 1, wherein $R^2$ is hydrogen.

10. The compound of claim 1, wherein $R^1$ is selected from the group consisting of methyl, ethyl, n-propyl, $CH_2C(CH_3)_3$, $CH_2CH(CH_3)_2$, $CF_3$, $C_2$-$C_6$-alkenyl, $C_2$-$C_6$-alkynyl and $C_3$-$C_6$-cycloalkyl.

11. The compound of claim 1, wherein A is N and $R^2$ is H:

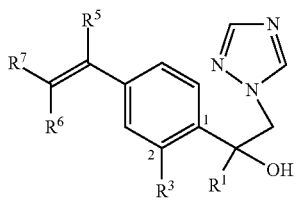

and wherein the remaining substituents are as follows:

| | $R^1$ | $R^3$ | $R^5$ | $R^6$ | $R^7$ |
|---|---|---|---|---|---|
| I-1 | cyclopropyl ($C_3H_5$) | Cl | H | $CH_3$ | H |
| I-2 | cyclopropyl ($C_3H_5$) | Cl | H | H | $C(CH_3)_3$ |
| I-3 | cyclopropyl ($C_3H_5$) | Cl | H | $CH_3$ | $CH_3$ |
| I-4 | cyclopropyl ($C_3H_5$) | Cl | H | H | cyclopropyl ($C_3H_5$) |
| I-5 | cyclopropyl ($C_3H_5$) | $CF_3$ | H | H | cyclopropyl ($C_3H_5$) |
| I-6 | cyclopropyl ($C_3H_5$) | H | H | H | cyclopropyl ($C_3H_5$) |
| I-7 | $CH_3$ | Cl | H | H | cyclopropyl ($C_3H_5$) |
| I-8 | $CH_3$ | $CF_3$ | H | H | cyclopropyl ($C_3H_5$) |
| I-9 | $CH_3$ | H | H | H | cyclopropyl ($C_3H_5$) |
| I-10 | cyclopropyl ($C_3H_5$) | H | H | H | $C(CH_3)_3$ |
| I-11 | cyclopropyl ($C_3H_5$) | $CF_3$ | H | H | $C(CH_3)_3$ |
| I-12 | $CH_3$ | H | H | H | $C(CH_3)_3$ |
| I-13 | $CH_3$ | Cl | H | H | $C(CH_3)_3$ |
| I-14 | $CH_3$ | $CF_3$ | H | H | $C(CH_3)_3$ |
| I-15 | cyclopropyl ($C_3H_5$) | Cl | H | Br | Br |
| I-16 | cyclopropyl ($C_3H_5$) | Cl | H | Cl | Cl |
| I-17 | cyclopropyl ($C_3H_5$) | Cl | H | H | $CH_3$ |
| I-18 | cyclopropyl ($C_3H_5$) | Cl | H | H | H |
| I-19 | cyclopropyl ($C_3H_5$) | Cl | H | H | C(=O)OCH$_3$ |
| I-20 | cyclopropyl ($C_3H_5$) | Cl | H | H | Cl |
| I-21 | cyclopropyl ($C_3H_5$) | Cl | H | H | $CH(CH_3)_2$ |
| I-22 | $CF_2(CH_3)$ | Cl | H | H | cyclopropyl ($C_3H_5$) |
| I-23 | cyclopropyl ($C_3H_5$) | Cl | H | cyclopropyl ($C_3H_4$) | |
| I-24 | cyclopropyl ($C_3H_5$) | Cl | H | cyclobutyl ($C_4H_6$) | |
| I-25 | cyclopropyl ($C_3H_5$) | Cl | H | cyclopentyl ($C_5H_8$) | |
| I-26 | $C(CH_3)_3$ | Cl | H | H | cyclopropyl ($C_3H_5$) |
| I-27 | $C(CH_3)_3$ | $CF_3$ | H | H | cyclopropyl ($C_3H_5$) |
| I-28 | $C(CH_3)_3$ | H | H | H | cyclopropyl ($C_3H_5$) |
| I-29 | $CH_2CH_3$ | Cl | H | H | cyclopropyl ($C_3H_5$) |
| I-30 | $CH_2CH_3$ | H | H | H | cyclopropyl ($C_3H_5$) |
| I-31 | cyclopropyl ($C_3H_5$) | Cl | H | H | $CH_3$ |
| I-32 | cyclopropyl ($C_3H_5$) | Cl | $CH_3$ | H | H |
| I-33 | cyclopropyl ($C_3H_5$) | Cl | $CH_3$ | $CH_3$ | $CH_3$ |
| I-34 | cyclopropyl ($C_3H_5$) | Cl | $CF_3$ | H | H |
| I-35 | cyclopropyl ($C_3H_5$) | Cl | $R^5$ and $R^7$ form cyclohexenyl, $R^6$ is H | | |
| I-36 | cyclopropyl ($C_3H_5$) | Cl | $R^5$ and $R^7$ form cyclopentenyl, $R^6$ is H | | |
| I-37 | cyclopropyl ($C_3H_5$) | Cl | H | H | $Si(CH_3)_3$ |
| I-38 | cyclopropyl ($C_3H_5$) | Cl | $CH_3$ | H | $CH_3$ |
| I-39 | cyclopropyl ($C_3H_5$) | Cl | $CH_3$ | $CH_3$ | H |
| I-40 | cyclopropyl ($C_3H_5$) | Cl | H | H | $CH_3$ |
| I-41 | $C(CH_3)_3$ | Cl | H | H | $CH_3$ |
| I-42 | $CH_3$ | $CF_3$ | H | H | $CH_3$ |
| I-43 | cyclopropyl ($C_3H_5$) | Cl | H | H | C≡CH |
| I-44 | cyclopropyl ($C_3H_5$) | Cl | H | H | CH=CBr$_2$ |
| I-45 | cyclopropyl ($C_3H_5$) | Cl | H | H | F |
| I-46 | $CH_2CH_3$ | Cl | H | H | $CH_3$ |
| I-47 | cyclopropyl ($C_3H_5$) | Cl | H | H | $CF_3$ |
| I-48 | $C(CH_3)_3$ | H | H | H | $CF_3$ |
| I-49 | $CH_3$ | $CF_3$ | H | H | $CF_3$ |
| I-50 | $CH_3$ | $CF_3$ | $CH_3$ | $CH_3$ | $CH_3$ |
| I-51 | $CH_2CH_3$ | Cl | H | H | $CF_3$ |
| I-52 | cyclopropyl ($C_3H_5$) | Cl | H | H | Br. |

12. A composition comprising the compound of claim 1, an N-oxide or an agriculturally acceptable salt thereof.

13. The composition of claim 12, comprising additionally a further active substance.

14. A method for combating phytopathogenic fungi comprising treating the fungi or the materials, plants, the soil or seeds to be protected against fungal attack with an effective amount of a composition comprising at least one compound claim 1.

15. The method of claim 14, wherein A is N.

16. The method of claim 14, wherein $R^5$ is H.

17. The method of claim 14, wherein $R^6$ is H.

18. The method of claim 14, wherein $R^7$ is H.

19. The method of claim 14, wherein A is N and $R^2$ is H:

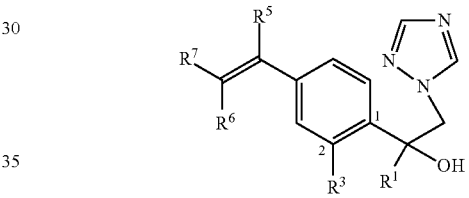

and wherein the remaining substituents are as follows:

| | $R^1$ | $R^3$ | $R^5$ | $R^6$ | $R^7$ |
|---|---|---|---|---|---|
| I-53 | cyclopropyl ($C_3H_5$) | Cl | H | $CH_3$ | H |
| I-54 | cyclopropyl ($C_3H_5$) | Cl | H | H | $C(CH_3)_3$ |
| I-55 | cyclopropyl ($C_3H_5$) | Cl | H | $CH_3$ | $CH_3$ |
| I-56 | cyclopropyl ($C_3H_5$) | Cl | H | H | cyclopropyl ($C_3H_5$) |
| I-57 | cyclopropyl ($C_3H_5$) | $CF_3$ | H | H | cyclopropyl ($C_3H_5$) |
| I-58 | cyclopropyl ($C_3H_5$) | H | H | H | cyclopropyl ($C_3H_5$) |
| I-59 | $CH_3$ | Cl | H | H | cyclopropyl ($C_3H_5$) |
| I-60 | $CH_3$ | $CF_3$ | H | H | cyclopropyl ($C_3H_5$) |
| I-61 | $CH_3$ | H | H | H | cyclopropyl ($C_3H_5$) |
| I-62 | cyclopropyl ($C_3H_5$) | H | H | H | $C(CH_3)_3$ |
| I-63 | cyclopropyl ($C_3H_5$) | $CF_3$ | H | H | $C(CH_3)_3$ |
| I-64 | $CH_3$ | H | H | H | $C(CH_3)_3$ |
| I-65 | $CH_3$ | Cl | H | H | $C(CH_3)_3$ |
| I-66 | $CH_3$ | $CF_3$ | H | H | $C(CH_3)_3$ |
| I-67 | cyclopropyl ($C_3H_5$) | Cl | H | Br | Br |
| I-68 | cyclopropyl ($C_3H_5$) | Cl | H | Cl | Cl |
| I-69 | cyclopropyl ($C_3H_5$) | Cl | H | H | $CH_3$ |
| I-70 | cyclopropyl ($C_3H_5$) | Cl | H | H | H |
| I-71 | cyclopropyl ($C_3H_5$) | Cl | H | H | C(=O)OCH$_3$ |
| I-72 | cyclopropyl ($C_3H_5$) | Cl | H | H | Cl |
| I-73 | cyclopropyl ($C_3H_5$) | Cl | H | H | $CH(CH_3)_2$ |
| I-74 | $CF_2(CH_3)$ | Cl | H | H | cyclopropyl ($C_3H_5$) |
| I-75 | cyclopropyl ($C_3H_5$) | Cl | H | cyclopropyl ($C_3H_4$) | |
| I-76 | cyclopropyl ($C_3H_5$) | Cl | H | cyclobutyl ($C_4H_6$) | |
| I-77 | cyclopropyl ($C_3H_5$) | Cl | H | cyclopentyl ($C_5H_8$) | |
| I-78 | $C(CH_3)_3$ | Cl | H | H | cyclopropyl ($C_3H_5$) |
| I-79 | $C(CH_3)_3$ | $CF_3$ | H | H | cyclopropyl ($C_3H_5$) |
| I-80 | $C(CH_3)_3$ | H | H | H | cyclopropyl ($C_3H_5$) |
| I-81 | $CH_2CH_3$ | Cl | H | H | cyclopropyl ($C_3H_5$) |
| I-82 | $CH_2CH_3$ | H | H | H | cyclopropyl ($C_3H_5$) |

-continued

| | R¹ | R³ | R⁵ | R⁶ | R⁷ |
|---|---|---|---|---|---|
| I-83 | cyclopropyl (C₃H₅) | Cl | H | H | CH₃ |
| I-84 | cyclopropyl (C₃H₅) | Cl | CH₃ | H | H |
| I-85 | cyclopropyl (C₃H₅) | Cl | CH₃ | CH₃ | CH₃ |
| I-86 | cyclopropyl (C₃H₅) | Cl | CF₃ | H | H |
| I-87 | cyclopropyl (C₃H₅) | Cl | R⁵ and R⁷ form cyclohexenyl, R⁶ is H | | |
| I-88 | cyclopropyl (C₃H₅) | Cl | R⁵ and R⁷ form cyclopentenyl, R⁶ is H | | |
| I-89 | cyclopropyl (C₃H₅) | Cl | H | H | Si(CH₃)₃ |
| I-90 | cyclopropyl (C₃H₅) | Cl | CH₃ | H | CH₃ |
| I-91 | cyclopropyl (C₃H₅) | Cl | CH₃ | CH₃ | H |
| I-92 | cyclopropyl (C₃H₅) | Cl | H | H | CH₃ |
| I-93 | C(CH₃)₃ | H | H | H | CH₃ |
| I-94 | CH₃ | CF₃ | H | H | CH₃ |
| I-95 | cyclopropyl (C₃H₅) | Cl | H | H | C≡CH |
| I-96 | cyclopropyl (C₃H₅) | Cl | H | H | CH=CBr₂ |
| I-97 | cyclopropyl (C₃H₅) | Cl | H | H | F |
| I-98 | CH₂CH₃ | Cl | H | H | CH₃ |
| I-99 | cyclopropyl (C₃H₅) | Cl | H | H | CF₃ |
| I-100 | C(CH₃)₃ | H | H | H | CF₃ |
| I-101 | CH₃ | CF₃ | H | H | CF₃ |
| I-102 | CH₃ | CF₃ | CH₃ | CH₃ | CH₃ |
| I-103 | CH₂CH₃ | Cl | H | H | CF₃ |
| I-104 | cyclopropyl (C₃H₅) | Cl | H | H | Br. |

20. A seed coated with at least one compound of the formula I, as defined in claim 1, and/or an agriculturally acceptable salt thereof, in an amount of from 0.1 to 10 kg per 100 kg of seed.

21. A seed coated wth the composition of claim 12 in an amount of from 0.1 to 10 kg per 100 kg of seed.

* * * * *